United States Patent
Doronina et al.

(10) Patent No.: US 11,857,565 B2
(45) Date of Patent: Jan. 2, 2024

(54) HYDROPHOBIC AURISTATIN F COMPOUNDS AND CONJUGATES THEREOF

(71) Applicant: SEAGEN INC., Bothell, WA (US)

(72) Inventors: Svetlana O. Doronina, Snohomish, WA (US); Philip Moquist, Seattle, WA (US)

(73) Assignee: SEAGEN INC., Bothell, WA (US)

( * ) Notice: Subject to any disclaimer, the term of this patent is extended or adjusted under 35 U.S.C. 154(b) by 453 days.

(21) Appl. No.: 16/968,749

(22) PCT Filed: Feb. 20, 2019

(86) PCT No.: PCT/US2019/018825
§ 371 (c)(1),
(2) Date: Aug. 10, 2020

(87) PCT Pub. No.: WO2019/164987
PCT Pub. Date: Aug. 29, 2019

(65) Prior Publication Data
US 2021/0008099 A1    Jan. 14, 2021

Related U.S. Application Data

(60) Provisional application No. 62/633,059, filed on Feb. 20, 2018.

(51) Int. Cl.
| A61K 31/74 | (2006.01) |
| A61K 47/64 | (2017.01) |
| A61K 38/02 | (2006.01) |
| A61K 47/65 | (2017.01) |

(52) U.S. Cl.
CPC .............. *A61K 31/74* (2013.01); *A61K 38/02* (2013.01); *A61K 47/64* (2017.08); *A61K 47/65* (2017.08)

(58) Field of Classification Search
CPC ..................................................... A61K 31/74
See application file for complete search history.

(56) References Cited

U.S. PATENT DOCUMENTS

| 8,664,407 B2 | 3/2014 | Chen |
| 2009/0018086 A1 | 1/2009 | Doronina |
| 2012/0141509 A1 | 6/2012 | Doronina |

(Continued)

FOREIGN PATENT DOCUMENTS

| EP | 2832856 A1 | 2/2015 |
| EP | 2842575 A1 | 3/2015 |
| WO | 199819705 A1 | 5/1998 |

(Continued)

OTHER PUBLICATIONS

Doronina, S.O. et al. (Oct. 2008, e-pub. Sep. 20, 2008). "Novel Peptide Linkers for Highly Potent Antibody—Auristain Conjugate," Bioconugate Chem. 19:1960-1963.

(Continued)

*Primary Examiner* — Benjamin J Packard
(74) *Attorney, Agent, or Firm* — MORRISON & FOERSTER LLP

(57) ABSTRACT

Ligand Drug Conjugates of hydrophobically-modified auristatin F compounds that exhibit cytotoxic activities towards targeted cells, including abnormal cells such as cancer cells, that are MDR+ while also exhibiting bystander activities towards nearby cells having lower expression of the moeity targeted by the Conjugate.

12 Claims, 3 Drawing Sheets

(56) References Cited

U.S. PATENT DOCUMENTS

2017/0216391 A1 8/2017 Doronina

FOREIGN PATENT DOCUMENTS

| WO | 2004010957 A2 | 2/2004 |
|---|---|---|
| WO | 2004010957 A3 | 6/2004 |
| WO | 2007086083 A1 | 8/2007 |
| WO | 2009117531 A1 | 9/2009 |
| WO | 2013147153 A1 | 10/2013 |
| WO | 2013173393 A1 | 11/2013 |
| WO | 2015123679 A1 | 8/2015 |

OTHER PUBLICATIONS

Extended European Search Report, dated Oct. 2, 2017, for European Patent Application No. 15748980.8, 9 pages.

Harada, M. et al. (Dec. 31, 2000). "Determinants for the Drug Release From T-0128, Camptothecin Analogue-Carboxymethyl Dextran Conjugate," Journal of Controlled Release 69:399-412.

International Preliminary Report on Patentability, dated Aug. 23, 2016, for PCT Application No. PCT/US2015/16185, filed Feb. 17, 2016, 5 pages.

International Preliminary Report on Patentability, dated Aug. 27, 2020, for PCT Application No. PCT/US2019/018825, filed Feb. 20, 2020, 8 pages.

International Search Report and Written Opinion, dated May 1, 2015, for PCT Application No. PCT/US2015/16185, filed Feb. 17, 2015, 11 pages.

International Search Report and Written Opinion, dated May 15, 2019, for PCT Application No. PCT/US2019/018825, filed Feb. 20, 2019, 15 pages.

Shiose, Y. et al. (2009, e-pub. Dec. 18, 2008). "Systematic Research of Peptide Spacers Controlling Drug Release From Macromolecular Prodrug System, Carboxymethyldextran Polyalcohol-Peptide-Drug Conjugates," Bioconjugate Chem. 20:60-70.

Sutherland, M.S.K. et al. (2006, e-pub. Feb. 16, 2006). "Lysosomal Trafficking and Cysteine Protease Metabolism Confer Target-specific Cytotoxicity by Peptide-linked Anti-CD30-Auristatin Conjugates," Journal of Biological Chemistry 281(15):10540-10547, 19 pages.

Lyon, R.P et al. (Jul. 2015; e-pub. Jun. 15, 2015). "Reducing Hydrophobicity of Homogeneous Antibody-Drug Conjugates Improves Pharmacokinetics and Therapeutic Index," Nat Biotechnol 33(7):733-735.

R¹ = unbranched alkyl

HYDROPHOBIC AURISTATIN F COMPOUNDS AND CONJUGATES THEREOF

CROSS REFERENCE TO RELATED APPLICATIONS

This application is a national stage application under 35 U.S.C. § 371 of International Application No. PCT/US2019/018825, filed internationally on Feb. 20, 2019, which claims priority to U.S. Provisional Application 62/633,059 filed Feb. 20, 2018, the contents of which are incorporated herein by reference in their entirety.

BACKGROUND OF THE INVENTION

The invention relates to hydrophobic Auristatin F (AF) compounds and related compounds and conjugates thereof that exhibit activity against MDR$^+$ cancer cells having higher copy number of the targeted antigen while exhibiting bystander activity against cancer cells with lower copy number or undetectable levels of that antigen.

Traditional antibody auristatin drug conjugates either exhibit activity against MDR$^+$ cancer cells or have bystander activity but no single-agent antibody auristatin drug conjugate has been reported that exhibits both of these desirable activities. Activity against MDR$^+$ cells is considered desirable as emergence of resistance to therapy is often associated with clonal expansion of cancer cells within a tumor in which the surviving cells that remain after initial therapy have been selected on average to have higher copy numbers of multiple drug resistant transporters. Bystander activity is also a desirable property because of the heterogeneous population of cancer cells within a tumor. Thus, cancer cells in a solid tumor have varying copy numbers of targeted antigen, and it is not unusual for some of these cells to have no detectable levels of the antigen as determined by standard immunohistological methods. Again, survival of those cells from initial therapy leads to their clonal expansion, which allows for re-emergence of the tumor that is more resistant to subsequent rounds of the same therapy.

Significant amounts of research have been conducted for developing auristatin drug conjugates for the treatment of cancer (e.g., see Maderna A. and Leverett, C. A. "Recent Advances in the development of new auristatins: structural modifications and application in antibody drug conjugates" Mol. Pharmacol. (2015) 12: 1798-1812). Those conjugates may be broadly divided into two classes based upon the type of conjugated auristatin drug. One class is exemplified by auristatin E (AE) and monomethyl auristatin E (MMAE) and the other is exemplified by auristatin F (AF) and monomethyl auristatin F (MMAF) in which the neutral C-terminal norephedrine component of AE/MMAE has been replaced with phenylalanine, which is negatively charged at physiological pH. The absence of a negative charge on AE/MMAE as a free drug allows its entry into nearby cancer cells by passive diffusion once released from targeted cancer cells that have processed the AE or MMAE conjugate (Li, F. et al. "Intracellular released payload influences potency and bystander-killing effects of antibody-drug conjugates in preclinical models" Cancer Res. (2016) 76(9): 2710-2719) That permits action, commonly referred to as bystander activity, on those nearby cancer cells that otherwise would not be exposed to free drug released from the Conjugate due to low copy number or undetectable levels of the targeted antigen. However, the lack of a C-terminal negative charge in AE/MMAE significantly reduces or provides no detectable activity against MDR$^+$ cells compared to AF/MMAF, as such compounds are typically substrates for the MDR transporter (Chen, R. et al. "CD30 downregulation, MMAE resistance, and MDR1 upregulation are all associated with resistance to brentuximab vedotin" Mol. Cancer Ther. (2015) 14(6): 1376-1384). On the other hand, AF and MMAF as free drugs are significantly poorer MDR substrates in comparison to AE/MMAE, due to the presence of the negative charge of the phenylalanine C-terminal component. As a consequence AF/MMAF Conjugates have improved activity against MDR$^+$ cancer cells (Doronina, S. O. et al. "Enhanced activity of monomethylauristatin F through monoclonal antibody delivery: effects of linker technology on efficacy and toxicity" Bioconj. Chem. (2006) 17: 114-124). However, that same negative charge decreases the cell permeability of free drug so that AF/MMAF conjugates provide limited or no bystander activity despite potent activity against antigen-positive cells (Doronina, S. O. et al. "Novel peptide linkers for highly potent antibody-auristatin conjugate" Bioconj. Chem. (2008) 19: 1960-1963).

In view of the significant effort to date in developing single-agent auristatin-based Conjugates, there remains a long-standing need for such Conjugates to have dual MDR$^+$ and bystander activities. The present disclosure unexpectedly provides a solution to that problem by providing modified AF and AF-type compounds and single-agent auristatin ADCs having conjugation thereto through the C-terminal carboxylic acid functional group in which the hydrophobicity of the free drugs have been tuned through synthetically-accessible modifications of their structures. From those modifications, ADCs were obtained having bystander activity while sufficiently retaining the activity of the parent auristatin F Conjugate towards MDR$^+$ cancer cells.

Furthermore, the amount of bystander activity provided by those hydrophobically-modified AF Conjugates is tunable based upon the amount of increased hydrophobicity introduced into the AF or AF-type free drug relative to the parent free drug within a tolerable range in which MDR$^+$ activity of parent is essentially, substantially, or sufficiently retained. The ability to do so is an another important advantage provided by the present invention, since the interplay between favorable bystander activity by released free drug against nearby cancer cells with low copy number or undetectable levels of targeted antigen and bystander activity against more distant normal cells, which would lead to off-target toxicities, is context dependent. Thus, maximal bystander activity would typically be desired against solid tumors with the highest cancer cell heterogeneity, while lower bystander activity would typically be more desirable against more homogenous tumors, which have limited numbers of cancers cells with lower copy number compared to the bulk of the cancer cells or undetectable levels of targeted antigen, or those cancers where diffusion of free drug from the desired site of action is most likely, as would likely be the case for haematological malignancies (e.g., see Staudacher, A. H. and Brown, M. P. "Antibody drug conjugates and bystander killing: is antigen-dependent internalisation required?" Br. J. Cancer (2017) 117: 1736-1742).

SUMMARY OF THE INVENTION

One principle embodiment of the invention provides for synthetically-accessible hydrophobically-modified auristatin F (AF) and AF-type compounds, collectively referred to as hydrophobic AF compounds, that are suitable for conjugation to the C-terminal component of the auristatin structure for providing ADCs having dual MDR$^+$ and tunable bystander activities against targeted cells, wherein the hydrophobic AF compounds are related to auristatin F by having the structure of Formula H-AF:

(H-AF)

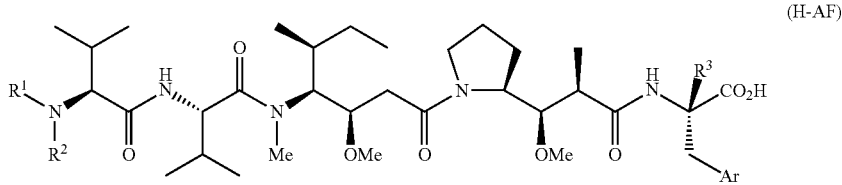

or a salt thereof, in particular, a pharmaceutically acceptable salt, wherein Ar is phenyl, thienyl, 1-napthyl, 2-napthyl or benzo[b]thiophen-3-yl, optionally substituted;

$R^2$ is $C_1$-$C_2$ alkyl;

$R^3$ is independently selected from the group consisting of hydrogen and $C_1$-$C_2$ alkyl; and $R^1$ is $C_1$-$C_9$ alkyl, which is inclusive of saturated $C_1$-$C_9$ alkyl and unsaturated $C_3$-$C_9$ alkyl, optionally substituted by a $C_3$-$C_6$ carbocyclyl to provide a (carbocyclyl)-alkylene- of up to 9 total carbon atoms, or $R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in the (carbocyclyl)alkyl(ene) moieties of $R^1$, $R^2$ and $R^3$ is between 3 and 10, and $R^1$, $R^2$ and $R^3$ are not each methyl, or wherein Ar is phenyl; $R^3$ is hydrogen; $R^1$ is a first non-aromatic hydrophobic moiety; and $R^2$ is a second non-aromatic hydrophobic moiety, wherein $R^1$ and $R^2$ provide the hydrophobic auristatin F compound of Formula H-AF characterized by a clogP value of between about 4.4 to about 7.2, and wherein the parent auristatin F compound has the structure of Formula H-AF in which $R^1$ and $R^2$ are methyl, $R^3$ is hydrogen, and Ar is phenyl.

Other hydrophobic AF compounds that are related to auristatin F and are synthetically accessible have the internal valine residue of AF or a Formula H-AF compound replaced with another α-amino acid residue having a different hydrophobic α-carbon side chain provided that the cLogP of the hydrophobic AF compound from said replacement is or remains within the range of between about 4.4 to about 7.2.

Still other hydrophobic AF compounds that are related to auristatin F have the structure of AF or any one of the previously described hydrophobically-modified AF compounds in which the N-methyl substituent of the Dil amino acid residue has been replaced with variable group $R^5$, wherein $R^5$ is $C_2$-$C_6$ alkyl or has the of formula —($C_2$-$C_6$ alkylene)-X'—$R^6$, wherein X' is an independently selected amide or carbamate functional group and $R^6$ is $C_1$-$C_6$ alkyl and the remaining variable groups retain their previous meanings, with the proviso that the total number of carbon atoms in the (carbocyclyl)alkyl(ene) moieties of R, $R^2$, $R^3$ and $R^5$ is between 3 and 10, or has been replaced with a more hydrophobic moiety provided that the cLogP from said replacement is or remains within the range of between about 4.4 to about 7.2, Another principal embodiment of the invention provides for a Ligand Drug Conjugate (LDC) composition represented by Formula 1:

$$L-[LU-(D')]_p \qquad (1)$$

or a salt thereof, in particular a pharmaceutically acceptable salt thereof, wherein L is a Ligand Unit; LU is a Linker Unit; and subscript p is a number ranging from 1 to 24; D' represents from 1 to 4 hydrophobic auristatin F Drug Units each of which is a hydrophobic AF drug of Formula H-AF conjugated to its C-terminal component, in particular through its carboxylic acid functional group, for each drug linker moiety of formula -LU-D', wherein in some aspects the Ligand Unit is an antibody or antigen-binding fragment thereof, thereby defining an antibody Ligand Unit of an Antibody Drug Conjugate (ADC), wherein the Ligand Unit is capable of selective binding to a targeted moiety of a targeted cell, which in some aspects is an antigen of a cancer cell, for subsequent release of free drug, wherein the targeted moiety is preferably capable of internalization along with bound Ligand Drug Conjugate compound into the targeted cell upon said binding to initiate intracellular release of free drug subsequent to said internalization, wherein each hydrophobic auristatin F drug linker moiety in a Ligand Drug Conjugate compound of the composition has the structure of Formula 1A:

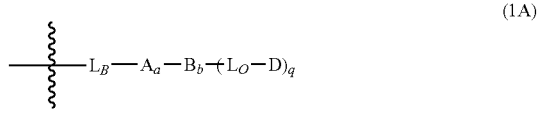

(1A)

or a salt thereof, in particular a pharmaceutically acceptable salt thereof, wherein the wavy line indicates covalent attachment to L; $L_B$ is an ligand covalent binding moiety, which is an antibody covalent binding moiety when L is an antibody Ligand Unit; A is a first optional Stretcher Unit; subscript a is 0 or 1 indicating the absence of presence of A, respectively; B is an optional Branching Unit; subscript b is 0 or 1, indicating the absence of presence of B, respectively; $L_O$ is an optional secondary linker moiety; D is the hydrophobic AF Drug Unit; and subscript q is an integer ranging from 1 to 4, provided that subscript b is 1 when subscript q ranges from 2 to 4 and is 0 when subscript q is 1, wherein the LDC compound has the structure of Formula 1 in which subscript p is replaced by subscript p', wherein subscript p' is an integer ranging from 1 to 24.

A related principle embodiment provides for a Drug Linker compound of Formula I:

$$LU'\text{-}(D') \qquad (I)$$

or a salt thereof, in particular a pharmaceutically acceptable salt thereof, wherein LU' is a LU precursor; and D' represents from 1 to 4 hydrophobic AF Drug Units, each of which is a hydrophobic AF drug of Formula H-AF conjugated to its C-terminal component, in particular through its carboxylic acid functional group, wherein the Drug Linker compound is further defined by the structure of Formula IA:

(IA)

wherein $L_B'$ is a ligand covalent binding moiety precursor and the remaining variable groups are as defined for Formula 1A.

Those and other embodiments of the invention are described in more detail in the following "Detailed Description of the Invention" and "Claims".

DETAILED DESCRIPTION OF THE INVENTION

General

Figure 1:
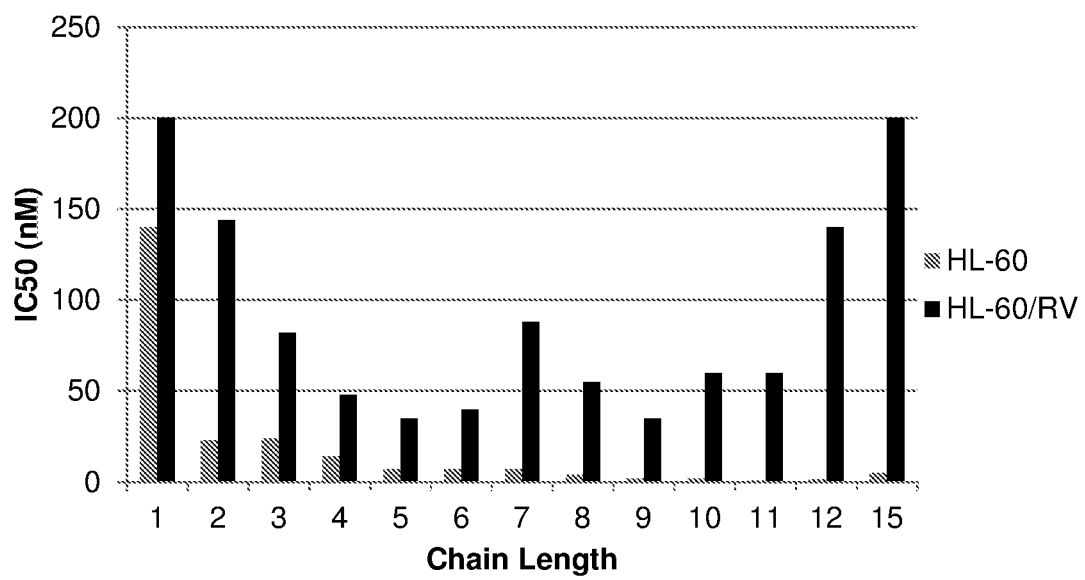
FIG. 1. Variation of in vitro $IC_{50}$ values for auristatin free drugs on MDR-HL60 and $MDR^+$ HL60/RV acute myeloid leukemia cells with increasing unbranched alkyl chain length replacing the N-terminal methyl of auristatin F (n=1)
Figure 1:
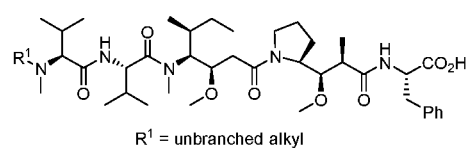
Figure 2:
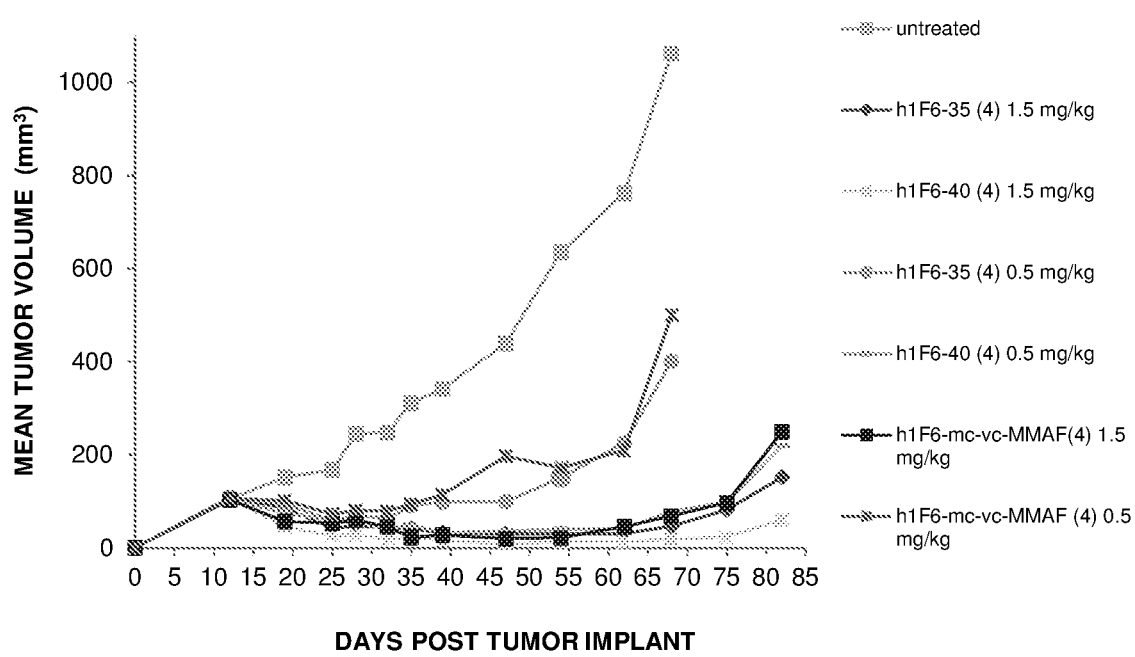
FIG. 2. In vivo efficacies of hydrophobic auristatin F ADCs targeting CD70 against a nude mouse xenograft model bearing subcutaneous 786-0 renal carcinoma tumors, which are $MDR^+$, administered i.p. at doses of 0.5 and 1.5 mg/Kg.
Figure 3:
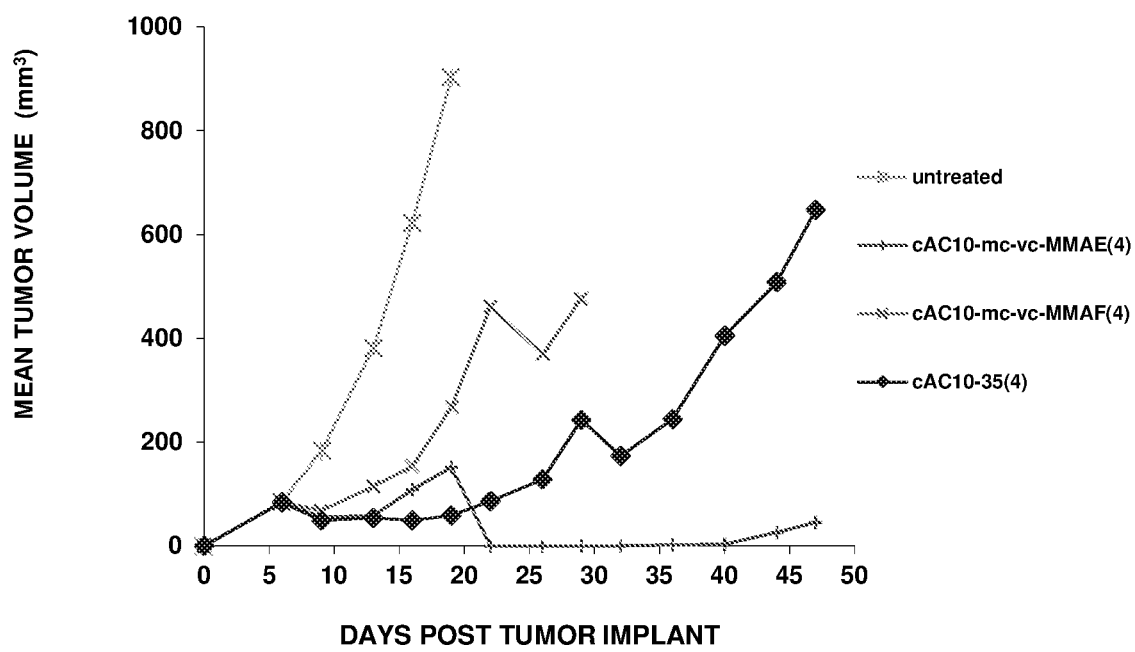
FIG. 3. In vivo efficacies of a hydrophobic auristatin F ADC targeting CD30 and comparator ADCs having MMAE and MMAF Drug Units against a nude mouse xenograft model bearing an admixed Karpas/KarpasBVR Hodgkin ($MDR^-/MDR^+$) lymphoma tumors, administered i.p. at doses of 3 mg/Kg.

The present invention is based, in part, on the unexpected finding that a hydrophobic auristatin F (AF) compound conjugated through its C-terminal carboxylic acid functional group provides an auristatin Antibody Drug Conjugate having immunologically-specific cytotoxic activity towards targeted cancer cells, which are characterized by higher copy number of the targeted antigen, and bystander activity against nearby cancer cells, which are characterized by a lower copy number or undetectable levels of the targeted antigen, and are sufficiently cytotoxic irrespective of the heterogeneity in MDR status of the tumor cells throughout the tumor. It was unpredictably found upon exposure of cancer cells to an ADC having conjugation to a hydrophobic AF compound, which is characterized by an increased hydrophobicity relative to AF in the parent ADC, that sufficient retention of $MDR^+$ activity, previously observed for the parent ADC having conjugation to AF through its C-terminal carboxylic acid functional group, occurred with emergence of bystander activity and that the dual bystander and $MDR^+$ activities were observed for a narrow range of that increase as a result of the hydrophobic modification of AF. That bystander activity has previously been shown to occur for uncharged hydrophobic auristatin conjugates such as AE and MMAE ADCs, the latter of which is conjugated through the N-terminal component through a carbamate functional group.

It is believed, without being bound by theory, that an ADC conjugated to a hydrophobic AF compound through its C-terminal component that is characterized by a hydrophobicity outside the narrow range disclosed herein for retaining the dual activities either fail to exhibit bystander effects by having insufficient permeability into cancer cells with low copy number or undetectable levels of targeted antigen or are so hydrophobic that the hydrophobically-modified AF free drug released after immunologically specific internalization of the ADC becomes an MDR substrate. Furthermore, those finding are extendable to a Conjugate that releases its Drug Unit as a modified AF free drug extracellularly subsequent to immunologically selective binding. In that instance, insufficient hydrophobicity of the modified free drug will not provide for sufficient cellular permeability to allow for directed cytotoxicity or bystander effect, which will be independent of the cells MDR status, whereas an excessively hydrophobic modified AF free drug, although readily cell-permeable for directed cytotoxicity, would not allow for bystander effect against nearby $MDR^+$ cancer cells due expulsion of that modified AF free drug by the MDR transporter.

The above principles for N-terminal modification also apply when hydrophobicity of the parent AF free drug is increased while remaining within the same narrow range disclosed herein for providing a hydrophobically-modified AF free drug having dual $MDR^+$ and bystander effects when hydrophobicity is introduced or additionally introduced at alternate sites within AF that do not adversely affect the tubulin binding activity of the free drug to an extent that cytotoxicity against auristatin-sensitive cancer cells is unacceptably diminished.

1. Definitions

Unless otherwise stated or implied by context, terms that are used herein have the meanings defined below. Unless otherwise contraindicated or implied, e.g., by including mutually exclusive elements or options, in those definitions and throughout this specification, the terms "a" and "an" mean one or more and the term "or" means and/or where permitted by context. Thus, as presented in the specification and the appended claims, the singular forms "a," "an," and "the" include plural referents unless the context clearly dictates otherwise.

At various locations in the present disclosure, e.g., in any disclosed embodiments or in the claims, reference is made to compounds, compositions, or methods that "comprise" one or more specified components, elements or steps. Invention embodiments also specifically include those compounds, compositions, compositions or methods that are, or that consist of, or that consist essentially of those specified components, elements or steps. The term "comprised of" is used interchangeably with the term "comprising" and are stated as equivalent terms. For example, disclosed compositions, devices, articles of manufacture or methods that "comprise" a component or step are open and they include or read on those compositions or methods plus an additional component(s) or step(s). However, those terms do not encompass unrecited elements that would destroy the functionality of the disclosed compositions, devices, articles of manufacture or methods for its intended purpose. Similarly, disclosed compositions, devices, articles of manufacture or methods that "consist of" a component or step are closed and they would not include or read on those compositions or methods having appreciable amounts of an additional component(s) or an additional step(s). Furthermore, the term "consisting essentially of" admits for the inclusion of unrecited elements that have no material effect on the functionality of the disclosed compositions, devices, articles of manufacture or methods for its intended purpose as further defined herein. The section headings used herein are for organizational purposes only and are not to be construed as limiting the subject matter described. Unless otherwise indicated, conventional methods of mass spectroscopy, NMR, HPLC, protein chemistry, biochemistry, recombinant DNA techniques, and pharmacology are employed.

"About", as the term is used herein, unless otherwise stated or implied by context, in connection with a numeric value or range of values to describe a particular property of a compound or composition, indicate that the value or range of values may deviate to an extent deemed reasonable to one of ordinary skill in the art while still describing the particular property. Reasonable deviations include those that are within the accuracy or precision of the instrument(s) used in measuring, determining or deriving the particular property. Specifically, the term "about" when used in this context, indicate that the numeric value or range of values can vary by 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, or 0.01% of the recited value or range of values, typically by 10% to 0.5%, more typically by 5% to 1%, while still describing the particular property.

With respect to subscript p, which denotes the average number of drug linker moieties in a Ligand Drug Conjugate composition as further defined herein, the term "about" reflects the accepted uncertainty in the art for determining that value from a distribution of Ligand Drug Conjugate compounds within that composition as determined by standard methods of size exclusion, HIC chromatography or HPLC-MS.

"Essentially retains", "essentially retaining" and like terms, as used herein, unless otherwise stated or implied by context, refers to a property, characteristic, function or activity of a compound or composition or moiety thereof that has not detectably changed or is within experimental error of determination of that same activity, characteristic or property of a compound or composition or moiety of related structure.

"Substantially retains", "substantially retaining" and like terms, as used herein, unless otherwise stated or implied by context, refers to a measured value of a physical property or characteristic of a compound or composition or moiety thereof that may be statistically different from the determination of that same physical property of another compound or composition or moiety of related structure, but which such difference does not translate to a statistically significant or meaningful difference in biological activity or pharmacological property in a suitable biological test system for evaluating that activity or property (i.e., biological activity or property is retained or is essentially retained). Thus, the phrase "substantially retains" is made in reference to the effect that a physical property or characteristic of a compound or composition has on a physiochemical or pharmacological property or biological activity that is explicitly associated with that physical property or characteristic.

"Bystander activity" and like terms, as used herein, unless otherwise stated or implied by context, refers to the ability of free drug once released into a targeted cell from a Ligand Drug Conjugate having that drug in the form of a Drug Unit, which in some aspects the targeted cell is an abnormal cell such as a cancer cell, to exit the initially targeted cell and enter into a nearby cell so as to exert a cytotoxic effect against that nearby cell. In some aspects, the nearby cells are a subset of the targeted abnormal cells that have lower or no detectable level of the targeted moiety. Conjugates having bystander activity are typically more effective against a heterogeneous population of target cells, which in some aspects is a solid mass of abnormal cells, such as cancer cells of a solid tumor. Bystander effect may be less desirable to some degree for non-solid tumors, due to the permeability of the free drug exiting the initially targeted cell, as it is able to diffuse from the site of its initial release into the periphery and enter into normal cells. In that event, the Conjugate may contribute to undesirable side effects normally attributable to administration of the drug in unconjugated form.

"Sufficiently retains", "sufficiently retaining" and like terms, as used herein, unless otherwise stated or implied by context, refers to a measured value of a desired physical property or characteristic of a structurally related compound or composition or moiety thereof, that does deviate from the determination of that same physical property of the parent compound, composition or moiety thereof to extent that would obviate the desired physical property or characteristic, or refers to a measured value of a desired physical property of parent compound or composition or moiety thereof, that is retained by a structurally related compound, composition or moiety thereof to extent that is sufficient for the same intended purpose.

In the context for determining if there will be sufficient retention of MDR$^+$ cytotoxicity of an auristatin Ligand Drug Conjugate having conjugation to a hydrophobically-modified auristatin F compound, alternatively referred to as a Conjugate having a hydrophobic AF Drug Unit or a hydrophobic AF Conjugate, the activity of that Conjugate against cells of an auristatin-sensitive, antigen-positive MDR$^+$ cell line is sufficiently retained from an otherwise identical LDC in which the auristatin Drug Unit is that of the parent AF compound if the potency of the hydrophobic AF Conjugate is essentially the same or greater than that of the parent AF conjugate or if it is reduced by no more than about 1.2 log units, typically no more than about 1.1 log units, or more than about 1.0 log units or no more than about 0.5 log units, from that of parent AF conjugate, when both are separately tested in the same test system, provided that the potency of the parent Conjugate against the MDR$^+$ cancer cells in that test system is from about 1 ng/mL to about 100 ng/mL or from about 2 to about 40, or from about 4 to about 20 ng/mL.

In the context of determining sufficient retention of bystander activity, it is accepted in the art that the in vitro cytotoxicity of the free auristatin drug, which is shown to correlate with the ability of the free drug to permeate cellular membranes, is considered as a surrogate for the drug-related bystander activity of a corresponding Ligand Drug Conjugate provided that the auristatin drug is conjugated via a cleavable linker allowing for facile intracellular release of free drug into a targeted cell. That activity is determined by comparing the potency of the unconjugated hydrophobic auristatin F compound to the potency of unconjugated monomethyl auristatin E (MMAE) or unconjugated auristatin E (AE) against a cell line that is to be targeted by a Conjugate having conjugation to that hydrophobic auristatin F compound. The bystander activity of the hydrophobic auristatin F compound is deemed to be sufficiently retained relative to that of MMAE or AE when the IC$_{50}$ value obtained for the unconjugated hydrophobic AF compound is about the same as the MMAE or AE free drug or is increased by no more than about 1.2 log units, about 1 log unit or about 0.5 log units, provided that the IC$_{50}$ value of MMAE ranges from about 0.1 nM to about 2 nM and the IC$_{50}$ value of AE ranges from about 0.1 nM to about 2 nM when tested separately in the same test system as the hydrophobic auristatin F compound.

Alternatively, in the context of determining sufficient retention of bystander activity for a Ligand Drug Conjugate (LDC), such as an Antibody Drug Conjugate (ADC) with conjugation to a hydrophobic auristatin F compound, that activity is determined by comparing its potency to the potency of a MMAE LDC against a co-culture of abnormal cell lines having an approximately equal mixture of cells from antigen-positive and antigen-negative abnormal cell lines otherwise having essentially the same genetic background and having similar growth rates. The said comparison is performed for Conjugates containing a cleavable linker allowing for efficient intracellular release of its Drug Unit as free drug. The bystander activity of the hydrophobic auristatin F LDC is deemed to be sufficiently retained from the comparator MMAE LDC when the $IC_{50}$ value obtained for the hydrophobic AF LDC is the same as that of the comparator MMAE LDC or is increased by about 1.2 log units, about 1 log unit or about 0.5 log units, provided that the $IC_{50}$ value of the comparator MMAE LDC is from about 5 ng/mL to about 25 ng/mL when tested separately in the same test system as the hydrophobic auristatin F compound.

Additionally, in the context of determining sufficient retention of bystander activity for an Ligand Drug Conjugate, such as an Antibody Drug Conjugate (ADC), having conjugation to a hydrophobic auristatin F compound, that activity is determined by comparing its efficacy to the efficacy of a MMAE LDC in vivo using an admixed tumor xenograft model. In those models, the tumor contains an approximately equal mixture of cells from antigen-positive and antigen-negative cell lines having essentially the same genetic background and having similar growth rates. The said comparison is performed for Conjugates containing a cleavable linker allowing for efficient release its Drug Unit as free drug. The bystander activity of the hydrophobic auristatin F LDC is deemed to be sufficiently retained relative that of the comparator MMAE LDC, when the dose level causing significant tumor regression, typically in the range of about 2 mg/Kg to about 6 mg/Kg, are observed to be the same or less than that of the comparator MMAE LDC or is increased to no more than about 5-fold, no more than about 3-fold or no more than about 2 fold.

"Negligibly", "negligible" and like terms, as used herein, unless otherwise stated or implied by context, is an amount of an impurity below the level of quantification by HPLC analysis and if optical impurities are present represents from about 0.5% to about 0.1 w/w % of the composition that it contaminates. Depending on context, those terms may alternatively mean that no statistically significant difference is observed between measured values or outcomes or are within experimental error of the instrumentation used to obtain those values. Negligible differences in values of a parameter determined experimentally do not imply that an impurity characterized by that parameter is present in negligible amount.

"Predominately containing", "predominately having" and like terms, as used herein, unless otherwise stated or implied by context, refers to the major component of a mixture. When the mixture is of two components, then the major component represents more than 50% by weight of the mixture. With a mixture of three or more components the predominant component is the one present in greatest amount in the mixture and may or may not represent the majority of the mass of the mixture.

"Electron-withdrawing group", as the term is used herein, unless otherwise stated or implied by context, refers to a functional group or electronegative atom that draws electron density away from an atom to which it is bonded either inductively and/or through resonance, whichever is more dominant (i.e., a functional group or atom may be electron-donating through resonance but may overall be electron withdrawing inductively), and tends to stabilize anions or electron-rich moieties. The electron-withdrawing effect is typically transmitted inductively, albeit in attenuated form, to other atoms attached to the bonded atom that has been made electron-deficient by the electron-withdrawing group (EWG), thus reducing the electron density of a more remote reactive center.

An electron-withdrawing group (EWG) is typically selected from the group consisting of —C(═O), —CN, —NO$_2$, —CX$_3$, —X, —C(═O)OR', —C(═O)NH$_2$, —C(═O)N(R')R$^{op}$, —C(═O)R', —C(═O)X, —S(═O)$_2$R$^{op}$, —S(═O)$_2$OR', —SO$_3$H$_2$, —S(═O)$_2$NH$_2$, —S(═O)$_2$N(R')R$^P$, —PO$_3$H$_2$, —P(═O)(OR')(OR$^{op}$)$_2$, —NO, —NH$_2$, —N(R')(R$^{op}$), —N(R$^{op}$)$_3{}^+$, and salts thereof, wherein X is —F, —Br, —Cl, or —I, and R$^{op}$ is, at each occurrence, independently selected from a grouping previously described for optional substituents and in some aspects is independently selected from the group consisting of $C_1$-$C_6$ alkyl and phenyl, and wherein R' is hydrogen and R$^{op}$ is selected from a grouping as described elsewhere for optional substituents and in some aspects is a $C_1$-$C_{12}$ alkyl, $C_1$-$C_8$ alkyl, $C_1$-$C_6$ alkyl or $C_1$-$C_4$ alkyl. An EWG can also be an aryl (e.g., phenyl) or heteroaryl depending on its substitution and certain electron deficient heteroaryl groups (e.g., pyridine). Thus, in some aspects, an "electron-withdrawing group" further encompasses electron-deficient $C_5$-$C_{24}$ heteroaryls and $C_6$-$C_{24}$ aryls in which the latter are substituted with electron-withdrawing substituents. More typically, an electron-withdrawing group is independently selected from the group consisting of —C(═O)OH, —C(═O)OR', —CN, —NO$_2$, —NH$_3$+, —N(R')H$_2$+, and —N(R')$_3$+, —CX$_3$, and —X, wherein X is halogen, typically independently selected from the group consisting of —F and —Cl, and wherein each R' is an independently selected from $C_1$-$C_{12}$ alkyl, typically $C_1$-$C_6$ alkyl. Depending on its substituents, an optionally substituted alkyl moiety may also be an electron withdrawing group and thus in such aspects would be encompassed by the term for an electron-withdrawing group.

"Electron-donating group", as the term is used herein, unless otherwise stated or implied by context, refers to a functional group or electropositive atom that increases electron density of an atom to which it is bonded either inductively and/or through resonance, whichever is more dominant (i.e., a functional group or atom may be electron-withdrawing inductively but may overall be electron-donating through resonance), and tends to stabilize cations or electron poor systems. The electron-donating effect is typically transmitted through resonance to other atoms attached to the bonded atom that has been made electron rich by the electron-donating group (EDG) thus increasing the electron density of a more remote reactive center. Typically, an electron donating group is selected from the group consisting of —OH, —OR' and —NH$_2$, —NHR' and N(R')$_2$, in unprotonated form, wherein each R' is an independently selected from $C_1$-$C_{12}$ alkyl, typically $C_1$-$C_6$ alkyl. Depending on its substituents, a $C_6$-$C_{24}$ aryl, $C_5$-$C_{24}$ heteroaryl, or unsaturated $C_1$-$C_{12}$ alkyl moiety may also be an electron-donating group and in some aspects, such moieties are encompassed by the term for an electron-donating group.

"Compound" as the term is used herein, unless otherwise stated or implied by context, refers to and encompasses the chemical compound itself, either named or represented by structure, and salt form(s) thereof, whether explicitly stated or not, unless context makes clear that such salt forms are to be excluded. Compound salts include zwitterionic salt forms and acid addition and base addition salt forms having organic counterions or inorganic counterions and salt forms involving two or more counterions, which may be the same or different. In some aspects, the salt form is a pharmaceutically acceptable salt form of the compound. The term "compound" further encompasses solvate forms of the compound, in which solvent is noncovalently associated with the compound or is reversibly associated covalently with the compound, as when a carbonyl group of the compound is hydrated to form a gem-diol. Solvate forms include those of the compound itself and its salt form(s) and are inclusive of hemisolvates, monosolvates, disolvates, including hydrates; and when a compound can be associated with two or more solvent molecules, the two or more solvent molecules may be the same or different. In some instances, a compound of the invention will include an explicit reference to one or more of the above forms, e.g., salts and solvates, which does not imply any solid state form of the compound; however, this reference is for emphasis only, and is not to be construed as excluding any other of the forms as identified above. Furthermore, when explicit reference to a salt and/or solvate form of a compound or a Ligand Drug Conjugate composition is not made, that omission is not to be construed as excluding the salt and/or solvate form(s) of the compound or Conjugate unless context make clear that such salt and/or solvate forms are to be excluded.

"Optical isomer", as the term is used herein, unless otherwise stated or implied by context, refers to a related compound in comparison to a reference compound both having identical atom connectivities but differing structurally by one or more chiral centers in opposite stereochemical configuration(s).

"Moiety", as the term is used herein, unless otherwise stated or implied by context, means a specified segment, fragment, or functional group of a molecule or compound. Chemical moieties are sometimes indicated as chemical entities that are embedded in or appended to (i.e., a substituent or variable group) a molecule, compound or chemical formula.

Unless indicated otherwise or implied by context, for any substituent group or moiety described herein by a given range of carbon atoms, the designated range means that any individual number of carbon atoms is described. Thus, reference to, e.g., "optionally substituted $C_1$-$C_4$ alkyl" or "optionally substituted $C_2$-$C_6$ alkenyl" specifically means that a 1, 2, 3, or 4 carbon alkyl moiety, optionally substituted, as defined herein, is present, or a 2, 3, 4, 5, or 6 carbon alkenyl moiety, optionally substituted, as defined herein, is present, respectively. All such numerical designations are expressly intended to disclose all of the individual carbon atom groups; and thus "optionally substituted $C_1$-$C_4$ alkyl" includes, methyl, ethyl, 3-carbon alkyls, and 4-carbon alkyls, including all of their positional isomers, whether substituted or unsubstituted. Thus, when an alkyl moiety is substituted, the numerical designations refer to an unsubstituted base moiety and are not intended to include carbon atoms not directly attached to the base moeity that may be present in the substituents of that base moiety. For esters, carbonates, carbamates, and ureas, as defined herein, that are identified by a given range of carbon atoms, the designated range includes the carbonyl carbon of the respective functional group. Thus, a $C_1$ ester refers to a formate ester and a $C_2$ ester refers to an acetate ester.

The organic substituents, moieties, and groups described herein, and for other any other moieties described herein, usually will exclude unstable moieties except where such unstable moieties are transient species that one can use to make a compound with sufficient chemical stability for the one or more of the uses described herein. Substituents, moieties or groups by operation of the definitions provided herein that results in those having a pentavalent carbon are specifically excluded.

"Alkyl" as the term is used herein, by itself or as part of another term, unless otherwise stated or implied by context, refers to methyl or a collection of contiguous carbon atoms, one of which is monovalent, wherein one or more of the carbon atoms are saturated (i.e., is comprised of one or more $sp^3$ carbons) and are covalently linked together in normal, secondary, tertiary or cyclic arrangements, i.e., in a linear, branched, cyclic arrangement or some combination thereof. When the contiguous saturated carbon atoms are in a cyclic arrangement such alkyl moieties are, in some aspects, referred to as carbocyclyls as further defined herein.

When referring to an alkyl moiety or group as an alkyl substituent, that alkyl substituent to a Markush structure, or another organic moiety with which it is associated, is methyl or that chain of contiguous carbon atoms covalently attached to the structure or moiety through a $sp^3$ carbon of the alkyl substituent. An alkyl substituent, as used herein, therefore contains at least one saturated moiety and may also be optionally substituted with cycloalkyl or aromatic or heteroaromatic moieties or groups or contain an alkenyl or alkynyl moiety resulting in an unsaturated alkyl. Thus, an optionally substituted alkyl substituent may additionally contain one, two, three or more independently selected double bonds and/or triple bonds, which in some aspects is derived from a saturated alkyl in which one or more hydrogen atoms is replaced by alkenyl or alkynyl moieties or some combination thereof, to define an unsaturated alkyl substituent, and may be substituted by other moieties that include appropriate optional substituents as described herein. The number of carbon atoms in a saturated alkyl can vary and typically is 1-50, 1-30 or 1-20, and more typically is 1-8 or 1-6, and the number of carbon atoms in an unsaturated alkyl moiety or group typically varies between 3-50, 3-30 or 3-20, and more typically varies between 3-8.

A saturated alkyl moiety contains saturated, acyclic carbon atoms (i.e., acyclic $sp^3$ carbons) and no $sp^2$ or sp carbon atoms, but may be substituted with an optional substituent as described herein, provided that such substitution is not through an $sp^3$, $sp^2$ or sp carbon atom of the optional substituent as that would affect the identity of the base alkyl moiety so substituted, except in those instances in which the optional substituent is a Basic Unit as described herein. Unless otherwise indicated or implied by context, the term "alkyl" will indicate a saturated, non-cyclic hydrocarbon radical, wherein the hydrocarbon radical has the indicated number of covalently linked saturated carbon atoms so that terms such as "$C_1$-$C_6$ alkyl", "$C_1$-$C_6$ alkyl", $C_{1-6}$ alkyl or $C_{1-6}$ alkyl means an alkyl moiety or group containing 1 saturated carbon atom (i.e., is methyl) or 2, 3, 4, 5 or 6 contiguous, non-cyclic saturated carbon atoms and "$C_1$-$C_8$ alkyl" refers to an alkyl moiety or group having 1 saturated carbon atom or 2, 3, 4, 5, 6, 7 or 8 contiguous saturated, non-cyclic carbon atoms. Typically, a saturated alkyl is a $C_1$-$C_6$ or $C_1$-$C_4$ alkyl moiety containing no $sp^2$ or sp carbon atoms, if other than methyl, in its contiguous carbon chain, with the latter sometimes referred to as lower alkyl, and in some aspects will refer to a saturated $C_1$-$C_8$ alkyl moiety having from 1 carbon atom to 8 contiguous acyclic $sp^3$ carbon atoms containing no $sp^2$ or sp carbon atoms, if other than methyl, in its contiguous carbon chain when the number of carbon atoms is not indicated. In other aspects, when a range of carbon atoms that encompasses methyl or a contiguous chain of carbon atoms, defines the term "alkyl" but without specifying it as saturated or unsaturated, then that term encompasses saturated alkyl with the specified range and unsaturated alkyl in which the lower limit of the range is increased by two carbon atoms. For example, the term "$C_1$-$C_8$ alkyl without limitation encompasses saturated $C_1$-$C_8$ alkyl and $C_3$-$C_8$ unsaturated alkyl.

When a saturated alkyl substituent, moiety or group is specified, species include those derived from removing a hydrogen atom from a parent alkane (i.e., an alkyl moiety is monovalent) and in some aspects include methyl, ethyl, 1-propyl (n-propyl), 2-propyl (iso-propyl, —CH(CH$_3$)$_2$), 1-butyl (n-butyl), 2-methyl-1-propyl (iso-butyl, —CH$_2$CH(CH$_3$)$_2$), 2-butyl (sec-butyl, —CH(CH$_3$)CH$_2$CH$_3$), 2-methyl-2-propyl (t-butyl, —C(CH$_3$)$_3$), amyl, isoamyl, sec-amyl and other linear and branch chain alkyl moieties.

"Alkylene," as the term is used herein, by itself of as part of another term, unless otherwise stated or implied by context, refers to a saturated, branched or straight chain hydrocarbon diradical, substituted or unsubstituted, wherein one or more of the carbon atoms is saturated (i.e., is comprised of one or more sp$^3$ carbons), of the stated number of carbon atoms ranging from 1 to 50 or 1 to 30, typically 1 to 20 or 1 to 12 carbon atoms, more typically 1 to 8, 1 or 6, or 1 to 4 carbon atoms and having two radical centers (i.e., is divalent) derived by the removal of two hydrogen atoms from the same or two different saturated (i.e., sp$^3$) carbon atoms of a parent alkane. An alkylene moiety in some aspects is an alkyl radical as described herein in which a hydrogen atom has been removed from another of its saturated carbons or from the radical carbon of an alkyl radical to form a diradical. In other aspects, an alkylene moiety is or is further encompassed by a divalent moiety derived from removing a hydrogen atom from a saturated carbon atom of a parent alkyl moiety and are exemplified without limitation by methylene (—CH$_2$—), 1,2-ethylene (—CH$_2$CH$_2$—), 1,3-propylene (—CH$_2$CH$_2$CH$_2$—), 1,4-butylene (—CH$_2$CH$_2$CH$_2$CH$_2$—), and like diradicals. In some aspects, an alkylene is a branched or straight chain hydrocarbon containing only sp$^3$ carbons (i.e., is fully saturated notwithstanding the radical carbon atoms) and in some of these and other aspects is unsubstituted. In other aspects, an alkylene contains an internal site of unsaturation(s) in the form of one or more double and/or triple bond functional groups, typically 1 or 2, more typically 1, such functional group(s) so that the terminal carbons of the unsaturated alkylene moeity are monovalent sp$^3$ carbon atoms or an alkylene contains one terminal site of unsaturation in the form of a double or triple bond functional group, so that one terminal carbon of the unsaturated alkylene moeity is a monovalent sp$^2$ or sp carbon atom and the other terminal carbon atom is a monovalent sp$^3$ carbon atom. In still other aspects, the alkylene is substituted with 1 to 4, typically 1 to 3, or 1 or 2 substituents, as defined herein for optional substituents, excluding alkyl, arylalkyl, alkenyl, alkynyl and any other moiety when the substituted alkylene differs only by the number of contiguous non-aromatic carbon atoms relative to the unsubstituted alkylene, at saturated carbon atom(s) of a saturated alkylene moiety or saturated and/or unsaturated carbon atom(s) of an unsaturated alkylene moiety.

"Carbocyclyl" as the term is used herein, by itself of as part of another term, unless otherwise stated or implied by context, refers to a radical of a monocyclic, bicyclic or tricyclic ring system, wherein each of the atoms forming the ring system (i.e., skeletal atoms) is a carbon atom and wherein one or more of these carbon atoms in each ring of the cyclic ring system is saturated (i.e., is comprised of one or more sp$^3$ carbons). Thus, a carbocyclyl is a cyclic arrangement of saturated carbons but may also contain unsaturated carbon atom(s) and therefore its carbocyclic ring may be saturated or partially unsaturated or may be fused with an aromatic moiety, wherein the points of fusion to the cycloalkyl and aromatic rings are to adjacent unsaturated carbons of the carbocyclyl moiety and adjacent aromatic carbons of the aromatic moiety.

Unless otherwise specified, a carbocyclyl can be substituted (i.e. optionally substituted) with moieties described for alkyl, alkenyl, alkynyl, aryl, arylalkyl, alkylaryl and the like or can be substituted with another cycloalkyl moiety. Cycloalkyl moieties, groups or substituents include cyclopropyl, cyclopentyl, cyclohexyl, adamantly or other cyclic moieties that have only carbon atoms in their cyclic ring systems.

When carbocyclyl is used as a Markush group (i.e., a substituent) the carbocyclyl is attached to a Markush formula or another organic moiety with which it is associated through a carbon that is involved in the carbocyclic ring system of the carbocyclyl moiety provided that carbon is not an aromatic carbon. When an unsaturated carbon of an alkene moiety comprising the carbocyclyl substituent is attached to a Markush formula, or another organic moiety with which it is associated, that carbocyclyl is sometimes referred to as a cycloalkenyl substituent. The number of carbon atoms in a carbocyclyl substituent is defined by the total number of skeletal atoms of its carbocyclic ring system. That number can vary and typically ranges from 3 to 50, 1-30 or 1-20, and more typically 3-8 or 3-6 unless otherwise specified, e.g., $C_3$-$C_8$ carbocyclyl means an carbocyclyl substituent, moiety or group containing 3, 4, 5, 6, 7 or 8 carbocyclic carbon atoms and $C_3$-$C_6$ carbocyclyl means an carbocyclyl substituent, moiety or group containing 3, 4, 5 or 6 carbocyclic carbon atoms. In some aspects a carbocyclyl is derived by the removal of one hydrogen atom from a ring atom of a parent cycloalkane or cycloalkene. Representative $C_3$-$C_8$ carbocyclyls include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl.

Therefore, carbocyclyl substituents, moieties or groups typically have 3, 4, 5, 6, 7, 8 carbon atoms in its carbocyclic ring system and in some aspects contain exo or endo-cyclic double bonds or endo-cyclic triple bonds or a combination of both wherein the endo-cyclic double or triple bonds, or the combination of both, do not form a cyclic conjugated system of 4n+2 electrons. A bicyclic ring system may share two carbon atoms and a tricyclic ring system may share a total of 3 or 4 carbon atoms. In some aspects, a carbocyclyl is a $C_3$-$C_8$ or $C_3$-$C_6$ carbocyclyl, which sometimes is substituted (i.e. optionally substituted) with one or more, 1 to 4, typically 1 to 3, or 1 or 2 moieties described herein for alkyl, alkenyl, alkynyl, aryl, arylalkyl, and alkylaryl and/or with other moieties as including substituent(s) as defined herein for optional substituents, and other times is unsubstituted. In other aspects, a cycloalkyl moiety, group or substituent is a $C_3$-$C_6$ cycloalkyl selected from the group consisting of cyclopropyl, cyclopentyl and cyclohexyl, or is a $C_3$-$C_8$ cycloalkyl that encompasses that group and is further encompasses other cyclic moieties that have no more than 8 carbon atoms in their cyclic ring systems. When the number of carbon atoms is not indicated, a carbocyclyl moiety, group or substituent has from 3 to 8 carbon atoms in one carboxylic ring system.

"Carbocyclo", as the term is used herein by itself or as part of another term, unless otherwise stated or implied by context, refers to an optionally substituted carbocyclyl as defined above wherein another hydrogen atom of its cycloalkyl ring system has been removed (i.e., it is divalent) and is a $C_3$-$C_{50}$ or $C_3$-$C_{30}$ carbocyclo, typically a $C_3$-$C_{20}$ or $C_3$-$C_{12}$ carbocyclo, more typically a $C_3$-$C_8$ or $C_3$-$C_6$ carbocyclo and in some aspects is unsubstituted or an optionally substituted $C_3$, $C_5$ or $C_6$ carbocyclo. When the number of carbon atoms is not indicated, a carbocyclo moiety, group or substituent has from 3 to 8 carbon atoms in its carboxcylic ring system.

In some aspects, that other hydrogen atom is removed from the monovalent carbon atom of the cycloalkyl to provide a divalent carbon atom, which in some instances becomes a spiro carbon atom that interrupts an alkyl moiety with that carbocyclic carbon atom. In such instances, the spiro carbon atom is attributed to the carbon atom count of the interrupted alkyl moiety and also to the carbocyclo ring system with the carbocyclo indicated as being incorporated into the alkyl moiety. In those aspects, a carbocyclo moiety, group or substituent is a $C_3$-$C_6$ carbocyclo in the form of a spiro ring system and is selected from the group consisting of cycloprop-1,1-diyl, cyclobutyl-1,1-diyl, cyclopent-1,1-diyl and cyclohex-1,1-diyl, or is a $C_3$-$C_8$ carbocyclo, which encompasses that group and is further encompassed by other divalent cyclic moieties that have no more than 8 carbon atoms in their cyclic ring systems. A carbocyclo may be a saturated or an unsaturated carbocyclo, and/or may be unsubstituted or unsubstituted in the same manner as described for a carbocyclyl moiety. In some aspects, if unsaturated, one or both monovalent carbon atoms of the carbocyclo moiety are $sp^2$ carbon atoms from the same or a different double bond functional group and in other aspects both monovalent carbon atoms are either adjacent or non-adjacent $sp^3$ carbon atoms.

"Alkenyl" as the term is used herein, by itself or as part of another term, unless otherwise stated or implied by context, refers to an organic moiety, substituent or group that comprises one or more double bond functional groups (e.g., a —CH=CH— moiety) or 1, 2, 3, 4, 5 or 6 or more, typically 1, 2 or 3 of such functional groups, more typically one such functional group, and in some aspects may be substituted (i.e., is optionally substituted) with an aryl moiety or group such as phenyl, or may contain non-aromatic linked normal, secondary, tertiary or cyclic carbon atoms, i.e., linear, branched, cyclic or any combination thereof as part of the base moeity unless the alkenyl substituent, moiety or group is a vinyl moiety (e.g., a —CH=CH$_2$ moiety). An alkenyl moiety, group or substituent having multiple double bonds may have the double bonds arranged contiguously (i.e., a 1,3-butadienyl moiety) or non-contiguously with one or more intervening saturated carbon atoms or a combination thereof, provided that a cyclic, contiguous arrangement of double bonds do not form a cyclic conjugated system of 4n+2 electrons (i.e., is not aromatic).

An alkenyl moiety, group or substituent contains at least one $sp^2$ carbon atom in which that carbon atom is divalent and is doubly bonded to another organic moiety or Markush structure to which it is associated, or contains at least two $sp^2$ carbon atoms in conjugation to each other in which one of the $sp^2$ carbon atoms is monovalent and is singly bonded to another organic moiety or Markush structure to which it is associated. Typically, when alkenyl is used as a Markush group (i.e., is a substituent) the alkenyl is singly bonded to a Markush formula, or another organic moiety with which it is associated, through a $sp^2$ carbon of an alkene functional group of the alkenyl moiety. In some aspects, when an alkenyl moiety is specified, species encompasses those corresponding to any of the optionally substituted alkyl or carbocyclyl, groups moieties or substituents described herein that has one or more endo double bonds in which a $sp^2$ carbon atom thereof is monovalent and monovalent moieties derived from removal of a hydrogen atom from a $sp^2$ carbon of a parent alkene compound. Such monovalent moieties are exemplified without limitation by vinyl (—CH=CH$_2$), allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, and cyclohexenyl. In some aspects, the term alkenyl encompasses those and/or other linear, cyclic and branched chained, all carbon-containing moieties containing at least one double bond functional group in which one of the $sp^2$ carbon atoms is monovalent.

The number of carbon atoms in an alkenyl moiety is defined by the number of $sp^2$ carbon atoms of the alkene functional group(s) that defines it as an alkenyl substituent and the total number of contiguous non-aromatic carbon atoms appended to each of these $sp^2$ carbons not including any carbon atom of the other moiety or Markush structure for which the alkenyl moiety is a variable group and carbon atoms from any optional substituent to the alkenyl moeity. That number ranges from 1 to 50 or 1 to 30, typically 1 to 20 or 1 to 12, more typically, 1 to 8, 1 to 6 or 1 to 4 carbon atoms when the double bond functional group is doubly bonded to a Markush structure (e.g. =CH$_2$), or ranges from 2 to 50, typically 2 to 30, 2 to 20 or 2 to 12, more typically 2 to 8, 2 to 6 or 2 to 4 carbon atoms, when the double bond functional group is singly bonded to the Markush structure (e.g., —CH=CH$_2$). For example, $C_2$-$C_8$ alkenyl or $C_2$-$C_8$ alkenyl means an alkenyl moiety containing 2, 3, 4, 5, 6, 7 or 8 carbon atoms in which at least two are $sp^2$ carbon atoms in conjugation with each other with one of these carbon atoms being monovalent, and $C_2$-$C_6$ alkenyl or $C_2$-$C_6$ alkenyl means an alkenyl moiety containing 2, 3, 4, 5 or 6 carbon atoms in which at least two are $sp^2$ carbons that are in conjugation with each other with one of these carbon atoms being monovalent. In some aspects, an alkenyl substituent or group is a $C_2$-$C_6$ or $C_2$-$C_4$ alkenyl moiety having only two $sp^2$ carbons that are in conjugation with each other with one of these carbon atoms being monovalent, and in other aspects that alkenyl moiety is unsubstituted or is substituted with 1 to 4 or more, typically 1 to 3, more typically 1 or 2, independently selected moieties as disclosed herein, including substituents as defined herein for optional substituents, excluding alkyl, arylalkyl, heteroarylalkyl, alkenyl, alkynyl and any other moiety when the substituted alkenyl differs only by the number of contiguous non-aromatic carbon atoms relative to the unsubstituted alkenyl, wherein the substitution(s) may be at any of the alkenyl moiety's contiguous $sp^2$ carbon and $sp^3$ carbon atoms, if any. Typically, an alkenyl substituent is a $C_2$-$C_6$ or $C_2$-$C_4$ alkenyl moiety having only two $sp^2$ carbons that are in conjugation with each other. When the number of carbon atoms is not indicated, an alkenyl moiety has from 2 to 8 carbon atoms.

"Alkenylene" as the term is used herein, by itself of as part of another term, unless otherwise stated or implied by context, refers to an organic moiety, substituent or group that comprises one or more double bond moieties, as previously described for alkenyl, of the stated number of carbon atoms and has two radical centers derived by the removal of two hydrogen atoms from the same or two different $sp^2$ carbon atoms of an alkene functional group or removal of two hydrogen atoms from two separate alkene functional groups in a parent alkene. In some aspects, an alkenylene moiety is that of an alkenyl radical as described herein in which a hydrogen atom has been removed from the same or different $sp^2$ carbon atom of a double bond functional group of the alkenyl radical, or from a $sp^2$ carbon from a different double bonded moiety to provide a diradical. Typically, alkenylene moieties encompass diradicals containing the structure of —C═C— or —C═C—X$^1$—C═C— wherein X$^1$ is absent or is an optionally substituted saturated alkylene as defined herein, which is typically a $C_1$-$C_6$ alkylene, which is more typically unsubstituted. The number of carbon atoms in an alkenylene moiety is defined by the number of sp$^2$ carbon atoms of its alkene functional group(s) that defines it as an alkenylene moiety and the total number of contiguous non-aromatic carbon atoms appended to each of its sp$^2$ carbons not including any carbon atoms of the other moiety or Markush structure in which the alkenyl moiety is a present as a variable group. That number, unless otherwise specified, ranges from 2 to 50 or 2 to 30, typically from 2 to 20 or 2 to 12, more typically from 2 to 8, 2 to 6 or 2 to 4 carbon atoms. For example, $C_2$-$C_8$ alkenylene or $C_2$-$C_8$ alkenylene means an alkenylene moiety containing 2, 3, 4, 5, 6, 7 or 8 carbon atoms, in which at least two are sp$^2$ carbons in which one is divalent or both are monovalent, that are in conjugation with each other and $C_2$-$C_6$ alkenylene or $C_2$-$C_6$ alkenylene means an alkenyl moiety containing 2, 3, 4, 5 or 6 carbon atoms in which at least two are sp$^2$ carbons, in which at least two are sp$^2$ carbons in which one is divalent or both are monovalent, that are in conjugation with each other. In some aspects, an alkenylene moiety is a $C_2$-$C_6$ or $C_2$-$C_4$ alkenylene having two sp$^2$ carbons that are in conjugation with each other in which both sp$^2$ carbon atoms are monovalent, and in some aspects is unsubstituted. When the number of carbon atoms is not indicated, an alkenylene moiety has from 2 to 8 carbon atoms and is unsubstituted or substituted in the same manner described for an alkenyl moiety.

"Alkynyl" as the term is used herein, by itself or as part of another term, unless otherwise stated or implied by context, refers to an organic moiety, substituent or group that comprises one or more triple bond functional groups (e.g., a —C≡C— moiety) or 1, 2, 3, 4, 5, or 6 or more, typically 1, 2, or 3 of such functional groups, more typically one such functional group, and in some aspects may be substituted (i.e., is optionally substituted) with an aryl moiety such as phenyl, or by an alkenyl moiety or linked normal, secondary, tertiary or cyclic carbon atoms, i.e., linear, branched, cyclic or any combination thereof unless the alkynyl substituent, moiety or group is —C≡CH). An alkynyl moiety, group or substituent having multiple triple bonds may have the triple bonds arranged contiguously or non-contiguously with one or more intervening saturated or unsaturated carbon atoms or a combination thereof, provided that a cyclic, contiguous arrangement of triple bonds do not form a cyclic conjugated system of 4n+2 electrons (i.e., is not aromatic).

An alkynyl moiety, group or substituent contains at least two sp carbon atom in which the carbon atoms are conjugation to each other and in which one of the sp carbon atoms is singly bonded, to another organic moiety or Markush structure to which it is associated. When alkynyl is used as a Markush group (i.e., is a substituent) the alkynyl is singly bonded to a Markush formula or another organic moiety with which it is associated through a triple-bonded carbon (i.e., a sp carbon) of a terminal alkyne functional group. In some aspects when an alkynyl moiety, group or substituent is specified, species encompasses are any of the optionally substituted alkyl or carbocyclyl, groups moieties or substituents described herein that has one or more endo triple bonds and monovalent moieties derived from removal of a hydrogen atom from a sp carbon of a parent alkyne compound. Such monovalent moieties are exemplified without limitation by —C≡CH, and —C≡C—CH$_3$, and —C—C-Ph.

The number of carbon atoms in an alkynyl substituent is defined by the number of sp carbon atoms of the alkene functional group that defines it as an alkynyl substituent and the total number of contiguous non-aromatic carbon atoms appended to each of these sp carbons not including any carbon atom of the other moiety or Markush structure for which the alkenyl moiety is a variable group. That number can vary ranging from 2 to 50, typically 2 to 30, 2 to 20, or 2 to 12, more typically 2 to 8, 2 to 6, or 2 to 4 carbon atoms, when the triple bond functional group is singly bonded to the Markush structure (e.g., —CH≡CH). For example, $C_2$-$C_8$ alkynyl or $C_2$-$C_8$ alkynyl means an alkynyl moiety containing 2, 3, 4, 5, 6, 7, or 8 carbon atoms in which at least two are sp carbon atoms in conjugation with each other with one of these carbon atoms being monovalent, and $C_2$-$C_6$ alkynyl or $C_2$-$C_6$ alkynyl means an alkynyl moiety containing 2, 3, 4, 5, or 6 carbon atoms in which at least two are sp carbons that are in conjugation with each other with one of these carbon atoms being monovalent. In some aspects, an alkynyl substituent or group is a $C_2$-$C_6$ or $C_2$-$C_4$ alkynyl moiety having two sp carbons that are in conjugation with each other with one of these carbon atoms being monovalent, and in other aspects that alkynyl moeity is unsubstituted. When the number of carbon atoms is not indicated, an alkynyl moiety, group or substituent has from 2 to 8 carbon atoms. An alkynyl moiety may be substituted or unsubstituted in the same manner as described for an alkenyl moiety, except that substitution at the monovalent sp carbon is not permitted.

"Aryl" as the term is used herein, by itself or as part of another term, unless otherwise stated or implied by context, refers to an organic moiety, substituent or group having an aromatic or fused aromatic ring system with no ring heteroatoms comprising or consisting of 1, 2, 3 or 4 to 6 aromatic rings each of which are independently optionally substituted, typically consisting of 1 to 3 aromatic rings, more typically 1 or 2 aromatic rings each of which are independently optionally substituted, wherein the rings are composed of only carbon atoms that participate in a cyclically conjugated system of 4n+2 electrons (Hückel rule), typically 6, 10 or 14 electrons, some of which may additionally participate in exocyclic conjugation with a heteroatom (cross-conjugated, e.g., quinone). Aryl substituents, moieties or groups are typically formed by six, eight, ten or more contiguous aromatic carbon atoms up to 24 to include $C_6$-$C_{24}$ aryl and in some aspects is a $C_6$-$C_{20}$ or $C_6$-$C_{12}$ aryl. Aryl substituents, moieties or groups are optionally substituted and in some aspects are unsubstituted or substituted with 1, 2, 3 or more, typically 1 or 2, independently selected substituents as defined herein for alkyl, alkenyl, alkynyl or other moiety described herein including another aryl or a hetereoaryl to form a biaryl and other optional substituents as defined herein. In other aspects, aryls are $C_6$-$C_{10}$ aryls such as phenyl and naphthalenyl and phenanthryl. As aromaticity in a neutral aryl moiety requires an even number or electrons, it will be understood that a given range for that moiety will not encompass species with an odd number of aromatic carbons. When aryl is used as a Markush group (i.e., a substituent) the aryl is attached to a Markush formula or another organic moiety with which it is associated through an aromatic carbon of the aryl group.

"Heterocyclyl" as the term is used herein, by itself or as part of another term, unless otherwise stated or implied by context, refers to a carbocyclyl in which one or more, but not all of the skeletal carbon atoms with their attached hydrogen atoms within the carbocyclic ring system are replaced by independently selected heteroatoms or heteroatom moieties, optionally substituted where permitted, including without limitation N/NH, O, S, Se, B, Si and P, wherein two or more heteroatoms or heteroatom moieties, typically 2, may be adjacent to each other or separated by one or more carbon atoms within the same ring system, typically by 1 to 3 carbon atoms. Those heteroatoms or heteroatom moieties typically are N/NH, O and S. A heterocyclyl typically contains a monovalent skeletal carbon atom or a monovalent heteroatom or heteroatom moeity and has a total of one to ten heteroatoms and/or heteroatom moieties, typically a total of 1 to 5, or more typically a total of 1 to 3, or 1 or 2, provided that not all of the skeletal atoms in any one of the heterocyclic ring(s) in the heterocyclyl are heteroatoms and/or heteroatom moieties (i.e. at least one carbon atom is not replaced in each ring with at least one having been replaced in one of the rings), wherein each heteroatom or heteroatom moiety in the ring(s), optionally substituted where permitted, is independently selected from the group consisting of N/NH, O and S, with the proviso that any one ring does not contain two adjacent O or S atoms. Exemplary heterocyclyls and heteroaryls are collectively referred to as heterocycles, are provided by Paquette, Leo A.; "Principles of Modem Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* 1960, 82:5545-5473 particularly 5566-5573).

When heterocyclyl is used as a Markush group (i.e., a substituent) a saturated or partially unsaturated heterocyclic ring of the heterocyclyl is attached to a Markush structure or other moiety with which it is associated through a carbon atom or a heteroatom of that heterocyclic ring, where such attachment does not result in an unstable or disallowed formal oxidation state of that carbon or heteroatom. A heterocyclyl in that context is a monovalent moiety in which a heterocyclic ring of the heterocyclic ring system defining it as a heterocyclyl is non-aromatic, but may be fused with a carbocyclic, aryl or heteroaryl ring and includes phenyl- (i.e., benzo) fused heterocyclic moieties.

A heterocyclyl is a $C_3$-$C_{50}$ or $C_3$-$C_{30}$ carbocyclyl, typically a $C_3$-$C_{20}$ or $C_3$-$C_{12}$ carbocyclyl, more typically a $C_3$-$C_8$ or $C_3$-$C_6$ carbocyclyl wherein 1, 2 or 3 or more, but not all of its carbons of its cycloalkyl ring system are replaced along with its attached hydrogens, typically 1, 2, 3 or 4, more typically 1 or 2, are replaced with a heteroatom or heteroatom moeity independently selected from the group consisting of N/NH, O and S, optionally substituted where permitted, and thus is a $C_3$-$C_{50}$ or $C_3$-$C_{30}$ heterocyclyl, typically a $C_3$-$C_{20}$ or $C_3$-$C_{12}$ heterocyclyl, more typically a $C_3$-$C_6$, or $C_5$-$C_6$ heterocyclyl, in which the subscript indicates the total number of skeletal atoms (inclusive of its carbon atoms and heteroatoms) of the heterocyclic ring system(s) of the heterocyclyl. In some aspects, a heterocyclyl contains 0 to 2 N, 0 to 2 O or 0 to 1 S skeletal heteroatoms, optionally substituted or some combination thereof provided at least one of said heteroatoms is present in a heterocyclic ring system of the heterocyclyl. A heterocyclyl may be saturated or partially unsaturated and/or unsubstituted or substituted at a skeletal carbon atom with an oxo (=O) moiety, as in pyrrolidin-2-one, and/or at a skeletal heteroatom with one or two oxo moieties so as to contain an oxidized heteroatom as exemplified, but not limited to, —N(=O), —S(=O)— or —S(=O)$_2$—. A fully saturated or partially unsaturated heterocyclyl may be substituted or further substituted with an alkyl, (hetero)aryl, (hetero)arylalkyl, alkenyl, alkynyl or other moiety as described herein, including optional substituents as defined herein or a combination of 2, 3 or more, typically 1 or 2, such substituents. In certain aspects, heterocyclyl is selected from the group consisting of pyrrolidinyl, piperidinyl, morpholinyl and piperazinyl.

"Heterocyclo", as the term is used herein, by itself or as part of another term, unless otherwise stated or implied by context, refers to a heterocyclyl moiety, group or substituent as defined above wherein a hydrogen atom from its monovalent carbon atom, if optical impurities are present, a hydrogen atom from a different skeletal atom (carbon or nitrogen atom if the latter is present), or an electron from a skeletal nitrogen atom, where permitted and if optical impurities are present, is removed or an electron from a nitrogen ring atom that is not already monovalent, if optical impurities are present, is removed and is replaced with a bond (i.e., it is divalent). In some aspects, the replaced second hydrogen is that of the monovalent carbon atom of the parent heterocyclyl thus forming a spiro carbon atom, which in some instances may interrupt an alkyl moiety with that carbocyclic carbon atom. In such instances, the spiro carbon atom is attributed to the carbon atom count of the interrupted alkyl moiety and the skeletal atom count of the heterocyclic ring system with the heterocyclo indicated as being incorporated into the alkyl moiety.

"Heteroaryl" as the term is used herein, by itself or as part of another term, unless otherwise stated or implied by context, refers to an aryl moiety, group or substituent as defined herein in which one or more but not all of the aromatic carbons of an aromatic ring system of an aryl is replaced by a heteroatom. A heteroaryl typically contains a total one to four skeletal heteroatoms in the ring(s) of the heteroaryl ring system, provided that not all of the skeletal atoms of any one ring system in the heteroaryl are heteroatoms, which are optionally substituted where permitted, and have 0 to 3 N, 1 to 3 N or 0 to 3 N skeletal heteroatoms, typically 0 to 10 and/or 0 to 1 S skeletal heteroatoms, provided that at least one skeletal heteroatom is present. A heteroaryl may be monocyclic, bicyclic or polycyclic. A polycyclic heteroaryl is typically a $C_5$-$C_{50}$ or $C_5$-$C_{30}$ heteroaryl, more typically a $C_5$-$C_{20}$ or $C_5$-$C_{12}$ heteroaryl, a bicyclic heteroaryl is typically a $C_5$-$C_{10}$ heteroaryl, and a monocyclic heteroaryl is a typically is $C_5$-$C_6$ heteroaryl, in which the subscript indicates the total number of skeletal atoms (inclusive of its carbon atoms and heteroatoms) of the aromatic ring system(s) of the heteroaryl. In some aspects, a heteroaryl is a bicyclic aryl moiety wherein one 1, 2, 3, 4 or more, typically 1, 2 or 3, of the carbon atoms of the aromatic ring(s) and their attached hydrogen atoms of a parent bicyclic aryl moiety are replaced by an independently selected heteroatom or heteroatom moiety, or is a monocyclic aryl moiety wherein one 1, 2, 3 or more, typically 1 or 2, of the carbon atoms of the aromatic ring(s) and their attached hydrogen atoms of a parent monocyclic aryl moiety are replaced by an independently selected heteroatom or heteroatom moeity, wherein the heteroatom or heteroatom moiety is optionally substituted where permitted, including N/NH, O and S, provided that not all of the skeletal atoms of any one aromatic ring system in the parent aryl moiety are replaced by heteroatoms and more typically are replaced by oxygen (—O—), sulfur (—S—) nitrogen (=N—) or —NR—, so that the nitrogen heteroatom is optionally substituted, wherein R is —H, a nitrogen protecting group or optionally substituted $C_1$-$C_{20}$ alkyl or is an optionally substituted $C_6$-$C_{24}$ aryl or $C_5$-$C_{24}$ heteroaryl to form a heterobiaryl. In other aspects, 1, 2 or 3 of the carbon atoms of the aromatic ring(s) and their attached hydrogen atoms of a parent aryl moiety are replaced by nitrogen substituted with another organic moiety in a manner which retains the cyclic conjugated system. In still other aspects, the aromatic carbon radical of a parent aryl moeity is replaced with an aromatic nitrogen radical. In either of those aspects, the nitrogen, sulfur or oxygen heteroatom participates in the conjugated system either through pi-bonding with an adjacent atom in the ring system or through a lone pair of electrons on the heteroatom. In still other aspects, a heteroaryl has the structure of a heterocyclyl as defined herein in which its ring system has been aromatized.

Typically, a heteroaryl is monocyclic, which in some aspects has a 5-membered or 6-membered heteroaromatic ring system. A 5-membered heteroaryl is a monocyclic $C_5$-heteroaryl containing 1 to 4 aromatic carbon atoms and the requisite number of aromatic heteroatoms within its heteroaromatic ring system. A 6-membered heteroaryl is a monocyclic $C_6$ heteroaryl containing 1 to 5 aromatic carbon atoms and the requisite number of aromatic heteroatoms within its heteroaromatic ring system. Heteroaryls that are 5-membered have four, three, two or one aromatic heteroatom(s), and heteroaryls that are 6-membered include heteroaryls having five, four, three, two or one aromatic heteroatom(s).

$C_5$-heteroaryls, also referred to as 5-membered heteroaryl, are monovalent moieties derived from removing a hydrogen atom from a skeletal aromatic carbon or an electron from a skeletal aromatic heteroatom, where permitted, from a parent aromatic heterocycle compound, which is some aspects is selected from the group consisting of pyrrole, furan, thiophene, oxazole, isoxazole, thiazole, isothiazole, imidazole, pyrazole, triazole and tetrazole. In other aspects, the parent heterocycle is selected from the group consisting of thiazole, imidazole, oxazole, and triazole and is typically thiazole or oxazole, more typically thiazole.

$C_6$ heteroaryls, which are 6-membered, are monovalent moieties derived from removing a hydrogen atom from an aromatic carbon or an electron from an aromatic heteroatom, where permitted, from a parent aromatic heterocycle compound, which is certain aspects is selected from the group consisting of pyridine, pyridazine, pyrimidine, and triazine. A heteroaryl may be substituted or further substituted with an alkyl, (hetero)arylalkyl, alkenyl or alkynyl, or with an aryl or another heteroaryl to form a biaryl, or with other moieties as described herein, including optional substituents as defined herein, or a combination of 2, 3 or more, typically 1 or 2, such substituents.

"Arylalkyl" or "heteroarylalkyl" as the terms are used herein, by itself or as part of another term, refers to an aryl or heteroaryl moiety bonded to an alkyl moiety, i.e., (aryl)-alkyl-, where alkyl and aryl groups are as described above. Typically, an arylalkyl is a ($C_6$-$C_{24}$ aryl)-$C_1$-$C_{12}$ alkyl-moeity, group or substituent, and heteroarylalkyl is a ($C_5$-$C_{24}$ heteroaryl)-$C_1$-$C_{12}$ alkyl- moeity, group or substituent. When (hetero)arylalkyl is used as a Markush group (i.e., a substituent) the alkyl moiety of the (hetero)arylalkyl is attached to a Markush formula with which it is associated through a sp³ carbon of its alkyl moiety. In some aspects, an arylalkyl is a ($C_6$-$C_{24}$ aryl)-$C_1$-$C_{12}$ alkyl- or a ($C_6$-$C_{20}$ aryl)-$C_1$-$C_{20}$ alkyl-, typically a ($C_6$-$C_{12}$ aryl)-$C_1$-$C_{12}$ alkyl- or ($C_6$-$C_{10}$ aryl)-$C_1$-$C_{12}$ alkyl-, more typically a ($C_6$-$C_{10}$ aryl)-$C_1$-$C_6$ alkyl-exemplified without limitation, by $C_6H_5$—$CH_2$—, $C_6H_5$—$CH(CH_3)CH_2$— and $C_6H_5$—$CH_2$—$CH(CH_2CH_2CH_3)$—. An (hetero)arylalkyl may be unsubstituted or substituted in the same manner as described for (hetero)aryl and/or alkyl moieties.

"Arylene," or "heteroarylene" as the terms are used herein, by itself or as part of another term, unless otherwise stated or implied by context, is an aromatic or heteroaromatic diradical moiety that forms two covalent bonds (i.e., it is divalent) within another organic moiety, for which the bonds are in the ortho, meta, or para configuration. Arylene and some heteroarylenes include divalent species by removal of a hydrogen atom from a parent aryl or heteroaryl moiety, group or substituent as defined herein. Other heteroarylenes are divalent species in which hydrogen atoms have been removed from two different aromatic carbon atoms of a parent aromatic heterocycle to form a diradical species, or from removal of a hydrogen atom from an aromatic carbon atom or heteroatom and of another hydrogen atom or electron from a different aromatic heteroatom from a parent aromatic heterocycle to form a diradical species in which one aromatic carbon atom and one aromatic heteroatom is monovalent or two different aromatic heteroatoms are each monovalent. Heteroarylene further include those in which heteroatom(s) and/or heteroatom moiety(ies) replace one or more but not all of the aromatic carbon atoms of a parent arylene.

Non-limiting exemplary arylenes, which are optionally substituted at the remaining positions, are phenyl-1,2-ene, phenyl-1,3-ene, and phenyl-1,4-ene, as shown in the following structures:

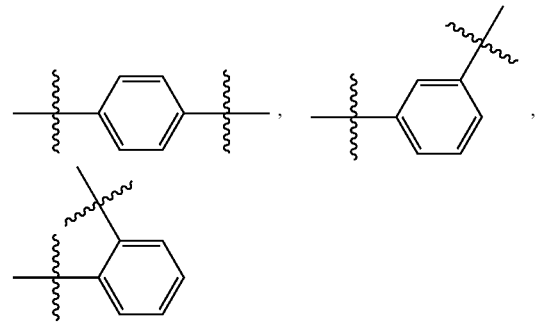

"Heteroalkyl," as the term is used herein by itself or in combination with another term, unless otherwise stated or implied by context, refers to an optionally substituted straight or branched chain hydrocarbon, fully saturated or containing from 1 to 3 degrees of unsaturation and having 1 to 12 carbon atom and 1 to 6 heteroatoms, typically 1 to 5 heteroatoms, more typically one or two heteroatoms or heteroatom moieties, selected from the group consisting of O, N/NH, Si and S, optionally substituted where permitted, and includes each nitrogen and sulfur atom independently optionally oxidized to an N-oxide, a sulfoxide or sulfone, or wherein one or more of the nitrogen atoms is optionally substituted or quaternized. The heteroatom(s) or heteroatom moeity(ies) 0, N/NH, S, and/or Si may be placed at any interior position of the heteroalkyl group or at a terminal position of the optionally substituted alkyl group of the heteroalkyl. In some aspects, the heteroalkyl is fully saturated or contains 1 degree of unsaturation and contain 1 to 6 carbon atoms and 1 to 2 heteroatoms, and in other aspects that heteroalkyl is unsubstituted. Non-limiting examples are —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —NH—$CH_2$—$CH_2$—NH—C(O)—$CH_2$—$CH_3$, —$CH_2$—$CH_2$—S(O)$_2$—$CH_3$, —CH=CHO—$CH_3$, —Si($CH_3$)$_3$, —$CH_2$—CH=NO—$CH_3$, and —CH=CH—N($CH_3$)—$CH_3$. Up to two heteroatoms may be consecutive, as exemplified by —CH$_2$—NH—OCH$_3$ and —CH$_2$—O—Si(CH$_3$)$_3$.

A heteroalkyl is typically denoted by the number of its contiguous heteroatom(s) and non-aromatic carbon atoms, which includes those contiguous carbon atom(s) attached to the heteroatom(s), unless indicated otherwise or by context. Thus, —CH$_2$—CH$_2$—O—CH$_3$ and —CH$_2$—CH$_2$—S(O)—CH$_3$ are both C$_4$-heteroalkyls and —CH$_2$—CH=N—O—CH$_3$, and —CH=CH—N(CH$_3$)$_2$ are both C$_5$ heteroalkyls. A heteroalkyl may be unsubstituted or substituted (i.e., optionally substituted) at its heteroatom or heteroatom component with any one of the moieties described herein, including an optional substituent as defined herein, and/or at its alkyl component with 1 to 4 or more, typically 1 to 3 or 1 or 2 independently selected moieties as described herein, including optional substituent(s) as defined herein, excluding alkyl, (hetero)arylalkyl, alkenyl, alkynyl and another heteroalkyl.

An aminoalkyl as defined herein is an exemplary heteroalkyl in which a terminal carbon atom of an alkyl moiety other than its monovalent carbon atom is replaced by an amino group. When indicated as a substituent to a Markush structure or other organic moiety to which it is associated, the monovalent carbon atom of the alkyl moeity is attached to another organic moiety with which it is to be associated, which typically is a different carbon atom to that attached to the amino group. An aminoalkyl differs from other heteroalkyls by denotation in numbering by only indicating the number of contiguous carbon atoms of its alkylene moiety.

"Heteroalkylene" as the term is used herein by itself or in combination with another term, unless otherwise stated or implied by context, means a divalent group derived from a heteroalkyl (as discussed above), by removal of a hydrogen atom or a heteroatom electron form a parent heteroalkyl to provide a divalent moeity exemplified by, but not limited to, —CH$_2$—CH$_2$—S—CH$_2$—CH$_2$— and —CH$_2$—S—CH$_2$—CH$_2$—NH—CH$_2$—. For a heteroalkylene, heteroatom(s) thereof may be interior to or may occupy either or both termini of its optionally substituted alkylene chain so that one or both of these heteroatoms are monovalent. When a heteroalkylene is a component of a Linker Unit both orientations of that component within the Linker Unit is permitted unless indicated or implied by context. A heteroalkylene is typically denoted by the number of its contiguous heteroatom(s) and non-aromatic carbon atoms, which includes those contiguous carbon atom(s) attached to the heteroatom (s), unless indicated otherwise or by context. A alkylene diamine is a heteroalkylene in which the two monovalent carbon atoms of an alkylene are replaced by amino groups so that each of their nitrogen atoms is monovalent and differs from other heteroalkylenes by denotation in numbering by only indicating the number of contiguous carbon atoms of its alkylene moiety.

"Aminoalkyl" as the term is used herein by itself or in combination with another term, unless otherwise stated or implied by context, refers to a moiety, group or substituent having a basic nitrogen bonded to one radical terminus of an alkylene moiety as defined above to provide a primary amine in which the basic nitrogen is not further substituted, or to provide a secondary or tertiary amine in which the basic amine is further substituted by one or two independent selected optional substituted C$_1$-C$_{12}$ alkyl moieties, respectively, as described above. In some aspects, the optionally substituted alkyl is a C$_1$-C$_8$ alkyl or C$_1$-C$_6$ alkyl and in other aspects that alkyl is unsubstituted. In still other aspects, the basic nitrogen together with its substituents defines an optionally substituted C$_3$-C$_8$ heterocyclyl containing the basic nitrogen as a skeletal atom, typically in the form of a nitrogen-containing C$_3$-C$_6$ or C$_5$-C$_6$ heterocyclyl, optionally substituted. When aminoalkyl is used as a variable group to a Markush structure, the alkylene moeity of the aminoalkyl is attached to a Markush formula with which it is associated through a sp$^3$ carbon of that moiety, which in some aspects is the other radical terminus of the aforementioned alkylene. An aminoalkyl is typically denoted by the number of contiguous carbon atoms of its alkylene moiety. Thus, a C$_1$ aminoalkyl is exemplified without limitation by —CH$_2$NH$_2$, —CH$_2$NHCH$_3$ and —CH$_2$N(CH$_3$)$_2$ and a C$_2$ amino alkyl is exemplified without limitation by —CH$_2$CH$_2$NH$_2$, —CH$_2$CH$_2$NHCH$_3$ and —CH$_2$CH$_2$N(CH$_3$)$_2$.

"Optionally substituted alkyl", "optionally substituted alkenyl", "optionally substituted alkynyl", "optionally substituted arylalkyl", "optionally substituted heterocycle", "optionally substituted aryl", "optionally substituted heteroaryl", "optionally substituted heteroarylalkyl" and like terms as used herein, unless otherwise stated or implied by context, refer to an alkyl, alkenyl, alkynyl, arylalkyl, heterocycle, aryl, heteroaryl, heteroarylalkyl, or other substituent, moiety or group as defined or disclosed herein wherein hydrogen atom(s) of that substituent, moiety or group has been optionally replaced with different moiety(ies) or group (s), or wherein an alicyclic carbon chain that comprise one of those substituents, moiety or group is interrupted by replacing carbon atom(s) of that chain with different moiety (ies) or group(s). In some aspects, an alkene functional group replaces two contiguous sp$^3$ carbon atoms of an alkyl substituent, provided that the radical carbon of the alkyl moiety is not replaced, so that the optionally substituted alkyl becomes an unsaturated alkyl substituent.

Optional substituents replacing hydrogen(s) in any one of the foregoing substituents, moieties, or groups is independently selected from the group consisting of C$_6$-C$_{24}$ aryl, C$_5$-C$_{24}$ heteroaryl, hydroxyl, C$_1$-C$_{20}$ alkoxy, C$_6$-C$_{24}$ aryloxy, cyano, halogen, nitro, C$_1$-C$_{20}$ fluoroalkoxy, and amino, which encompasses —NH$_2$ and mono-, di-, and tri-substituted amino groups, and the protected derivatives thereof, or is selected from the group consisting of —X, —OR', —SR', —NH$_2$, —N(R')(R$^{op}$), —N(R$^{op}$)$_3$, =NR', —CX$_3$, —CN, —NO$_2$, —NR'C(=O)H, —NR'C(=O)R$^{op}$, —NR'C(=O)R$^{op}$, —C(=O)R', —C(=O)NH$_2$, —C(=O)N(R')R$^{op}$, —S(=O)$_2$R$^{op}$, —S(=O)$_2$NH$_2$, —S(=O)$_2$N(R')R$^{op}$, —S(=O)$_2$NH$_2$, —S(=O)$_2$N(R')R$^{op}$, —S(=O)$_2$OR', —S(=O)R$^{op}$, —OP(=O)(OR')(OR$^{op}$), —OP(OH)$_3$, —P(=O)(OR')(OR$^{op}$), —PO$_3$H$_2$, —C(=O)R', —C(=S)R$^{op}$, —CO$_2$R', —C(=S)OR$^{op}$, —C(=O)SR', —C(=S)SR', —C(=S)NH$_2$, —C(=S)N(R')(R$^{op}$)$_2$, —C(=NR')NH$_2$, —C(=NR')N(R')R$^{op}$, and salts thereof, wherein each X is independently selected from the group consisting of halogens: —F, —Cl, —Br, and —I; and wherein each R$^c$p is independently selected from the group consisting of C$_1$-C$_{20}$ alkyl, C$_2$-C$_2$ alkenyl, C$_2$-C$_{20}$ alkynyl, C$_6$-C$_{24}$ aryl, C$_3$-C$_{24}$ heterocyclyl, C$_5$-C$_{24}$ heteroaryl, a protecting group, and a prodrug moiety or two of R$^{op}$ together with the heteroatom to which they are attached defines a C$_3$-C$_{24}$ heterocyclyl; and R' is hydrogen or R$^{op}$, wherein R$^{op}$ is selected from the group consisting of C$_1$-C$_{20}$ alkyl, C$_6$-C$_{24}$ aryl, C$_3$-C$_{24}$ heterocyclyl, C$_5$-C$_{24}$ heteroaryl, and a protecting group.

Typically, optional substituents that are present are selected from the group consisting of —X, —OH, —OR$^{op}$, —SH, —SR$^{op}$, —NH, —NH$_2$, —NH(R$^{op}$), —NR'(R$^{op}$)$_2$, —N(R$^{op}$)$_3$, =NH, =NR$^{op}$, —CX$_3$, —CN, —NO$_2$, —NR'C(=O)H, NR'C(=O)R$^{op}$, —CO$_2$H, —C(=O)H, —C(=O)R$^{op}$, —C(=O)NH$_2$, —C(=O)NR'R$^{op}$, —S(=O)$_2$R$^{op}$, —S(=O)$_2$NH$_2$, —S(=O)$_2$N(R')R$^{op}$, —S(=O)$_2$NH$_2$, —S(=O)$_2$N(R')(R$^{op}$), —S(=O)$_2$OR', —S(=O)R$^{op}$, —C(=S)R$^{op}$, —C(=S)NH$_2$, —C(=S)N(R')R$^{op}$, —C(=NR')N(R$^{op}$)$_2$, and salts thereof, wherein each X is independently selected from the group consisting of —F and —Cl, wherein R$^{op}$ is typically selected from the group consisting of C$_1$-C$_6$ alkyl, C$_6$-C$_{10}$ aryl, C$_3$-C$_{10}$ heterocyclyl, C$_5$-C$_{10}$ heteroaryl, and a protecting group; and R' is independently selected from the group typically consisting of hydrogen, C$_1$-C$_6$ alkyl, C$_6$-C$_{10}$ aryl, C$_3$-C$_{10}$ heterocyclyl, C$_5$-C$_{10}$ heteroaryl, and a protecting group, independently selected from R$^{op}$.

More typically, optional substituents that are present are selected from the group consisting of —X, —R$^{op}$, —OH, —OR$^{op}$, —NH$_2$, —NH(R$^{op}$), —N(R$^{op}$)$_2$, —N(R$^{op}$)$_3$, —CX$_3$, —NO$_2$, —NHC(=O)H, —NHC(=O)R$^{op}$, —C(=O)NH$_2$, —C(=O)NHR$^{op}$, —C(=O)N(R$^{op}$)$_2$, —CO$_2$H, —CO$_2$R$^{op}$, —C(=O)H, —C(=O)R$^{op}$, —C(=O)NH$_2$, —C(=O)NH(R$^{op}$), —C(=O)N(R$^{op}$)$_2$, —C(=NR')NH$_2$, —C(=NR')NH(R$^{op}$), —C(=NR')N(R$^{op}$)$_2$, a protecting group and salts thereof, wherein each X is —F, wherein R$^{op}$ is independently selected from the group consisting of C$_1$-C$_6$ alkyl, C$_6$-C$_{10}$ aryl, C$_5$-C$_{10}$ heteroaryl and a protecting group; and R' is selected from the group consisting of hydrogen, C$_1$-C$_6$ alkyl and a protecting group, independently selected from R$^{op}$.

In some aspects, an optional alkyl substituent that is present is selected from the group consisting of —NH$_2$, —NH(R$^{op}$), —N(R$^{op}$)$_2$, —N(R$^{op}$)$_3$, —C(=NR')NH$_2$, —C(=NR')NH(R$^{op}$), and —C(=NR')N(R$^{op}$)$_2$, wherein R' and R$^{op}$ is as defined for any one of the R' or R$^{op}$ groups above. In some of those aspects, the R' and/or R$^{op}$ substituents together with the nitrogen atom to which they are attached provide for the basic functional group of a Basic Unit (BU), as when R$^{op}$ is independently selected from the group consisting of hydrogen and C$_1$-C$_6$ alkyl. Alkylene, carbocyclyl, carbocyclo, aryl, arylene, heteroalkyl, heteroalkylene, heterocyclyl, heterocyclo, heteroaryl, and heteroarylene groups as described above are similarly substituted or are unsubstituted, with exceptions, if any, described in the definitions of these moieties.

"Optionally substituted heteroatom", as the term is used herein by itself or in combination with another term, unless otherwise stated or implied by context, refers to a heteroatom or heteroatom moeity within a functional group or other organic moiety in which the heteroatom is not further substituted or is substituted by any one of the aforementioned moieties having a monovalent carbon atom including, but not limited to alkyl, cycloalkyl, alkenyl, aryl, heterocyclyl, heteroaryl, heteroalkyl and (hetero)arylalkyl- or is oxidized by substitution with one or two =O substituents. In some aspects, "optionally substituted heteroatom" refers an aromatic or non-aromatic —NH— moeity that is unsubstituted or in which the hydrogen atom is replaced by any one of the aforementioned substituents. In other aspects, "optionally substituted heteroatom" refers to an aromatic skeletal nitrogen atom of a heteroaryl in which an electron of that heteroatom is replaced by any one of the aforementioned substituents. For encompassing both of those aspects, the nitrogen heteroatom is sometime referred to as an optionally substituted N/NH.

Therefore, in some aspects, an optional substituent of a nitrogen atom that is present is selected from the group consisting of C$_1$-C$_2$ alkyl, C$_2$-C$_{20}$ alkenyl, C$_2$-C$_{20}$ alkynyl, C$_6$-C$_{24}$ aryl, C$_5$-C$_{24}$ heteroaryl, (C$_6$-C$_{24}$ aryl)-C$_1$-C$_{20}$ alkyl-, and (C$_5$-C$_{24}$ heteroaryl)-C$_1$-C$_{20}$ alkyl-, optionally substituted, as those terms are defined herein. In other aspects, optional substituents of a nitrogen atom that are present are independently selected from the group consisting of C$_1$-C$_{12}$ alkyl, C$_2$-C$_{12}$ alkenyl, C$_2$-C$_{12}$ alkynyl, C$_6$-C$_{24}$ aryl, C$_5$-C$_{24}$ heteroaryl, (C$_6$-C$_{24}$ aryl)-C$_1$-C$_{12}$ alkyl-, and (C$_5$-C$_{24}$ heteroaryl)-C$_1$-C$_{12}$ alkyl-, optionally substituted, from the group consisting of C$_1$—C alkyl, C$_2$-C$_8$ alkenyl, C$_2$-C$_8$ alkynyl, C$_6$-C$_{10}$ aryl, C$_5$-C$_{10}$ heteroaryl, (C$_6$-C$_{10}$ aryl)-C$_1$-C$_8$ alkyl-, and (C$_5$-C$_6$ heteroaryl)-C$_1$-C$_8$ alkyl, or from the group consisting of C$_1$-C$_6$ alkyl, C$_2$-C$_6$ alkenyl, C$_2$-C$_6$ alkynyl, C$_6$-C$_{10}$ aryl, C$_5$-C$_{10}$ heteroaryl, (C$_6$-C$_{10}$ aryl)-C$_1$-C$_6$ alkyl-, and (C$_5$-C$_{10}$ heteroaryl)-C$_1$-C$_6$ alkyl-.

In some aspects, an optional substituent that is present replaces a carbon atom in the acyclic carbon chain of an alkyl or alkylene moeity, group or substituent to provide for a C$_3$-C$_{12}$ heteroalkyl or C$_3$-C$_{12}$ heteroalkylene and for that purpose is typically selected from the group consisting of —O—, —C(=O)—, —C(=O)O—, —S—, —S(=O)—, —S(=O)$_2$—, —NH—, —NHC(=O)—, —C(=O)NH—, S(=O)$_2$NH—, —NHS(=O)$_2$—, —OC(=O)NH—, and —NHC(=O)O, optionally substituted in which —NH— is an optionally substituted heteroatom moeity by replacement of its hydrogen atom by an independently selected substituent from a group previously described for an —NH— optional substituent.

"O-linked moiety", as the term is used herein by itself or in combination with another term, unless otherwise stated or implied by context, refers to a moeity, group or substituent that is attached to a Markush structure or another organic moiety with which it is associated directly through an oxygen atom of the O-linked moeity. A monovalent O-linked moeity has that attachment through a monovalent oxygen and is typically —OH, —OC(=O)R$^b$ (acyloxy), wherein R$^b$ is —H, optionally substituted saturated C$_1$-C$_2$ alkyl, optionally substituted unsaturated C$_1$-C$_{20}$ alkyl, optionally substituted C$_3$-C$_{20}$ cycloalkyl, wherein the cycloalkyl moeity is saturated or partially unsaturated, optionally substituted C$_3$-C$_{20}$ alkenyl, optionally substituted C$_2$-C$_{20}$ alkynyl, optionally substituted C$_6$-C$_{24}$ aryl, optionally substituted C$_5$-C$_{24}$ heteroaryl or optionally substituted C$_3$-C$_{24}$ heterocyclyl, or R$^b$ is optionally substituted C$_1$-C$_{12}$ alkyl, optionally substituted C$_3$-C$_{12}$ cycloalkyl, optionally substituted C$_3$-C$_{12}$ alkenyl or optionally substituted C$_2$-C$_{12}$ alkynyl, and wherein an monovalent O-linked moeity further encompasses ether groups which are C$_1$-C$_{12}$ alkyloxy (i.e., C$_1$-C$_{12}$ aliphatic ether) moieties, optionally substituted, wherein the alkyl moeity is saturated or unsaturated.

In other aspects, a monovalent O-linked moeity is a monovalent moeity selected from the group consisting of optionally substituted phenoxy, optionally substituted C$_1$-C$_8$ alkyloxy (i.e., C$_1$-C$_8$ aliphatic ether) and —OC(=O)R$^b$, wherein R$^b$ is optionally substituted C$_1$-C$_8$ alkyl, which is typically saturated or is an unsaturated C$_3$-C$_6$ alkyl, optionally substituted.

In still other aspects, an O-linked moeity is a monovalent moeity selected from the group consisting of —OH, and saturated C$_1$-C$_6$ alkyl ether, unsaturated C$_3$-C$_6$ alkyl ether, optionally substituted, and —OC(=O)R$^b$, wherein R$^b$ is typically C$_1$-C$_6$ saturated alkyl, C$_3$-C$_6$ unsaturated alkyl, C$_3$-C$_6$ cycloalkyl, C$_2$-C$_6$ alkenyl, or phenyl, optionally substituted, or is selected from that group excluding —OH and/or phenyl, or R$^b$ is a monovalent moeity selected from the group consisting of C$_1$-C$_6$ saturated alkyl, C$_3$-C$_6$ unsaturated alkyl and C$_2$-C$_6$ alkenyl, optionally substituted, or an Monovalent O-linked moeity is an unsubstituted O-linked substituent selected from the group consisting of saturated C$_1$-C$_6$ alkyl ether, unsaturated C$_3$-C$_6$ alkyl ether, and —OC(=O)R$^1$, wherein R is an unsubstituted, saturated C$_1$-C$_6$ alkyl or unsubstituted, unsaturated C$_3$-C$_6$ alkyl.

Other exemplary O-linked substituents are provided by definitions for carbamate, ether and carbonate as disclosed herein in which the monovalent oxygen atom of the carbamate, ether and carbonate functional group is bonded to the Markush structure or other organic moiety with which it is associated.

In other aspects, an O-linked moiety to carbon is divalent and encompasses =O and —X—(CH$_2$)$_n$—Y—, wherein X and Y independently are S and O and subscript n is 2 or 3, to form a spiro ring system with the carbon to which X and Y are both attached.

"Halogen" as the term is used herein by itself or in combination with another term, unless otherwise stated or implied by context, refers to fluorine, chlorine, bromine or iodine and is typically —F or —Cl.

"Protecting group" as the term is used herein by itself or in combination with another term, unless otherwise stated or implied by context, refers to a moiety that prevents or substantially reduces the ability of the atom or functional group to which it is linked from participating in unwanted reactions. Typical protecting groups for atoms or functional groups are given in Greene (1999), "Protective groups in organic synthesis, 3$^{rd}$ ed.", Wiley Interscience. Protecting groups for heteroatoms such as oxygen, sulfur and nitrogen are sometime used to minimize or avoid their unwanted reactions with electrophilic compounds. Other times the protecting group is used to reduce or eliminate the nucleophilicity and/or basicity of the unprotected heteroatom. Non-limiting examples of protected oxygen are given by —OR$^{PR}$, wherein R$^{PR}$ is a protecting group for hydroxyl, wherein hydroxyl is typically protected as an ester (e.g., acetate, propionate or benzoate). Other protecting groups for hydroxyl avoid its interference with the nucleophilicity of organometallic reagents or other highly basic reagents, for which purpose hydroxyl is typically protected as an ether, including without limitation alkyl or heterocyclyl ethers, (e.g., methyl or tetrahydropyranyl ethers), alkoxymethyl ethers (e.g., methoxymethyl or ethoxymethyl ethers), optionally substituted aryl ethers, and silyl ethers (e.g., trimethylsilyl (TMS), triethylsilyl (TES), tert-butyldiphenylsilyl (TBDPS), tert-butyldimethylsilyl (TBS/TBDMS), triisopropylsilyl (TIPS) and [2-(trimethylsilyl)ethoxy]-methylsilyl (SEM)). Nitrogen protecting groups include those for primary or secondary amines as in —NHR$^{PR}$ or —N(R$^{PR}$)$_2$, wherein least one of R$^{PR}$ is a nitrogen atom protecting group or both R$^{PR}$ together define a nitrogen atom protecting group.

A protecting group is a suitable for protecting when it is capable of preventing or substantially avoiding unwanted side-reactions and/or premature loss of the protecting group under reaction conditions required to effect desired chemical transformation(s) elsewhere in the molecule and during purification of the newly formed molecule when desired, and can be removed under conditions that do not adversely affect the structure or stereochemical integrity of that newly formed molecule. In some aspects, suitable protecting groups are those previously described for protecting functional groups. In other aspects, a suitable protecting group is a protecting group used in peptide coupling reactions. For example, a suitable protecting group for the basic nitrogen atom of an acyclic or cyclic Basic Unit is an acid-labile carbamate protecting group such as t-butyloxycarbonyl (BOC).

"Ester" as the term is used herein by itself or in combination with another term, unless otherwise stated or implied by context, refers to a substituent, moiety or group having the structure of —C(=O)—O— to define an ester functional group in which the carbonyl carbon atom of that structure is not directly connected to another heteroatom but is directly connected to hydrogen or another carbon atom of an organic moiety with which it is associated, and wherein the monovalent oxygen atom is either attached to the same organic moiety at a different carbon atom to provide a lactone or to a Markush structure or to some other organic moiety. Typically, esters in addition to the ester functional group comprise or consist of an organic moiety containing 1 to 50 carbon atoms, typically 1 to 20 carbon atoms or more typically 1 to 8, 1 to 6 or 1 to 4 carbon atoms and 0 to 10 independently selected heteroatoms (e.g., O, S, N, P, Si, but usually O, S and N), typically 0 to 2 heteroatoms, wherein the organic moiety is bonded to the —C(=O)—O— structure (i.e., through the ester functional group) so as to provide structure having the formula of organic moiety-C(=O)—O— or —C(=O)—O— organic moiety.

When an ester is a substituent or variable group of a Markush structure or other organic moiety with which it is associated, that substituent is bonded to the structure or other organic moiety through the monovalent oxygen atom of the ester functional group so that it is an monovalent O-linked substituent, which sometimes referred to as an acyloxy. In such instances, the organic moiety attached to the carbonyl carbon of the ester functional group typically is a C$_1$-C$_2$ alkyl, C$_2$-C$_2$ alkenyl, C$_2$-C$_2$ alkynyl, C$_6$-C$_{24}$ aryl, C$_5$-C$_{24}$ heteroaryl, C$_3$-C$_{24}$ heterocyclyl or is a substituted derivative of any one of these, e.g., having 1, 2, 3 or 4 substituents, more typically is C$_1$-C$_{12}$ alkyl, C$_2$-C$_{12}$ alkenyl, C$_2$-C$_{12}$ alkynyl, C$_6$-C$_{10}$ aryl, C$_5$-C$_{10}$ heteroaryl, C$_3$-C$_{10}$ heterocyclyl or a substituted derivative of one any of these, e.g., having 1, 2, or 3 substituents or is C$_1$-C$_8$ alkyl, C$_2$-C$_8$ alkenyl, C$_2$-C$_8$ alkynyl, or phenyl or a substituted derivative of any one of these, e.g., having 1 or 2 substituents, wherein each independently selected substituent is as defined herein for optional alkyl substituents, or is unsubstituted C$_1$-C$_6$ alkyl or unsubstituted C$_2$-C$_6$ alkenyl.

Exemplary esters by way of example and not limitation, are acetate, propionate, isopropionate, isobutyrate, butyrate, valerate, isovalerate, caproate, isocaproate, hexanoate, heptanoate, octanoate, phenylacetate esters and benzoate esters or have the structure of —OC(=O)R$^b$ in which R$^b$ is as defined for acyloxy O-linked substituents and is typically selected from the group consisting of methyl, ethyl, propyl, iso-propyl, 2-methyl-prop-1-yl, 2,2-dimethyl-prop-1-yl, prop-2-ene-1-yl, and vinyl.

"Ether" as the term is used herein by itself or in combination with another term, unless otherwise stated or implied by context, refers to an organic moiety, group or substituent that comprises 1, 2, 3, 4 or more —O— (i.e., oxy) moieties that are not bonded to carbonyl moiety(ies), typically 1 or 2, wherein no two —O— moieties are immediately adjacent (i.e., directly attached) to each other. Typically, an ether contains the formula of —O-organic moiety wherein organic moiety is as described for an organic moiety bonded to an ester functional group or is as described herein for an optionally substituted alkyl group. When ether is recited as a substituent or variable group of a Markush structure or other organic moiety with which it is associated, the oxygen of the ether functional group is attached to a Markush formula with which it is associated and is sometimes designated as an "alkoxy" group, which is an exemplary O-linked substituent. In some aspects an ether O-linked substituent is a C$_1$-C$_{20}$ alkoxy or a C$_1$-C$_{12}$ alkoxy, optionally substituted with 1, 2, 3 or 4 substituents, typically 1, 2 or 3, and in other aspects is a C$_1$-C$_8$ alkoxy or C$_1$-C$_6$ alkoxy, optionally substituted with 1 or 2 substituents, wherein each independently selected substituent is as defined herein for optional alkyl substituents, and in still other aspects an ether O-linked substituent is an unsubstituted, saturated or unsaturated $C_1$-$C_4$ alkoxy such as, by way of example and not limitation, methoxy, ethoxy, propoxy, iso-propoxy, butoxy and allyloxy (i.e., —OCH$_2$CH=CH$_2$).

"Amide" as the term is used herein by itself or in combination with another term, unless otherwise stated or implied by context, refers to a moiety having an optionally substituted functional group having the structure of R—C(=O)N(R$^c$)— or —C(=O)N(R$^c$)$_2$ to which no other heteroatom is directly attached to the carbonyl carbon and wherein each R$^c$ is independently hydrogen, a protecting group or an independently selected organic moiety, and R is hydrogen or an organic moiety, wherein organic moiety, independently selected from R$^c$, is as described herein for an organic moiety bonded to an ester functional group or is as described herein for an optionally substituted alkyl group. When an amide is recited as a substituent or variable group of a Markush structure or other organic moiety with which it is associated, the amide nitrogen atom or carbonyl carbon atom of the amide functional group is bonded to that structure or other organic moiety. Amides are typically prepared by condensing an acid halide, such an acid chloride, with a molecule containing a primary or secondary amine. Alternatively, amide coupling reactions well-known in the art of peptide synthesis, which in some aspects proceeds through an activated ester of a carboxylic acid-containing molecule, are used. Exemplary preparations of amide bonds through peptide coupling methods are provided in Benoiton (2006) "Chemistry of peptide synthesis", CRC Press; Bodansky (1988) "Peptide synthesis: A practical textbook" Springer-Verlag; Frinkin, M. et al. "Peptide Synthesis" *Ann. Rev. Biochem*. (1974) 43: 419-443. Reagents used in the preparation of activated carboxylic acids is provided in Han, et al. "Recent development of peptide coupling agents in organic synthesis" *Tet*. (2004) 60: 2447-2476.

Thus, in some aspects, amides are be prepared by reacting a carboxylic acid with an amine in the presence of a coupling agent. As used herein, "in the presence of a coupling agent" includes contacting the carboxylic acid with the coupling agent thereby converting the acid to its activated derivative, such as an activated ester or a mixed anhydride, with or without isolation of the resulting activated derivative of the acid, followed by or simultaneously contacting the resulting activated derivative with the amine. In some instances, the activated derivative is prepared in situ. In other instances, the activated derivative may be isolated to remove any undesired impurities.

"Carbonate" as the term is used herein by itself or in combination with another term, unless otherwise stated or implied by context, means a substituent, moiety or group that contains a functional group having the structure —O—C(=O)—O— which defines a carbonate functional group. Typically, carbonate groups as used herein are comprised of an organic moiety bonded to the —O—C(=O)—O— structure, wherein the organic moiety is as described herein for an organic moiety bonded to an ester functional group, e.g., organic moiety-O—C(=O)—O—. When carbonate is recited as a substituent or variable group of a Markush structure or other organic moiety with which it is associated, one of the monovalent oxygen atoms of the carbonate functional group is attached to that structure or organic moiety and the other is bonded to a carbon atom of another organic moiety as previously described for an organic moiety bonded to an ester functional group or is as described herein for an optionally substituted alkyl group. In such instances, carbonate is an exemplary O-linked substituent.

"Carbamate" as the term is used herein by itself or in combination with another term, unless otherwise stated or implied by context, means a substituent, moiety or group that contains a optionally substituted carbamate functional group structure represented by —O—C(=O)N(R$^c$)— or —O—C(=O)N(R$^c$)$_2$, or —O—C(=O)NH (optionally substituted alkyl)- or —O—C(=O)N (optionally substituted alkyl)$_2$ in which the independently selected optionally substituted alkyl(s) are exemplary carbamate functional group substituents, and typically are $C_1$-$C_{12}$ alkyl or $C_1$-$C_8$ alkyl, optionally substituted, more typically $C_1$-$C_6$ alkyl or $C_1$-$C_4$ alkyl, optionally substituted, wherein each R$^c$ is independently selected, wherein independently selected R$^c$ is hydrogen, a protecting group or an organic moiety, wherein the organic moiety is as described herein for an organic moiety bonded to an ester functional group or is as described herein for an optionally substituted alkyl group. Typically, carbamate groups are additionally comprised of an organic moiety, independently selected from R$^c$, wherein the organic moiety is as described herein for an organic moiety bonded to an ester functional group, bonded through the —O—C(=O)—N(R$^c$)— structure, wherein the resulting structure has the formula of organic moiety-O—C(=O)—N(R$^c$)— or —O—C(=O)—N(R$^c$)-organic moiety. When carbamate is recited as a substituent or variable group of a Markush structure or other organic moeity with which it is associated, the monovalent oxygen (O-linked) or nitrogen (N-linked) of the carbamate functional group is attached to a Markush formula with which it is associated. The linkage of the carbamate substituent is either explicitly stated (N- or O-linked) or implicit in the context to which this substituent is referred. O-linked carbamates described herein are exemplary monovalent O-linked substituents.

"Ligand Drug Conjugate", as the term is used herein, unless otherwise stated or implied by context, refers to a construct comprised of a Ligand Unit (L) incorporating or corresponding to a targeting agent and a auristatin Drug Unit (D) incorporating or corresponding in structure to an auristatin free drug, wherein L and D are bonded to each other through a Linker Unit (LU), wherein the Ligand Drug Conjugate is capable of selective binding to a targeted moiety of a targeted cell. The term Ligand Drug Conjugate (LDC) in one aspect refers to a plurality (i.e., composition) of individual Conjugate compounds having the same or differing to some extent by the number of auristatin Drug Units conjugated to each Ligand Unit and/or the location on the Ligand Unit to which the auristatin Drug Units are conjugated. In some aspects the term refers to a collection (i.e., population or plurality) of Conjugate compounds having essentially the same Ligand Unit, and the same auristatin Drug Unit and Linker Unit, which in some aspects have variable loading and/or distribution of auristatin drug linker moieties attached to each antibody residue (as, for example, when the number of auristatin Drug Units of any two Ligand Drug Conjugate compounds in a plurality of such compounds is the same but the locations of their sites of attachment to the Ligand Unit are different). In those instances a Ligand Drug Conjugate is described by the averaged auristatin drug loading of the Conjugate compounds. In the context of the present invention, an auristatin Drug Unit incorporates or corresponds to a hydrophobically-modified auristatin F or auristatin F-type compound, and is sometimes collectively referred to as an hydrophobic auristatin F Drug Unit.

The average number auristatin Drug Units per Ligand Unit in a Ligand Drug Conjugate composition, which is an averaged number for a population of Ligand Drug Conjugate compounds and in some aspects is a distribution of these compounds differing primarily by the number of conjugated auristatin Drug Units to the Ligand Unit and/or by their location.

An LDC of the present invention is typically represented by the structure of Formula 1:

$$L\text{-}[LU\text{-}(D')]_p \qquad (1)$$

or a salt thereof, which in some aspects is a pharmaceutically acceptable salt, wherein L is a Ligand Unit, in particular an antibody Ligand Unit; LU is a Linker Unit; and subscript p is a number ranging from 1 to 24, D' represents from 1 to 4 auristatin Drug Units, each of which is that of a hydrophobically-modified auristatin F or auristatin F-type free drug, sometimes collectively referred to as a hydrophobic AF Drug Unit, conjugated through its C-terminal component, in particular through its carboxylic acid functional group, wherein the antibody Ligand Unit is capable of specific and selective binding to an antigen of a targeted cell for subsequent release of free drug, wherein the targeted antigen in one aspect is a cancer cell antigen selectively recognized by an antibody Ligand Unit and is capable of internalization into said cancer cell upon said binding for initiating intracellular release of free drug subsequent to said internalization, wherein each drug linker moiety in a Ligand Drug Conjugate compound of the composition has the structure of Formula 1A:

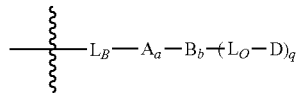

$$\text{---}L_B\text{---}A_a\text{---}B_b\text{---}(L_O\text{---}D)_q \qquad (1A)$$

or a salt thereof, which is some aspects is a pharmaceutically acceptable salt, wherein D in each drug linker moiety, is the hydrophobic auristatin Drug; the wavy line indicates covalent attachment to L; $L_B$ is an antibody covalent binding moiety; A is a first optional Stretcher Unit; subscript a is 0 or 1 indicating the absence of presence of A, respectively; B is an optional Branching Unit; subscript b is 0 or 1, indicating the absence of presence of B, respectively; $L_O$ is an optional secondary linker moiety; D is a modified AF Drug Unit; and subscript q is an integer ranging from 1 to 4, wherein the Ligand Drug Conjugate compound has the structure of Formula 1 in which subscript p is replaced by subscript p', wherein subscript p' is an integer ranging from 1 to 24.

"Ligand Unit" as the term is used herein, unless otherwise stated or implied by context, refers to a targeting moiety of a Ligand Drug Conjugate composition or compound that is capable of binding selectively to its cognate targeted moiety and incorporates or corresponds to the structure of a targeting agent. A Ligand Unit (L) includes without limitation those from receptor ligands, antibodies to cell-surface antigens, and transporter substrates. In some aspects, the receptor, antigen or transporter to be bound by a Conjugate compound of a Ligand Drug Conjugate composition is present in greater abundance on abnormal cells in contrast to normal cells so as to effect a desired improvement in tolerability or reduce the potential occurrence or severity of one or more adverse events that are associated with administration of a drug in unconjugated form. In other aspects, the receptor, antigen or transporter to be bound by a Ligand Drug Conjugate compound of the composition is present in greater abundance on normal cells in the vicinity of abnormal cells in contrast to normal cells that are distant from the site of the abnormal cells, so as to selectively expose the nearby abnormal cells to free drug. Various aspects of Ligand Units, including antibody Ligand Units, are further described by embodiments of the invention.

"Targeting agent" as used herein, unless otherwise stated or implied by context, refers to an agent that is capable of selective binding to a targeted moiety and which substantially retains that capability when it is incorporated into a Ligand Drug Conjugate as a Ligand Unit. The Ligand Unit of a Ligand Drug Conjugate therefore corresponds in structure to the targeting agent so that the Ligand Unit is the targeting moiety of the Conjugate. In some aspects, the targeting agent is an antibody or fragment thereof that selectively and specifically binds to an accessible antigen that is characteristic of an abnormal cell or is present in higher copy number in comparison to normal cells or is an accessible antigen that is particular to the surrounding environment in which these cells are found to an extent that achieves an improved tolerability in comparison to administration of free drug. In other aspects, the targeting agent is a receptor ligand that selectively binds to an accessible receptor characteristic of, or in greater abundance on, abnormal cells, or to an accessible receptor on nominally normal cells that are peculiar to environment surrounding the abnormal cells. Typically, a targeting agent is an antibody as defined herein that binds selectively to a targeted moiety of an abnormal mammalian cell, more typically a targeted moiety of an abnormal human cell.

"Targeted moiety" as defined herein is a moiety to be specifically recognized by a targeting agent or the targeting moiety of a Ligand Drug Conjugate, which is its Ligand Unit that corresponds to or incorporates the targeting agent. In some aspects, a targeted moiety is present on, within, or in the vicinity of abnormal cells and is typically present in greater abundance or copy number on these cells in comparison to normal cells or the environment of normal cells distant from the site of abnormal cells so as to provide for improved tolerability relative to administration of free drug or reduce the potential for one or more adverse events from that administration. In some aspects, the targeted moiety is an antigen accessible to selective binding by an antibody, which is an exemplary targeting agent that is incorporated as or corresponds to an antibody Ligand Unit in an Antibody Drug Conjugate composition or compound thereof. In other aspects, the targeting moiety is that of a ligand for an extracellularly accessible cell membrane receptor, which may be internalized upon binding of the cognate targeting moiety provided by the Ligand Unit of a Ligand Drug Conjugate or compound thereof that incorporates or corresponds in structure to the receptor ligand, or is capable of passive or facilitative transport of a Ligand Drug Conjugate compound subsequent to binding of the cell-surface receptor. In some aspects, the targeted moiety is present on abnormal mammalian cells or on mammalian cells characteristic of the environment of such abnormal cells. In some aspects, the targeted moiety is an antigen of an abnormal mammalian cell, more typically a targeted moiety of an abnormal human cell.

"Targeted cells", as the term is used herein, unless otherwise stated or implied by context, are the intended cells to which Ligand Drug Conjugate is designed to interact in order to inhibit the proliferation or other unwanted activity of abnormal cells. In some aspects, the targeted cells are hyper-proliferating cells or hyper-activated immune cells, which are exemplary abnormal cells. Typically, those abnormal cells are mammalian cells and more typically are human cells. In other aspects, the targeted cells are within the vicinity of the abnormal cells so that action of the Ligand Drug Conjugate on the nearby cells has an intended effect on the abnormal cells. For example, the nearby cells may be epithelial cells that are characteristic of the abnormal vasculature of a tumor. Targeting of those vascular cells by a Ligand Drug Conjugate composition or compound thereof will either have a cytotoxic or a cytostatic effect on these cells, which is believed to result in inhibition of nutrient delivery to the nearby abnormal cells of the tumor. Such inhibition indirectly has a cytotoxic or cytostatic effect on the abnormal cells and may also have a direct cytotoxic or cytostatic effect on the nearby abnormal cells by releasing its auristatin drug payload, such as a hydrophobic auristatin F compound, in the vicinity of these cells.

"Antigen" as the term is used herein, unless otherwise stated or implied by context, is a moiety that is capable of specific binding by an unconjugated antibody or an antigen-binding fragment thereof or to an Antibody Drug Conjugate compound, which is comprised of an antibody Ligand Unit that incorporates or corresponds in structure to the unconjugated antibody. In some aspects, the antigen is an extracellularly-accessible cell-surface protein, glycoprotein, or carbohydrate preferentially displayed by abnormal cells in comparison to normal cells distant from the site of the abnormal cells. In some instances, the abnormal cells displaying the antigen are hyper-proliferating cells, which includes cancer cells, in a mammal. In other instances, the abnormal cells displaying the antigen are hyper-activated immune cells in a mammal. In other aspects, the antigen to be specifically bound by an antibody Ligand Unit of an Antibody Drug Conjugate compound having a auristatin Drug Unit, including a hydrophobic auristatin F Drug Unit, is present in the particular environment of hyper-proliferating cells or hyper-activated immune cells in a mammal in contrast to the environment typically experienced by normal cells in the absence of such abnormal cells. In still other aspects, the cell-surface antigen is capable of internalization upon selective binding by a Conjugate compound of an Antibody Drug Conjugate composition having a auristatin Drug Unit, inclusive of an auristatin F Drug Unit and hydrophobic auristatin F Drug Units. Subsequent to internalization, intracellular processing of a Linker Unit of an Antibody Drug Conjugate compound of the composition releases its auristatin Drug Unit as a free auristatin drug, which is inclusive of release of a hydrophobic auristatin F Drug Unit as a hydrophobic auristatin compound. Antigens associated with hyper-proliferating cells that are cell-surface accessible to an Antibody Drug Conjugate include by way of example and not limitation CD19, CD70, CD30 and CD33.

"Antibody Drug Conjugate", as the term is used herein, unless otherwise stated or implied by context, is a subset of Ligand Drug Conjugates of Formula 1 and therefore refers to a construct comprised of an antibody Ligand Unit (L) incorporating or corresponding to an antibody or antigen-binding fragment thereof, and a auristatin Drug Unit (D) incorporating or corresponding in structure to an auristatin free drug, wherein L and D are bonded to each other through a Linker Unit (LU), wherein the Antibody Drug Conjugate is capable of selective binding to a targeted antigen of a targeted cell, which in some aspects is an antigen of an abnormal cell such as a cancer cell, through its targeting antibody Ligand Unit.

The term Antibody Drug Conjugate (ADC) in one aspect refers to a plurality (i.e., composition) of individual Conjugate compounds having the same or differing to some extent by the number of auristatin Drug Units conjugated to each antibody Ligand Unit and/or the location on the antibody Ligand Unit to which the auristatin Drug Units are conjugated. In some aspects the term refers to a collection (i.e., population or plurality) of Conjugate compounds having the same antibody Ligand Unit, allowing for mutational amino acid variations and varying glycosylation patterns as described herein occurring during production of antibodies from cell culture, and the same auristatin Drug Unit and Linker Unit, which in some aspects have variable loading and/or distribution of auristatin drug linker moieties attached to each antibody residue (as, for example, when the number of auristatin Drug Units of any two Antibody Drug Conjugate compounds in a plurality of such compounds is the same but the location of their sites of attachment to the targeting antibody ligand Unit differ). In those instances an Antibody Drug Conjugate is described by the averaged drug loading of the Conjugate compounds. In the context of the present invention, an auristatin Drug Unit of an Antibody Drug Conjugates incorporates or corresponds to a hydrophobically-modified auristatin F or auristatin F-type compound, and is sometimes collectively referred to as an auristatin F compound.

The average number auristatin Drug Units per antibody Ligand Unit, or antigen-binding fragment thereof, having intact drug linker moieties in an Antibody Drug Conjugate composition, which is an averaged number for a population of Antibody Drug Conjugate compounds and in some aspects is a distribution of these compounds differing primarily by the number of conjugated auristatin Drug Units to the antibody Ligand Unit and/or by their location. In that context p is a number ranging from about 2 to about 24 or about 2 to about 20 and is typically about 2, about 4, or about 10 or about 8. In other contexts, p represents the number of auristatin Drug Units that are covalently bonded to a single antibody Ligand Unit of an Antibody Drug Conjugate within a population of Antibody Drug Conjugate compounds in which the compounds of that population in some aspects primarily differ by the number and/or location of the Drug Units. In that context p is designated as p' and is an integer ranging from 1 to 24 or from 1 to 20, typically from 1 to 12 or 1 to 10, and more typically from 1 to 8. In other aspects, essentially all of the available reactive functional groups of an antibody targeting agent form covalent bonds to auristatin drug linker moieties to provide an antibody Ligand Unit attached to the maximum number of drug linker moieties, so that the p value of the Antibody Drug Conjugate composition is the same or nearly the same as each of the p' values for each of the Antibody Drug Conjugate compounds of the composition, so that only minor amounts of Antibody Drug Conjugate compounds with lower p' values are present, if at all, as detected using an appropriate chromatographic method, such as electrophoresis, HIC, reverse phase HPLC or size-exclusion chromatography.

The average number of auristatin Drug Units per antibody Ligand Unit in a preparation from a conjugation reaction in some aspects is characterized by conventional chromatographic means as described above in conjunction with mass spectroscopy detection. In other aspects, the quantitative distribution of conjugate compounds in terms of p' values are determined. In those instances, separation, purification, and characterization of homogeneous Antibody Drug Conjugate compounds in which p' is a certain value from an Antibody Drug Conjugate composition from those with other Drug Unit loadings is achievable by means such as an aforementioned chromatographic method.

In some aspects, an ADC of the present invention is compared to an MMAE ADC, sometimes referred to as a comparator MMAE conjugate having the same antibody Ligand Unit. In other aspects, an ADC of the present invention is compared to an ADC in which the Drug Unit incorporates or corresponds the parent AF free drug, sometimes referred herein as a comparator AF conjugate, having the same release mechanism, antibody Ligand Unit and site of conjugation as the hydrophobically-modified AF Conjugate.

"Drug Linker compound" as the terms are used herein, unless otherwise stated or implied by context, refers to a compound having an auristatin Drug Unit, in which the auristatin Drug Unit in a principle embodiment is that of a hydrophobically-modified auristatin F or auristatin F-type free drug, sometimes collectively referred to as a hydrophobic AF Drug Unit, covalently attached to a Linker Unit precursor (LU') through it C-terminal component, in particular through its carboxylic acid functional group, wherein LU' is comprised of a ligand covalent binding precursor ($L_b'$) moiety capable of reacting with a targeting agent to form a covalent bond between a ligand covalent binding moiety ($L_b'$) and a Ligand Unit, in particular an antibody Ligand Unit that incorporates or corresponds to an antibody thus providing a drug linker moiety of Formula 1A of an Antibody Drug Conjugate compound of Formula 1.

A Drug Linker compound of the present invention typically has the general formula of Formula I:

LU'-(D')  (I)

or a salt thereof, which in some aspects is a pharmaceutically acceptable salt, wherein LU' is a LU precursor; and D' represents from 1 to 4 hydrophobic AF Drug Units, each of which is a hydrophobic AF drug of Formula H-AF conjugated to its C-terminal component, in particular through its carboxylic acid functional group, wherein the Drug Linker compound is further defined by the structure of Formula IA:

$L_B'$——$A_a$—$B_b$—($L_O$—$D)_q$  (IA)

wherein $L_B'$ is an antibody covalent binding moiety precursor and the remaining variable groups are as defined for Formula 1A.

"Cytotoxic agent" as the term is used herein, unless otherwise stated or implied by context, is a compound capable of inducing cell death or inhibiting the proliferation or continued survival of cells, which typically are abnormal mammalian cells, in vitro or in vivo. Cytostatic agents, which primarily exert a therapeutic effect by inhibiting proliferation of abnormal cells and not by direct cell killing, are encompassed by the definition of cytotoxic agent. In some aspects, a cytotoxic agent is the free drug resulting from release of a Drug Unit from an Antibody Drug Conjugate, and includes a hydrophobically-modified auristatin F free drug or free drug of related structure, the parent AF free drug, or MMAE.

"Hydrophobic auristatin F compound", "free hydrophobic auristatin F drug" or like term as used herein, unless otherwise stated or implied by context, refers to auristatin F (AF) or AF-type compound that has been hydrophobically modified so as to exhibit cytotoxic activity as free drug against targeted cells irrespective of their MDR status.

In one aspect, a hydrophobic AF compound has the structure represented by Formula H-AF:

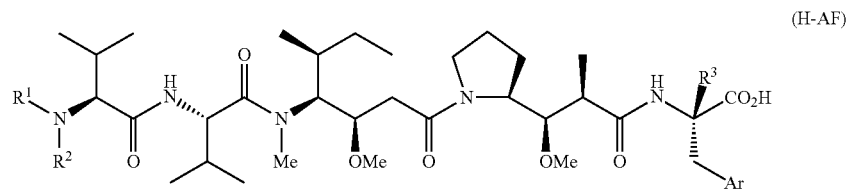

(H-AF)

or a salt thereof, which in some aspects is a pharmaceutically acceptable salt, wherein Ar is phenyl, thienyl, 1-napthyl, 2-napthyl or benzo[b]thiophen-3-yl, optionally substituted; $R^2$ is $C_1$-$C_2$ alkyl; $R^3$ is independently selected from the group consisting of hydrogen and $C_1$-$C_2$ alkyl; and $R^1$ is $C_1$-$C_9$ alkyl, which is inclusive of saturated $C_1$-$C_9$ alkyl and unsaturated $C_3$-$C_9$ alkyl, optionally substituted by a $C_3$-$C_6$ carbocyclyl, to provide a (carbocyclyl)-alkylene- of up to 9 total carbon atoms, or $R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in the (carbocyclyl)alkyl(ene) moieties of $R^1$ $R^2$ and $R^3$ is between 3 and 10 and $R^1$, $R^2$ and $R^3$ are not methyl, or $R^1$ is a first non-aromatic hydrophobic moiety, $R^2$ is hydrogen or a second non-aromatic hydrophobic moiety, $R^3$ is hydrogen and Ar is phenyl, wherein $R^1$ and $R^2$ provide the hydrophobic auristatin F compound of Formula H-AF characterized by an clogP of between about 4.4 to about 7.2 wherein auristatin F has the structure of Formula H-AF in which $R^1$ and $R^2$ are each methyl, $R^3$ is hydrogen and Ar is phenyl.

In another aspect, a hydrophobic AF compound is a hydrophobically-modified auristatin F-type compound related to Formula H-AF in which the C-terminal phenylalanine amino acid residue is replaced with another carboxylic acid-containing amine residue and/or has the internal valine amino acid residue replaced with another α-amino acid residue having a different hydrophobic α-carbon side chain provided that its cLogP value from said replacement(s) remains in the range of between about 4.4 to about 7.2.

In yet another aspect, a hydrophobic AF compound is a hydrophobically-modified auristatin F-type compound having the structure of auristatin F or any one of the previously described hydrophobically-modified AF compounds in which the amide —N-methyl of the DiI residue of the compound is replaced by variable group $R^5$, wherein $R^5$ is $C_2$-$C_6$ alkyl or has the formula —($C_2$-$C_6$ alkylene)-X'—$R^6$, wherein X' is an independently selected amide or carbamate functional group and $R^6$ is $C_1$-$C_6$ alkyl with the proviso that the total number of carbon atoms in the carbocyclyl (when present) and alkyl(ene) moieties of $R^1$ $R^2$, $R^3$ and $R^5$ is between 3 and 10, or is replaced by a more hydrophobic moiety provided that its cLogP value from said replacement remains in the range of between about 4.4 to about 7.2.

Those and other aspects hydrophobic AF compounds are further described by the embodiments of the invention and claims.

"Drug Unit" as the phrase is used herein, unless otherwise stated or implied by context, refers to a residue of a drug that is covalently attached to a Linker Unit (LU) in a drug linker moiety of a Ligand Drug Conjugate (LDC) or is covalently attached to the Linker Unit precursor (LU') of a Drug Linker compound and is releasable from the drug linker moiety or Drug linker compound as free drug. The free drug may be directly incorporated into a Drug Unit, or a component of the free drug may be covalently attached to LU or LU' or an intermediate thereof followed by further elaboration to complete the structure of the Drug Unit. In the context of the present invention, the Drug Unit is a hydrophobic auristatin F Drug Unit, which is a residue of a hydrophobically-modified AF or AF-type compound having covalent attachment to LU/LU' through the compound's C-terminal component, in particular through a residue of a carboxylic acid functional group, such that release of the hydrophobic AF Drug Unit provides the hydrophobic AF compound in which the carboxylic acid has been restored.

"Salt thereof" as the phrase is used herein, unless otherwise stated or implied by context, refers to a salt form of a compound (e.g., a Drug, a Drug Linker compound or a HMW LDC compound). A salt form of a compound is of one or more internal salt forms and/or involves the inclusion of another molecule such as an acetate ion, a succinate ion or other counterion. The counterion in a salt form of a compound is typically an organic or inorganic moiety that stabilizes the charge on the parent compound. A salt form of a compound has one or more than one charged atoms in its structure. In instances where multiple charged atoms are part of the salt form, multiple counter ions and/or multiple charged counter ions are present. Hence, a salt form of a compound typically has one or more charged atoms corresponding to those of the non-salt form of the compound and one or more counterions. In some aspects, the non-salt form of a compound contains at least one amino group or other basic moiety, and accordingly in the presence of an acid, an acid addition salt with the basic moiety is obtained. In other aspects, the non-salt form of a compound contains at least one carboxylic acid group or other acidic moiety, and accordingly in the presence of a base, a carboxylate or other anionic moiety is obtained.

Exemplary counteranion and countercations in compound salt forms include, but are not limited to, sulfate, trifluoroacetate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2-hydroxy-3-naphthoate)) salts.

Selection of a salt form of a compound is dependent on properties the drug product must exhibit, including adequate aqueous solubility at various pH values, depending upon the intended route(s) of administration, crystallinity with flow characteristics and low hygroscopicity (i.e., water absorption versus relative humidity) suitable for handling and required shelf life by determining chemical and solid-state stability under accelerated conditions (i.e., for determining degradation or solid-state changes when stored at 40° C. and 75% relative humidity).

A "pharmaceutically acceptable salt" is a salt form of a compound that is suitable for administration to a subject as described herein and in some aspects includes countercations or counteranions as described by P. H. Stahl and C. G. Wermuth, editors, *Handbook of Pharmaceutical Salts: Properties, Selection and Use*, Weinheim/Zurich:Wiley-VCH/VHCA, 2002.

"Antibody" as the term is used herein is used in the broadest sense, unless otherwise stated or implied by context, and specifically encompasses intact monoclonal antibodies, polyclonal antibodies, monospecific antibodies, multispecific antibodies (e.g., bispecific antibodies), and antibody fragments that exhibit the desired biological activity which requires the antibody fragment to have the requisite number of sites for attachment to the desired number of drug-linker moieties and be capable of specific and selective binding to the targeted cancer cell antigen. The native form of an antibody is a tetramer and typically consists of two identical pairs of immunoglobulin chains, each pair having one light chain and one heavy chain. In each pair, the light and heavy chain variable regions (VL and VH) are together primarily responsible for binding to an antigen. The light chain and heavy chain variable domains consist of a framework region interrupted by three hypervariable regions, also called "complementarity determining regions" or "CDRs". In some aspects, the constant regions are recognized by and interact with the immune system (see, e.g., Janeway et al., 2001, *Immunol. Biology, 5th Ed.*, Garland Publishing, New York) so as to exert an effector function. An antibody includes any isotype (e.g., IgG, IgE, IgM, IgD, and IgA) or subclass thereof (e.g., IgG1, IgG2, IgG3, IgG4, IgA1 and IgA2). The antibody is derivable from any suitable species. In some aspects, the antibody is of human or murine origin. Such antibodies include human, humanized or chimeric antibodies.

"Monoclonal antibody" as used herein refers to an antibody obtained from a population of substantially homogeneous antibodies, i.e., the individual antibodies comprising the population are identical except for possible naturally-occurring mutations that may be present in minor amounts and/or differences in glycosylation patterns. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

"Selective binding" and "selectively binds" as the terms are used herein, unless otherwise stated or implied by context, refers to an antibody, a fragment thereof, or an antibody Ligand Unit of an Antibody Drug Conjugate that is capable of binding in an immunologically selective and specific manner with its cognate cancer cell antigen and not with a multitude of other antigens. Typically, the antibody or antigen-binding fragment thereof binds its targeted cancer cell antigen with an affinity of at least about $1 \times 10^{-7}$ M, and preferably about $1 \times 10^{-8}$ M to $1 \times 10^{-9}$ M, $1 \times 10^{-10}$ M, or $1 \times 10^{-11}$ M and binds to that predetermined antigen with an affinity that is at least two-fold greater than its affinity for binding to a non-specific antigen (e.g., BSA, casein) other than for a closely-related antigen, wherein said affinities are substantially retained when the antibody or antigen-binding fragment thereof corresponds to or is incorporated into an Antibody Drug Conjugate as an antibody Ligand Unit.

"Antigen" is an entity that is capable of being selective bound by an unconjugated antibody or an antigen-binding fragment thereof or by the antibody Ligand Unit of an Antibody Drug Conjugate corresponding to or incorporating that antibody or antigen-binding fragment thereof. In the context of the present invention, the antigen is a cancer cell antigen, which is some aspects is an extracellularly-accessible cell-surface protein, glycoprotein, or carbohydrate of a cancer cell, and in preferred aspects is a glycoprotein, preferentially displayed by cancer cells in comparison to normal cells that are not localized to the abnormal cells. In some of those aspects, the cancer cells displaying the cancer cells are mammalian cancer cells. In other aspects the cancer cell antigen is an extracellularly-accessible antigen preferentially displayed by nearby normal cells that are peculiar to the environment of the cancer cells in comparison to normal cells distant from the site of the cancer cells. For example, the nearby cells may be epithelial cells that are characteristic of the abnormal vasculature of a tumor. Targeting of those vascular cells by an Antibody Drug Conjugate will have a cytotoxic or a cytostatic effect on these cells, which is believed to result in inhibition of nutrient delivery to the nearby cancer cells of the tumor. Such inhibition will indirectly have a cytotoxic or cytostatic effect on the cancer cells and may also have a direct cytotoxic or cytostatic effect on nearby cancer cells subsequent to release of its auristatin Drug Unit as an auristatin free drug subsequent to immunological selective binding by an Antibody Drug Conjugate (ADC) compound. In either of those aspects, the cell-surface antigen is preferably capable of internalization to allow for intracellular delivery of the auristatin free drug into the targeted cell.

Antigens associated with cancer cells that are cell-surface accessible to an ADC include by way of example and not limitation CD19, CD70, CD30, CD33, NTB-A, and $\alpha v \beta 6$.

"Linker Unit" as the term is used herein, unless otherwise stated or implied by context, refers to an organic moiety in a Ligand Drug Conjugate intervening between and covalently attached to a Drug Unit and a Ligand Unit (L) as these terms are defined herein, or is an organic moiety in a Drug Linker compound that is covalently attached to a Drug Unit and has a reactive functional group or moiety for interaction with a targeting agent to form a covalent bond between L and the Linker Unit (LU). As the Linker Unit in a Drug Linker is capable of forming such a bond, it is considered a precursor to a Linker Unit in a Ligand Drug Conjugate and is so indicated as LU'. A Linker Unit is comprised of a primary linker ($L_R$) and a secondary linker ($L_O$) that intervenes between $L_R$ and D within a drug linker moiety of a Ligand Drug Conjugate compound or between $L_R$ and D of a Drug Linker compound, which in the latter instance may be represented as $L_R$' to explicitly indicate that is a precursor to $L_R$ in a Ligand Drug Conjugate.

"Primary linker" as the term is used herein, unless otherwise stated or implied by context, refers to a required component of a Linker Unit (LU) in Antibody Drug Conjugate (ADC) that is covalently attached to the antibody Ligand Unit and the remainder of LU. One component of the primary linker is a ligand covalent binding moiety ($L_b$), which in some aspects of ADCs and Drug Linker compounds described herein provides for a self-stabilizing ($L_{SS}$) linker, thereby defining a $L_{SS}$ primary linker, and in other aspects of ADCs provides for a self-stabilized ($L_S$) linker derivable from $L_{SS}$, thereby defining a $L_S$ primary linker, as these terms are further described herein. The primary linker optionally contains a Branching Unit (B) and a first optional Stretcher Unit, dependent on the values of subscripts a and b in Formula 1A.

A $L_{SS}$ primary linker in a ADC or Drug Linker compound is characterized by a succinimide ($M^2$) or maleimide ($M^1$) moiety, respectively in proximity to a Basic Unit, while a $L_S$ primary linker in a ADC composition or compound thereof is characterized by a succinic acid amide ($M^3$) moiety in proximity to a Basic Unit. An $L_{SS}$ or $L_S$ primary linker of the present invention may also be characterized by a first optional Stretcher Unit (A) and/or an optional Branching Unit, wherein A, when present, is comprised of an optionally substituted $C_1$-$C_{12}$ alkylene moiety bonded to the imide nitrogen of the maleimide or succinimide ring system of $M^1$ or $M^2$ or the amide nitrogen of $M^3$, wherein the alkylene moiety in some aspects is substituted by an acyclic Basic Unit and may be further substituted by optional substituents, or in other aspects is optionally substituted and incorporates a cyclic Basic Unit that is optionally substituted.

A maleimide ($M^1$) moiety of a ligand covalent binding precursor or of a $L_{SS}$ primary linker in a Drug Linker Compound, sometimes shown as $L_{SS}$' to explicitly indicate that it is a precursor to $L_{SS}$ in a Ligand Drug Conjugate, is capable of reacting with a thiol functional group of a high molecular weight targeting agent to form a thio-substituted succinimide moiety ($M^2$) in a ligand covalent binding moiety or a $L_{SS}$ primary linker of an Antibody Drug Conjugate, wherein the thio-substituent is an antibody Ligand Unit incorporating or corresponding to the structure of an antibody or antigen-binding fragment thereof, and wherein the antibody Ligand Unit is bonded to $M^2$ through a sulfur atom from one of the antibody's thiol functional groups. As a result of that reaction, the antibody or antigen-binding fragment thereof becomes covalently bonded to the $L_{SS}$ primary linker as an antibody Ligand Unit. Subsequent hydrolysis of $M^2$ in a $L_{SS}$ primary linker results in a $L_S$ primary linker in which $M^2$ is converted to a succinic acid amide moiety ($M^3$). That linker moiety may exist as a mixture of two regioisomers ($M^{1A}$ and $M^{3B}$), depending on the relative reactivity of the two carbonyl groups of the succinimide ring system to hydrolysis.

"Ligand covalent binding moiety" as the term is used herein, unless otherwise stated or implied by context, refers to a moiety of a Linker Unit (LU) in Ligand Drug Conjugate that interconnects its Ligand Unit (L) and the remainder of the Linker Unit and is derived from reaction between the corresponding ligand covalent binding precursor ($L_b$') moiety of a Linker Unit precursor (LU') in a Drug Linker compound and an antibody or antigen-binding fragment thereof. For example, when $L_B$' is comprised of a maleimide moiety (M'), reaction of that moiety with a reactive thiol functional group of an antibody converts $L_B$' to a ligand covalent binding ($L_B$) moiety so that a thio-substituted succinimide moiety is obtained, wherein its thio-substituent is comprised of a sulfur atom of an antibody Ligand Unit, which in some aspects is provided by a cysteine residue obtained by interchain disulfide bond reduction or genetic engineering. In another example, when $L_B$' is comprised of an activated carboxylic acid functional group, reaction of that functional group with an epsilon amino group of a lysine residue in an antibody converts the functional group to an amide, wherein that amide functional group is shared between $L_B$ and the attached antibody Ligand Unit resulting from that reaction. Other $L_B$ moieties and their conversion from $L_B$'-containing moieties are described in the embodiments of the invention. In yet another example, an antibody is derivitized with a bi-functional molecule to provide an intermediate, which in some instances results in a reactive thiol functional group, that is condensed with a $L_B'$ moiety. As a result of that condensation the $L_B$ moiety so formed has atoms attributable to the bi-functional molecule and $L_B'$.

"Ligand covalent binding precursor moiety" is a moiety of a Linker Unit of a Drug Linker compound or Intermediate thereof that is capable of covalent binding to a targeting agent such as an antibody or antigen-binding fragment thereof during the preparation of a Ligand Drug Conjugate (LDC), including an Antibody Drug Conjugate (ADC), whereupon the ligand binding moiety precursor ($L_B'$) moeity is converted to a ligand covalent binding ($L_b$) moiety. In some aspects, a $L_B'$ moiety has a functional group capable of reacting with a nucleophile or electrophile native to an antibody or antigen-binding fragment thereof, or is introduced into an antibody or antigen binding fragment thereof by chemical transformation or genetic engineering (vide supra) for its conversion to an antibody Ligand Unit. In some of those aspects the nucleophile is an N-terminal amino group of a light or heavy chain of an antibody, or antigen-binding fragment thereof, or the epsilon amino group of a lysine residue of that light or heavy chain. In other aspects, the nucleophile of an antibody, or antigen-binding fragment thereof, is the sulfhydryl group of a cysteine residue introduced by genetic engineering into a light or heavy chain of an antibody or antigen-binding fragment thereof or from chemical reduction of an interchain disulfide of the antibody or fragment thereof. In some aspects, the electrophile is an aldehyde introduced by selective oxidation of a carbohydrate moiety in a glycan component of an antibody or antigen-binding fragment thereof, or is a ketone from an unnatural amino acid introduced into a light or heavy chain of an antibody or antigen-binding fragment thereof using a genetically engineered tRNA/tRNA synthetase pair. Those and other methods for introducing a reactive functional group to provide for a conjugation site in an antibody are reviewed by Behrens and Liu "Methods for site-specific drug conjugation to antibodies" *mAB* (2014) 6(1): 46-53.

"Secondary linker", "secondary linker moiety" and like terms as used herein, unless otherwise stated or implied by context, refer to an organic moiety in a Linker Unit (LU), wherein the secondary linker ($L_O$) is a component of that Unit that interconnects a Drug Unit to a primary linker ($L_R$), which contains a ligand covalent binding ($L_b$) moiety, optionally a first optional Stretcher Unit and/or an optional Branching Unit (B) and in some aspects provides for a self-stabilizing ($L_{SS}$) primary linker of a Ligand Drug Conjugate (LDC), such as an Antibody Drug Conjugate (ADC), or a Drug Linker compound useful for the preparation of the Conjugate or provides for a self-stabilized ($L_S$) primary linker of a ADC compound upon hydrolysis of $L_{SS}$. In some aspects, $L_R$ is attached to $L_O$ through a heteroatom or functional group from a first optional Stretcher Unit (A) that is present.

A secondary linker typically has the structure:

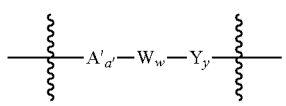

wherein the wavy line adjacent to A' indicates the site of covalent attachment to the primary linker; the wavy line adjacent to Y indicates the site of covalent attachment to the auristatin Drug Unit; A' is a second optional Spacer Unit, subscript a' is 0 or 1, indicating the absence or presence of A', respectively, W is a Cleavable Unit, and subscript w is 0 or 1, indicating the absence or presence of A'; Y is a Spacer Unit, and subscript y is 0 or 1, indicating the absence or presence of a Spacer Unit, respectively.

For AF and hydrophobically-modified AF and AF-type free drugs, collectively referred to as auristatin F free drugs, the corresponding LDCs have conjugation of the auristatin F Drug Units through their C-terminal component, in particular through the carboxylic acid functional group of that component such that release of the Drug Unit from a drug linker moiety of the LDC provides the free drug in which the carboxylic acid functional group is restored. In some of those aspects, W is a peptide Cleavable Unit that provides for a recognition site for an endopeptidase and is directly attached to the auristatin Drug Unit so that subscript y is 0. In other aspects, the peptide sequence comprised of the peptide Cleavable Unit has additional amino acid residues that provide for a Spacer Unit so that subscript y is 1. In those aspects W, Y and D are arranged in a linear configuration, as represented by —W—$Y_y$-D, in which W is the peptide Cleavable Unit and subscript y is 0 or 1. When subscript y is 1, cleavage by the endopeptidase is typically followed by enzymatic action of a exopeptidase to remove remaining amino acid residues contributed by the Spacer Unit so as to complete the release of the auristatin free drug. In some of those aspects the sequence of amino acids providing the endopeptidase recognition sequence and the amino acid residues contributed by the Spacer Unit that remain after endopeptidase cleavage of the recognition sequence are contained within a single peptide sequence.

In other aspects, subscript a' is 1, subscript w is 1 and subscript y is 0 and a second optional Spacer Unit (A') or subunit thereof provides part of the endopeptidase recognition site in the peptide Cleavable Unit (W). In that aspect, an optional secondary linker ($L_O$) is present since the recognition site is within or part of the peptide sequence of W. In other aspects in which $L_O$ is present, subscript a' is 0, subscript w is 1 and subscript y is 0 and a subunit of a first optional Spacer Unit (A) provides part of the endopeptidase recognition site in the peptide Cleavable Unit. In still other aspects in which subscript a' is 0 and subscript y is 0, an amide bond between the primary linker and the C-terminally conjugated Drug Unit provides the recognition site so that A also serves as the peptide Cleavable Unit. In that aspect subscript w is 0 so that $L_O$ is absent as there is no discreet peptide Cleavable Unit although there is the presence of a endopeptidase recognition site for release for auristatin F free drug.

A secondary linker ($L_O$) bonded to D in a Linker Unit as exemplified when only one Drug Unit is attached to LU in which W is a peptide Cleavable Unit is typically represented by structure $S_1$:

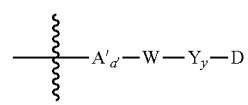

(S₁)

wherein D is an auristatin F Drug Unit and the remaining variable groups are as defined herein for $L_O$;

and a drug linker moiety or a Drug Linker compound comprised of that secondary linker typically has the structure of Formula 1B Formula IB, respectively:

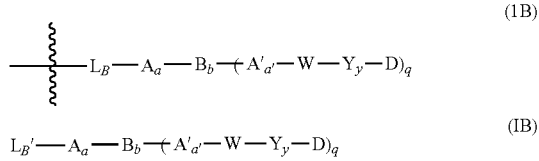

(IB)

$L_B'$—$A_a$—$B_b$—$(A'_{a'}$—$W$—$Y_y$—$D)_q$ wherein $L_B$ is a ligand covalent binding moiety; $L_B'$ is a ligand covalent binding precursor moiety as defined herein for a primary linker ($L_R$) in the Linker Unit (LU) of a drug linker moiety or Drug Linker compound; A is a first optional Stretcher Unit; subscript a is 0 or 1, indicating the absence or presence of A; B is an optional Branching Unit, subscript b is 0 or 1, indicating the absence or presence of B; subscript q ranges from 1 to 4, wherein $L_B/L_B'$, A and B are components of $L_R/L_R'$ provided that subscript b is 1, when subscript q ranges from 2 to 4; and the remaining variable groups are as defined herein for $L_O$.

"Maleimide moiety" as used herein, unless otherwise stated or implied by context, refers to a component of a primary linker of a Drug Linker compound, which in some aspects is a self-stabilizing linker, and is sometimes represented as $L_R'$ or $L_{SS}'$ to explicitly indicated that it is a precursor to $L_R/L_{SS}$ of a Drug Linker compound. A maleimide moiety ($M^1$) is capable of participating in Michael addition (i.e., 1,4-conjugate addition) by a sulfur atom of a reactive thiol functional group of targeting agent, such as an antibody or antigen-binding fragment thereof, to provide a thio-substituted succinimide ($M^2$) moiety, wherein the thio substituent is an Ligand Unit that incorporates or correspond to the structure of the targeting agent as exemplified herein for an antibody Ligand Unit of an Antibody Drug Conjugate composition or compound thereof. That $M^1$ moiety of a Drug Linker compound is attached to the remainder of the primary linker, typically to a first optional Stretcher Unit (A) that is present or to a secondary linker ($L_O$) if both A and B are absent, through its imide nitrogen atom. Other than the imide nitrogen atom, an $M^1$ moiety is typically unsubstituted, but may be asymmetrically substituted at the cyclic double bond of its maleimide ring system. Such substitution can result in regiochemically preferred conjugate addition of a sulfur atom of a reactive thiol functional group of a high molecular weight targeting agent to the less hindered or more electronically deficient double bonded carbon atom (dependent on the more dominant contribution) of the maleimide ring system. That conjugate addition results in a succinimide ($M^2$) moiety, which is thio-substituted by an antibody Ligand Unit though a sulfur atom from a thiol functional group provided by the high molecular weight targeting agent.

"Succinimide moiety" as used herein, unless otherwise stated or implied by context, refers one type of ligand covalent binding ($L_b$) moiety in of primary linker, which in turn is a component of a Linker Unit of a Ligand Drug Conjugate, such as an Antibody Drug Conjugate, and results from Michael addition of a sulfur tom of a reactive thiol functional group of an antibody or antigen-binding fragment thereof to the maleimide ring system of a maleimide moiety ($M^1$), which is one type of ligand covalent binding precursor ($L_b'$) moiety in a Drug Linker compound or a $M^1$-containing intermediate thereof. A succinimide ($M^2$) moiety is therefore comprised of a thio-substituted succinimide ring system that has its imide nitrogen atom substituted with the remainder of the primary linker. In some aspects, that nitrogen atom is attached to a first optional Stretcher Unit (A) that is present through an optionally substituted $C_1$-$C_{12}$ alkylene moiety comprising that Unit. When the primary linker is a self-stabilizing linker, that alkylene moiety incorporates a cyclic Basic Unit into a first optional Stretcher Unit that is required to be present or is substituted by an acyclic Basic Unit as described elsewhere, and is otherwise optionally substituted, and its $M^2$ moiety is optionally substituted with substituent (s) at its succinimide ring system that may have been present on the $M^1$ precursor.

Thus, the optionally substituted $C_1$-$C_{12}$ alkylene moiety of A, in optional combination with [HE], is either covalently attached directly to the optional secondary linker ($L_O$) that is present, optionally through [HE] or indirectly to $L_O$ through -[HE]-$A_O$ wherein $A_O$ is an optional subunit of A that is present in a drug linker moiety of Formula 1A or the Drug Linker compound of Formula IA. In those instances in which $A_O$ is present, A is represented by the formula -$A_1$[HE]-$A_2$-, wherein $A_1$ is a first subunit of A, which is comprised of the optionally substituted $C_1$-$C_{12}$ alkylene moiety, and $A_O$ has become $A_2$, which is the second subunit of A. When present in a self-stabilizing linker ($L_{SS}$) in a Ligand Drug Conjugate compound, hydrolysis of the succinimide ring system of the thio-substituted succinimide ($M^2$) moiety, which is pH controllable due to the nearby presence of the acyclic or cyclic Basic Unit, provides in some instances regiochemical isomers of succinic acidamide ($M^3$) moieties in a self-stabilized linker ($L_S$) due to its asymmetric substitution by the thio substituent. The relative amounts of those isomers will be due at least in part to differences in reactivity of the two carbonyl carbons of $M^2$, which can be attributed at least in part to any substituent(s) that were present in the $M^1$ precursor. Hydrolysis is also expected to occur to some extent when $L_R$ having a $M^2$ moiety that does not contain a Basic Unit, but is highly variable in comparison to the controlled hydrolysis provided by the Basic Unit.

In some aspects, those optional substituents on the succinimide ring system of $M^2$ are not present and the first optional Stretcher Unit is present and is comprised of an optionally substituted $C_1$-$C_{12}$ alkylene moiety optionally attached to [HE], which is an optional hydrolysis-enhancing unit, at a position distal to its attachment site to the imide nitrogen atom. In that aspect, A is a single unit or is further comprised of $A_O$ which is an optional subunit of A that is present and is attached to [HE] that is also present.

"Succinic acid-amide moiety" as used herein, unless otherwise stated or implied by context, refers to component of a self-stabilized linker ($L_S$) of a Linker Unit within a Ligand Drug Conjugate, such as an Antibody Drug Conjugate, and has the structure of a succinic amide hemi-acid residue with substitution of its amide nitrogen by another component of $L_S$, wherein that component is typically a first optional Stretcher Unit (A) or subunit thereof that is present and is comprised of an $C_1$-$C_{12}$ alkylene moiety optionally attached to [HE]. The possible structures for A are indicated by the formula of -A[HE]-$A_O$ in which $A_O$ is the optional subunit. When that subunit is present, A is represented by the formula of A1[HE]-$A_2$-, wherein $A_1$ is the first subunit of A, which is comprised of the optionally substituted $C_1$-$C_{12}$ alkylene moiety optionally attached to [HE], and $A_2$ is the second subunit of A, previously indicated as $A_O$. In some aspects, the alkylene moiety incorporates a cyclic Basic Unit and in other aspects is substituted by an acyclic Basic Unit and in either aspect is otherwise optionally substituted, wherein the succinic acid amide ($M^3$) moiety has further substitution by L-S—, wherein L is antibody Ligand Unit incorporating or corresponding to an antibody or antigen-binding fragment thereof as the targeting agent and S is a sulfur atom from that antibody or fragment. A $M^3$ moiety results from the thio-substituted succinimide ring system of a succinimide ($M^2$) moiety in self-stabilizing primary linker having undergone breakage of one of its carbonyl-nitrogen bonds by hydrolysis, which is assisted by the Basic Unit.

Thus, a $M^3$ moiety has a free carboxylic acid functional group and an amide functional group whose nitrogen heteroatom is attached to the remainder of the primary linker and is substituted by L-S— at the carbon that is alpha to that carboxylic acid or amide functional group, depending on the site of hydrolysis of its $M^2$ precursor. Without being bound by theory, it is believed the aforementioned hydrolysis resulting in a $M^3$ moiety provides a Linker Unit (LU) in an Ligand Drug Conjugate that is less likely to suffer premature loss from the Conjugate of its targeting Ligand Unit (L) through elimination of the thio substituent.

"Self-stabilizing linker" as used herein, unless otherwise stated or implied by context, refers to a primary linker of a Linker Unit (LU) in a Ligand Drug Conjugate, such as an Antibody Drug Conjugate having a $M^2$-containing component or a primary linker of a Linker Unit precursor (LU') in a Drug Linker compound having a $M^1$-containing component, wherein that component may be designated as $L_{SS}$' to indicate that it is a precursor to the $M^2$-containing component of $L_{SS}$ in an LDC, that subsequently undergoes conversion under controlled hydrolysis conditions to the corresponding self-stabilized linker ($L_S$). That hydrolysis is facilitated by the Basic Unit component of $L_{SS}$, such that an ADC comprised of $L_{SS}$ becomes more resistant to premature loss of its antibody Ligand Unit by virtue of its Linker Unit (LU) now being comprised of $L_S$. The $L_{SS}$ primary linker, in addition to its $M^1$ or $M^2$ moiety, is further comprised of a first optional Stretcher Unit (A) that is required to be present, wherein A is comprised of an $C_1$-$C_{12}$ alkylene moiety optionally in combination with [HE], which is sometimes designated as $A_1$ when A is further comprised of an optional subunit ($A_O$) that is present, wherein that subunit is designated a $A_2$. When A may be a single discrete unit or in the form of two discrete units, both possibilities are represented by the formula of -A[HE]-$A_O$-, which becomes -A[HE]- or -$A_1$[HE]-$A_2$-, depending on the absence or presence, respectively, of a second subunit. In either variation of A within $L_{SS}$ its alkylene moiety incorporates a cyclic Basic Unit or is substituted by an acyclic Basic Unit and is otherwise optionally substituted.

Thus, when the primary linker of a Drug Linker compound is $L_{SS}$, sometimes shown as $L_{SS}$' to indicate that it is a precursor of $L_{SS}$ in a Ligand Drug Conjugate, that primary linker contains a first optional Stretcher Unit (A) that is required to be present and a maleimide (MI) moiety through which an antibody is to be attached as an antibody Ligand Unit. In those aspects, the $C_1$-$C_{12}$ alkylene moiety of A is attached to the imide nitrogen of the maleimide ring system of $M^1$ and to the remainder of the Linker Unit, the latter of which optionally occurs through [HE]-$A_O$ of $L_{SS}$, depending on the absence or presence of $A_O$ and [HE]. In some of those aspects, [HE], which is a hydrolysis-enhancing moiety, consists or is comprised of an optionally substituted electron withdrawing heteroatom or functional group, which in some aspects in addition to BU may enhance the hydrolysis rate of the $M^2$ moiety in the corresponding $L_{SS}$ moeity of a ADC compound. After incorporation of the Drug Linker compound into an ADC compound, $L_{SS}$ now contains a succinimide ($M^2$) moiety that is thio-substituted by the antibody Ligand Unit (i.e., attachment of the antibody Ligand Unit to its drug linker moiety occurs through Michael addition of a sulfur atom of a reactive thiol functional group of an antibody to the maleimide ring system of $M^1$).

In some aspects, a cyclized Basic unit (cBU) corresponds in structure to an acyclic Basic Unit through formal cyclisation to the basic nitrogen of that Unit so that the cyclic Basic Unit structure is incorporated into the first optional Stretcher Unit that is present as an optionally substituted spiro $C_4$-$C_{12}$ heterocyclo. In such constructs, the spiro carbon is attached to the maleimide imide nitrogen of $M^1$, and hence to that nitrogen in $M^2$, and is further attached to the remainder of the $L_{SS}$ primary linker, which is comprised of the afore-described first optional Stretcher Unit (A) that is present optionally through -[HE]-$A_O$-, in a drug linker moiety of Formula 1A or a Drug Linker compound of Formula IA. In those aspects, a cyclic BU assists in the hydrolysis of the succinimide moiety of $M^2$ to its corresponding ring-opened form(s) represented by $M^3$ in qualitatively similar manner to that of an acyclic Basic Unit, which may also be enhanced by [HE].

In some aspects, $L_b$'-A- of a $L_{SS}$ primary linker, which is sometimes shown as $L_{SS}$' to explicitly indicate that it is a precursor to a self-stabilizing ($L_{SS}$) primary linker in a Drug Linker compound of Formula IA, is represented by the general formula of $M^1$-A(BU)—[HE]-$A_O$-, wherein M is a maleimide moiety and A is a $C_1$-$C_{12}$ alkylene that incorporates or is substituted by BU and is otherwise optionally substituted and is in optional combination with [HE], which is an optional hydrolysis-enhancing moiety, wherein that formula becomes A(BU)—[HE]- when A is a single discreet unit or A1(BU)—[HE]-$A_2$- when A is of two subunits, wherein $A_1$ and $A_2$ are the subunits of A.

In other aspects, a $L_{SS}$ primary linker in a drug linker moiety of Formula 1A of an ADC of Formula 1, is represented by the general formula of -$M^2$-A(BU)—[HE]-$A_O$-, wherein $M^2$ is a succinimide moiety, A is a first optional Stretcher Unit that is present and is comprised of an $C_1$-$C_{12}$ alkylene that incorporates or is substituted by BU and is otherwise optionally substituted and is in optional combination with [HE], which is an optional hydrolysis-enhancing moiety, and $A_O$ is an optional subunit of A. When A is a single discreet unit, $L_{SS}$ is represented by the formula of -$M^2$-A(BU)—[HE]- and when A is of two subunits $L_{SS}$ is represented by the formula of -$M^2$-A1(BU)—[HE]-$A_2$-.

In still other aspects, a $L_S$ primary linker in a drug linker moiety of Formula 1A of a ADC of Formula 1 is represented by the general formula of -$M^3$-A(BU)—[HE]-$A_O$-, wherein $M^3$ is a succinimide acid amide moiety and A is a $C_1$-$C_{12}$ alkylene that incorporates or is substituted by BU, and is otherwise optionally substituted, and is in optional combination with [HE], which is an optional hydrolysis-enhancing moiety, and $A_O$ is an optional subunit of A, wherein A(BU)—[HE]-$A_O$- becomes -A(BU)—[HE]- when A is a single discreet unit or -A1(BU)—[HE]-$A_2$- when A is or is comprised of two subunits.

Exemplary, but non-limiting -$L_b$-A- structures comprising a $L_{SS}$ primary linker within a drug linker moiety of Formula 1A for some Antibody Ligand Drug Conjugates of Formula 1 are represented by:

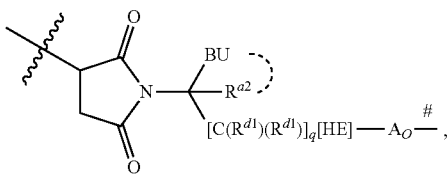

wherein the wavy line indicates the site of covalent attachment to a Ligand Unit, the pound sign (#) indicates the site of covalent attachment in Formula 1 to a Branching Unit (B) or an optional secondary linker ($L_O$) that is present depending on the value of subscript b or to D if both B and $L_O$ are absent and wherein the dotted curved line indicates optional cyclization which is present when present BU is a cyclic Basic Unit or is absent when BU is an acyclic Basic Unit, wherein [HE] is an optional hydrolysis-enhancing moiety, $A_O$ is an optional subunit of A, subscript q is 0 or an integer ranging from 1 to 6; each $R^{d1}$ is independently selected from the group consisting of hydrogen and optionally substituted $C_1$-$C_6$ alkyl, or two of $R^{d1}$, the carbon atom(s) to which they are attached and any intervening carbon atoms define an optionally substituted $C_3$-$C_8$ carbocyclo, and the remaining $R^{d1}$, if any, are independently hydrogen or optionally substituted $C_1$-$C_6$; and $R^2$ is an optionally substituted $C_1$-$C_8$ alkyl, which in a cyclic Basic Unit along with the carbon atom to which BU and $R^2$ are attached define an optionally substituted spiro $C_4$-$C_{12}$ heterocyclo having a skeletal secondary or tertiary basic nitrogen atom, such that the cyclic Basic Unit is capable of increasing the rate of hydrolysis of the shown succinimide ($M^2$) moiety to provide a succinic acid amide ($M^3$) moiety at a suitable pH in comparison to the corresponding Conjugate in which $R^2$ is hydrogen and BU is replaced by hydrogen, and/or substantially retains the increase in the rate of hydrolysis in the for the drug linker moeity corresponding to that of the ADC in which in $R^{a2}$ is hydrogen and BU is an acyclic BU over the aforementioned Conjugate in which $R^2$ is hydrogen and BU is replaced by hydrogen.

Exemplary, but non-limiting, $L_b$'-A- structures comprising $L_{SS}$', which are sometimes present in Drug Linker compounds of Formula I used as intermediates in the preparation of Antibody Drug Conjugate compositions, are represented by:

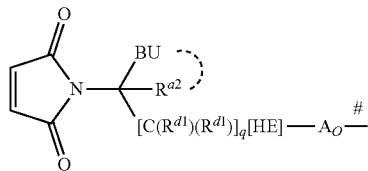

wherein BU and the other variable groups are as defined above for $L_b$'-A-structures of ADCs having $L_{SS}$ primary linkers. When a Drug Linker compound having a self-stabilizing linker precursor ($L_{SS}$'), which is comprised of a maleimide moeity, is used in the preparation of a ADC, that $L_{SS}$' moiety is converted into a $L_{SS}$ primary linker comprised of a succinimide moeity. Prior to condensation with a reactive thiol functional group from an antibody, the basic nitrogen atom of BU is typically protonated or protected by an acid-labile protecting group.

"Self-stabilized linker" is an organic moiety derived from a $M^2$-containing moiety of a self-stabilizing linker ($L_{SS}$) in a Ligand Drug Conjugate, such as an Antibody Drug Conjugate, that has undergone hydrolysis under controlled conditions so as to provide a corresponding $M^3$-moiety of a self-stabilized linker ($L_S$), wherein that LU component is less likely to reverse the condensation reaction of a targeting moiety with a $M^1$-containing moiety that provided the original $M^2$-containing $L_{SS}$ moiety. In addition to the $M^3$ moiety, a self-stabilized linker ($L_S$) is comprised of a first optional Stretcher Unit (A) that is present and incorporates a cyclic Basic Unit or is substituted by an acyclic Basic Unit, wherein A is covalently attached to $M^3$ and the remainder of the $L_S$ primary linker (i.e., B) or to an optional secondary linker ($L_O$) that is present when B is absent or to D when both B and $L_O$ are absent. The $M^3$ moiety is obtained from conversion of a succinimide moiety ($M^2$) of $L_{SS}$ in an Ligand Drug Conjugate, wherein the $M^2$ moiety has a thio-substituted succinimide ring system resulting from Michael addition of a sulfur atom of a reactive thiol functional group of a targeting agent to the maleimide ring system of $M^1$ of a $L_{SS}$' moiety in a Drug Linker compound, wherein that $M^2$-derived moiety has reduced reactivity for elimination of its thio-substituent in comparison to the corresponding substituent in $M^2$. In those aspects, the $M^2$-derived moiety has the structure of a succinic acid-amide ($M^3$) moiety corresponding to $M^2$ wherein $M^2$ has undergone hydrolysis of one of its carbonyl-nitrogen bonds of its succinimide ring system, which is assisted by the basic functional group of BU due to its appropriate proximity as a result of that attachment. The product of that hydrolysis therefore has a carboxylic acid functional group and an amide functional group substituted at its amide nitrogen atom, which corresponds to the imide nitrogen atom in the $M^2$-containing $L_{SS}$ precursor to $L_S$, with the remainder of the primary linker. In some aspects, the basic functional group is a primary, secondary or tertiary amine of an acyclic Basic Unit or secondary or tertiary amine of a cyclic Basic Unit. In other aspects, the basic nitrogen of BU is a heteroatom of an optionally substituted basic functional group as in a guanidino moeity. In either aspect, the reactivity of the basic functional group of BU for base-catalyzed hydrolysis is controlled by pH by reducing the protonation state of the basic nitrogen atom.

Thus, a self-stabilized linker ($L_S$) typically has the structure of an $M^3$ moiety covalently bond to an first optional Stretcher Unit that is present and incorporating a cyclic Basic Unit or substituted by an acyclic Basic Unit. In some aspects, A is a discrete single unit and in other aspects is of two or more subunits, typically represented by $A_1$-$A_2$ if two subunits are present with A/$A_1$ optionally in combination with [HE]. Stretcher Unit A in turn is covalently bonded to the remainder of the primary linker $L_S$ with its $M^3$, A/$A_1$, $A_O$/$A_2$, BU components arranged in the manner represented by the general formula of -$M^3$-A(BU)—[HE]-$A_O$- when A is a single discreet unit represented by $M^3$-A(BU)—[HE]- or is of two subunits represent by -$M^3$-$A_1$(BU)-$A_2$-, wherein BU represents either type of Basic Unit (cyclic or acyclic).

Exemplary non-limiting structures of $L_b$-A- in $L_{SS}$ and $L_S$ primary linkers for ADCs in which $L_B$ is $M^2$ or $M^3$; and A(BU)/$A_1$(BU), $A_O$/$A_2$ and [HE] within these structures are arranged in the manner indicated above in which BU is an acyclic Basic Unit is shown by way of example but not limitation by the structures of:

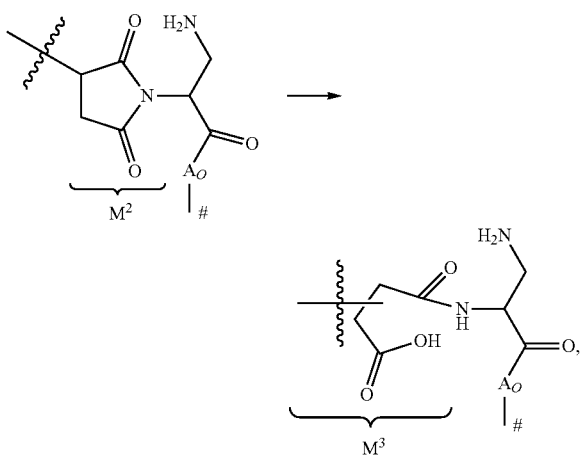

wherein the —CH(CH$_2$NH$_2$)C(=O)— moiety is A, when A is a single discreet unit so that A$_O$ is absent or is A$_1$ when A$_O$ is present as A$_2$, and wherein A/A$_1$ is substituted by BU, wherein BU is an acyclic Basic Unit, which is —CH$_2$NH$_2$, the basic nitrogen atom, optionally protonated, and —C(=O)— within that moiety is the optional hydrolysis enhancing moiety [HE] that is present. Those exemplary structures contain a succinimide (M$^2$) moiety or a succinic acid-amide (M$^3$) moiety resulting from succinimide ring hydrolysis of M$^2$ assisted —CH$_2$NH$_2$ by in the conversion of L$_{SS}$ to L$_S$.

Exemplary non-limiting structures of -L$_b$-A- in L$_{SS}$ and L$_S$ primary linkers for ADCs in which L$_B$ is M$^2$ or M$^3$; and A(BU)/A1(BU), A$_O$/A$_2$ and [HE] within these structures are arranged in the manner indicated above in which BU is a cyclic Basic Unit is shown by way of example but not limitation by the structures of:

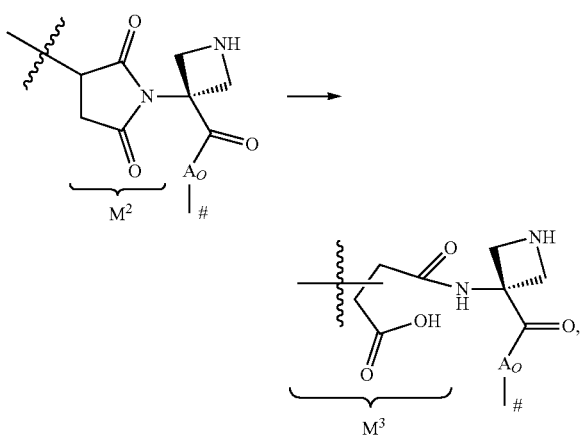

wherein these -M$^2$-A(BU)—[HE]-A$_O$- and -M$^3$-A(BU)—[HE]-A$_O$- structures become -M$^2$-A(BU)—[HE]- and -M$^3$-A(BU)—[HE]-, when A$_O$ is absent so that A is present as a single discreet unit or -M$^2$-A1(BU)—[HE]-A$_2$- and -M$^3$-A1(BU)—[HE]-A$_2$- in which A$_O$ is present as a subunit of A indicated as A$_2$ and wherein BU is a cyclic Basic Unit in the form of an optionally protonated azetidin-3,3-diyl, the structure of which is an exemplary heterocyclo Basic Unit incorporated into A/A$_1$ that corresponds to the aminoalkyl of an acyclic Basic Unit in an A$_1$(BU) or A(BU) moiety in which the basic nitrogen of the acyclic Basic Unit has been formally cyclized at least in part back through R$^{a2}$ to the carbon atom that is alpha to the succinimide nitrogen of M$^2$ to which the acyclic Basic Unit is attached.

The wavy line in each of the above -L$_b$-A- structures indicates the site of covalent attachment of a sulfur atom of a Ligand Unit derived from a reactive thiol functional group of a targeting agent upon Michael addition of that sulfur atom to the maleimide ring system of an M$^1$ moiety in a corresponding Drug Linker compound. The pound sign (#) in each of the above -L$_b$-A- structures indicates the site of covalent attachment to the remainder of the L$_{SS}$ or L$_S$ primary linker. Since the succinimide ring system of M$^2$ is asymmetrically substituted due to its thio substituent, regiochemical isomers of succinic acid-amide (M$^3$) moieties as defined herein differing in position relative to the liberated carboxylic acid group may result on M$^2$ hydrolysis. In the above structures, the carbonyl functional group shown adjacent to A$_O$ exemplifies a hydrolysis enhancer [HE] as defined herein.

The above -M$^3$-A(BU)—[HE]-A$_O$-, -M$^3$-A(BU)— and -M$^3$-A$_1$(BU)—[HE]-A$_2$-moieties wherein BU is acyclic or cyclic Basic Unit represent exemplary -L$_b$-A- structures of self-stabilized linker (L$_S$) primary linkers, so named because these structures are less likely to eliminate the thio substituent of the Ligand Unit, and thus cause loss of that targeting moiety, in comparison to the corresponding L$_{SS}$ moieties of formula -M$^2$-A(BU)—[HE]-A$_O$-, -M$^2$-A(BU)— and -M$^2$-A$_1$(BU)—[HE]-A$_2$- from which they are derived. Without being bound by theory, it is believed the increased stability results from the greater conformational flexibility in M$^3$ in comparison to M$^2$, which no longer constrains the thio substituent in a conformation favorable for E2 elimination.

"Basic Unit" as used herein, unless otherwise stated or implied by context, refers to an organic moiety within a self-stabilizing linker (L$_{SS}$) primary linker, as described herein, which is carried forward into a corresponding L$_S$ moiety by BU participating in base catalyzed hydrolysis of the succinimide ring system within a M$^2$ moiety comprising L$_{SS}$ (i.e., catalyzes addition of a water molecule to one of the succinimide carbonyl-nitrogen bonds). In some aspects, the base-catalyzed hydrolysis is initiated under controlled conditions tolerable by the targeting antibody Ligand Unit attached to L$_{SS}$. In other aspects, the base-catalyzed hydrolysis is initiated on contact of the Drug Linker compound comprised of L$_{SS}$' with a targeting antibody in which Michael addition of a sulfur atom of a reactive thiol functional group of the antibody effectively competes with hydrolysis of the L$_{SS}$' M$^1$ moeity of the Drug Linker compound. Without being bound by theory, the following aspects describe various considerations for design of a suitable Basic Unit. In one such aspect, the basic functional group of an acyclic Basic Unit and its relative position in L$_{SS}$ with respect to its M$^2$ component are selected for the ability of BU to hydrogen bond to a carbonyl group of M$^2$, which effectively increases its electrophilicity and hence its susceptibility to water attack. In another such aspect, those selections are made so that a water molecule, whose nucleophilicity is increased by hydrogen bonding to the basic functional group of BU, is directed to an M$^2$ carbonyl group. In a third such aspect, those selections are made so the basic nitrogen on protonation does not increase the electrophilicity of the succinimide carbonyls by inductive electron withdrawal to an extent that would promote premature hydrolysis requiring compensation from an undesired excess of Drug Linker compound. In a final such aspect, some combination of those mechanistic effects contributes to catalysis for controlled hydrolysis of $L_{SS}$ to $L_S$.

Typically, an acyclic Basic Unit, which may act through any of the above mechanistic aspects, is comprised of 1 carbon atom or 2 to 6 contiguous carbon atoms, more typically of 1 carbon atom or 2 or 3 contiguous carbon atoms, wherein the carbon atom(s) connect the basic amino functional group of the acyclic Basic Unit to the remainder of the $L_{SS}$ primary linker to which it is attached. In order for that basic amine nitrogen atom to be in the required proximity to assist in the hydrolysis of a succinimide ($M^2$) moiety to its corresponding ring-opened succinic acid amide ($M^3$) moiety, the amine-bearing carbon chain of an acyclic Basic Unit is typically attached to A of the -$L_b$-A-moiety of $L_{SS}$ at the alpha carbon of the $C_1$-$C_{12}$ alkylene of that moiety relative to the site of attachment of A to the succinimide nitrogen of $M^2$ (and hence to the maleimide nitrogen of its corresponding $M^1$-A- structure). Typically, that alpha carbon in an acyclic Basic Unit has the (S) stereochemical configuration or the configuration corresponding to that of the alpha carbon of L-amino acids.

As previously described, BU in acyclic form or BU in cyclized form is typically connected to $M^1$ or $M^2$ of $L_{SS}$ or $M^3$ of $L_S$ through an otherwise optionally substituted $C_1$-$C_{12}$ alkylene moiety in which that moiety incorporates the cyclized Basic Unit or is substituted by the acyclic Basic Unit and is bonded to the maleimide or succinimide nitrogen of $M^1$ or $M^2$, respectively, or the amide nitrogen atom of $M^3$. In some aspects, the otherwise optionally substituted $C_1$-$C_{12}$ alkylene moiety incorporating the cyclic Basic Unit is covalently bonded to [HE] and typically occurs through intermediacy of an ether, ester, carbonate, urea, disulfide, amide carbamate or other functional group, more typically through an ether, amide or carbamate functional group. Likewise, BU in acyclic form is typically connected to $M^1$ or $M^2$ of $L_{SS}$ or $M^3$ of $L_S$ through an otherwise optionally substituted $C_1$-$C_{12}$ alkylene moiety of A in $L_B$'-A-, wherein $L_B$' is $M^1$ or -$L_b$-A-, wherein $L_B$ is $M^2$ or $M^3$ which is substituted by the acyclic Basic unit at the same carbon of the $C_1$-$C_{12}$ alkylene moiety that is attached to the imino nitrogen atom of the maleimide or succinimide ring system of $M^1$ or $M^2$ or the amide nitrogen of $M^3$ subsequent to hydrolysis of the succinimide ring system of $M^2$.

In some aspects, a cyclic Basic Unit incorporates the structure of an acyclic BU by formally cyclizing an acyclic Basic Unit to an otherwise optionally substituted $C_1$-$C_{12}$ alkyl ($R^{a2}$) independently selected from that of A/$A_1$ and bonded to the same alpha carbon as the acyclic Basic Unit, thus forming a spirocyclic ring system so that a cyclic Basic Unit is incorporated into the structure of A/$A_1$ rather than being a substituent of A/$A_1$ as when BU is acyclic. In those aspects, the formal cyclization is to the basic amine nitrogen of an acyclic Basic Unit thus providing a cyclic Basic Unit as an optionally substituted symmetrical or asymmetrical spiro $C_4$-$C_{12}$ heterocyclo, depending on the relative carbon chain lengths in the two alpha carbon substituents, in which the basic nitrogen is now a basic skeletal heteroatom. In order for that cyclization to substantially retain the basic properties of the acyclic Basic Unit in a cyclic Basic Unit, the basic nitrogen atom of the acyclic Basic Unit nitrogen should be that of a primary or secondary amine and not a tertiary amine since that would result in a quaternized skeletal nitrogen in the heterocyclo of the cyclic Basic Unit. In that aspect of formal cyclization of an acyclic Basic Unit to a cyclic Basic Unit, in order to substantially retain the ability of the basic nitrogen to assist in hydrolysis of $M^2$ to $M^3$ in conversion of $L_{SS}$ to $L_S$, the resulting structure of the cyclic Basic Unit in these primary linkers will typically have its basic nitrogen located so that no more than three, and typically one or two, intervening carbon atoms are between the basic nitrogen atom and the spiro carbon of the spiro $C_4$-$C_{12}$ heterocyclo component. Cyclic Basic Units incorporated into A/$A_1$ and the $L_{SS}$ and $L_S$ primary linkers having these as components are further described by the embodiments of the invention.

"Hydrolysis-enhancing moeity" as used herein, unless otherwise stated or implied by context, refers to is electron withdrawing group or moiety that is an optionally present within a first optional Stretcher Unit (A) in $L_b$'-A- or $L_b$-A- of an $L_{SS}$ primary linker and its hydrolysis product $L_S$. A hydrolysis-enhancing [HE] moiety when present as component of A/$A_1$ of $L_{SS}$ in a drug linker moiety of an ADC, wherein A/$A_1$ is bonded to the imide nitrogen of an $M^2$ moiety can increase the electrophilicity of the succinimide carbonyl groups in that moiety, depending on its proximity to that $M^2$ moiety can exert and electron withdrawing effect of [HE], to facilitate its conversion to a $M^3$ moiety of a $L_S$ primary linker With A/$A_1$ incorporating or substituted by a cyclic Basic Unit or an acyclic Basic Unit, respectively, the potential effect of [HE] on the carbonyl groups of $M^2$ for increasing the hydrolysis rate to $M^3$ by induction and the aforementioned effect(s) of either type of BU, are adjusted so that premature hydrolysis of $M^1$ does not occur to an appreciable extent during preparation of a Ligand Drug Conjugate from a Drug Linker compound comprised of the $L_b$'-A- structure of formula $M^1$-A(BU)—[HE]-$A_O$-, with the two variations represented by the formulae of $M^1$-A(BU)— and $M^1$-A(BU)—[HE]-$A_2$-, in which A/$A_1$ is in combination with [HE]. Instead, the combined effects of BU and [HE] to promote hydrolysis, which covert the -$L_b$-A- structure of general formula -$M^2$-A(BU)—[HE]-$A_O$-, or more specifically of formula -$M^2$-A(BU)— or -$M^2$-$A_1$(BU)-$A_2$-, of a Ligand Drug Conjugate compound to its corresponding -$M^3$-A(BU)—[HE]-$A_O$-, -$M^3$-A(BU)— or $M^3$-A1(BU)—[HE]-$A_2$- formula, under controlled conditions (as when pH is purposely increased so as to decrease protonation of the Basic Unit) are such that an undue molar excess of Drug Linker compound to compensate for hydrolysis of its $M^1$ moiety is not required. Therefore, Michael addition of the sulfur atom of a reactive thiol functional group of the targeting agent to the maleimide ring system of $M^1$, which provides a targeting Ligand Unit attached to a succinimide ring system of $M^2$, typically occurs at a rate that effectively competes with $M^1$ hydrolysis. Without being bound by theory, it is believed that at low pH, as for example when the basic amine of BU is in the form of a TFA salt, premature hydrolysis of $M^1$ in a Drug Linker product is much slower than when the pH is raised to that suitable for base catalysis using an appropriate buffering agent and that an acceptable molar excess of Drug Linker compound can adequately compensate for any loss due to premature $M^1$ hydrolysis that does occur during the time course for completion or near completion of the Michael addition of a sulfur atom of a targeting agent's reactive thiol functional group to a Drug Linker compound's $M^1$ moiety.

As previously discussed, enhancement of carbonyl hydrolysis by either type of Basic Unit is dependent on the basicity of its functional group and the distance of that basic functional group in relation to the $M^1$/$M^2$ carbonyl groups. Typically, [HE] is a carbonyl moiety or other carbonyl-containing functional group located distal to the end of the $C_1$-$C_{12}$ alkylene of A/$A_1$ that is bonded to $M^2$, or $M^3$ derived therefrom and also provides for covalent attachment to $A_2$ or to the optional secondary linker this is present, when B is absent and A is a single discreet unit. Carbonyl-containing functional groups other than ketone include esters, carbamates, carbonates and ureas. When [HE] is a carbonyl-containing functional group other than ketone in a drug linker moiety of an ADC having a $L_{SS}$ primary linker, the carbonyl moiety of that functional group, which is shared with A/A$_1$, is typically bonded to the otherwise optionally substituted $C_1$-$C_{12}$ alkylene of A/A$_1$ distal to its attachment site to the imide nitrogen atom of M$^2$ as when [HE] is —C(=O)—X—, wherein X is —O— or optionally substituted —NH—. In some aspects, the [HE] moiety may be sufficiently distant from the imide nitrogen to which of A/A$_1$ is covalently bonded so that no discernable or minor effect on hydrolytic sensitivity of the succinimide carbonyl-nitrogen bonds of an M$^2$-containing moiety is observable, but instead is driven primarily by BU.

"Stretcher Unit" as used herein, unless otherwise stated or implied by context, refers to an optional organic moiety in a primary or secondary linker of a Linker Unit in a Drug Linker compound or drug linker moiety of Ligand Drug Conjugate, such as an Antibody Drug Conjugate, that physically separates the targeting Ligand Unit (L) from an optional secondary linker that typically is present. When the Linker Unit is comprised of a $L_{SS}$ or $L_S$ primary linker a first option Stretcher is present since it provides the Basic Unit for these types of primary linkers. The presence of a first optional Stretcher Unit (A) in $L_R$ may also be required in any type of primary linker when there is insufficient steric relief from the Ligand Unit absent that optional Stretcher Unit to allow for efficient processing of the secondary linker for release of the Drug Unit as a free auristatin drug, which includes a hydrophobic auristatin F compound as described herein. Alternatively, or in addition to steric relief, those optional components may be included for synthetic ease in preparing a Drug Linker compound. A first or second optional Stretcher Unit (A or A', respectively) can each be a single unit or can contain multiple subunits (as for example when A has two subunits represented by -A$_1$-[HE]-A$_2$-). Typically, A or A' is one distinct unit or has 2 to 4 distinct subunits.

In some aspects, when $L_R$ is $L_{SS}$/$L_S$, in addition to covalent attachment to M$^1$ of a Drug Linker compound or M$^2$/M$^3$ of a drug linker moiety in a ADC compound, A is bonded to a Branching Unit (B), an optional secondary linker ($L_O$) that is present or directly to D when $L_O$ is absent optionally through A$_O$ as in A[HE] or A$_1$-[HE]-A$_2$ represented in general as A-[HE]-A$_O$- in which A/A$_1$ and A$_O$/A$_2$ is also a component of $L_{SS}$/$L_S$.

In some aspects, A or A' or a subunit of either of these Stretcher Units has the formula of -L$^P$(PEG)- in which L$^P$ is a Parallel Connecter Unit and PEG is a PEG Unit as defined elsewhere. Thus, in some of those aspects a Linker Unit in drug linker moiety of an Antibody Drug Conjugate or Drug Linker compound contains the formula of -A$_1$-[HE]-L$^P$(PEG)-A$_a$'- in which -L$^P$(PEG)- is A$_2$ or A-[HE]-A$_O$-L$^P$(PEG)- in which A'$_{a'}$ is -L$^P$(PEG)- when subscript a' is 1.

In some aspects when subscript a is 1 so that a first optional Stretcher Unit (A) is present, that Unit typically has at least one carbon atom that connects $L_B$/$L_B$' to [HE]. In some of those aspects in which $L_B$' is that of a $L_{SS}$' primary linker of a Drug Linker compound, that Stretcher Unit is comprised of $C_1$-$C_{12}$ alkylene moiety substituted by or incorporating a Basic Unit and is otherwise optionally substituted and has one of its radical carbon atoms attached to the maleimide nitrogen atom and the other to [HE], wherein [HE] is an optional hydrolysis enhancing moiety that is present. In other aspects, when $L_R$' is other than $L_{SS}$', but nonetheless is comprised of a maleimide moiety or some other $L_B$' moeity, $L_B$' is attached to an optional first Stretcher Unit (A), which in some aspects is an optionally substituted $C_1$-$C_{12}$ alkylene, which is optionally in combination with [HE]. Thus, in some aspects in which $L_R$' is $L_{SS}$' the first optional Stretcher Unit is present and is comprised of a $C_1$-$C_{12}$ alkylene moiety, [HE] and an optional subunit (A$_O$), all of which are components of $L_{SS}$, wherein A is attached to B, $L_O$ or D at a position distal to the attachment site of the $C_1$-$C_{12}$ alkylene moiety to the imide nitrogen atom. In other aspects, when subscript a is 1 and A is present as a single discreet unit or of two subunits, A has the general formula of -A-[HE]-A$_O$- wherein A$_O$ is an optional subunit of A, or more specifically has the formula of -A$_1$-[HE]-A$_2$- when A$_O$ is present as a second subunit of A. In such aspects, A$_O$/A$_2$ is an α-amino acid, a β-amino acid or other amine-containing acid residue.

"Branching Unit" as used herein, unless otherwise stated or implied by context, refers to a tri-functional organic moiety that is an optional component of a Linker Unit (LU). A Branching Unit (B) is present in a primary linker of drug linker moiety of Formula 1A of antibody drug conjugate (ADC) of Formula 1A. In a ADC having the afore-described generalized formula, the absence or presence of a Branching Unit is indicated by subscript b of B$_b$ in which subscript b is 0 or 1, respectively. A Branching Unit is trifunctional in order to be incorporated into a primary linker. Drug Linker or ADC compound having a Branching Unit, which is due to multiple -L$_O$-D moieties per drug linker moiety of formula -LU-D, typically have each secondary linker (L$_O$) containing the formula -A'$_a$-W$_w$-Y$_y$-, wherein A' is a second optional Stretcher Unit; subscripts a' is 0 or 1, indicating the absence or presence of A', respectively; W is a Cleavable Unit; subscript w is 0 or 1, indicating the absence or presence of W, respectively; Y is a Spacer Unit; and subscript y is 0 or 1, indicating the absence or presence a Spacer Unit, respectively, provided that if $L_O$ is present a'+w+y is not 0.

In some aspects, a natural or un-natural amino acid residue or residue of another amine-containing acid compound having a functionalized side chain serves as a Branching Unit. In some aspects B is a lysine, glutamic acid or aspartic acid residue in the L- or D-configuration in which the epsilon-amino, gamma-carboxylic acid or beta-carboxylic acid functional group, respectively, along with their amino and carboxylic acid termini, interconnects B within the remainder of LU.

"Natural amino acid" as used herein, unless otherwise stated or implied by context, refers to a naturally occurring amino acid, namely, arginine, glutamine, phenylalanine, tyrosine, tryptophan, lysine, glycine, alanine, histidine, serine, proline, glutamic acid, aspartic acid, threonine, cysteine, methionine, leucine, asparagine, isoleucine, and valine or a residue thereof, in the L or D-configuration, unless otherwise specified or implied by context.

"Un-natural amino acid" as used herein, unless otherwise stated or implied by context, refers to an alpha-amino-containing acid or residue thereof, which has the basic structure of a natural amino acid, but has a side chain group attached to the alpha carbon that is not present in natural amino acids.

"Non-classical amino acid" as used herein, unless otherwise stated or implied by context, refers to an amine-containing acid compound that does not have its amine substituent bonded to the carbon alpha to the carboxylic acid and therefore is not an alpha-amino acid. Non-classical amino acids include β-amino acids in which a methylene is inserted between the carboxylic acid and amino functional groups in a natural amino acid or an un-natural amino acid.

"Peptide" as used herein, unless otherwise stated or implied by context, refers to a polymer of two or more amino acids wherein carboxylic acid group of one amino acid forms an amide bond with the alpha-amino group of the next amino acid in the peptide sequence. Methods for preparing amide bonds in polypeptides are additionally provided in the definition of amide. Peptides may be comprised of naturally occurring amino acids in the L- or D-configuration and/or unnatural and/or non-classical amino acids.

"Protease" as defined herein refers to a protein capable of enzymatic cleavage of a carbonyl-nitrogen bond such as an amide bond typically found in a peptide. Proteases are classified into major six classes: serine proteases, threonine proteases, cysteine proteases, glutamic acid proteases, aspartic acid proteases and metalloproteases so named for the catalytic residue in the active site that is primarily responsible for cleaving the carbonyl-nitrogen bond of its substrate. Proteases are characterized by various specificities, which are dependent of identities of the residues at the N-terminal and/or C-terminal side of the carbonyl-nitrogen bond and various distributions (intracellular and extracellular).

Regulatory proteases are typically intracellular proteases that are required for the regulation of cellular activities that sometimes becomes aberrant or dysregulated in abnormal or other unwanted cells. In some instances, when a Peptide Cleavable Unit is directed to a protease having preferential distribution intracellularly, that protease is a regulatory protease, which is involved in cellular maintenance or proliferation. Those proteases include cathepsins. Cathepsins include the serine proteases, Cathepsin A, Cathepsin G, aspartic acid proteases Cathepsin D, Cathepsin E and the cysteine proteases, Cathepsin B, Cathepsin C, Cathepsin F, Cathepsin H, Cathepsin K, Cathepsin L1, Cathepsin L2, Cathepsin O, Cathepsin S, Cathepsin W and Cathepsin Z.

"Peptide Cleavable Unit" as used herein, unless otherwise stated or implied by context, refers to an organic moiety within a secondary linker of a Ligand Drug Conjugate compound's auristatin drug linker moiety, as exemplified by a hydrophobic auristatin F drug linker moiety of Formula 1A, or an auristatin Drug Linker compound, as exemplified by a hydrophobic auristatin F Drug Linker compound of Formula IA, that provides for a recognition site for a protease and is capable of enzymatically releasing its conjugated Drug Unit (D) as a free auristatin drug, such as a hydrophobic auristatin F compound as defined herein, upon action of that protease.

A recognition site for cleavage by a protease is sometimes limited to those recognized by proteases found in abnormal cells, such as cancer cells, or within nominally normal cells targeted by the Ligand Drug Conjugate that are particular to the environment of the nearby abnormal cells. For that purpose, the peptide is typically resistant to circulating proteases in order to minimize premature release of free drug or precursor thereof that otherwise could cause off-target adverse events from systemic exposure to that drug. In some aspects, the peptide will have one or more D-amino acids or an unnatural or non-classical amino acids in order to have that resistance. In some of those aspects the sequence will comprise a dipeptide or tripeptide in which the P2' site contains a D-amino acid and the P1' site contains one of the 20 naturally-occurring L-amino acids other than L-proline.

In some aspects, the reactive site is more likely operated upon enzymatically subsequent to immunologically selective binding to the targeted antigen. In some of those aspects, the targeted antigen is on abnormal cells so that the recognition site is more likely operated upon enzymatically subsequent to cellular internalization of an Antibody Drug Conjugate compound into targeted abnormal cells. As a consequence, those abnormal cells should display the targeted antigen in higher copy number in comparison to normal cells to mitigate on-target adverse events.

In other of those aspects, the targeted antigen is on normal cells that are within and are peculiar to the environment of abnormal cells so that the recognition site is more likely operated upon enzymatically subsequent to cellular internalization of an Antibody Drug Conjugate compound into these targeted normal cells. As a consequence, those normal cells should display the targeted antigen in higher copy number in comparison to normal cells distant from the site of the cancer cells to mitigate on-target adverse events.

In some instances, protease reactivity towards the recognition site is greater within targeted cancer cells or targeted nearby normal cells in comparison to normal cells that are not present at the site or are distant from the site of the cancer cells. That greater reactivity in some aspects is due to a greater amount of intracellular protease activity within the targeted cells. However, the protease is not necessarily required to be preferentially present or found in greater abundance in targeted cells since a Conjugate compound will have poorer access to cells that do not preferentially display the targeted moiety. In some instances, the intracellular protease is a regulatory protease and typically the peptide bond of the Peptide Cleavable Unit is capable of being selective cleaved by a intracellular regulatory protease in comparison to serum proteases.

In other aspects, the protease is preferentially excreted by cancer cells or by nominally normal cells in the environment in which those cancer cells are found in comparison to normal cells in their typical environment, which typically are not under the influence of the targeted abnormal cells. Thus, in those instances where the protease is excreted, the protease is necessarily required to be preferentially present or found in greater abundance in the vicinity of cells targeted by the Conjugate in comparison to that of distant normal cells so as to reduce unwanted off-target effects. When W is a Peptide Cleavable Unit directed to a protease that is preferentially distributed extracellularly in the vicinity of targeted cancer cells due to preferential excretion by such cells or by neighboring nominally normal cells whose excretion is peculiar to the environment of the abnormal cells, that protease is usually a metalloprotease. Typically, such proteases are involved in tissue remodeling, which aids in the invasiveness of abnormal cells or their accumulation at inappropriate sites that results in further recruitment of such cells.

A secondary linker containing a Peptide Cleavable Unit typically has the formula of $-A'_{a'}-W_w-Y_y-$, wherein A' is a second optional Spacer Unit; subscript a' is 0 or 1, W is a peptide Cleavable Unit; subscript w is 1; Y is an optional Spacer Unit; and subscript y is 0 or 1, in which protease action on the peptide sequence comprising the peptide Cleavable Unit results in direct release of D when subscript y is 0 or when subscript y is 1 results in a drug-peptide fragment of formula Y-D as the precursor to free drug, in which Y typically undergoes enzymatic processing by an exo-peptidase to provide free drug.

In some aspects, Drug Linker compounds in which the secondary linker contains a peptide Cleavable Unit are represented by the structures of Formula IC:

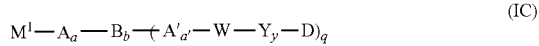

and corresponding drug linker moieties of Antibody Drug Conjugates are represented by the structures of Formula 1D or Formula 1E:

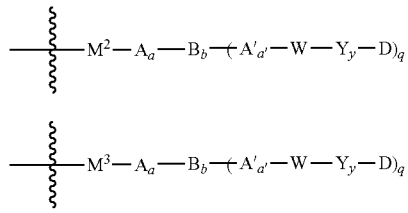

wherein W is the peptide Cleavable Unit and $M^1$-$A_a$-$B_b$— of Formula IC, -$M^2$-$A_a$-$B_b$— of Formula 1D and -$M^3$-$A_a$-$B_b$— of Formula 1E are primary linkers, wherein MI is a maleimide moiety; $M^2$ is a succinimide moiety; $M^3$ is a succinic acid amide moiety; Y is an optional Spacer Unit and the remaining variable groups are as defined for Drug Linker compounds of Formula IA and for drug linker moieties of Formula 1A. $L_{SS}'$ primary linkers of Drug Linker compounds, which contain an $M^1$ moiety, and $L_{SS}$ primary linkers of drug linker moieties in some ADCs, which contain $M^2$ moieties, of the present invention are those formulae in which A or a subunit thereof is substituted by or incorporates a Basic Unit. Other primary linkers are $L_S$ primary linkers that are derived from the above $M^2$-containing $L_{SS}$ primary linker of Formula 1C by hydrolysis of their succinimide moieties to provide $M^3$-containing moieties of Formula 1D.

In any one of the above aspects, the amide bond that is specifically cleaved by a protease produced by or within a targeted cell is to the C-terminal end of the auristatin AF or hydrophobically-modified AF Drug Unit or related structure thereof, collective referred to as an auristatin F Drug Unit. In other aspects, an internal peptide bond of a peptide sequence attached to the C-terminal end of the AF Drug Unit is specifically cleaved, which results in a secondary drug linker fragment having one or more amino acid residues attached through an amide bond to the C-terminal end of the auristatin AF Drug Unit. Subsequent exopeptidase action on that fragment then provides free drug. Thus, protease action on either type of peptide sequence in W results in release of D as free drug or its precursor Y-D, which is further processed to provide the free drug.

"Spacer Unit" as used herein, unless otherwise stated or implied by context, refers to a component in a secondary linker ($L_O$) within a Linker Unit (LU) of an Antibody Drug Conjugate or Drug Linker compound that is covalently bonded to auristatin F (AF) or a hydrophobically-modified AF Drug Unit or related structure thereof, collectively referred to as an auristatin F Drug Unit, and in some aspects when subscript a' is 1 is also covalently bonded to a second optional Stretcher Unit (A') when present in the generalized secondary linker of structure $S_1$. In those aspects, $Y_y$ is covalently bonded to W and D, wherein W is a peptide Cleavable Unit and Y attached to W is typically absent (subscript y is 0) or if present (subscript y is 1) is an amino acid residue or peptide fragment derived from the Peptide Cleavable Unit.

In one aspect, a secondary linker ($L_O$) of LU-D has the generalized formula -$A'_{a'}$-$W_{w'}$-$Y_y$—, in which subscript a' is 0 or 1, subscript w' is 1, and subscript y is 0 or 1. In those aspects, W, $Y_y$, and D are in a linear configuration with respect to each other so that W as a Peptide Cleavable Unit and the Drug Unit are covalently bonded to the Spacer Unit. In that linear configuration protease action upon W initiates release of the auristatin Drug Unit as free auristatin drug. In some aspects, the amide bond between Y and W provides the site of cleavage and in other aspects Y serve to separate the cleavage site of the Peptide Cleavable Unit from the Drug Unit to avoid steric interactions from the Drug Unit that would interfere with cleavage of W.

"PEG Unit" as used herein refers to a group comprising a polyethylene glycol moiety (PEG) having a repetition of ethylene glycol subunits having the formula of

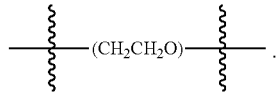

PEGs include polydisperse PEGs, monodisperse PEGs and discrete PEGs. Polydisperse PEGs are a heterogeneous mixture of sizes and molecular weights whereas monodisperse PEGs are typically purified from heterogeneous mixtures and are therefore provide a single chain length and molecular weight. Discrete PEGs are compounds that are synthesized in step-wise fashion and not via a polymerization process. Discrete PEGs provide a single molecule with defined and specified chain length.

A PEG Unit comprises at least 2 subunits, at least 3 subunits, at least 4 subunits, at least 5 subunits, least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. Some PEG Units comprise up to 72 subunit.

"PEG Capping Unit" as used herein is a nominally unreactive organic moeity or functional group that terminates the free and untethered end of a PEG Unit and in some aspects is other than hydrogen. In those aspects a PEG Capping Unit is methoxy, ethoxy, or other $C_1$-$C_6$ ether, or is —$CH_2$—$CO_2H$, or other suitable moeity. The ether, —$CH_2$—$CO_2H$, —$CH_2CH_2CO_2H$, or other suitable organic moeity thus acts as a cap for the terminal PEG subunit of the PEG Unit.

"Parallel Connector Unit" as used herein, unless otherwise stated or implied by context, refers to an organic moiety of a Drug Linker compound or a Ligand Drug Conjugate compound's drug linker moiety, which is typically present in its Linker Unit as a subunit of a first or second Stretcher Unit, wherein the Parallel Connector Unit ($L^P$) is capable of orienting the PEG Unit attached thereto in parallel orientation to a hydrophobic Drug Unit so as to reduce at least in part the hydrophobicity of that Drug Unit. In some aspects, the hydrophobicity being reduced is from a hydrophobic auristatin F free drug so as to mask at least in part the increased hydrophobicity of the corresponding Drug Unit relative to the parent auristatin F Drug Unit when needed to achieve comparable drug loadings between the hydrophobically-modified and parent auristatin LDCs. Structures of $L^P$ and associated PEG Units and PEG Capping Units are described by WO 2015/5057699, which are specifically incorporated by reference herein, and in some aspects $L^P$ is a tri-functional α-amino acid, β-amino acid or other tri-functional amine-containing acid residue.

"Intracellularly cleaved", "intracellular cleavage" and like terms used herein refer to a metabolic process or reaction within a targeted cell occurring upon a Ligand Drug Conjugate or the like, whereby covalent attachment through its Linker Unit between the auristatin Drug Unit and the Ligand Unit of the Conjugate is broken, resulting in release of D as an auristatin compound, such as release as a hydrophobic auristatin F compound, within the targeted cell.

"Hematological malignancy" as used herein, unless otherwise stated or implied by context, refers to a blood cell tumor that originates from cells of lymphoid or myeloid origin and is synonymous with the term "liquid tumor". Hematological malignancies may be categorized as indolent, moderately aggressive or highly aggressive.

"Lymphoma" as used herein, unless otherwise stated or implied by context, refers to is hematological malignancy that usually develops from hyper-proliferating cells of lymphoid origin. Lymphomas are sometimes classified into two major types: Hodgkin lymphoma (HL) and non-Hodgkin lymphoma (NHL). Lymphomas may also be classified according to the normal cell type that most resemble the cancer cells in accordance with phenotypic, molecular or cytogenic markers. Lymphoma subtypes under that classification include without limitation mature B-cell neoplasms, mature T cell and natural killer (NK) cell neoplasms, Hodgkin lymphoma and immunodeficiency-associated lymphoproliferative disorders. Lymphoma subtypes include precursor T-cell lymphoblastic lymphoma (sometimes referred to as a lymphoblastic leukemia since the T-cell lymphoblasts are produced in the bone marrow), follicular lymphoma, diffuse large B cell lymphoma, mantle cell lymphoma, B-cell chronic lymphocytic lymphoma (sometimes referred to as a leukemia due to peripheral blood involvement), MALT lymphoma, Burkitt's lymphoma, mycosis fungoides and its more aggressive variant Sézary's disease, peripheral T-cell lymphomas not otherwise specified, nodular sclerosis of Hodgkin lymphoma, and mixed-cellularity subtype of Hodgkin lymphoma.

"Leukemia" as used herein, unless otherwise stated or implied by context, refers to a hematological malignancy that usually develops from hyper-proliferating cells of myeloid origin, and include without limitation, acute lymphoblastic leukemia (ALL), acute myelogenous leukemia (AML), chronic lymphocytic leukemia (CLL), chronic myelogenous leukemia (CML) and acute monocyctic leukemia (AMoL). Other leukemias include hairy cell leukemia (HCL), T-cell lymphatic leukemia (T-PLL), large granular lymphocytic leukemia and adult T-cell leukemia.

"Hyper-proliferating cells" as used herein, unless otherwise stated or implied by context, refer to abnormal cells that are characterized by unwanted cellular proliferation or an abnormally high rate or persistent state of cell division or other cellular activity that is unrelated or uncoordinated with that of the surrounding normal tissues. In some aspects, hyper-proliferating cells are hyper-proliferating mammalian cells. In other aspects, hyper-proliferating cells are hyper-stimulated immune cells as defined herein whose persistent state of cell division or activation occurs after the cessation of the stimulus that may have initially evoked the change in their cell division. In other aspects, the hyper-proliferating cells are transformed normal cells or cancer cells and their uncontrolled and progressive state of cell proliferation may result in a tumor that is benign, potentially malignant (premalignant) or frankly malignant. Hyperproliferation conditions resulting from transformed normal cells or cancer cells include, but are not limited to, those characterized as a precancer, hyperplasia, dysplasia, adenoma, sarcoma, blastoma, carcinoma, lymphoma, leukemia or papilloma. Precancers are usually defined as lesions that exhibit histological changes and are associated with an increased risk of cancer development and sometimes have some, but not all, of the molecular and phenotypic properties that characterize the cancer. Hormone associated or hormone sensitive pre-cancers include without limitation, prostatic intraepithelial neoplasia (PIN), particularly high-grade PIN (HGPIN), atypical small acinar proliferation (ASAP), cervical dysplasia and ductal carcinoma in situ. Hyperplasias generally refers to the proliferation of cells within an organ or tissue beyond that which is ordinarily seen that may result in the gross enlargement of an organ or in the formation of a benign tumor or growth. Hyperplasias include, but are not limited to, endometrial hyperplasia (endometriosis), benign prostatic hyperplasia and ductal hyperplasia.

"Normal cells" as used herein, unless otherwise stated or implied by context, refer to cells undergoing coordinated cell division related to maintenance of cellular integrity of normal tissue or replenishment of circulating lymphatic or blood cells that is required by regulated cellular turnover, or tissue repair necessitated by injury, or to a regulated immune or inflammatory response resulting from pathogen exposure or other cellular insult, where the provoked cell division or immune response terminates on completion of the necessary maintenance, replenishment or pathogen clearance. Normal cells include normally proliferating cells, normal quiescent cells and normally activated immune cells. Normal cells include normal quiescent cells, which are noncancerous cells in their resting G₀ state and have not been stimulated by stress or a mitogen or are immune cells that are normally inactive or have not been activated by pro-inflammatory cytokine exposure.

"Abnormal cells" as used herein, unless otherwise stated or implied by context, refer to unwanted cells that are responsible for promoting or perpetuating a disease state to which a Ligand Drug Conjugate is intended to prevent or treat. Abnormal cells include hyper-proliferating cells and hyper-stimulated immune cells as these term are define elsewhere. Abnormal cells may also refer to nominally normal cells that are in the environment of other abnormal cells, but which nonetheless support the proliferation and/or survival of these other abnormal cells, such as tumor cells, so that targeting the nominally normal cells indirectly inhibits the proliferation and/or survival of the tumor cells.

"Hyper-stimulated immune cells" as used herein, unless otherwise stated or implied by context, refer to cells involved in innate or adaptive immunity characterized by an abnormally persistent proliferation or inappropriate state of stimulation that occurs after the cessation of the stimulus that may have initially evoked the change in proliferation or stimulation or that occurs in the absence of any external insult. Oftentimes, the persistent proliferation or inappropriate state of stimulation results in a chronic state of inflammation characteristic of a disease state or condition. In some instances, the stimulus that may have initially evoked the change in proliferation or stimulation is not attributable to an external insult but is internally derived, as in an autoimmune disease. In some aspects, a hyper-stimulated immune cell is a pro-inflammatory immune cell that has been hyper-activated through chronic pro-inflammatory cytokine exposure.

In some aspects of the invention, a Ligand Drug Conjugate compound of a Ligand Drug Conjugate composition binds to an antigen preferentially displayed by pro-inflammatory immune cells that are abnormally proliferating or are inappropriately or persistently activated. Those immune cells include classically activated macrophages or Type 1 T helper (Th1) cells, which produce interferon-gamma (INF-γ), interleukin-2 (IL-2), interleukin-10 (IL-10), and tumor necrosis factor-beta (TNF-β), which are cytokines that are involved in macrophage and CD8$^+$ T cell activation.

"Bioavailability" unless otherwise stated or implied by context, refers to the systemic availability (i.e., blood/plasma levels) of a given amount of a drug administered to a patient. Bioavailability is an absolute term that indicates measurement of both the time (rate) and total amount (extent) of drug that reaches the general circulation from an administered dosage form.

"Subject" unless otherwise stated or implied by context, refers to a human, non-human primate or mammal having a hyper-proliferation, inflammatory or immune disorder or other disorder attributable to abnormal cells or is prone to such a disorder who would benefit from administering an effective amount of a Ligand Drug Conjugate. Non-limiting examples of a subject include human, rat, mouse, guinea pig, monkey, pig, goat, cow, horse, dog, cat, bird and fowl. Typically, the subject is a human, non-human primate, rat, mouse or dog.

"Carrier" unless otherwise stated or implied by context refers to a diluent, adjuvant or excipient, with which a compound is administered. Such pharmaceutical carriers can be liquids, such as water and oils, including those of petroleum, animal, vegetable or synthetic origin, such as peanut oil, soybean oil, mineral oil, sesame oil. The carriers can be saline, gum acacia, gelatin, starch paste, talc, keratin, colloidal silica, urea. In addition, auxiliary, stabilizing, thickening, lubricating and coloring agents can be used. In one embodiment, when administered to a subject, the compound or compositions and pharmaceutically acceptable carriers are sterile. Water is an exemplary carrier when the compounds are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. The present compositions, if desired, can also contain minor amounts of wetting or emulsifying agents, or pH buffering agents.

"Salt form" as used herein, unless otherwise indicated by context, refers to a charged compound in ionic association with a countercation(s) and/or counteranions so as to form an overall neutral species. In some aspects, a salt form of a compound occurs through interaction of the parent compound's basic or acid functional group with an external acid or base, respectively. In other aspects the charged atom of the compound that is associated with a counteranion is permanent in the sense that spontaneous disassociation to a neural species cannot occur without altering the structural integrity of the parent compound as when a nitrogen atom is quaternized. Accordingly, a salt form of a compound may involve a quaternized nitrogen atom within that compound and/or a protonated form of a basic functional group and/or ionized carboxylic acid of that compound each of which is in ionic association with a counteranion. In some aspects a salt form may result from interaction of a basic functional group and an ionized acid functional group within the same compound or involve inclusion of a negatively charged molecule such as an acetate ion, a succinate ion or other counteranion. Thus, a compound in salt form may have more than one charged atom in its structure. In instances where multiple charged atoms of the parent compound are part of the salt form, that salt from can have multiple counter ions so that a salt form of a compound may have one or more charged atoms and/or one or more counterions. The counterion may be any charged organic or inorganic moiety that stabilizes an opposite charge on the parent compound.

A protonated salt form of a compound is typically obtained when a basic functional group of a compound, such as a primary, secondary or tertiary amine or other basic amine functional group interacts with an organic or inorganic acid of suitable pKa for protonation of the basic functional group, or when an acid functional group of a compound with a suitable $pK_a$, such as a carboxylic acid, interacts with a hydroxide salt, such as NaOH or KOH, or an organic base of suitable strength, such as triethylamine, for deprotonation of the acid functional group. In some aspects, a compound in salt form contains at least one basic amine functional group, and accordingly acid addition salts can be formed with this amine group, which includes the basic amine functional group of a cyclic or acyclic Basic Unit. A suitable salt form in the context of a Drug Linker compound is one that does not unduly interfere with the condensation reaction between a targeting agent and the Drug Linker compound that provides a Ligand drug Conjugate.

"Pharmaceutically acceptable salt" as used herein, unless otherwise indicated by context, refers to a salt form of a compound in which its counterion is acceptable for administration of the salt form to an intended subject and include inorganic and organic countercations and counteranions. Exemplary pharmaceutically acceptable counteranions for basic amine functional groups, such as those in cyclic or acyclic Basic Units, include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, mesylate, besylate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

Typically, a pharmaceutically acceptable salt is selected from those described in P. H. Stahl and C. G. Wermuth, editors, *Handbook of Pharmaceutical Salts: Properties, Selection and Use*, Weinheim/Zirich:Wiley-VCH/VHCA, 2002. Salt selection is dependent on properties the drug product must exhibit, including adequate aqueous solubility at various pH values, depending upon the intended route(s) of administration, crystallinity with flow characteristics and low hygroscopicity (i.e., water absorption versus relative humidity) suitable for handling and required shelf life by determining chemical and solid-state stability as when in a lyophilized formulation under accelerated conditions (i.e., for determining degradation or solid-state changes when stored at 40° C. and 75% relative humidity).

"Inhibit", "inhibition of" and like terms, unless otherwise stated or implied by context, means to reduce by a measurable amount, or to prevent entirely an undesired activity or outcome. In some aspects, the undesired outcome or activity is related to abnormal cells and includes hyper-proliferation, or hyper-stimulation or other dysregulated cellular activity underlying a disease state. Inhibition of such a dysregulated cellular activity by a Ligand Drug Conjugate is typically determined relative to untreated cells (sham treated with vehicle) in a suitable test system as in cell culture (in vitro) or in a xenograft model (in vivo). Typically, a Ligand Drug Conjugate that targets an antigen that is not present or has low copy number on the abnormal cells of interest or is genetically engineered to not recognize any known antigen is used as a negative control.

"Treat", "treatment," and like terms, unless otherwise indicated by context, refer to a therapeutic treatment, including prophylactic measures to prevent relapse, wherein the object is to inhibit or slow down (lessen) an undesired physiological change or disorder, such as the development or spread of cancer or tissue damage from chronic inflammation. Typically, beneficial or desired clinical benefits of such therapeutic treatments include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival or quality of life as compared to expected survival or quality of life if not receiving treatment. Those in need of treatment include those already having the condition or disorder as well as those prone to have the condition or disorder.

In the context of cancer, the term "treating" includes any or all of inhibiting growth of tumor cells, cancer cells, or of a tumor; inhibiting replication of tumor cells or cancer cells, inhibiting dissemination of tumor cells or cancer cell, lessening of overall tumor burden or decreasing the number of cancerous cells, or ameliorating one or more symptoms associated with cancer.

"Therapeutically effective amount" as the term is used herein, unless otherwise stated or implied by context, refers to an amount of free drug or Ligand Drug Conjugate having a Drug Unit, which is released as a free drug, effective to treat a disease or disorder in a mammal. In the case of cancer, the therapeutically effective amount of the free drug or Ligand Drug Conjugate may reduce the number of cancer cells; reduce the tumor size, inhibit (i.e., slow to some extent and preferably stop) cancer cell infiltration into peripheral organs, inhibit (i.e., slow to some extent and preferably stop) tumor metastasis, inhibit, to some extent, tumor growth, and/or relieve to some extent one or more of the symptoms associated with the cancer. To the extent the free drug or Ligand Drug Conjugate may inhibit growth and/or kill existing cancer cells, it may be cytostatic or cytotoxic. For cancer therapy, efficacy can, for example, be measured by assessing the time to disease progression (TTP) determining the response rate (RR) and/or overall survival (OS).

In the case of immune disorders resulting from hyper-stimulated immune cells, a therapeutically effective amount of the drug may reduce the number of hyper-stimulated immune cells, the extent of their stimulation and/or infiltration into otherwise normal tissue and/or relieve to some extent one or more of the symptoms associated with a dysregulated immune system due to hyper-stimulated immune cells. For immune disorders due to hyper-stimulated immune cells, efficacy can, for example, be measured by assessing one or more inflammatory surrogates, including one or more cytokines levels such as those for IL-1$\beta$, TNF$\alpha$, INF$\gamma$ and MCP-1, or numbers of classically activated macrophages.

In some aspects of the invention, a Ligand Drug Conjugate compound associates with an antigen on the surface of a targeted cell (i.e., an abnormal cell such as a hyper-proliferating cell or a hyper-stimulated immune cell), and the Conjugate compound is then taken up inside the targeted cell through receptor-mediated endocytosis. Once inside the cell, one or more Cleavage Units within a Linker Unit of the Conjugate are cleaved, resulting in release of Drug Unit (D) as free drug. The free drug so released is then able to migrate within the cytosol and induce cytotoxic or cytostatic activities, or in the case of hyper-stimulated immune cells may alternatively inhibit pro-inflammatory signal transduction. In another aspect of the invention, the Drug Unit (D) is released from a Ligand Drug Conjugate compound outside the targeted cell but within the vicinity of the targeted cell so that the resulting free drug from that release is localized to the desired site of action and is able to subsequently penetrate the cell rather than being prematurely released at distal sites.

2. Embodiments

A number of embodiments of the invention are described below followed by a more detailed discussion of the components, e.g., groups, reagents, and steps that are useful in the processes of the present invention. Any of the selected embodiments for the components of the processes can apply to each and every aspect of the invention as described herein or they may relate to a single aspect. The selected embodiments may be combined together in any combination appropriate for describing an auristatin Ligand Drug Conjugate, Drug Linker compound or Intermediate thereof having a hydrophobic auristatin F Drug Unit.

2.1 Hydrophobic Auristatin Drug Units

A hydrophobic auristatin Drug Unit relates to a hydrophobically-modified auristatin F or auristatin F-type compound in conjugated form in which the hydrophobicity of the parent compound has been increased so as to exhibit dual MDR$^+$ and bystander activities when released as free drug. Ligand Drug Conjugates having such Drug Units combines bystander cytotoxicity observed for auristatin E (AE) and monomethyl auristatin E (MMAE) Conjugates and MDR$^+$ cytotoxicity of auristatin F (AF) and monomethyl auristatin F (MMAF). Conjugation is through the C-terminal component of the hydrophobic AF compound, in particular through that component's carboxylic acid functional group such that release of the Drug Unit from a Drug Linker compound or a drug linker moiety of a Ligand Drug Conjugate compound obtained from that conjugation provides free drug in which the carboxylic acid functional group has been restored. The required increase in hydrophobicity is achieved is some embodiments by replacing one or more substituents of AF with independently selected non-aromatic substituents of greater hydrophobicity, particularly by replacing one or both of the N-terminus methyl substituents and/or by replacement of the N-methyl substituent of the Dil residue. In other embodiments the replacement(s) are effected with an AF-type compound in which the C-terminal component is replaced with another acid-containing amine residue and/or by replacing the internal valine residue with an $\alpha$-amino acid residue having a different hydrophobic, non-aromatic $\alpha$-carbon side chain.

In any one of those embodiments, the replacement(s) provide a hydrophobic AF compound having a cLogP value of between about 4.4 and 7.2, calculated according to a method that provides a cLogP value for the parent AF compound of about 4.1 and cLogP values for monomethyl auristatin F (MMAF) and monomethyl auristatin E (MMAE) of about 3.7 and about 3.5, respectively. In a preferred embodiment, the method of Viswanadhan, V. N. et al. *J. Chem. Inf. Comput.* (1989) 29: 163-172 is used in calculations of the cLogP values. Those and other cLogP values for specific hydrophobic AF compounds described herein in neutral form are provided by Table 1.

TABLE 1
Calculated Log P values for auristatin free drugs
| Compd No. | Auristatin compound | cLogP | cLogD (at PI) | Example |
|---|---|---|---|---|
| 1 | Auristatin F | 4.09 | 1.36 | |
| 2 | Monomethyl auristatin F | 3.71 | 1.23 | |
| 3 | Monomethyl auristatin E | 3.51 | NA | |
| 4 | 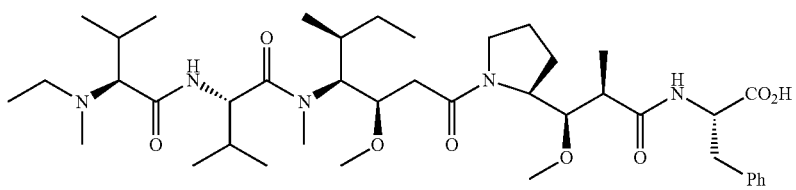 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CC)C(C)C] | 4.45 | 1.72 | 6 |
| 5 | 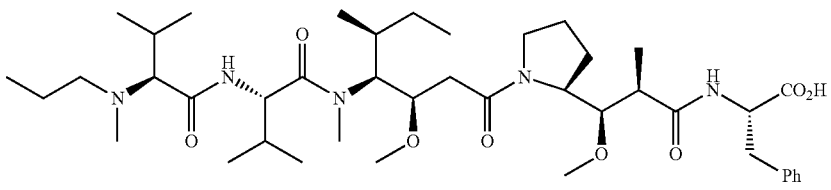 [SMILES: CCCN(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C] | 4.97 | 2.24 | 7 |
| 6 | 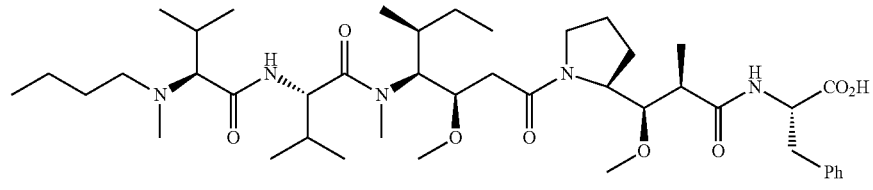 [SMILES: CCCCN(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C] | 5.41 | 2.68 | 8 |
| 7 | 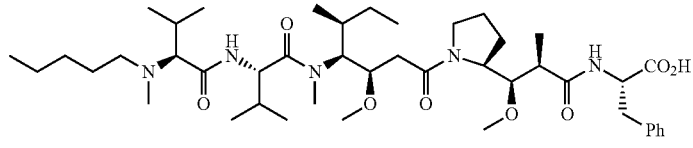 [SMILES: CCCCCN(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C] | 5.86 | 3.13 | 9 |
| 8 | 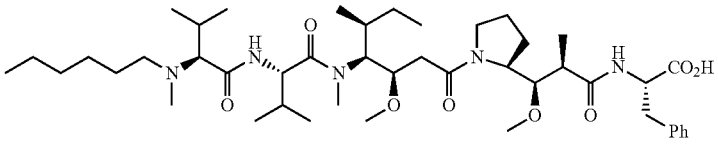 [SMILES: CCCCCCN(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C] | 6.3 | 3.57 | 10 |
| 9 | 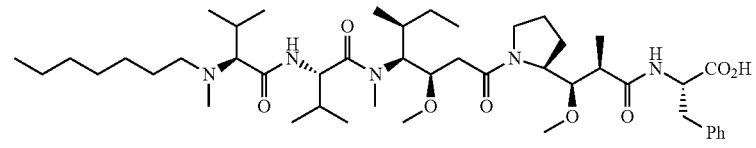 [SMILES: CCCCCCCN(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C] | 6.75 | 4.02 | 11 |
| 10 | 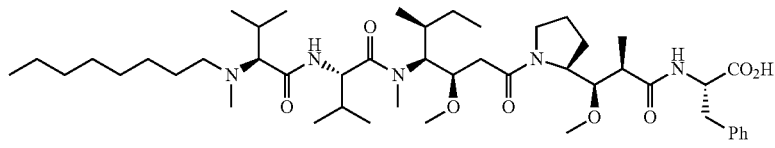 [SMILES: CCCCCCCCN(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C] | 7.19 | 4.46 | 12 |
| 11 | 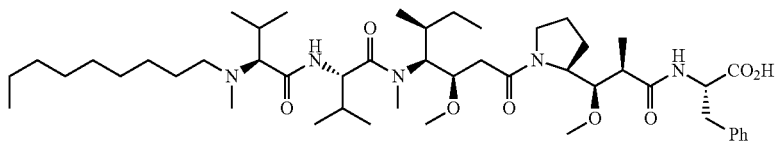 [SMILES: CCCCCCCCCN(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C] | 7.64 | 4.9 | 13 |

TABLE 1-continued
Calculated Log P values for auristatin free drugs
| Compd No. | Auristatin compound | cLogP | cLogD (at PI) | Example |
|---|---|---|---|---|
| 12 | 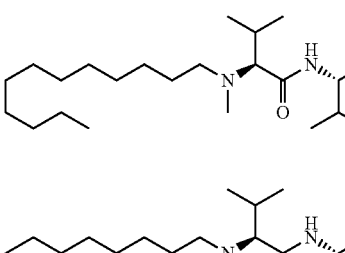 | 8.08 | 5.35 | 14 |
| 13 | | 8.52 | 5.79 | 15 |
| 14 | | 8.97 | 6.24 | 16 |
| 15 | | 10.3 | 7.57 | 17 |
| 16 | 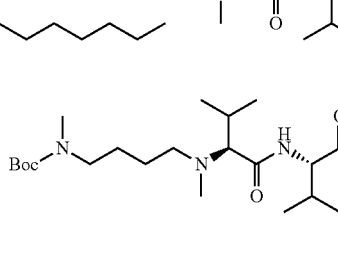 | 5.58 | 2.86 | 25 |
| 17 | 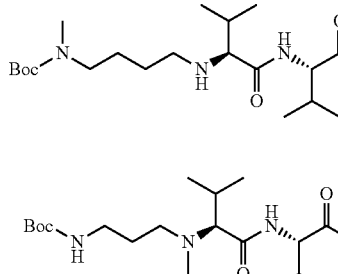 | 5.2 | 2.73 | 26 |
| 18 | 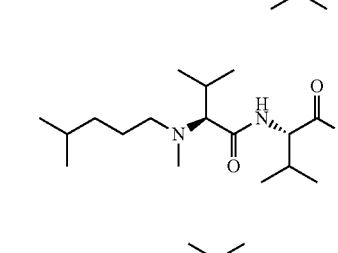 | 4.84 | 2.12 | 23 |
| 19 | 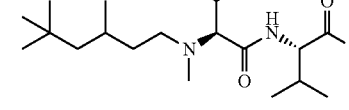 | 6.14 | 3.41 | 18 |
| 20 |  | 7.18 | 4.44 | 22 |

TABLE 1-continued

Calculated Log P values for auristatin free drugs

| Compd No. | Auristatin compound | cLogP | cLogD (at PI) | Example |
|---|---|---|---|---|
| 21 | | 5.7 | 2.97 | 19 |
| 22 | | 4.8 | 2.07 | 20 |
| 23 | | 5.85 | 3.12 | 21 |
| 24 | | 5.01 | 2.3 | 27 |
| 25 | | 5.07 | 2.34 | 28 |
| 26 | | 6.04 | 4.4 | 29 |
| 27 | | 5.71 | 2.98 | 30 |

In preferred embodiments, the desired hydrophobicity increase is obtained by replacing one or more N-methyl substituents in the N-terminal component of AF with an independently selected non-aromatic substituents so that the resulting hydrophobic AF compound has the Formula H-AF structure of:

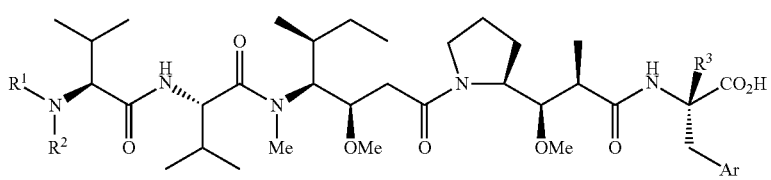

(H-AF)

or a salt thereof, in particular, a pharmaceutically acceptable salt, wherein Ar is phenyl, thienyl, 1-napthyl, 2-napthyl or benzo[b]thiophen-3-yl, optionally substituted;

$R^2$ is $C_1$-$C_2$ alkyl;

$R^3$ is hydrogen or $C_1$-$C_2$ alkyl; and $R^1$ is $C_1$-$C_9$ alkyl, which is inclusive of saturated $C_1$-$C_9$ alkyl and unsaturated $C_3$-$C_9$ alkyl, optionally substituted by a $C_3$-$C_6$ carbocyclyl to provide a carbocyclyl-alkyl- of up to 9 total carbon atoms, or $R^1$ is ($C_2$-$C_6$ alkyl)-X—$R^4$, wherein X is and amide or carbamate functional group and $R^4$ is $C_1$-$C_6$ alkyl, wherein the parent AF compound has the structure of the above formula in which $R^1$ and $R^2$ are methyl, $R^3$ is hydrogen and Ar is phenyl, with the proviso that the total number of carbon atoms in the carbocyclyl (if and) and alkyl(ene) moieties of $R^1$, $R^2$ and $R^3$ is between 3 and 10 and $R^1$, $R^2$ and $R^3$ are not methyl.

In other preferred embodiments, a hydrophobic AF compound has Formula H-AF or a salt thereof, in particular, a pharmaceutically acceptable salt, wherein Ar is phenyl, $R^3$ is hydrogen and $R^1$ is a first non-aromatic hydrophobic moiety; and $R^2$ is a second non-aromatic hydrophobic moiety, wherein $R^1$ and $R^2$ provide the hydrophobic auristatin F compound of Formula H-AF characterized by an clogP of between about 4.4 to about 7.2.

In other preferred embodiments, the desired hydrophobicity increase is obtained by replacing the N-methyl substituent of the Dil amino acid residue of AF with variable group $R^5$ wherein $R^5$ is a $C_2$-$C_6$ alkyl or has the formula of ($C_2$-$C_6$ alkylene)-X'—$R^6$, wherein X' is an independently selected amide or carbamate functional group and $R^6$ is $C_1$-$C_6$ alkyl, with the proviso that the total number of carbon atoms in the alkyl moieties of $R^1$, $R^2$, $R^3$ and $R^5$ is between 3 and 10. Representative $R^5$ substituents are —CH$_2$CH$_2$CH$_3$, —CH$_2$CH$_2$CH$_2$CH(CH$_3$)$_2$, —CH$_2$CH$_2$NH(C=O)—O-t-Bu and —CH$_2$CH$_2$NH(C=O)—CH(CH$_3$)$_2$.

In other preferred embodiments, a hydrophobic AF compound has the structure of Formula H-AF in which the internal valine residue is replaced by an L-α-amino acid residue having a different hydrophobic, non-aromatic α-carbon side chain. Representative internal valine residue replacements have the following structures:

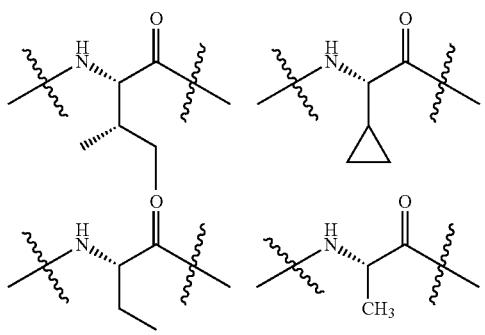

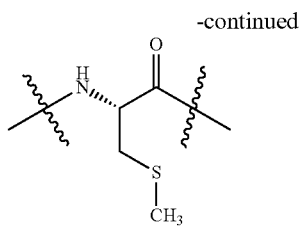

In still other preferred embodiments, a hydrophobic AF compound has the structure of Formula H-AF in which the C-terminal component is replaced by another acid-containing amine residue. Representative C-terminal component replacements have the structure of:

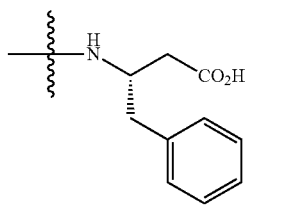

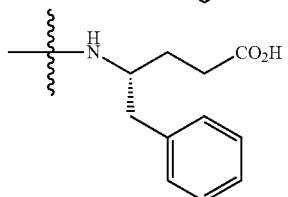

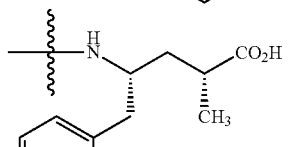

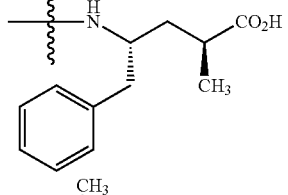

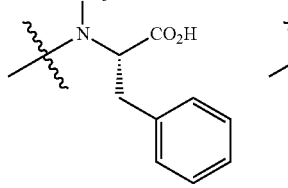

-continued

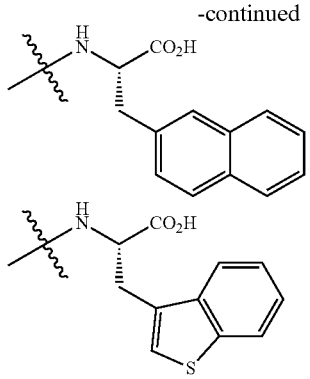

or salts thereof, in particular pharmaceutically acceptable salts.

In more preferred embodiments $R^2$ is methyl and $R^3$ is hydrogen, or $R^3$ is hydrogen and Ar is phenyl, or $R^2$ is methyl and Ar is phenyl, or $R^2$ is methyl; $R^3$ is hydrogen; and Ar is phenyl.

In any one of the above embodiments more preferred are those in which $R^1$ is optionally branched $C_4$-$C_9$ alkyl, or has the formula of —(CH$_2$)$_{3-5}$—N(R$^7$)—C(=O)—R$^4$ or —(CH$_2$)$_{3-5}$—N(R$^7$)—C(=O)—OR$^4$, wherein $R^4$ is $C_1$-$C_4$ alkyl and $R^7$ is hydrogen or unbranched $C_1$-$C_3$ alkyl, or $R^1$ is a branched $C_4$-$C_9$ alkyl or has the formula of —(CH$_2$)$_{3-5}$—N(R$^7$)—C(=O)—R$^4$ or —(CH$_2$)$_{3-5}$—N(R$^7$)—C(=O)—OR$^4$, wherein $R^4$ is t-butyl or —CH$_2$C=CH$_2$; and $R^7$ is hydrogen or methyl; and $R^2$ is methyl.

In particularly preferred embodiments, $R^2$ is methyl; $R^3$ is hydrogen; Ar is phenyl; and $R^1$ is —(CH$_2$)$_{3-5}$—N(CH$_3$)—C(=O)—O-t-Bu, —(CH$_2$)$_3$—NH—C(=O)—O-t-Bu, —CH$_2$CH$_2$CH$_2$NH—C(=O)-t-Bu or $R^1$ is —CH$_2$CH$_2$CH$_2$CH$_3$, or —CH$_2$CH$_2$CH$_2$CH$_2$CH$_3$, or $R^1$ has the structure of:

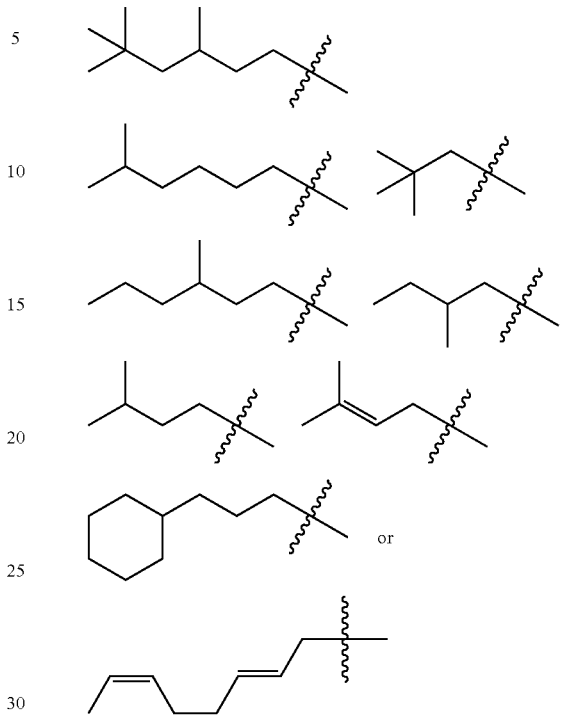

In more particularly preferred embodiments, the hydrophobic AF compound has the structure of one of compounds 1-10:

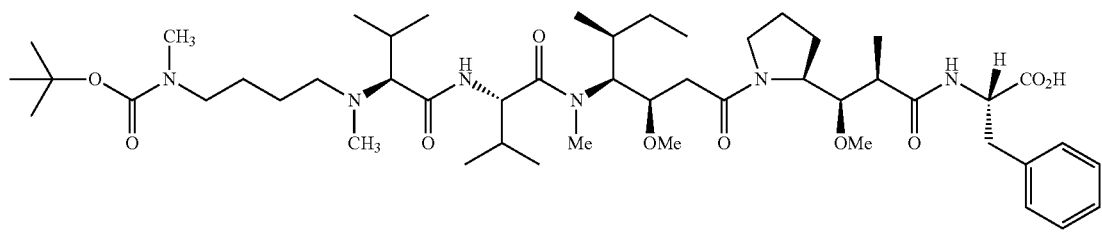

(1)

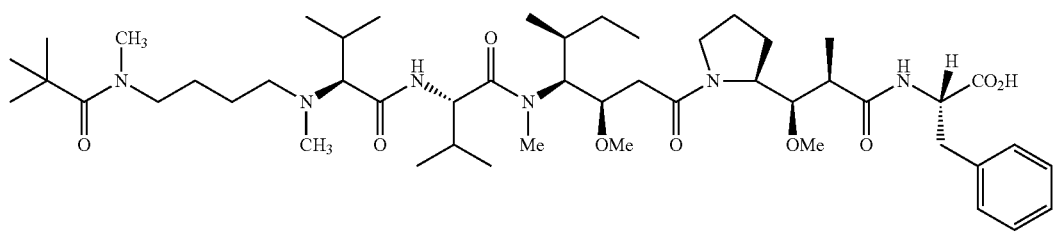

(2)

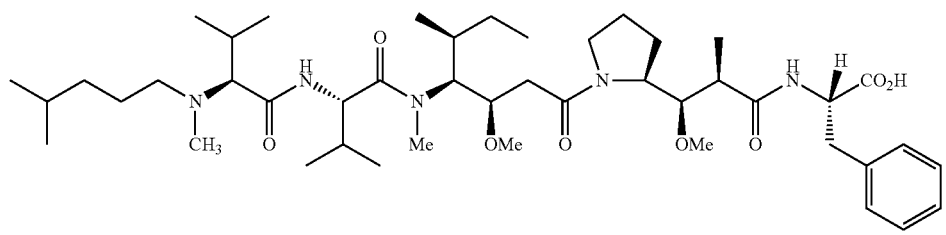

(3)

(4)
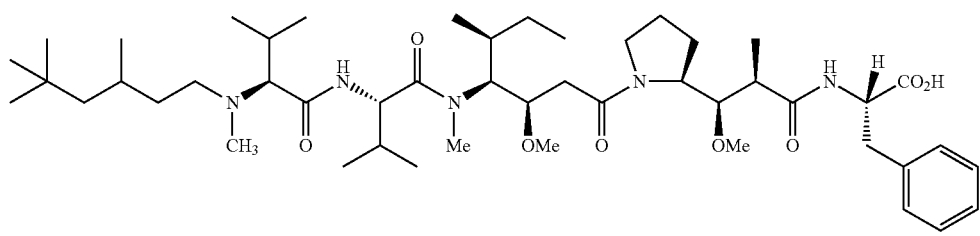
(5)
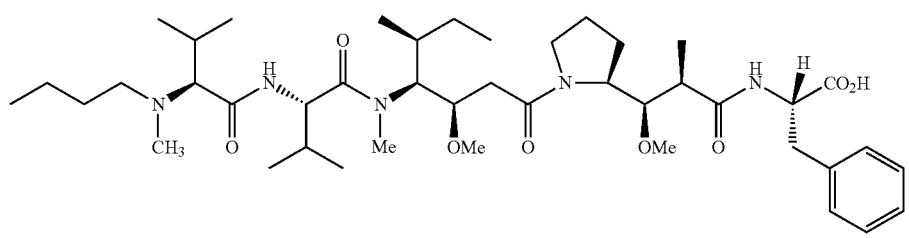
(6)
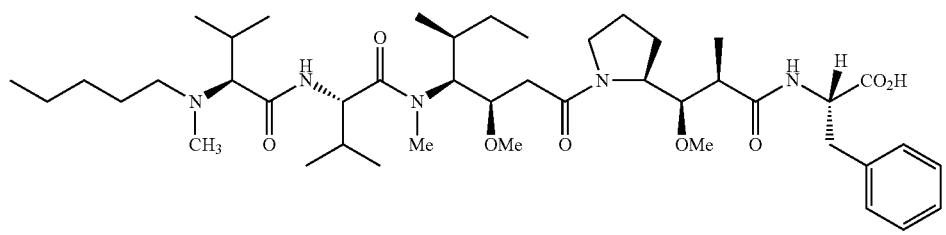
(7)
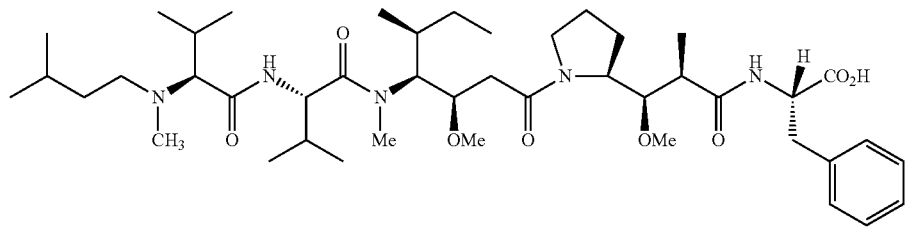
(8)
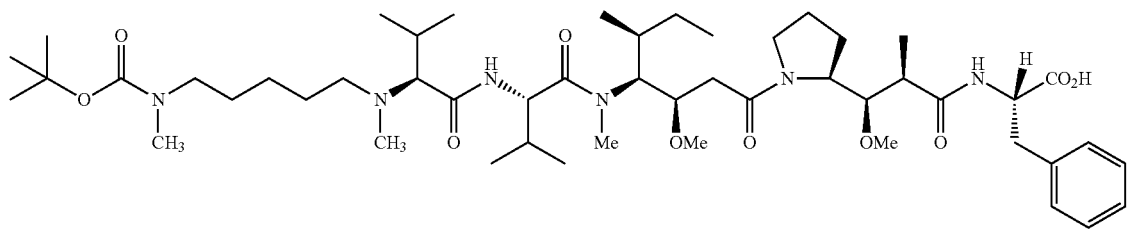
(9)
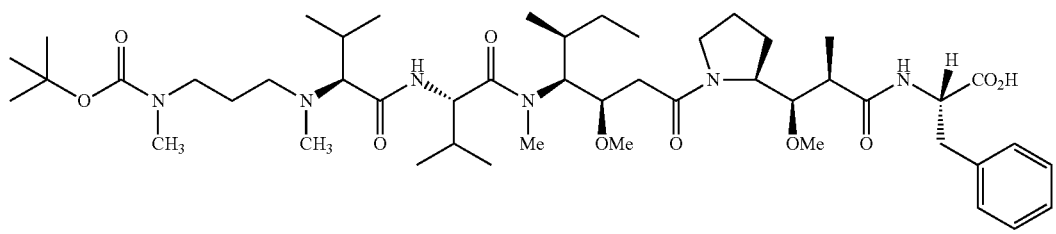

-continued

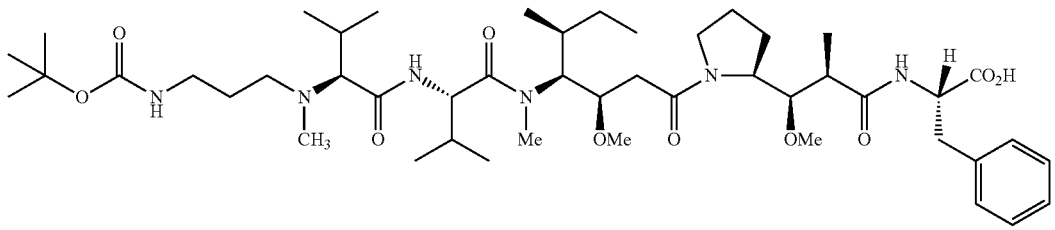

(10)

or a salt thereof, in particular a pharmaceutically acceptable salt.

In especially preferred embodiments, the hydrophobic AF compound has the structure of one of compounds 1-4.

2.2 Auristatin Ligand Drug Conjugates

An auristatin Ligand Drug Conjugate (AF LDC) is a composition or compound thereof having an auristatin Drug Unit connected to a Ligand Unit through an intervening Linker Unit (LU). Auristatin Ligand Drug Conjugates, including auristatin F (AF) and hydrophobic AF Drug Units in general are represented by Formula 1:

L-[LU-(D')]$_p$  (1)

or a salt thereof, in particular a pharmaceutically acceptable salt thereof, wherein L is a Ligand Unit; LU is a Linker Unit; and subscript p is a number ranging from 1 to 24, D' represents from 1 to 4 auristatin Drug Units, incorporating or corresponding to the same auristatin free drug for each drug linker moiety of formula -LU-D', wherein the Ligand Unit is capable of specific and selective binding to a targeted moiety for subsequent release of free auristatin drug, wherein each auristatin drug linker moeity, in an Ligand Drug Conjugate compound of the composition has the structure of Formula 1A:

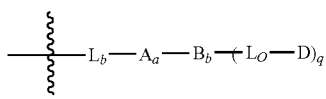

(1A)

or a salt thereof, in particular a pharmaceutically acceptable salt thereof, wherein the wavy line indicates covalent attachment to L; L$_B$ is a Ligand covalent binding moiety; A is a first optional Stretcher Unit; subscript a is 0 or 1 indicating the absence of presence of A, respectively; B is an optional Branching Unit; subscript b is 0 or 1, indicating the absence of presence of B, respectively; L$_O$ is an optional secondary linker moiety; D is a hydrophobic AF Drug Unit; and subscript q is an integer ranging from 1 to 4, wherein the LDC compound has the structure of Formula 1 in which subscript p is replaced by subscript p', wherein subscript p' is an integer ranging from 1 to 24.

In a principle embodiment of the invention, D is a hydrophobic auristatin F Drug Unit and the targeting Ligand Unit (L) is capable of selective binding to a targeted moiety for subsequent release of D as a free hydrophobic auristatin F drug of Formula H-AF, wherein the targeted moiety is preferably capable of internalization of a bound hydrophobic auristatin F Ligand drug Conjugate compound into an abnormal cell upon said binding to initiate intracellular release of the free drug upon said internalization. In those embodiments D' of Formula 1 represents 1 to 4 hydrophobic AF Drug Units and D of Formula 1A is a single hydrophobic AF Drug Unit incorporating or corresponding to the Formula H-AF free drug.

A -L$_b$-A$_a$-B$_b$— moiety of a drug linker moiety of Formula 1A in general represents the primary linker (L$_R$) of the Linker Unit (LU) of Formula 1 and L$_O$ is the optional secondary linker of LU that when present has the formula of:

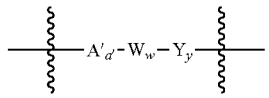

wherein the wavy line adjacent to A' indicates the site of covalent attachment to the primary linker; the wavy line adjacent to Y indicates the site of covalent attachment to the auristatin Drug Unit; A' is a second optional Spacer Unit, subscript a' is 0 or 1, indicating the absence or presence of A', respectively, W is a Cleavable Unit, and subscript w is 0 or 1, indicating the absence or presence of A'; Y is a Spacer Unit, and subscript y is 0 or 1, indicating the absence or presence of a Spacer Unit, respectively.

For AF, AF-type compounds and hydrophobically-modified AF free drugs of Formula H-AF related thereto, collectively referred to as auristatin F free drugs, the corresponding LDCs have conjugation of the auristatin F Drug Units through their C-terminal component, in particular through the carboxylic acid functional group of that component. In some of those embodiments, W is a Peptide Cleavable Unit that provides for a recognition site for a protease and is directly attached to the auristatin F Drug Unit so that subscript w is 1 and subscript y is 0. In other of those embodiments, the peptide sequence, of which the Peptide Cleavable Unit is comprised, has additional amino acid residues that provide for a Spacer Unit so that subscript w is 1 and subscript y is 1. In those embodiments W, Y and D are arranged in a linear configuration, as represented by —W—Y$_y$-D, in which W is the Peptide Cleavable Unit, Y is an optional Spacer Unit with subscript y is 0 or 1 indicating its absence or presence, respectively and D is the auristatin F Drug Unit, which in a principle embodiment of the invention is a hydrophobic AF Drug Unit. When subscript y is 1, cleavage by the protease provides a secondary drug linker fragment of formula Y-D and is followed by enzymatic action of a exopeptidase to remove remaining amino acid residue(s) contributed by the Spacer Unit (Y) so as to complete the release of the auristatin F free drug, which in principle embodiments has the structure of Formula H-AF. In some of those embodiments the sequence of amino acids providing the protease recognition sequence and the amino acid residues contributed by the Spacer Unit that remain after endopeptidase cleavage of the recognition sequence are contained within a single peptide sequence.

In other embodiments, subscript a' is 1, subscript w is 1 and subscript y is 0 and a second optional Spacer Unit A' or subunit thereof the provides part of the protease recognition site in the Peptide Cleavable Unit (W). In that aspect, an optional secondary linker ($L_O$) is present as when the recognition site is within the peptide sequence of W. In other aspects in which $L_O$ is present, subscript a' is 0, subscript w is 1 and subscript y is 0 and a subunit of a first optional Spacer Unit provides part of the protease recognition site in the peptide Cleavable Unit. In still other embodiments in which subscript a' is 0 and subscript y is 0, an amide bond between the primary linker and the C-terminally conjugated AF Drug Unit provides the recognition site so that no discreet peptide Cleavable Unit is present since A also serves as the Peptide Cleavable Unit. Although a protease cleavage site is present, in that embodiment subscript w is 0, so $L_O$ is an optional secondary linker that is not present.

In embodiments in which a secondary linker is present, a drug linker moiety of Formula 1A will have the structure represented by Formula 1B:

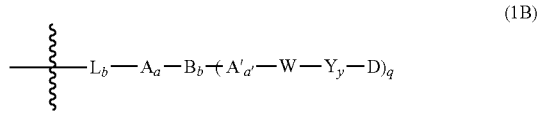

(1B)

wherein $L_B$ is a ligand covalent binding moiety as defined herein for a primary linker ($L_R$) in the Linker Unit (LU) of a drug linker moiety or Drug Linker compound; A and B are a first optional Stretcher Unit and an optional Branching Unit, respectively, of $L_R$; subscript q ranges from 1 to 4; and the remaining variable groups are as defined herein for $L_O$. Those and other components of auristatin F Ligand Drug Conjugates, which includes the parent auristatin F and hydrophobic auristatin F Ligand Drug Conjugates, are further discussed as follows.

2.2.1 Ligand Unit

A Ligand Unit (L) of an auristatin F Ligand Drug Conjugate is the targeting moiety of the Conjugate that specifically binds to a targeted moiety. The Ligand Unit can specifically bind to a cell component (a Cell Binding Agent), which serves as the targeted moiety, or to other target molecules of interest. The Ligand Unit acts to target and present the auristatin F Drug Unit of the Ligand Drug Conjugate to the particular target cell population with which the Ligand Unit interacts in order to selectively release D as a NAMPTi compound or derivative thereof. Targeting agents that provide for Ligand Units include, but are not limited to, proteins, polypeptides and peptides. Exemplary Ligand Units include, but are not limited to, those provided by proteins, polypeptides and peptides such as antibodies, e.g., full-length antibodies and antigen binding fragments thereof, interferons, lymphokines, hormones, growth factors and colony-stimulating factors. Other suitable Ligand Units are those from vitamins, nutrient-transport molecules, or any other cell binding molecule or substance. In some embodiments a Ligand Unit is from non-antibody protein targeting agent. In other embodiments, a Ligand Unit is from protein targeting agent such as an antibody. Preferred targeting agents are larger molecular weight proteins, e.g., Cell Binding Agents having a molecular weight of at least about 80 Kd.

A targeting agent reacts with a ligand covalent binding precursor ($L_b$') moiety of a primary linker precursor ($L_R$') of a Drug Linker compound to form a Ligand Unit covalently attached to a ligand covalent binding ($L_b$) moeity of a primary linker ($L_R$) of a drug-linker moiety of Formula 1A. The targeting agent has or is modified to have to have the appropriate number of attachment sites to accommodate the requisite number of drug-linker moieties, defined by subscript p, whether they be naturally occurring or non-naturally occurring (e.g., engineered). For example, in order for the value of subscript p to be from 6 to 14, a targeting agent has to be capable of forming a bond to 6 to 14 drug-linker moieties. The attachment sites can be naturally-occurring or engineered into the targeting agent. A targeting agent can form a bond to the $L_{SS}$ moiety of the Linker Unit of a Drug Linker compound via a reactive or activateable heteroatom or a heteroatom-containing functional group of the targeting agent. Reactive or activateable heteroatoms or a heteroatom-containing functional groups that may be present on a targeting agent include sulfur (in one embodiment, from a thiol functional group of an targeting agent), C=O or (in one embodiment, from a carbonyl, carboxyl or hydroxyl group of a targeting agent) and nitrogen (in one embodiment, from a primary or secondary amino group of a targeting agent). Those heteroatoms can be present on the targeting agent in the targeting agent's natural state, for example a naturally-occurring antibody, or can be introduced into the targeting agent via chemical modification or genetic engineering.

In one embodiment, a targeting agent has a thiol functional group and the Ligand Unit therefrom is attached to a drug linker moiety of a Ligand Drug Conjugate compound via the thiol functional group's sulfur atom.

In another embodiment, the targeting agent has lysine residues that can react with an activated ester, including but are not limited to, N-hydroxysuccinimide, pentafluorophenyl, and p-nitrophenyl esters), of $L_R$ of the Linker Unit of a Drug Linker compound and thus results in an amide bond between the nitrogen atom from the Ligand Unit and the C=O functional group from the Linker Unit of the Drug Linker compound.

In yet another embodiment, the targeting agent has one or more lysine residues that can be chemically modified to introduce one or more thiol functional groups. The Ligand Unit from that targeting agent is attached to the Linker Unit via the introduced thiol functional group's sulfur atom. The reagents that can be used to modify lysines include, but are not limited to, N-succinimidyl S-acetylthioacetate (SATA) and 2-Iminothiolane hydrochloride (Traut's Reagent).

In another embodiment, the targeting agent can have one or more carbohydrate groups that can be chemically modified to have one or more thiol functional groups. The Ligand Unit from that targeting agent is attached to the Linker Unit via the introduced thiol functional group's sulfur atom, or the targeting agent can have one or more carbohydrate groups that can be oxidized to provide an aldehyde (—CHO) group (see, e.g., Laguzza, et al., 1989, *J. Med. Chem.* 32(3):548-55). The corresponding aldehyde can then react with a $L_{SS}$ moiety of a Drug Linker compound having nucleophillic nitrogen. Other reactive sites on $L_R$ that can react with a carbonyl group on a targeting agent include, but are not limited to, hydrazine and hydroxylamine. Other protocols for the modification of proteins for the attachment of drug linker moieties are described in Coligan et al., *Current Protocols in Protein Science*, vol. 2, John Wiley & Sons (2002) (incorporated herein by reference).

In preferred embodiments, the reactive group of $L_R$ of a Drug Linker compound is a maleimide ($M^1$) moiety and covalent attachment of L to $L_R$ is accomplished through a thiol functional group of a targeting agent so that a thio-substituted succinimide ($M^2$) moiety is formed through Michael addition. The thiol functional group can be present on the targeting agent in the targeting agent's natural state, for example a naturally-occurring residue, or can be introduced into the targeting agent via chemical modification and/or genetic engineering.

It has been observed for bioconjugates that the site of drug conjugation can affect a number of parameters including ease of conjugation, drug-linker stability, effects on biophysical properties of the resulting bioconjugates, and in-vitro cytotoxicity. With respect to drug-linker stability, the site of conjugation of a drug-linker to a ligand can affect the ability of the conjugated drug-linker moiety to undergo an elimination reaction and for the drug linker moiety to be transferred from the Ligand Unit of a bioconjugate to an alternative reactive thiol present in the milieu of the bio-conjugate, such as, for example, a reactive thiol in albumin, free cysteine, or glutathione when in plasma. Such sites include, for example, the interchain disulfides as well as select cysteine engineered sites. The Ligand-Drug Conjugates described herein can be conjugated to thiol residues at sites that are less susceptible to the elimination reaction (e.g., positions 239 according to the EU index as set forth in Kabat) in addition to other sites.

In preferred embodiments, the Ligand Unit (L) is of an antibody or antigen-binding fragment thereof, thereby defining an antibody Ligand Unit of an Antibody Drug Conjugate (ADC), wherein the antibody Ligand Unit is capable of selective binding to a targeted antigen of a cancer cell for subsequent release of free hydrophobic auristatin F drug of Formula H-AF, wherein the targeted antigen is preferably capable of internalization into said cancer cell upon said binding in order to initiate intracellular release of free drug of Formula H-AF.

Useful antibodies include polyclonal antibodies, which are heterogeneous populations of antibody molecules derived from the sera of immunized animals. Other useful antibodies are monoclonal antibodies, which are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, or chimeric human-mouse (or other species) monoclonal antibodies. The antibodies include full-length antibodies and antigen binding fragments thereof. Human monoclonal antibodies may be made by any of numerous techniques known in the art (e.g., Teng et al., 1983, *Proc. Natl. Acad. Sci. USA*. 80:7308-7312; Kozbor et al., 1983, *Immunology Today* 4:72-79; and Olsson et al., 1982, *Meth. Enzymol.* 92:3-16).

The antibody can be a functionally active fragment, derivative or analog of an antibody that immunospecifically binds to targeted cells (e.g., cancer cell antigens, viral antigens, or microbial antigens) or other antibodies bound to tumor cells or matrix. In this regard, "functionally active" means that the fragment, derivative or analog is able to immunospecifically binds to target cells. To determine which CDR sequences bind the antigen, synthetic peptides containing the CDR sequences can be used in binding assays with the antigen by any binding assay method known in the art (e.g., the BIA core assay) (See, e.g., Kabat et al., 1991, *Sequences of Proteins of Immunological Interest*, Fifth Edition, National Institute of Health, Bethesda, Md.; Kabat E et al., 1980, *J. Immunology* 125(3):961-969).

Other useful antibodies include fragments of antibodies such as, but not limited to, F(ab')$_2$ fragments, Fab fragments, Fvs, single chain antibodies, diabodies, triabodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. Nos. 4,816,567; and 4,816,397, which are incorporated herein by reference in their entirety). Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety). Such chimeric and humanized monoclonal antibodies can be produced by recombinant DNA techniques known in the art, for example using methods, each of which is specifically incorporated herein by reference, as described in International Publication No. WO 87/02671; European Patent Publication No. 0 184 187; European Patent Publication No. 0 171496; European Patent Publication No. 0 173 494; International Publication No. WO 86/01533; U.S. Pat. No. 4,816,567; European Patent Publication No. 012 023; Berter et al., *Science* (1988) 240:1041-1043; Liu et al., *Proc. Natl. Acad. Sci.* (USA) (1987) 84:3439-3443; Liu et al., *J. Immunol.* (1987) 139: 3521-3526; Sun et al. *Proc. Natl. Acad. Sci.* (USA) (1987) 84:214-218; Nishimura et al. *Cancer. Res.* (1987) 47:999-1005; Wood et al., *Nature* (1985) 314:446-449; Shaw et al., *J. Natl. Cancer Inst.* (1988) 80:1553-1559; Morrison, *Science* (1985) 229:1202-1207; Oi et al. *BioTechniques* (1986) 4:214; U.S. Pat. No. 5,225,539; Jones et al., Nature 1986) (321:552-525; Verhoeyan et al., *Science* (1988) 239:1534; and Beidler et al., *J. Immunol.* (1988)141:4053-4060.

Completely human antibodies are particularly preferred and can be produced using transgenic mice that are incapable of expressing endogenous immunoglobulin heavy and light chains genes, but which can express human heavy and light chain genes.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, PEGylation, phosphorylation, amidation, derivitization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

In a specific embodiment, known antibodies for the treatment of cancer can be used. In another specific embodiment, antibodies for the treatment of an autoimmune disease are used in accordance with the compositions and methods of the invention.

In certain embodiments, useful antibodies can bind to a receptor or a receptor complex expressed on an activated lymphocyte. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein.

In some embodiments, the antibody will specifically bind to CD19, CD20, CD30, CD33, CD70, alpha-v-beta-6, or Lewis Y antigen.

The antibody can be a humanized anti-CD33 antibody (US 2013/0309223 incorporated by reference herein in its entirety and for all purposes), a humanized anti-Beta6 antibody (see, e.g., WO 2013/123152 incorporated by reference herein in its entirety and for all purposes), a humanized anti-Liv-1 antibody (see, e.g., US 2013/0259860 incorporated by reference herein in its entirety and for all purposes), or a humanized AC10 antibody (see, e.g., U.S. Pat. No. 8,257,706 incorporated by reference herein in its entirety and for all purposes). Exemplary attachment of the Linker Unit to the antibody Ligand Unit is via thioether linkages. The thioether linkages can be via interchain disulfide bonds, introduced cysteines resides, and combinations thereof.

2.2.2 Primary Linkers

In one group of embodiments, a hydrophobic AF compound of Formula H-AF is conjugated through its C-terminal compound in any one of the —W—$Y_y$-D structures disclosed herein. In some of those embodiments, in which subscript b is 0 a drug linker moiety related to a hydrophobic AF compound of Formula H-AF has the structure of:

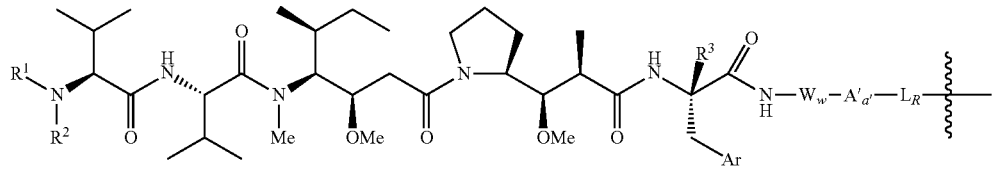

or a salt thereof, in particular a pharmaceutically acceptable salt, wherein $L_R$ is a primary linker.

In some embodiments $L_R$ of a drug linker moiety has the formula of -$L_b$-A-, wherein $L_B$ is a ligand covalent binding moiety and A is a first optional Stretcher Unit that is present.

In some preferred embodiments $L_R$ of formula -$L_b$-A- is a self-stabilizing linker ($L_{SS}$) moiety or a self-stabilized linker ($L_S$) moiety obtained from controlled hydrolysis of the succinimide ($M^2$) moiety of $L_{SS}$. Exemplary $L_{SS}$ and $L_S$ primary linkers of a drug linker moiety of an auristatin F Ligand Drug Conjugate composition or Conjugate compound thereof having either type of primary linker are represented by the structures of:

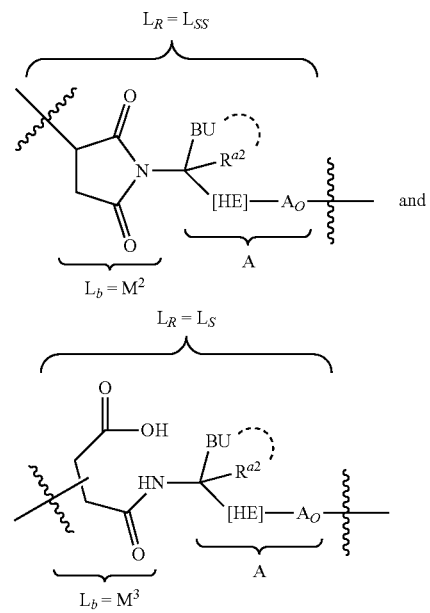

or a salt thereof, in particular a pharmaceutically acceptable salt, wherein the wavy line indicates the site of covalent attachments to A', W or the C-terminal component of an hydrophobic auristatin F Drug Unit, depending on the values of subscript a' and w; $A_O$ is an optional subunit of A; [HE] is an optional Hydrolysis Enhancing Unit, which is a component provided by A; BU is a Basic Unit; $R^{a2}$ is an optionally substituted $C_1$-$C_{12}$ alkyl group; and the dotted curved line indicates optional cyclization so that in the absence of said cyclization, BU is an acyclic Basic Unit having a primary, secondary or tertiary amine functional group as the basic function group of the acyclic Basic Unit, or in the presence of said cyclization BU is a cyclized Basic Unit in which $R^{a2}$ and BU together with the carbon atom to which both are attached, define an optionally substituted spiro $C_3$-$C_{20}$ heterocyclo containing a skeletal basic nitrogen atom of a secondary or tertiary amine functional group as the basic function group of the cyclic Basic Unit, wherein the basic nitrogen atom of the acyclic Basic Unit or cyclic Basic Unit is optionally suitably protected by a nitrogen protecting group, dependent on the degree of substitution of the basic nitrogen atom, or is optionally protonated, and the remaining variable groups are as described for any one of the embodiments of a hydrophobic AF compound of Formula H-AF.

In other preferred embodiments the primary linker of formula -$L_b$-A- does not contain a Basic Unit, which are exemplified by the structure of:

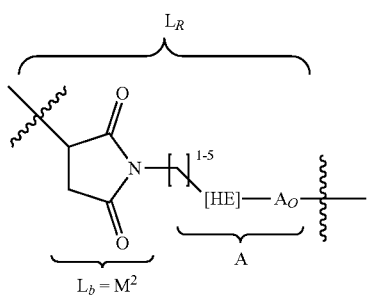

or a salt thereof, in particular a pharmaceutically acceptable salt, wherein the variable groups are as previously described for $L_{SS}$ or $L_S$ primary linkers.

Representative L-$L_R$- structures, in which $L_R$ is covalently attached to a Ligand Unit (L) of a hydrophobic AF LDC, are the following:

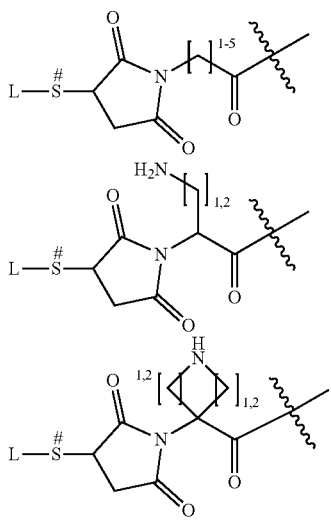

and salts thereof, in particular pharmaceutically acceptable salts, and structures in which the succinimide ring system is hydrolyzed to a ring opened form, wherein the indicated (#) sulfur atom is from the Ligand Unit; and wherein the wavy line indicates the site of covalent attachment to the remainder of the Conjugate structure.

Other representative L-$L_R$- structures are the following:

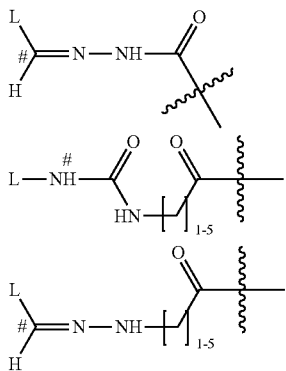

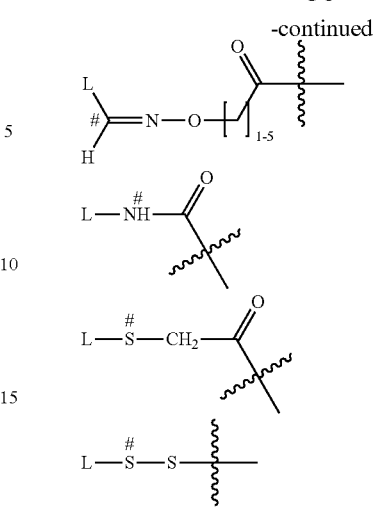

wherein the indicated (#) nitrogen, carbon or sulfur atom is from the Ligand Unit; and wherein the wavy line indicates the site of covalent attachment to the remainder of the Conjugate structure.

2.2.3 Peptide Cleavable Units

In any one of the above embodiments in which subscript w is 1, a Peptide Cleavable Unit (W) is present and is a peptide sequence comprised of a dipeptide or tripeptide residue that is recognized by a protease, in particular an intracellular protease, or is an amino acid residue that in combination with the C-terminal component of the auristatin F Drug Unit or additionally in combination with A' is recognized by the protease. In preferred embodiments, the amide bond between W and the carboxylic acid residue of the auristatin F Drug Unit's C-terminal component is cleaved by a protease, to provide free auristatin F or hydrophobic AF drug. In any one of the above embodiments in which subscript w is 0 and subscript a' is 0, the amide bond between A, or a subunit thereof as when $A_O$ is present as $A_2$, and the auristatin F Drug Unit is cleaved by the protease to provide free auristatin F drug or hydrophobic AF drug and in any one of the above embodiments in which subscript w is 0 or 1 and subscript a' is 1, the amide bond between A' and the auristatin F Drug Unit is cleaved by the protease to provide free auristatin F drug. In any one of the above embodiments the amide bond to release free drug is preferably cleavable by an intracellular protease, more preferably by a lysosomal protease, which can be a cathepsin protease such Cathepsin B.

A preferred amino acid residue, by itself or part of a peptide sequence of W, that is covalently attached to a hydrophobic auristatin Drug Unit through its C-terminal component's carboxylic acid residue as an amide bond that provides a recognition site for an protease for cleavage of that bond include any of the 20 naturally occurring L-α-amino acids, except proline. More preferred amino acids are L-alanine, L-lysine, L-aspartic acid and L-glutamic acid.

A preferred dipeptide residue, by itself or part of a peptide sequence of W, that provides a recognition site for a protease has the structures of:

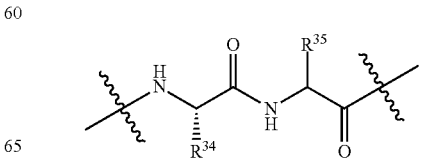

or a salt thereof, in particular a pharmaceutical acceptable salt, wherein the wavy line at the dipeptide N-terminal indicates the site of covalent attachment as an amide bond to an AF Drug Unit through its C-terminal component's carboxylic acid residue, wherein the amide bond is cleavable by the protease to release the Drug Unit as free drug, and the wavy line at the dipeptide C-terminal indicates the site of covalent attachment to the remainder of the peptide sequence or to A, or a subunit thereof, as when $A_O$ is present as $A_2$, of a primary linker of a drug linker moiety or Drug Linker compound; $R^{34}$ is hydrogen, —$CH_2CH_2CH_2NHC(=O)NH_2$ or the side chain of a naturally occurring α-amino acid except proline, in particular —$CH_2CH_2CH_2NHC(=O)NH_2$, —$CH_3$, —$C(CH_3)_2$, —$CH_2CH_2COOH$ or —$CH_2CH_2CH_2CH_2NH_2$—; and $R^{35}$ is hydrogen, methyl, isopropyl, sec-butyl, benzyl, p-hydroxy-benzyl, —$CH_2OH$, —$CH(OH)CH_3$, —$CH_2CH_2SCH_3$, —$CH_2C(=O)NH_2$, —$CH_2COOH$, —$CH_2CH_2C(=O)NH_2$, —$CH_2CH_2COOH$, —$CH_2CH_2CH_2NHC(=NH)NH_2$, —$CH_2CH_2CH_2NH_2$, —$CH_2CH_2CH_2NH$—$C(=O)CH_3$, —$CH_2CH_2CH_2NH$—$C(=O)H$, —$CH_2CH_2CH_2CH_2NHC(=NH)NH_2$, —$CH_2CH_2CH_2CH_2NH_2$—, —$CH_2CH_2CH_2CH_2NH$—$C(=O)CH_3$, —$CH_2CH_2CH_2CH_2NH$—$C(=O)H$, —$CH_2CH_2CH_2NHC(=O)NH_2$, —$CH_2CH_2CH_2CH_2NHC(=O)NH_2$, —$CH_2CH_2CH(OH)CH_2NH_2$, 2-pyridylmethyl, 4-pyridylmethyl, phenyl or cyclohexyl or $R^{35}$ has the structure of one of:

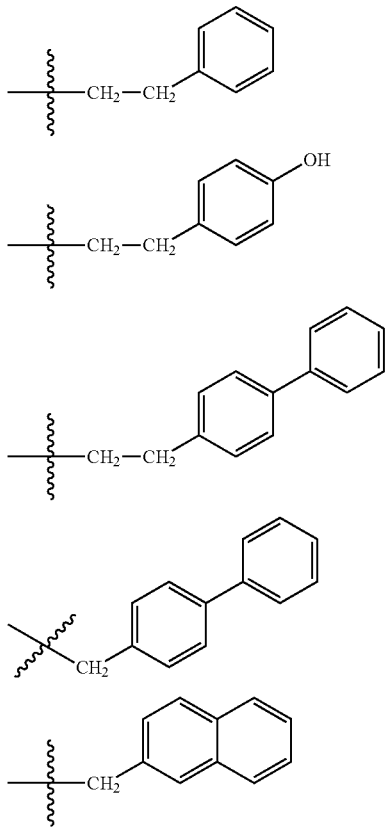

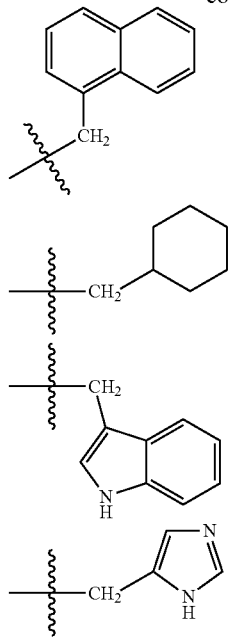

wherein the wavy line indicates the site of covalent attachment to the dipeptide backbone.

Other preferred recognition sites for an intracellular protease have or are comprised of the formula of -A'-W—, wherein W is a glutamic acid or aspartic acid residue attached to the C-terminal component's carboxylic acid residue of the AF Drug Unit through the α-amino nitrogen atom of the amino acid residue and to A', which is an optional second Stretcher Unit that is present, through the amino acid residue's α-carboxyl carbon atom, wherein both attachments are through amide bonds, wherein the amide bond to the C-terminal component is cleavable by a protease to release the Drug Unit as free drug, and wherein A' is alkylene diamine having a carboxylic acid side chain so that the nitrogen atom of one of its amines is covalently attached to the glutamic acid residue, and the nitrogen atom of the other amine is covalently attached A, or a subunit thereof, as when $A_O$ is present as $A_2$, wherein both attachments are through amide bonds.

A preferred structure of general formula A'-W is the following:

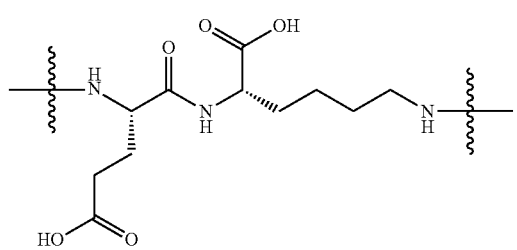

or a salt thereof, in particular a pharmaceutical acceptable salt, wherein the wavy line adjacent to the glutamic acid alpha-amino nitrogen atom indicates the site of covalent attachment as an amide bond to an AF Drug Unit through it C-terminal component's carboxylic acid residue, wherein the amide bond is cleavable by the protease to release the Drug Unit as free drug and the wavy line adjacent the lysine epsilon amine nitrogen atom indicates the site of covalent attachment to a first optional Stretcher Unit (A) or subunit thereof that is present.

2.2.4 Stretcher Units

In the above and following embodiments, a primary linker within a drug linker moiety of a Ligand Drug Conjugate exemplify the general formula of $M^2$-A(BU)-$A_O$-, $M^2$-A-$A_O$- or $M^3$-A(BU)-$A_O$-, and a primary linker of a Drug Linker compound, which can be used to prepare a Ligand Drug Conjugate, exemplify the general formula of $M^1$-A(BU)-$A_O$- or $M^1$-A-$A_O$-, wherein BU is an acyclic or cyclic Basic Unit; [HE] when present is—preferably C(=O)—, which is provided by a first optional Stretcher Unit that is present; $M^2$ is succinimide moiety; $M^3$ is succinic acid amide moiety and MI is a maleimide moiety, wherein A represents either a single discreet unit or a first subunit of A, which is sometimes indicated as $A_1$, when $A_O$ is present as a second subunit of A, which is sometimes indicated as $A_2$, is covalently attached to A' when subscript a' is 1, or to W when subscript a' is 0 and subscript w is 1 or to the carboxylic acid residue of the C-terminal component of a hydrophobic AF Drug Unit when subscript a' is 0 and subscript w is 0.

When $A_O$ is present in any one those embodiments that subunit of a first Stretcher Unit is indicated as $A_2$ to signify it as a subunit of A, wherein $A_2$ has a structure corresponding to an optionally substituted amine-containing acid (e.g., an amino acid) residue, wherein the residue of the carboxylic acid terminus of the amine-containing acid is covalently attached preferably to A' through an amide functional group and the residue of the amine terminus is covalently attached the remainder of A. If $A_O$ is absent, A is a single discreet unit that is preferably bonded to A' through [HE], which is provided by A, wherein [HE] is —C(=O)—.

In some of those embodiments, $A_2$ has or is comprised of the formula of -$L^P$(PEG)-, wherein $L^P$ is a Parallel Connector Unit and PEG is a PEG Unit. In those embodiments, the PEG Unit contains a total of 2 to 36 ethyleneoxy monomer units and $L^P$ is an amine-containing acid residue, preferably an amino acid residue, covalently attached preferably to A' and the remainder of A through amide functional groups. In preferred embodiments, the PEG Unit contains a total of 4 to 24 contiguous ethyleneoxy monomer units.

In other of those embodiments, $A_O$/$A_2$ is an amine-containing acid residue having the structure of formula 3a, formula 4a or formula 5a:

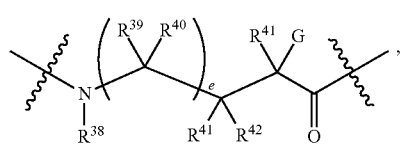

(3a)

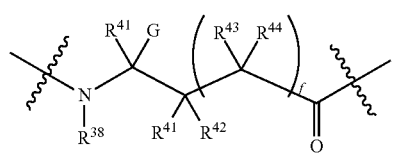

(4a)

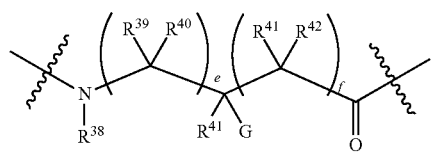

(5a)

wherein the wavy line adjacent to the nitrogen atom indicates the site of covalent attachment to the remainder of A, and the wavy line adjacent to the carbonyl carbon atom indicates the site of covalent attachment to A'; subscripts e and f are independently 0 or 1; and G is hydrogen, —OH, —$OR^{PR}$, —$CO_2H$, —$CO_2R^{PR}$ or an optionally substituted $C_1$-$C_6$ alkyl, wherein the optional substituent when present is selected from the group consisting of —OH, —$OR^{PR}$, —$CO_2H$, and —$CO_2R^{PR}$; and wherein $R^{PR}$ is a suitable protecting, or G is $N(R^{PR})(R^{PR})$ or an optionally substituted $C_1$-$C_6$ alkyl, wherein the optional substituent when present is $N(R^{PR})(R^{PR})$, wherein $R^{PR}$ are independently a protecting group or $R^{PR}$ together form a suitable protecting group, or G is —$N(R^{45})(R^{46})$, or an optionally substituted $C_1$-$C_6$ alkyl, wherein the optional substituent when present is —$N(R^{45})(R^{46})$, wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl;

$R^{38}$ is hydrogen or optionally substituted $C_1$-$C_6$ alkyl; and $R^{39}$-$R^{44}$ are independently selected from the group consisting of hydrogen, optionally substituted $C_1$-$C_6$ alkyl, optionally substituted $C_6$-$C_{20}$ aryl, and optionally substituted $C_5$-$C_{20}$ heteroaryl, or $R^{39}$, $R^{40}$ together with the carbon atom to which both are attached define a $C_3$-$C_6$ carbocyclo, and $R^{41}$-$R^{44}$ are as defined herein, or $R^{43}$, $R^{44}$ together with the carbon atom to which both are attached define a $C_3$-$C_6$ carbocyclo, and $R^{39}$-$R^{42}$ are as defined herein, or $R^{40}$ and $R^{41}$, or $R^{40}$ and $R^{43}$, or $R^{41}$ and $R^{43}$ to together with the carbon atom or heteroatom to which both are attached and the atoms intervening between those carbon atoms and/or heteroatoms define a $C_5$-$C_6$ carbocyclo or a $C_5$-$C_6$ heterocyclo, and $R^{39}$, $R^{40}$ and the remainder of $R^{40}$-$R^{43}$ are as defined herein, or $A_O$/$A_2$ is an α-amino or β-amino acid residue, wherein the nitrogen atom of it α-amino or α-amino residue is covalently attached to the remainder of A, and the carbonyl carbon atom of its carboxylic acid residue is covalently attached to A', wherein both attachments are preferably through amide functional groups.

When A' is present, A' is preferably an optionally substituted $C_2$-$C_{12}$ diamine, wherein the nitrogen atom of one of the amines is covalently attached to a first optional Stretcher Unit (A) or subunit thereof and the nitrogen atom of the other amine is covalently attached to W, wherein both covalent attachments are preferably through amide functional groups.

In some of those embodiments A' is an alkylene diamine reside having the structure of formula 3b formula 4b or formula 5b:

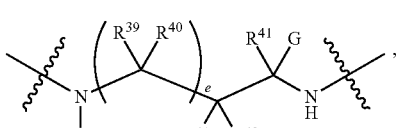

(3b)

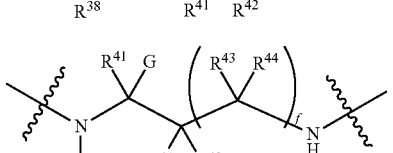

(4b)

-continued (5b)

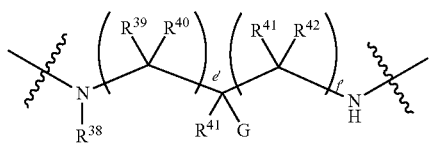

wherein subscript e and f range from 0 to 6; subscripts e' and f' range from 1 to 6; the wavy line next to the nitrogen atom of the amine residue to which $R^{38}$ is attached indicates the site of covalent attachment to a first optional Stretcher Unit that is present or a subunit thereof; the wavy line adjacent to the nitrogen atom of the other amine residue indicates the site of covalent attachment to W; and the remaining variable groups are as previously described for formula 3a, formula 4a or formula 5a.

In preferred embodiments, A' has the structure of formula 3b, wherein G is —$CO_2H$. In other preferred embodiments W is a glutamic acid or aspartic acid residue or a peptide sequence having a N-terminal glutamic acid or aspartic acid residue covalently attached to A' through the residue's α-amino nitrogen atom. In more preferred embodiments A' has the structure of formula 3b, wherein G is —$CO_2H$ and W is a glutamic acid residue attached to A'. In particularly preferred embodiments A' is a L-lysine residue in which the nitrogen atom of its epsilon amine residue is covalently attached to A or subunit thereof and the nitrogen atom of the alpha amine residue is covalently attached to W though an amide functional group.

2.2.5 Drug Linkers

In preferred embodiments of -$L_{SS}$ and -$L_S$-containing drug linker moieties of an auristatin F Ligand Drug Conjugate compound, the $L_{SS}$ and $L_S$ moieties contain a heterocyclo cyclic Basic Unit. Exemplary drug linker moieties having those primary linker in which the Peptide Cleavable Unit is a dipeptide are represented by the structures of:

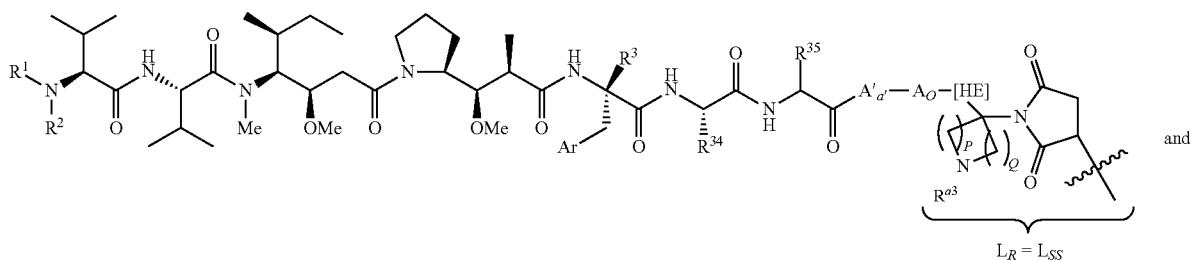

and

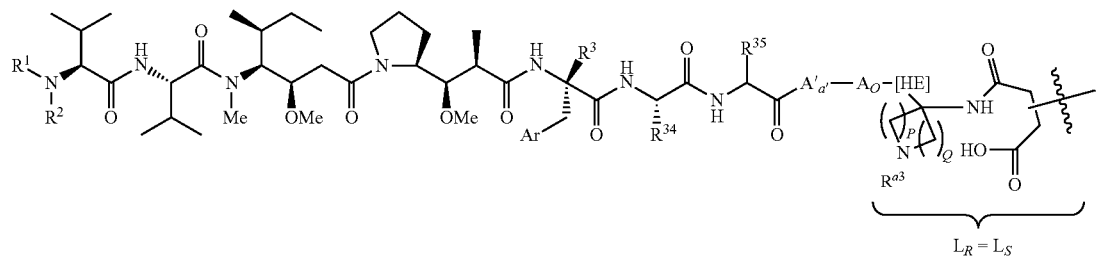

respectively, or a salt thereof, in particular a pharmaceutical acceptable salt, wherein HE is an optional Hydrolysis Enhancing Unit; $A_O$ is an subunit of first Stretcher Unit; A' is a second optional Stretcher Unit; subscript a' is 0 or 1, indicating the absence or presence of A', respectively; subscript P is 1 or 2; subscript Q ranges from 1 to 6; and wherein $R^{a3}$ is —H, optionally substituted $C_1$-$C_6$ alkyl, optionally substituted —$C_1$-$C_4$ alkylene-($C_6$-$C_{10}$ aryl), or —$R^{PEG1}$—O—$(CH_2CH_2O)_{1-36}$—$R^{PEG2}$, wherein $R^{PEG1}$ is $C_1$-$C_4$ alkylene, $R^{PEG2}$ is —H or $C_1$-$C_4$ alkylene, wherein the basic nitrogen bonded to $R^{a3}$ is optionally protonated or is in a salt form, preferably in a pharmaceutically acceptable salt form, or $R^{a3}$ is a nitrogen protecting group such as a suitable acid-labile protecting group; $R^{34}$ and $R^{35}$ are as previously defined for any one of the embodiments of Peptide Cleavable Units; and the remaining variable groups are as described for any one of the embodiments of a hydrophobic AF drug of Formula H-AF.

In other preferred embodiments of -$L_{SS}$ and -$L_S$-containing drug linker moieties of an auristatin F Ligand Drug Conjugate compound, the $L_{SS}$ and $L_S$ moieties contain a acyclic cyclic Basic Unit. Exemplary drug linker moieties having those primary linker in which the Peptide Cleavable Unit is a dipeptide are represented by the structures of:

or a salt thereof, in particular a pharmaceutical acceptable salt, wherein HE is an optional Hydrolysis Enhancing Unit; $A_O$ is an optional subunit of first optional Stretcher Unit that is present; A' is a second optional Stretcher Unit; subscript a' is 0 or 1, indicating the absence or presence of A'; $R^{34}$ and $R^{35}$ are as previously

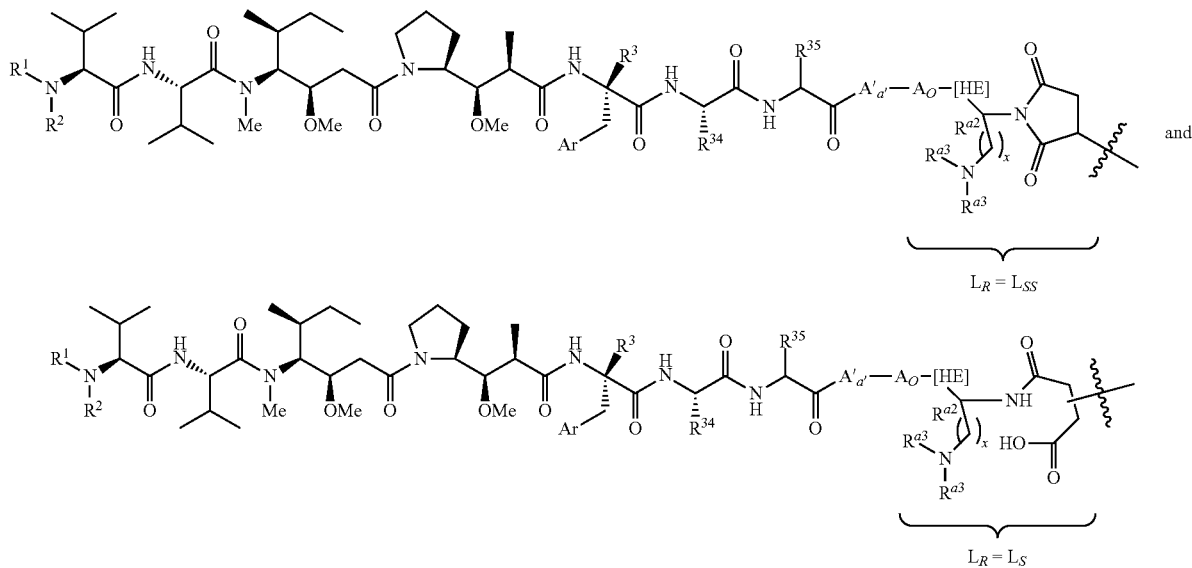

respectively, or a salt thereof, in particular a pharmaceutical acceptable salt, wherein HE is an optional Hydrolysis Enhancing Unit, $A_O$ is an optional subunit of an optional first Stretcher Unit that is present, A' is a second optional Stretcher Unit; subscript a' is 0 or 1, indicating the absence or presence of A', respectively; subscript x is 1 or 2, $R^2$ is hydrogen or —$CH_3$ or —$CH_2CH_3$; $R^{a3}$, at each instance, is independently hydrogen, —$CH_3$ or —$CH_2CH_3$, or both $R^{a3}$ together with the nitrogen to which they are attached define an azetidinyl, pyrrolidinyl or piperidinyl heterocyclyl, in which a basic primary, secondary or tertiary amine so defined is optionally protonated or is in a salt form, preferably a pharmaceutically acceptable salt form; $R^{34}$ and $R^{35}$ are as previously defined for any one of the embodiments of Peptide Cleavable Units; and the remaining variable groups are as described for any one of the embodiments of a hydrophobic AF drug of Formula H-AF.

In other preferred embodiments, a primary linker does not have a Basic Unit. Exemplary drug linker moieties having that primary linker in which the Peptide Cleavable Unit is a dipeptide are represented by the structure of:

defined for any one of the embodiments of Peptide Cleavable Units; and the remaining variable groups are as described for any one of the embodiments of a hydrophobic AF drug of Formula H-AF.

In other preferred embodiments the internal valine residue of an AF Drug Unit in any one of the foregoing drug linker moieties is replaced with one of the structures of:

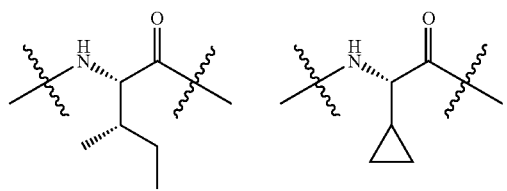

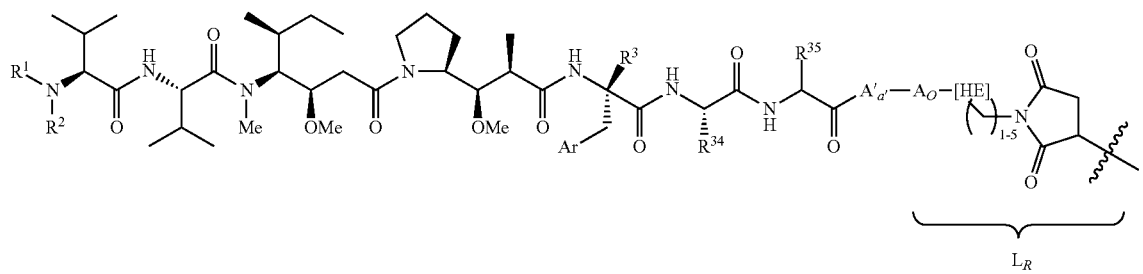

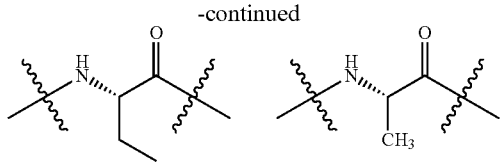
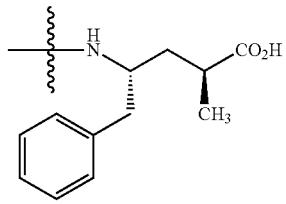

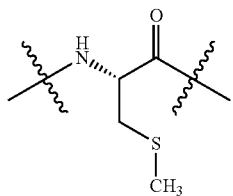

and/or the C-terminal component is replaced by another C-terminal component having the structure of one of:

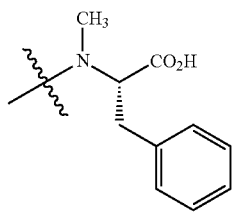
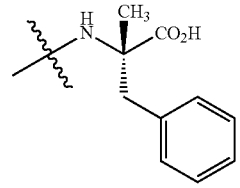

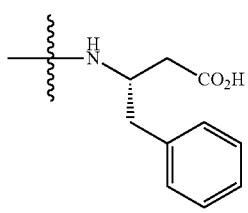

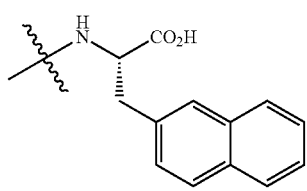

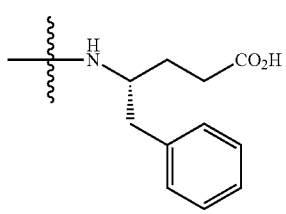

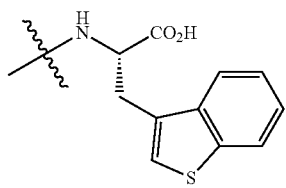

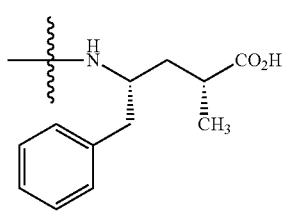

or a salt thereof, in particular pharmaceutically acceptable salt.

In more preferred embodiments the $L_{SS}$-containing drug linker moieties within a Ligand Drug Conjugate having a heterocyclo cyclic Basic Unit or an acyclic Basic Unit are represented by:

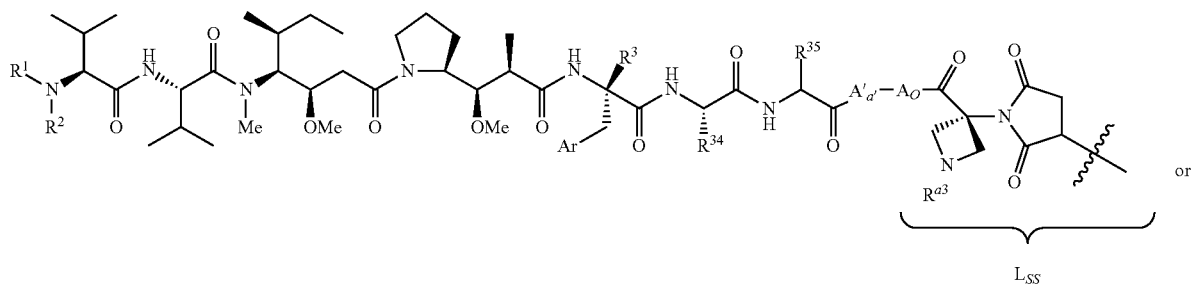

-continued

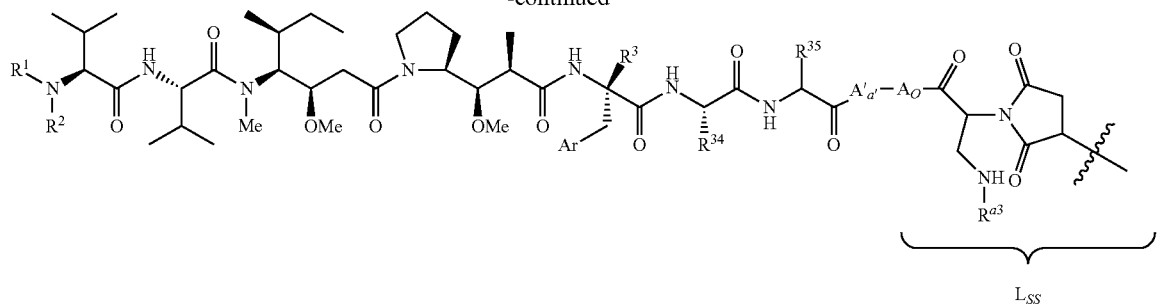

or a salt thereof, in particular a pharmaceutical acceptable salt, and more preferred $L_S$-containing drug linker moieties from controlled hydrolysis of the above drug linker moieties are represented by:

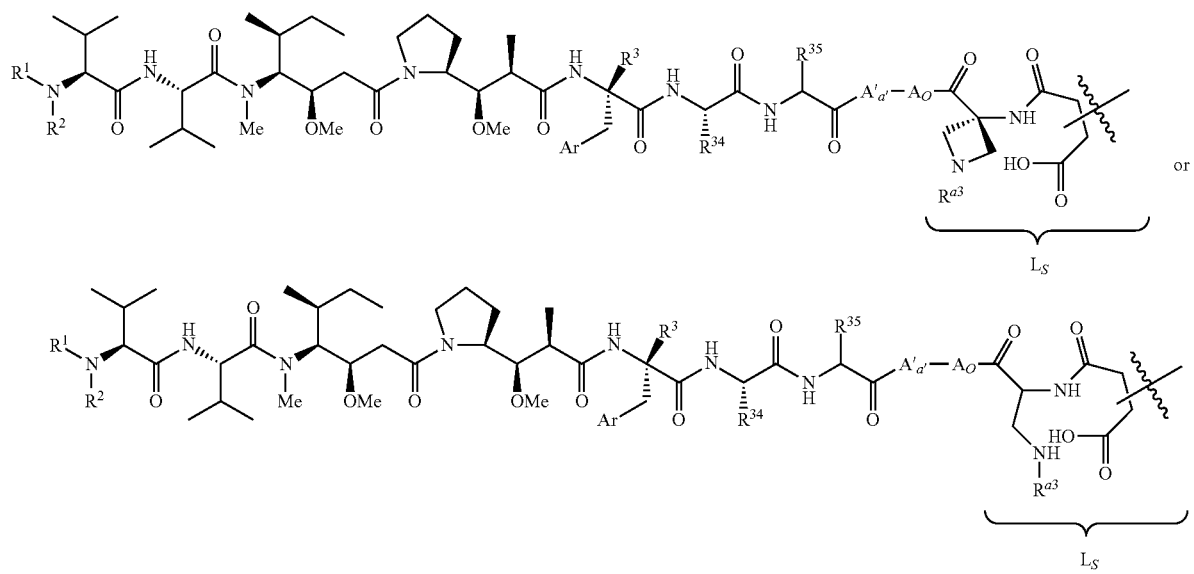

wherein the variable groups in each of the $L_{SS}$- or $L_S$-containing drug linker moieties are as previously described for drug linker moieties having a acyclic or heterocyclo cyclic Basic Unit and wherein the nitrogen atom to which $R^{a3}$ is bonded is optionally protonated and thus in a salt form, preferably in pharmaceutically acceptable salt from, in instances when $R^{a3}$ is other than a nitrogen protecting group; $R^{34}$ and $R^{35}$ are as previously defined for any one of the embodiments of Peptide Cleavable Units; and the remaining variable groups are as described for any one of the embodiments of a hydrophobic AF drug of Formula H-AF.

Particularly preferred drug linker moieties having a primary linker with a cyclic Basic Unit are represented by the structures of:

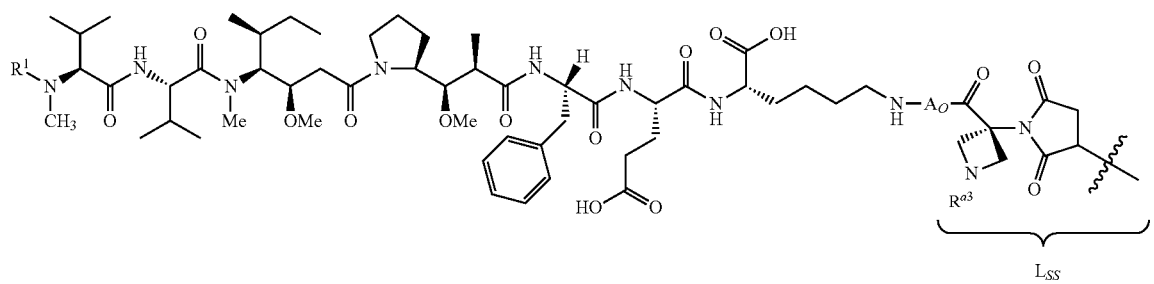

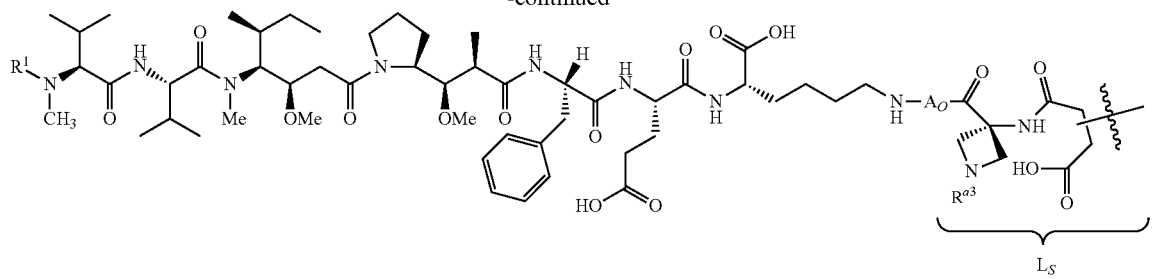

and salts thereof, in particular pharmaceutically acceptable salts;
wherein $A_O$ is an optional subunit of A, that if present is represented as $A_2$; $R^{a3}$ is hydrogen, —$CH_3$ or —$CH_2CH_3$, in which a basic secondary or tertiary amine so defined is optionally protonated or is in a salt form, preferably a pharmaceutically acceptable salt form; and the remaining variable groups are as described for any one of the embodiments of a hydrophobic AF drug of Formula H-AF.

and particularly preferred drug linker moieties having a primary linker with a acyclic Basic Unit are represented by the structures of;

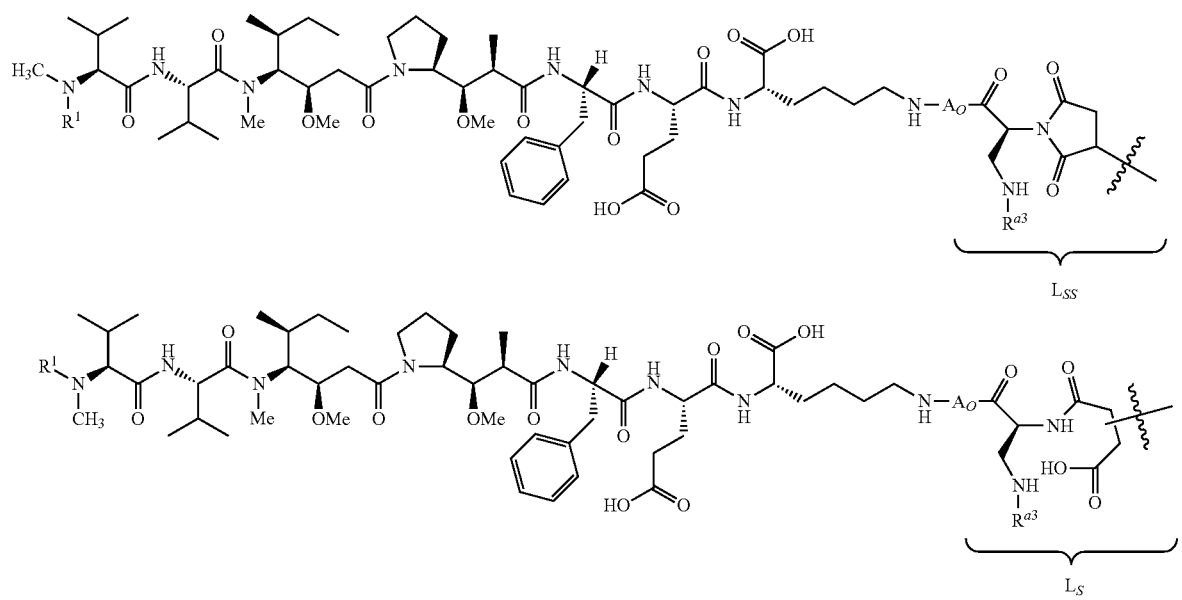

and salts thereof, in particular pharmaceutically acceptable salts;
wherein $A_O$ is an optional subunit of A, that if present is represented as $A_2$; $R^{a3}$ is hydrogen, —$CH_3$ or —$CH_2CH_3$, in which the basic primary or secondary tertiary amine so defined is optionally protonated or is in a salt form, preferably a pharmaceutically acceptable salt form; and the remaining variable groups are as described for any one of the embodiments of a hydrophobic AF drug of Formula H-AF.

and particularly preferred drug linker moieties having a primary linker without a Basic Unit are represented by the structures of:

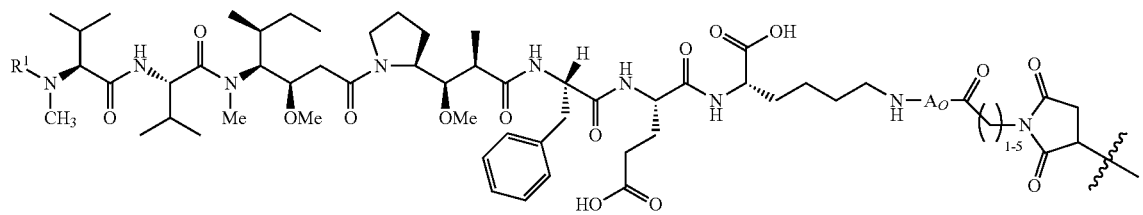

and salts thereof, in particular a pharmaceutical acceptable salts,
wherein $A_O$ is an optional subunit of A, that if present is represented as $A_2$; and the remaining variable groups are as described for any one of the embodiments of a hydrophobic AF drug of Formula H-AF.

In those particularly preferred embodiments W is a glutamic acid residue covalently attached to a second optional Stretcher Unit (A') that is present as a lysine residue, wherein the A'-W moiety in combination with the C-terminal component of the hydrophobic AF Drug Unit is recognized by an intracellular protease for cleavage of the amide bond between the glutamic acid residue and the C-terminal component for release of free hydrophobic AF drug.

In any one of the foregoing embodiments of drug linker moieties, $R^1$ preferably is —CH$_2$CH$_2$CH$_2$CH$_3$, —CH$_2$CH$_2$CH$_2$CH$_2$CH$_3$, —CH$_2$CH$_2$CH$_2$C(CH$_3$)$_2$, —CH$_2$CH$_2$CH$_2$CH$_2$N(CH$_3$)—C(=O)—O-t-Bu,
—CH$_2$CH$_2$CH$_2$CH$_2$N(CH$_3$)—C(=O)-t-Bu,
—CH$_2$CH$_2$CH$_2$N(CH$_3$)—C(=O)—O-t-Bu,
—CH$_2$CH$_2$CH$_2$NH—C(=O)—O-t-Bu, or has the structure of:

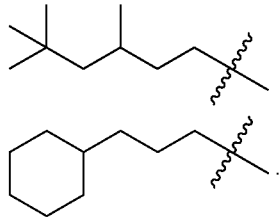

In especially preferred embodiments, a drug linker moiety having a hydrophobic AF Drug Unit has the structure of:

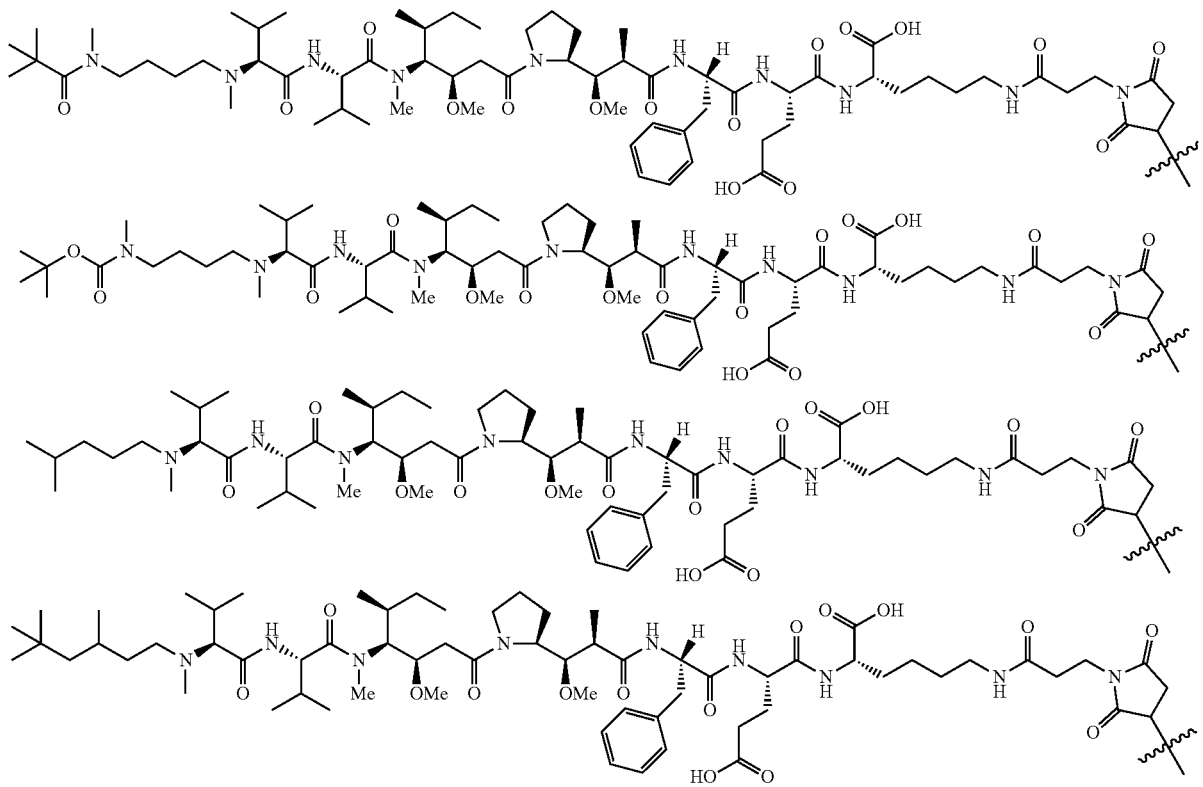

or a salt thereof, in particular a pharmaceutically acceptable salt.

2.2.6 Drug Linker Compounds

A Drug Linker compound is represented by the structure of Formula I:

$$LU'\text{-}(D') \tag{I}$$

or a salt thereof, wherein LU' is LU precursor; and D' represents from 1 to 4 hydrophobic AF Drug Units, which are preferably identical to each other, each of which is a hydrophobic AF drug of Formula H-AF conjugated to its C-terminal component, in particular through its carboxylic acid functional group, wherein the Drug Linker compound is further defined by the structure of Formula IA:

$$L_B'\text{—}A_a\text{—}B_b\text{—}(L_O\text{—}D)_q \tag{IA}$$

wherein $L_B'$ is an ligand covalent binding moiety precursor; A is a first optional Stretcher Unit; subscript a is 0 or 1 indicating the absence or presence of A, B is an optional Branching Unit; subscript b is 0 or 1 indicating the absence or presence of B, respectively, provided that subscript b is 1 when subscript q ranges from 2 to 4. A Drug Linker compound is particularly useful in preparing a Ligand Drug Conjugate of Formula 1 so that LU' is a LU precursor for a drug linker moiety of a Ligand Drug Conjugate compound.

In some embodiments $L_b'$-A- of a Drug Linker compound has or is comprised of one of the structures of:

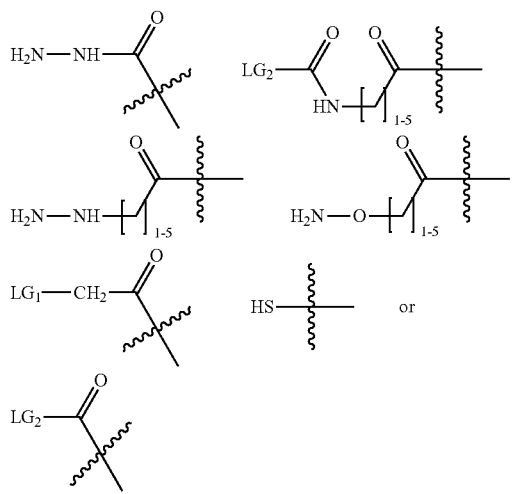

or a salt thereof, wherein $LG_1$ is a leaving group suitable for nucleophillic displacement by a targeting agent nucleophile; $LG_2$ is a leaving group suitable for amide bond formation to a targeting agent, or —OH to provide an activateable carboxylic acid suitable for amide bond formation to a targeting agent; and the wavy line indicates the site of covalent attachment to the remainder of the Drug Linker compound structure.

In other embodiments $L_b'$-A- of a Drug Linker compound has or is comprised of one of the structures of:

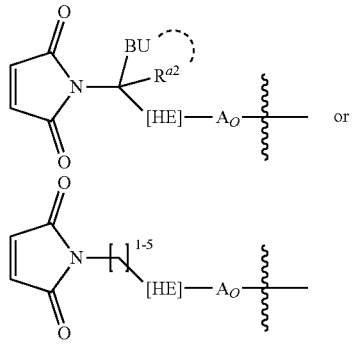

or a salt thereof, wherein the wavy line adjacent to $A_O$ indicates the site of covalent attachments to $L_O$; and the other wavy line indicates the site of covalent attachment to a sulfur atom of a Ligand Unit; $A_O$ is an optional second subunit of A; [HE] is an optional Hydrolysis Enhancing Unit, which is a component provided by A or a first subunit thereof;

BU is a Basic Unit; $R^1$ is an optionally substituted $C_1$-$C_{12}$ alkyl group; and the dotted curved line indicates optional cyclization so that in the absence of said cyclization, BU is an acyclic Basic Unit having a primary, secondary or tertiary amine functional group as the basic function group of the acyclic Basic Unit, or in the presence of said cyclization BU is a cyclized Basic Unit in which R' and BU together with the carbon atom to which both are attached, define an optionally substituted spiro $C_3$-$C_2$ heterocyclo containing a skeletal basic nitrogen atom of a secondary or tertiary amine functional group as the basic function group of the cyclic Basic Unit, wherein the basic nitrogen atom of the acyclic Basic Unit or cyclic Basic Unit is optionally suitably protected by a nitrogen protecting group, dependent on the degree of substitution of the basic nitrogen atom, or is optionally protonated as an acid addition salt.

In some preferred embodiments $L_b'$-A- of a Drug Linker compound has or is comprised of one of the structures of:

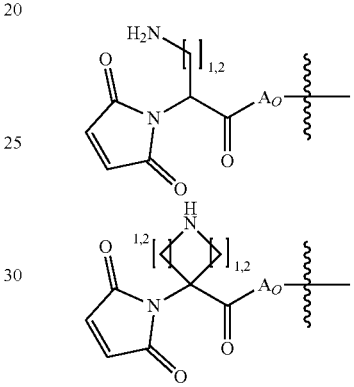

or a salt thereof, in particular as an acid addition salt, wherein $A_O$ is an optional second subunit of A.

In other preferred embodiments $L_b'$-A- of a Drug Linker compound has or is comprised of one of the structures of:

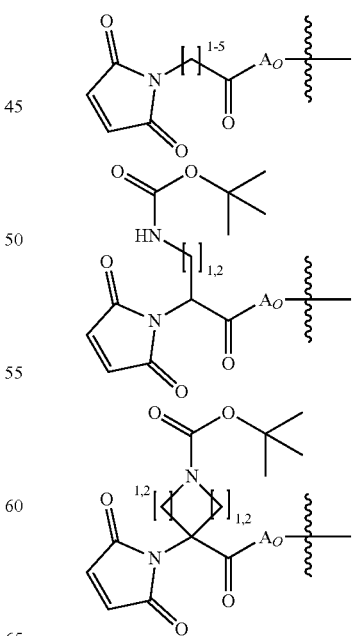

wherein $A_O$ is an optional second subunit of A.

In preferred embodiments of $L_{SS}$-containing Drug Linker compounds, the $L_{SS}$ moiety contains a heterocyclo cyclic Basic Unit. Exemplary Drug Linker compounds having those primary linker in which the Peptide Cleavable Unit is a dipeptide is represented by the structure of:

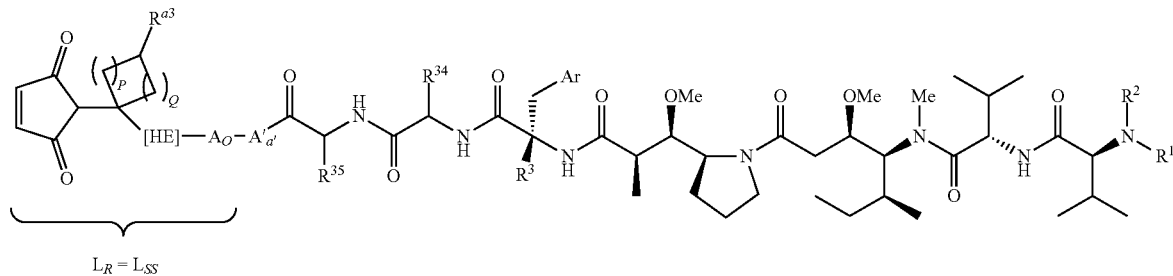

or a salt thereof, in particular a pharmaceutical acceptable salt, wherein HE is an optional Hydrolysis Enhancing Unit; $A_O$ is an subunit of first Stretcher Unit; A' is a second optional Stretcher Unit; subscript a' is 0 or 1, indicating the absence or presence of A', respectively; subscript P is 1 or 2; subscript Q ranges from 1 to 6; and wherein $R^{a3}$ is —H, optionally substituted $C_1$-$C_6$ alkyl, optionally substituted —$C_1$-$C_4$ alkylene-($C_6$-$C_{10}$ aryl), or —$R^{PEG1}$O—(CH$_2$CH$_2$)$_{1-36}$—$R^{PEG2}$, wherein $R^{PEG1}$ is $C_1$-$C_4$ alkylene, $R^{PEG2}$ is —H or $C_1$-$C_4$ alkylene, wherein the basic nitrogen bonded to $R^{a3}$ is optionally protonated or is in a salt form, preferably in a pharmaceutically acceptable salt form, or $R^{a3}$ is a nitrogen protecting group such as a suitable acid-labile protecting group; $R^{34}$ and $R^{35}$ are as previously defined for any one of the embodiments of Peptide Cleavable Units; and the remaining variable groups are as described for any one of the embodiments of a hydrophobic AF drug of Formula H-AF.

In other preferred embodiments of $L_{SS}$-containing Drug Linker compounds, the $L_{SS}$ moiety contains an acyclic cyclic Basic Unit. Exemplary Drug Linker compounds having that primary linker in which the Peptide Cleavable Unit is a dipeptide is represented by the structure of:

or a salt thereof, in particular a pharmaceutical acceptable salt, wherein HE is an optional Hydrolysis Enhancing Unit, $A_O$ is an optional subunit of an optional first Stretcher Unit that is present, A' is a second optional Stretcher Unit; subscript a' is 0 or 1, indicating the absence or presence of A', respectively; subscript x is 1 or 2, $R^2$ is hydrogen or —CH$_3$ or —CH$_2$CH$_3$; $R^1$, at each instance, is independently hydrogen, —CH$_3$ or —CH$_2$CH$_3$, or both $R^1$ together with the nitrogen to which they are attached define an azetidinyl, pyrrolidinyl or piperidinyl heterocyclyl, in which a basic primary, secondary or tertiary amine so defined is optionally protonated or is in a salt form, preferably a pharmaceutically acceptable salt form; $R^{34}$ and $R^{35}$ are as previously defined for any one of the embodiments of Peptide Cleavable Units; and the remaining variable groups are as described for any one of the embodiments of a hydrophobic AF drug of Formula H-AF.

In other preferred embodiments, a primary linker of a Drug Linker compound does not have a Basic Unit. Exemplary Drug Linker compounds having that primary linker in which the Peptide Cleavable Unit is a dipeptide are represented by the structure of:

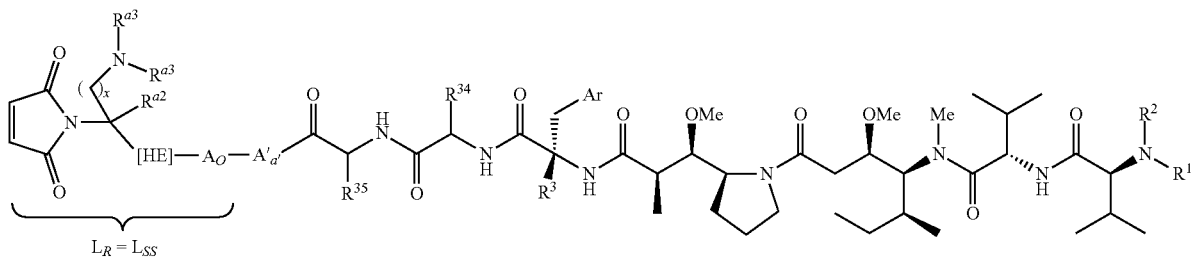

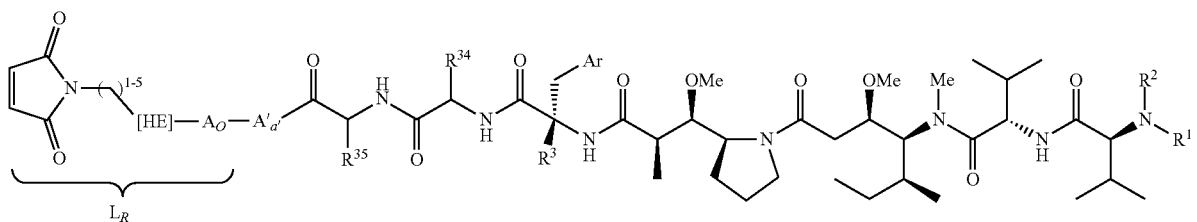

or a salt thereof, in particular a pharmaceutical acceptable salt, wherein HE is an optional Hydrolysis Enhancing Unit; $A_O$ is an optional subunit of first optional Stretcher Unit that is present; A' is a second optional Stretcher Unit; subscript a' is 0 or 1, indicating the absence or presence of A'; $R^{34}$ and $R^{35}$ are as previously defined for any one of the embodiments of Peptide Cleavable Units; and the remaining variable groups are as described for any one of the embodiments of a hydrophobic AF drug of Formula H-AF.

In other preferred embodiments the internal valine residue of an AF Drug Unit in any one of the foregoing Drug Linker compounds is replaced with one of the structures of:

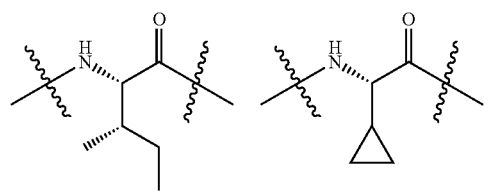

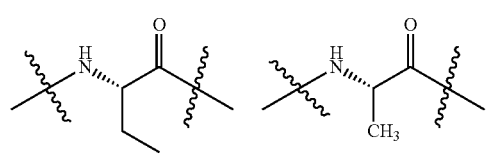

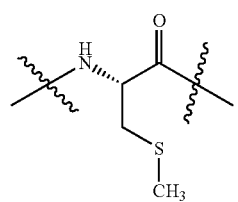

and/or the C-terminal component is replaced by another C-terminal component having the structure of one of:

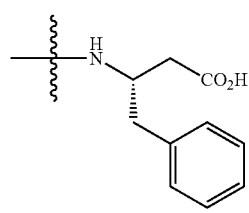

-continued

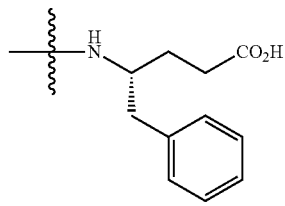

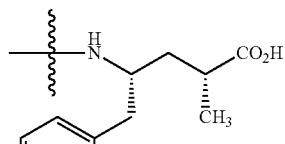

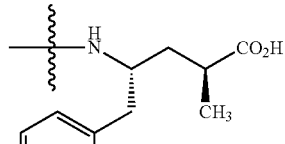

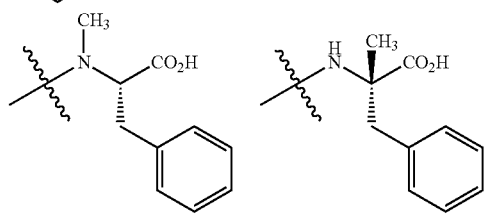

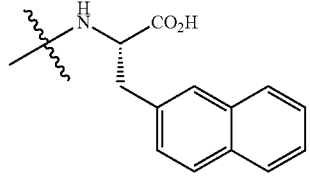

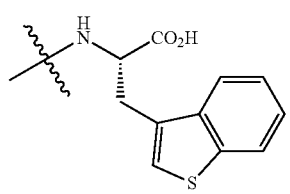

or a salt thereof, in particular pharmaceutically acceptable salt.

In more preferred embodiments a $L_{SS}$-containing Drug Linker compound having a heterocyclo cyclic Basic Unit or an acyclic Basic Unit is represented by:

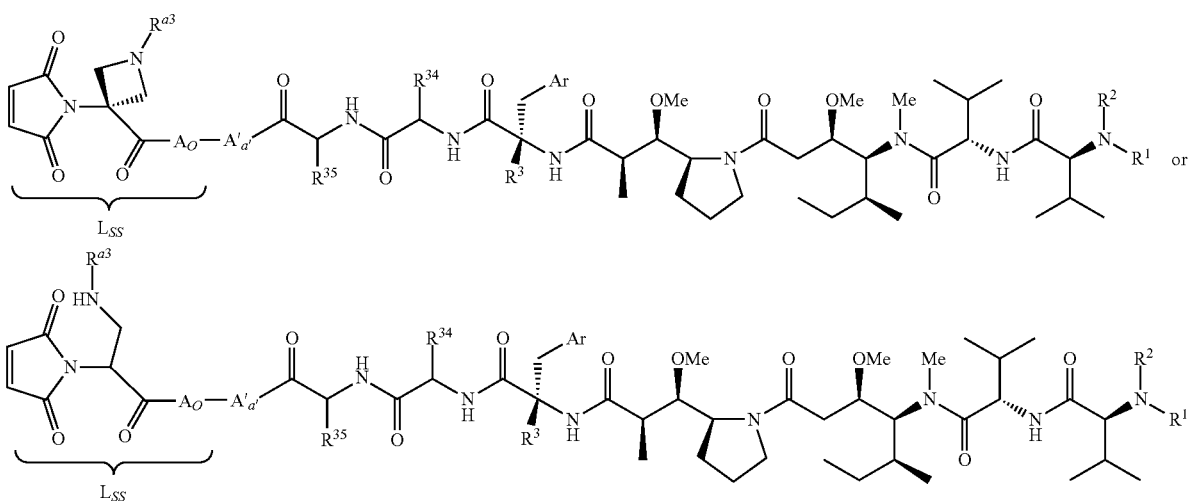

respectively, or a salt thereof, in particular a pharmaceutical acceptable salt, wherein the variable groups in each of the $L_{SS}$-containing Drug Linker compounds are as previously described for Drug Linker compounds having a acyclic or heterocyclo cyclic Basic Unit and wherein the nitrogen atom to which $R^{a3}$ is bonded is optionally protonated and thus in a salt form, preferably in pharmaceutically acceptable salt from, in instances when $R^{a3}$ is other than a nitrogen protecting group; $R^{34}$ and $R^{35}$ are as previously defined for any one of the embodiments of Peptide Cleavable Units; and the remaining variable groups are as described for any one of the embodiments of a hydrophobic AF drug of Formula H-AF.

Particularly preferred Drug Linker compounds having a primary linker with a cyclic Basic Unit are represented by the structure of:

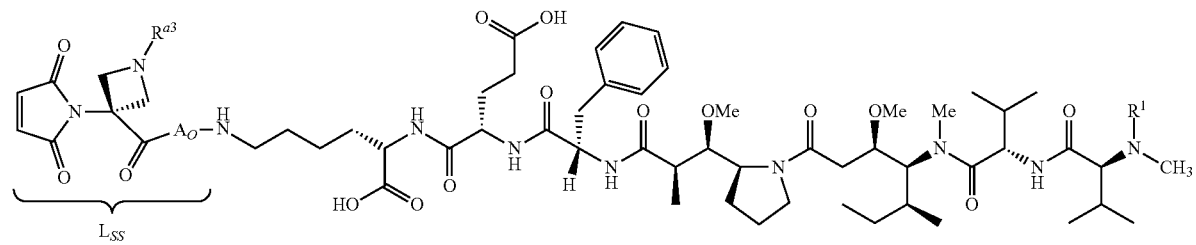

and salts thereof, in particular pharmaceutically acceptable salts, wherein $A_O$ is an optional subunit of A, that if present is represented as $A_2$; $R^{a3}$ is hydrogen, —$CH_3$ or —$CH_2CH_3$, in which a basic secondary or tertiary amine so defined is optionally protonated or is in a salt form, preferably a pharmaceutically acceptable salt form; and the remaining variable groups are as described for any one of the embodiments of a hydrophobic AF drug of Formula H-AF;

and particularly preferred Drug Linker compounds having a primary linker with a acyclic Basic Unit are represented by the structures of;

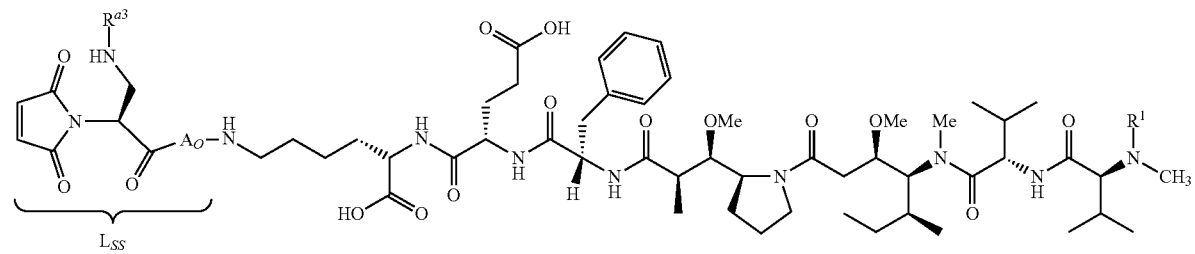

and salts thereof, in particular pharmaceutically acceptable salts;

wherein $A_O$ is an optional subunit of A, that if present is represented as $A_2$; $R^{a3}$ is hydrogen, —$CH_3$ or —$CH_2CH_3$, in which the basic primary or secondary tertiary amine so defined is optionally protonated or is in a salt form, preferably a pharmaceutically acceptable salt form; and the remaining variable groups are as described for any one of the embodiments of a hydrophobic AF drug of Formula H-AF;

and particularly preferred Drug Linker compounds having a primary linker without a Basic Unit are represented by the structures of:

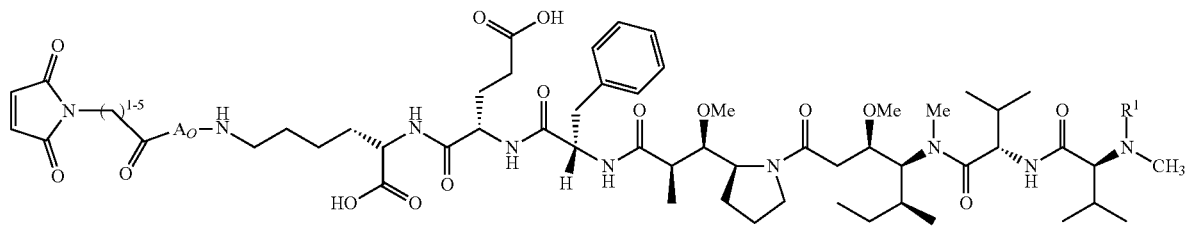

and salts thereof, in particular a pharmaceutical acceptable salts, wherein $A_O$ is an optional subunit of A, that if present is represented as $A_2$; and the remaining variable groups are as described for any one of the embodiments of a hydrophobic AF drug of Formula H-AF.

In those particularly preferred embodiments W is a glutamic acid residue covalently attached to a second optional Stretcher Unit (A') that is present as a lysine residue, wherein the A'-W moiety in combination with the C-terminal component of the hydrophobic AF Drug Unit is recognized by an intracellular protease for cleavage of the amide bond between the glutamic acid residue and the C-terminal component for release of free hydrophobic AF drug.

In any one of the foregoing embodiments of Drug Linker compounds, $R^1$ preferably is —$CH_2CH_2CH_2CH_3$, —$CH_2CH_2CH_2CH_2CH_3$, $CH_2CH_2CH_2C(CH_3)_2$, —$CH_2CH_2CH_2CH_2N(CH_3)$—C(=O)—O-t-Bu, —$CH_2CH_2CH_2N(CH_3)$—C(=O)—O-t-Bu, —$CH_2CH_2CH_2NH$—C(=O)—O-t-Bu, or has the structure of:

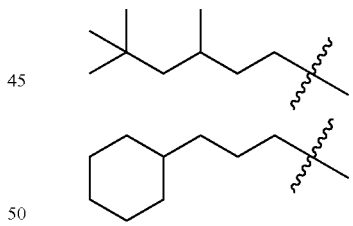

Especially preferred Drug Linker compounds having a hydrophobic AF Drug Unit have the structure of:

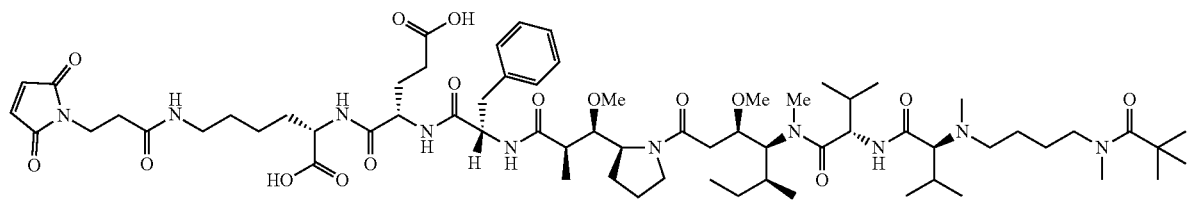

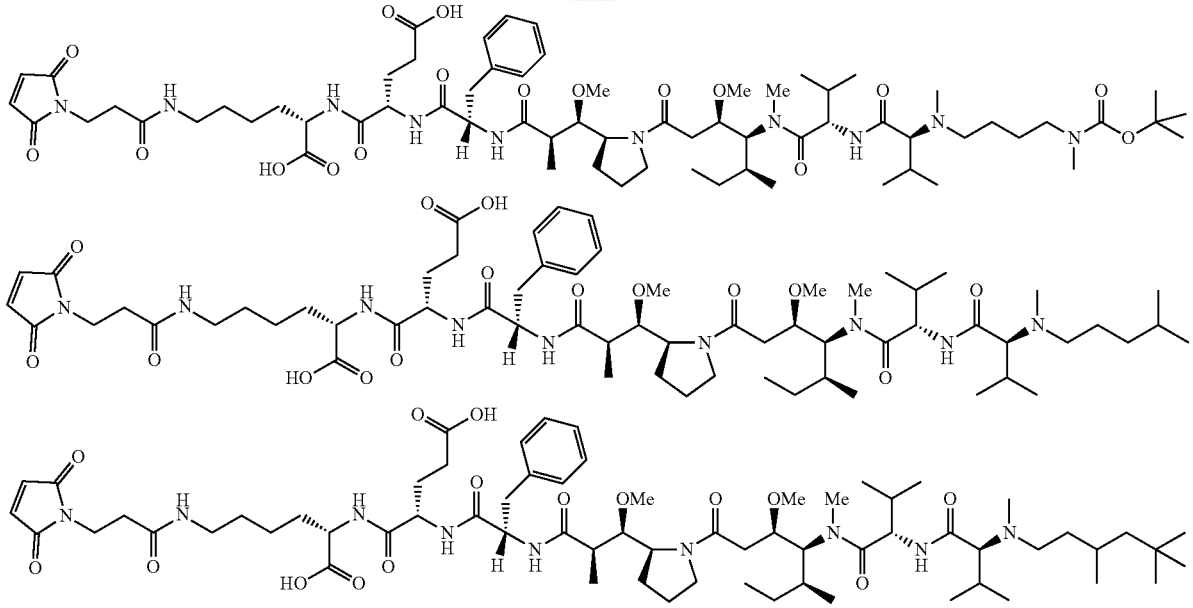

or a salt thereof, in particular a pharmaceutically acceptable salt.

3. Numbered Embodiments

The following embodiments further exemplify the invention and are not meant to limit the invention in any manner 1. A compound, wherein the compound is a hydrophobic auristatin F compound of Formula H-AF$_1$ having the structure of:

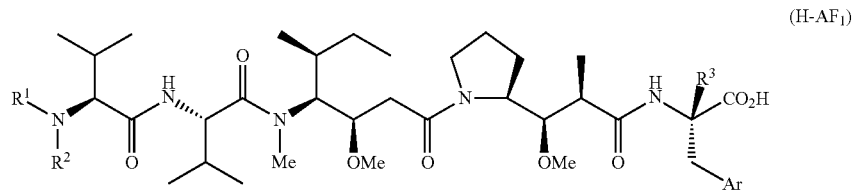

(H-AF$_1$)

or a salt thereof, wherein Ar is phenyl, thienyl, 1-napthyl, 2-napthyl or benzo[b]thiophen-3-yl; R$^3$ is independently selected from the group consisting of hydrogen and C$_1$-C$_2$ alkyl; R$^1$ is C$_1$-C$_9$ alkyl, optionally substituted by a C$_3$-C$_6$ carbocyclyl to provide a (carbocyclyl)-alkylene- of up to 9 total carbon atoms, or R' is —(C$_2$-C$_6$ alkylene)-X—R$^4$, wherein X is an amide or carbamate functional group and R$^4$ is C$_1$-C$_6$ alkyl; and R$^2$ is C$_1$-C$_2$ alkyl, with the proviso that the total number of carbon atoms in the (carbocyclyl)alkyl(ene) moieties of R$^1$, R$^2$ and R$^3$ is between 3 and 10 and R$^1$, R$^2$ and R$^3$ are not each methyl, or Ar is phenyl; R$^3$ is hydrogen; R$^1$ is a first non-aromatic hydrophobic moiety; and R$^2$ is a second non-aromatic hydrophobic moiety, wherein the first and second hydrophobic moieties provide the hydrophobic AF compound characterized by a clogP value of between about 4.4 to about 7.2.

2. The compound of embodiment 1, wherein R$^2$ is methyl and R$^3$ is hydrogen.

3. The compound of embodiment 1, wherein R$^3$ is hydrogen and Ar is phenyl.

4. The compound of embodiment 1, wherein R$^2$ is methyl; R$^3$ is hydrogen; and Ar is phenyl.

5. The compound of any one of embodiments 1 to 4, wherein R$^1$ is a saturated C$_1$-C$_9$ alkyl.

6. The compound of any one of embodiments 1 to 4, wherein R$^1$ is an unsaturated C$_3$-C$_9$ alkyl.

7. The compound of any one of embodiments 1 to 4, wherein R$^1$ is a carbocyclyl-alkyl- of up to 9 total carbon atoms.

8. The compound of any one of embodiments 1 to 4, wherein R$^1$ is an optionally branched C$_3$-C$_9$ alkyl, in particular an optionally branched C$_4$-C$_9$ alkyl.

9. The compound of any one of embodiments 1 to 4, wherein R$^1$ is —(C$_2$-C$_6$ alkylene)-X—R$^4$, wherein X is an amide functional group and R$^4$ is t-butyl.

10. The compound of any one of embodiments 1 to 4, wherein R$^1$ is —(C$_2$-C$_6$ alkylene)-X—R$^4$, wherein X is a carbamate functional group and R$^4$ is t-butyl or CH$_2$C═CH$_2$.

11. The compound of embodiment 9, wherein R$^1$ has the formula of —(CH$_2$)$_{3-5}$—N(R$^7$)—C(═O)-t-Bu wherein R$^7$ is hydrogen or —CH$_3$.

12. The compound of embodiment 10, wherein R$^1$ has the formula of —(CH$_2$)$_{3-5}$—N(R$^7$)—C(═O)—O-t-Bu, wherein R$^7$ is hydrogen or —CH$_3$.

13. The compound of any one of embodiments 1 to 4, wherein R¹ is a branched C₄-C₉ alkyl.

14. The compound of any one of embodiments 1 to 4, wherein R¹ has the structure of:

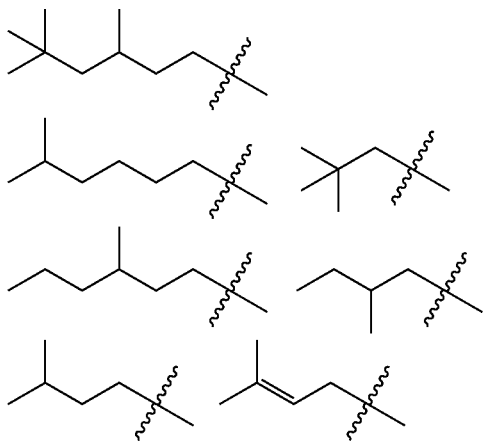

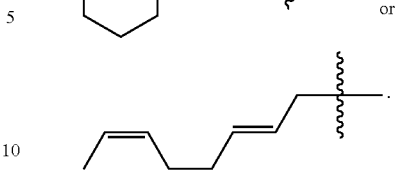

or

15. The compound of any one of embodiments 1 to 4, wherein R¹ is —CH₂CH₂CH(CH₃)CH₂C(CH₃)₃.

16. The compound of any one of embodiments 1 to 4, wherein R¹ is —CH₂CH₂CH₂CH₂N(CH₃)—C(=O)—O-t-Bu, —CH₂CH₂CH₂N(CH₃)—C(=O)—O-t-Bu or —CH₂CH₂CH₂NH—C(=O)—O-t-Bu.

17. The compound of any one of embodiments 1 to 4, wherein R¹ is —CH₂CH₂CH₂CH₂N(CH₃)—C(=O)-t-Bu.

18. The compound of embodiment 1, wherein the compound is:

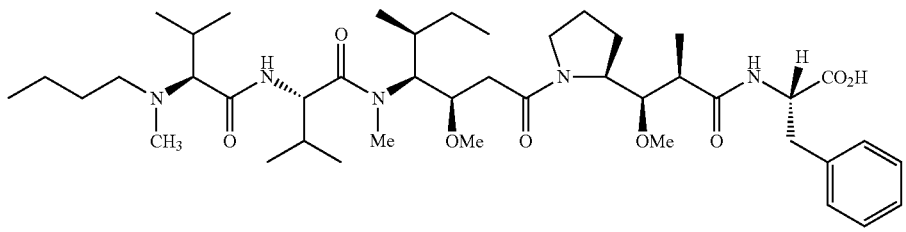

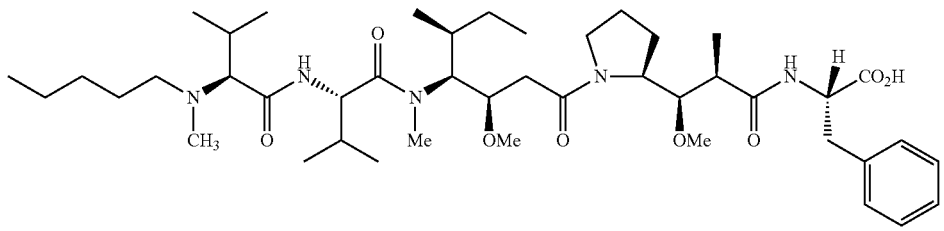

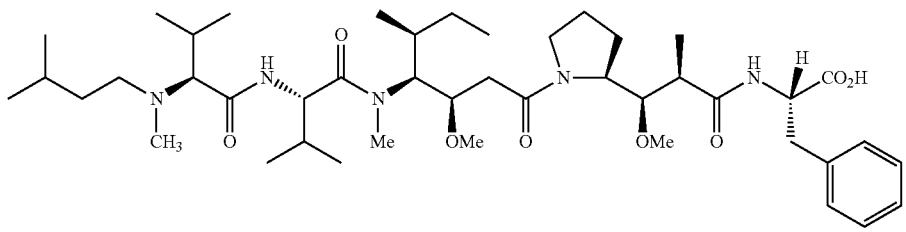

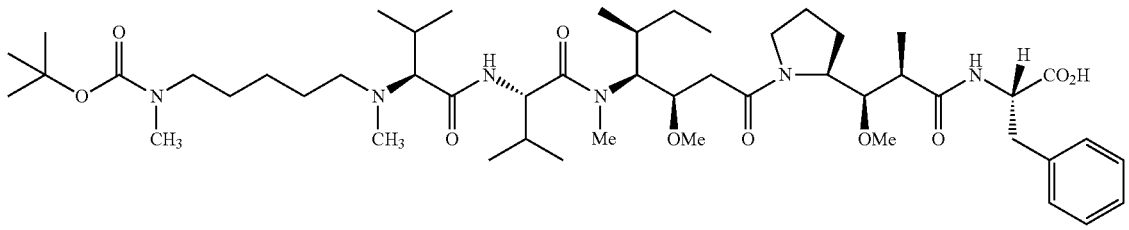

-continued
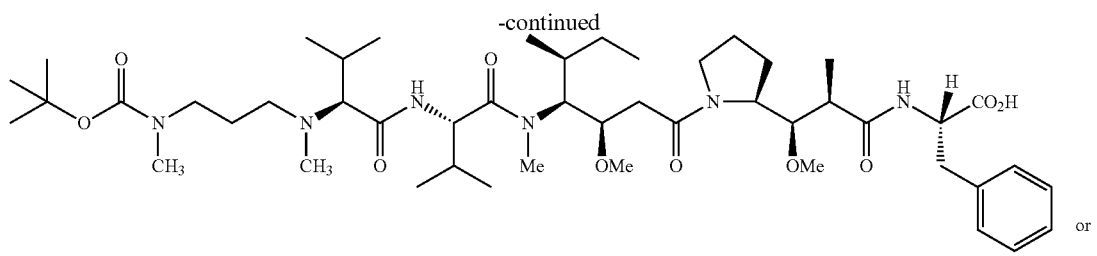
or
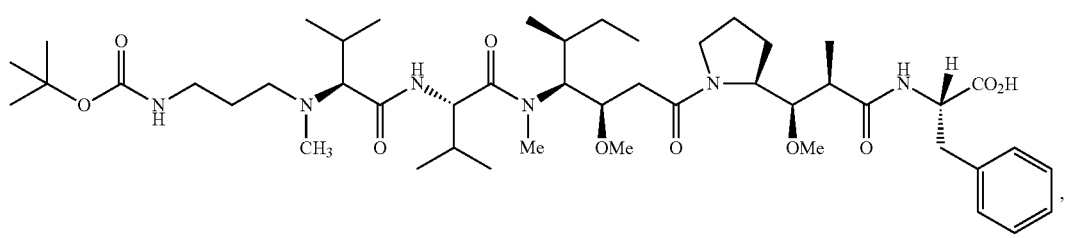
,
or a salt thereof.
19. The compound of embodiment 1, wherein the compound is:
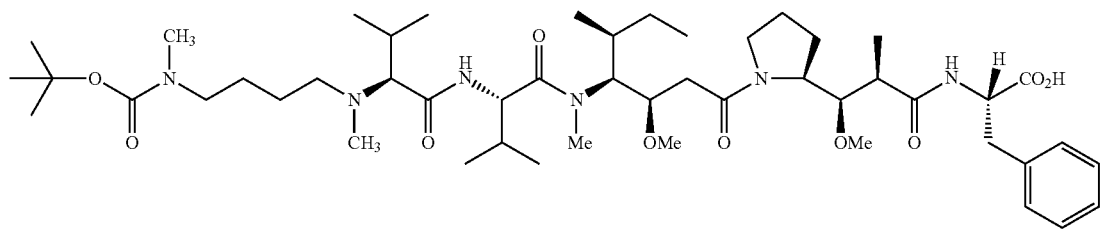
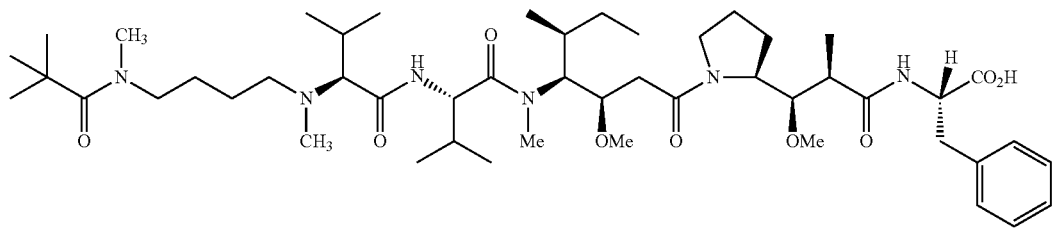
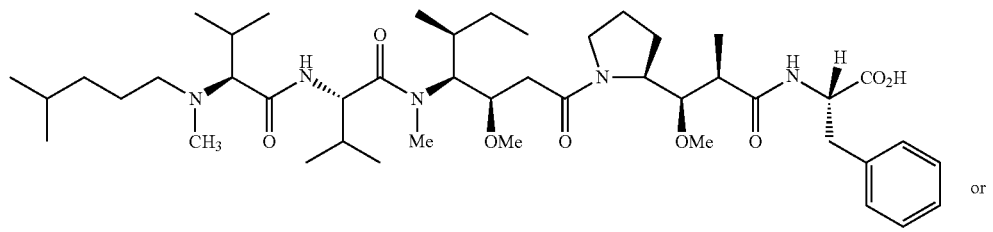
or

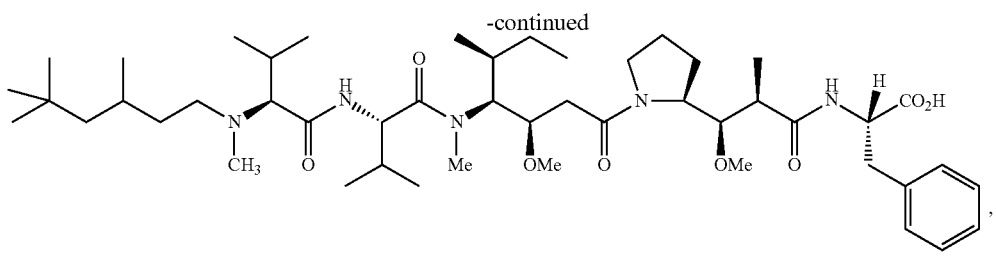

or a salt thereof.

20. A compound, wherein the compound is a hydrophobic auristatin F compound of Formula H-AF$_2$ having the structure of:

(H-AF$_2$)

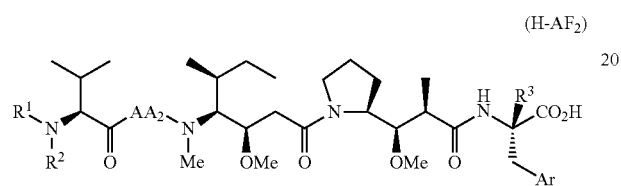

or a salt thereof, wherein Ar is phenyl, thienyl, 1-napthyl, 2-napthyl or benzo[b]thiophen-3-yl; R$^3$ is independently selected from the group consisting of hydrogen and C$_1$-C$_2$ alkyl; R$^1$ is C$_1$-C$_9$ alkyl, optionally substituted by a C$_3$-C$_6$ carbocyclyl to provide a (carbocyclyl)-alkylene- of up to 9 total carbon atoms, or R$^1$ is —(C$_2$-C$_6$ alkylene)-X—R$^4$, wherein X is an amide or carbamate functional group and R$^4$ is C$_1$-C$_6$ alkyl; and R$^2$ is C$_1$-C$_2$ alkyl.

and AA$_2$ is an amino acid residue having the structure of:

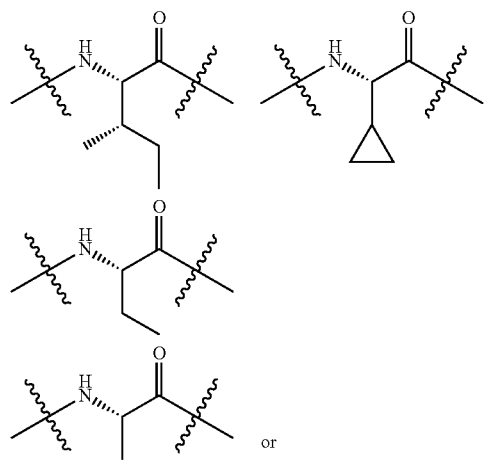

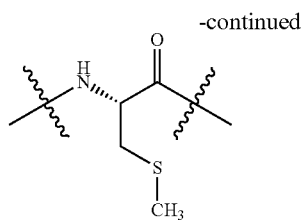

wherein the wavy lines indicate the sites of covalent attachment within the compound; and with the proviso that R and R$^2$ are not each methyl, and the compound is characterized by a clogP value of between about 4.4 to about 7.2.

21. The compound of embodiment 20, wherein the compound has the structure of:

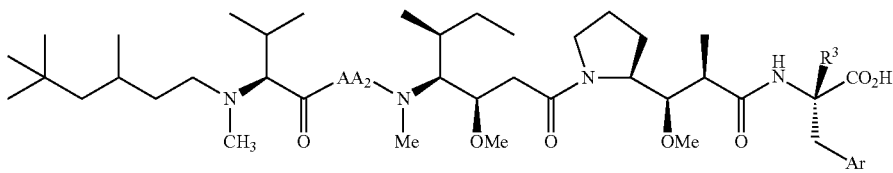

or a salt thereof.

22. The compound of embodiment 20 or 21 wherein Ar is phenyl and R$^3$ is hydrogen.

23. The compound of embodiment 20, 21 or 22, wherein -AA$_2$- has the structure of:

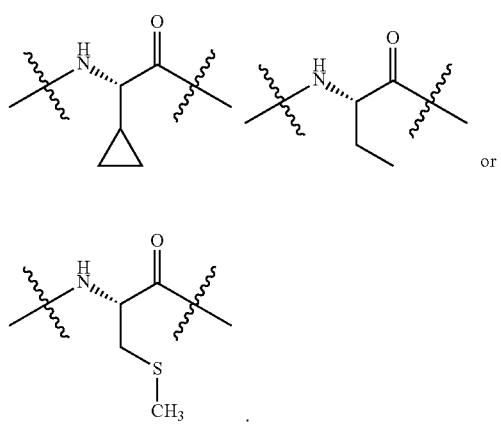

24. A compound, wherein the compound is a hydrophobic auristatin F compound of Formula H-AF$_3$ having the structure of:

(H-AF₃)

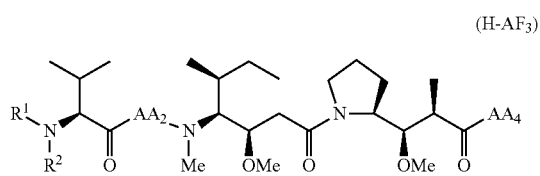

or a salt thereof, wherein R¹ is $C_1$-$C_9$ alkyl, optionally substituted by a $C_3$-$C_6$ carbocyclyl to provide a (carbocyclyl)-alkylene- of up to 9 total carbon atoms, or R¹ is —($C_2$-$C_6$ alkylene)-X—R⁴, wherein X is an amide or carbamate functional group and R⁴ is $C_1$-$C_6$ alkyl; R² is $C_1$-$C_2$ alkyl;

AA₂ is an amino acid residue having the structure of:

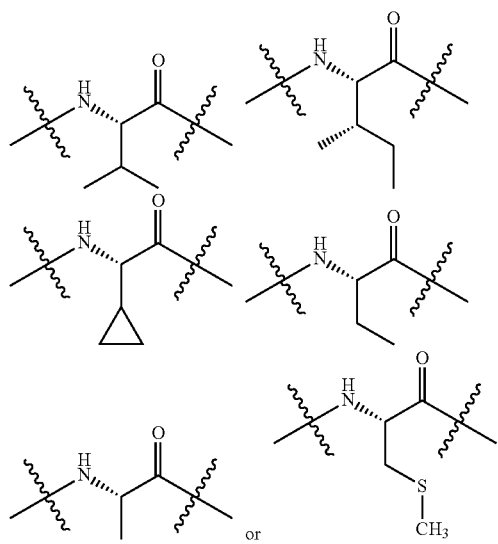

AA₄ has the structure of one of:

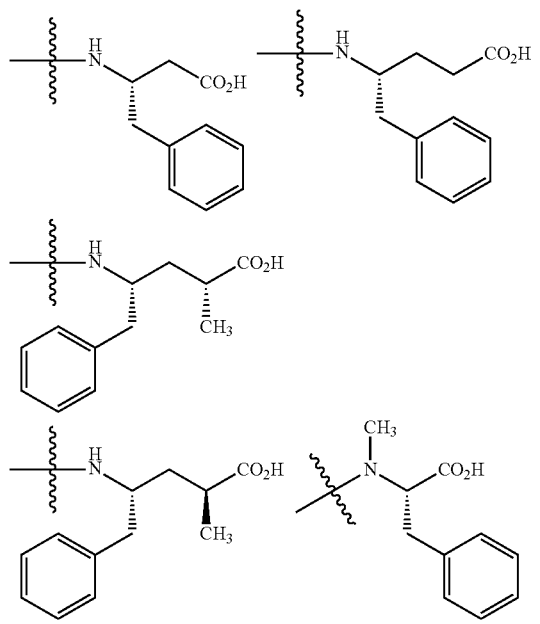

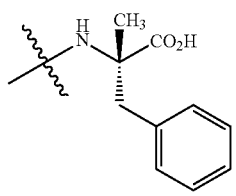

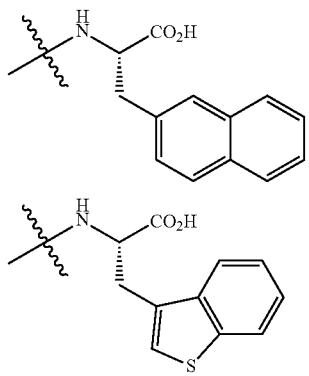

or a salt thereof, wherein the wavy lines indicate the sites of covalent attachment within the compound; and with the proviso that R¹ and R² are not methyl and the compound is characterized by a clogP value of between about 4.4 to about 7.2.

25. A compound, wherein the compound is a hydrophobic auristatin F compound of Formula H-AF₄ having the structure of:

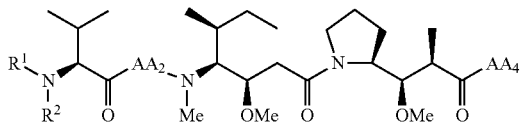

or a salt thereof, wherein R¹ is $C_1$-$C_9$ alkyl, optionally substituted by a $C_3$-$C_6$ carbocyclyl to provide a (carbocyclyl)-alkylene- of up to 9 total carbon atoms, or R¹ is —($C_2$-$C_6$ alkylene)-X—R⁴, wherein X is an amide or carbamate functional group and R⁴ is $C_1$-$C_6$ alkyl; R² is $C_1$-$C_2$ alkyl;

AA₂ is an amino acid residue having the structure of:

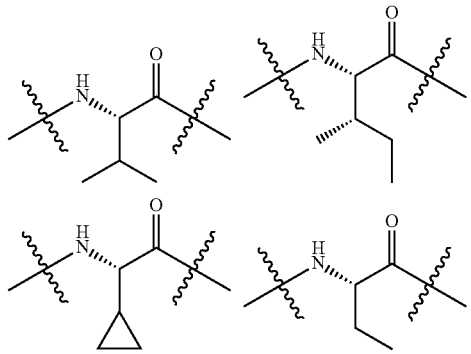

-continued

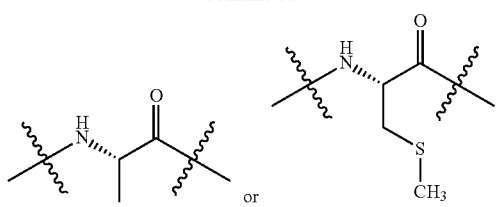

AA$_4$ has the structure of one of:

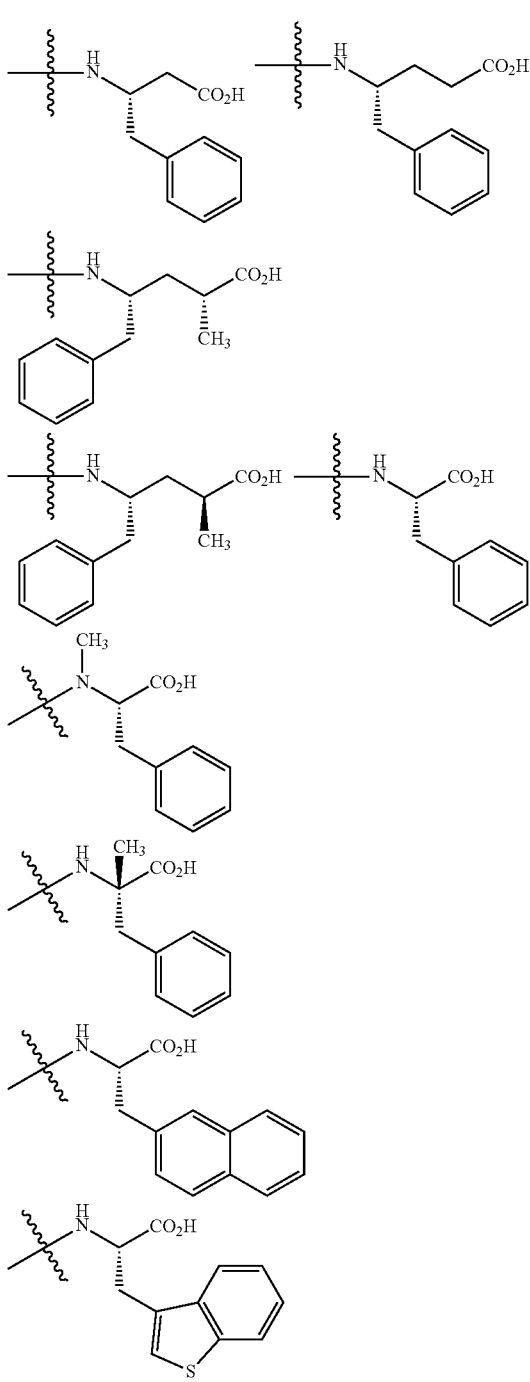

R$^5$ is a C$_2$-C$_6$ alkyl or has the formula of (C$_2$-C$_6$ alkylene)-X'—R$^6$, wherein X' is an independently selected amide or carbamate functional group and R$^6$ is C$_1$-C$_6$ alkyl, with the proviso that the total number of carbon atoms in the (carbocyclyl)alkyl(ene) moieties of R$^1$, R$^2$, R$^3$ and R$^5$ is between 3 and 10.

26. The compound of claim 25, wherein R$^5$ is —CH$_2$CH$_2$CH$_3$, —CH$_2$CH$_2$CH$_2$CH(CH$_3$)$_2$, —CH$_2$CH$_2$NH(C=O)—O-t-Bu or —CH$_2$CH$_2$NH(C=O)—CH(CH$_3$)$_2$.

27. The compound of embodiment 25 or 26, wherein AA$_2$ is:

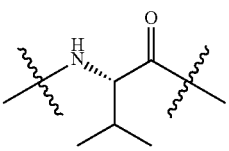

28. The compound of embodiment 25, 26 or 27, wherein AA$_4$ is:

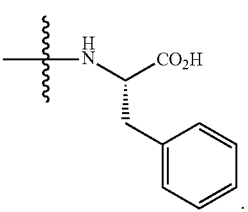 [SMILES: *N[C@@H](Cc1ccccc1)C(=O)O]

29. The compound of any one of embodiments 25 to 28, wherein R$^2$ is —CH$_3$ and R$^1$ is —CH$_3$, —CH$_2$CH$_3$, —CH$_2$CH$_2$CH$_3$, —CH$_2$CH$_2$CH$_2$CH$_3$, CH$_3$CH(CH$_3$)CH$_2$—, or has the structure of:

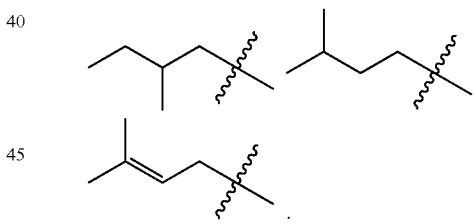

30. A Ligand Drug Conjugate composition represented by Formula 1:

L-[LU-D']p  (1)

or a salt thereof, wherein L is a Ligand Unit; LU is a Linker Unit; and D' represents from 1 to 4 hydrophobic auristatin F Drug Units (D) in each drug linker moiety of formula -LU-D', wherein each hydrophobic auristatin F Drug Unit is a hydrophobic auristatin F compound of any one of claims 1 to 29 conjugated through its C-terminal component's carboxylic acid functional group, wherein the Ligand Unit is capable of selective binding to a targeted moiety of a targeted cell for subsequent release of the hydrophobic auristatin F compound, wherein each drug linker moiety in a Ligand Drug Conjugate compound of the composition has the structure of Formula 1A:

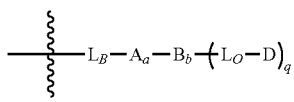
(IA)

or a salt thereof, wherein the wavy line indicates covalent attachment to L; D is the hydrophobic AF Drug Unit; $L_B$ is an ligand covalent binding moiety; A is a first optional Stretcher Unit; subscript a is 0 or 1 indicating the absence of presence of A, respectively; B is an optional Branching Unit; subscript b is 0 or 1, indicating the absence of presence of B, respectively; $L_O$ is an optional secondary linker moiety; subscript q is an integer ranging from 1 to 4, wherein the Ligand Drug Conjugate compound has the structure of Formula 1 in which subscript p is replaced by subscript p', wherein subscript p' is an integer ranging from 1 to 24.

31. The Ligand Drug Conjugate composition of embodiment 30, wherein $L_O$ is a secondary linker that is present and has the formula of:

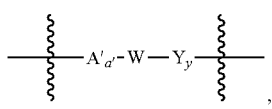

wherein the wavy line adjacent to Y indicates the site of covalent attachment of $L_O$ to the hydrophobic auristatin Drug Unit and the wavy line adjacent A' to indicates the site of covalent attachment of $L_O$ to the remainder of the drug linker moiety; A' is a second optional Stretcher Unit, subscript a' is 0 or 1, indicating the absence or presence of A', respectively, W is a peptide Cleavable Unit; Y is a peptide Spacer Unit; and subscript y is 0 or 1, indicating the absence or presence of Y, respectively.

32. The Ligand Drug Conjugate composition of embodiment 31, wherein each of its drug linker moieties has the structure of:

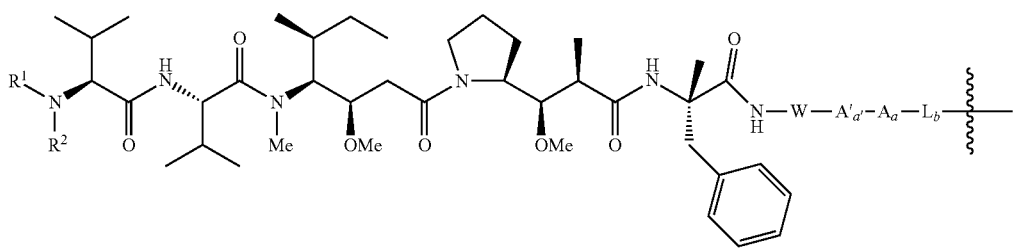

or a salt thereof, in particular a pharmaceutically acceptable salt, wherein $R^2$ is methyl; and $R^1$ is $C_3$-$C_9$ alkyl, optionally substituted by a $C_3$-$C_6$ carbocyclyl to provide a (carbocyclyl)-alkylene- of up to 9 total carbon atoms, or $R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in the (carbocyclyl)alkyl(ene) moiety of R is between 4 and 10.

33. The Ligand Drug Conjugate composition of embodiment 32, wherein L-$L_b$-A- has or is comprised of one of the structures of:

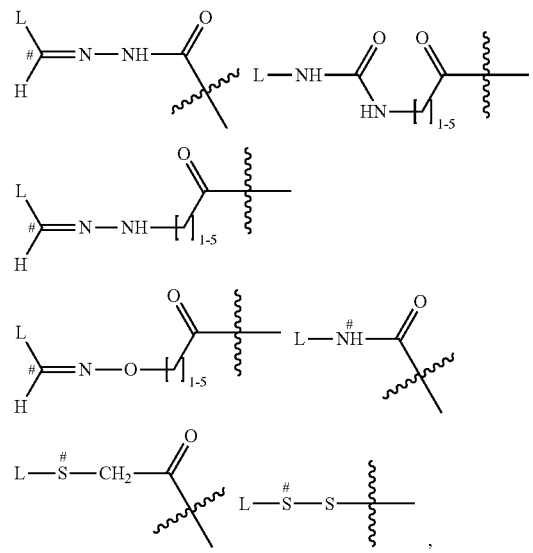

wherein the indicated (#) nitrogen, carbon or sulfur atom is from the Ligand Unit; and wherein the wavy line indicates the site of covalent attachment to the remainder of the Conjugate structure.

34. The Ligand Drug Conjugate composition of embodiment 32, wherein -$L_b$-A- in a plurality of drug linker moieties has the structure of:

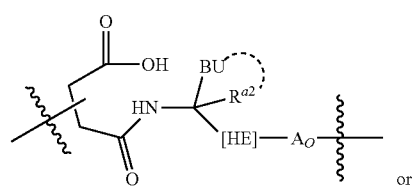

or

-continued

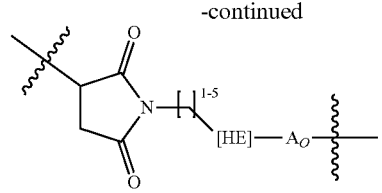

or a salt thereof, wherein the wavy line adjacent to $A_O$ indicates the site of covalent attachments to $L_O$; and the other wavy line indicates the site of covalent attachment to a sulfur atom of a Ligand Unit; $A_O$ is an optional second subunit of A; [HE] is an optional Hydrolysis Enhancing Unit, which is a component provided by A or a first subunit thereof; BU is a Basic Unit; $R^{a2}$ is an optionally substituted $C_1$-$C_{12}$ alkyl group; and the dotted curved line indicates optional cyclization so that in the absence of said cyclization, wherein BU is an acyclic Basic Unit having a primary, secondary or tertiary amine functional group as the basic function group of the acyclic Basic Unit, or in the presence of said cyclization BU is a cyclized Basic Unit in which $R^{a2}$ and BU together with the carbon atom to which both are attached, define an optionally substituted spiro $C_3$-$C_{20}$ heterocyclo containing a skeletal basic nitrogen atom of a secondary or tertiary amine functional group as the basic function group of the cyclic Basic Unit, wherein the basic nitrogen atom of the acyclic Basic Unit or cyclic Basic Unit is optionally suitably protected by a nitrogen protecting group, dependent on the degree of substitution of the basic nitrogen atom, or is optionally protonated.

35. The Ligand Drug Conjugate composition of embodiment 34, wherein -$L_b$-A- in a plurality of drug linker moieties has the structure of:

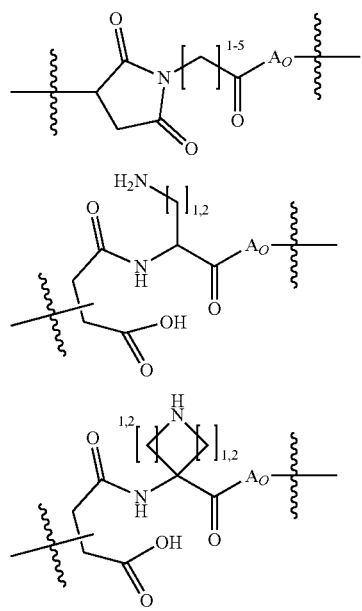

or a salt thereof.

36. The Ligand Drug Conjugate composition of embodiment 34 or 35, wherein $A_O$ is a second subunit of A that is present and is indicated as $A_2$, wherein $A_2$ is an amine-containing acid residue having the structure of formula 3a, formula 4a or formula 5a:

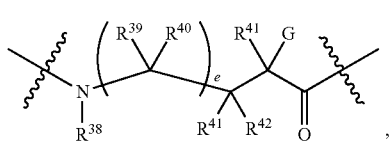

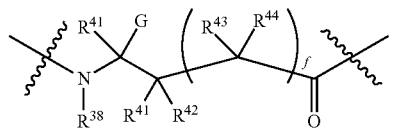

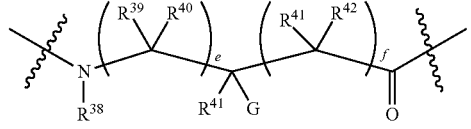

wherein the wavy line adjacent to the nitrogen atom indicates the site of covalent attachment to [HE] of the first subunit of A, wherein [HE] is —C(=O)— and the wavy line adjacent to the carbonyl carbon atom indicates the site of covalent attachment to $L_O$, wherein both attachments are through amide functional groups; subscripts e and f are independently 0 or 1; and G is hydrogen, —OH, —$OR^{PR}$, —$CO_2H$, —$CO_2R^{PR}$ or an optionally substituted $C_1$-$C_6$alkyl, wherein the optional substituent when present is selected from the group consisting of —OH, —$OR^{PR}$, —$CO_2H$, and —$CO_2R^{PR}$; and wherein $R^{PR}$ is a suitable protecting, or G is $N(R^{PR})(R^{PR})$ or an optionally substituted $C_1$-$C_6$ alkyl, wherein the optional substituent when present is $N(R^{PR})(R^{PR})$, wherein $R^{PR}$ are independently a protecting group or $R^{PR}$ together form a suitable protecting group, or G is —$N(R^{45})(R^{46})$, or an optionally substituted $C_1$-$C_6$ alkyl, wherein the optional substituent when present is —$N(R^{45})(R^{46})$, wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl;

$R^{38}$ is hydrogen or optionally substituted $C_1$-$C_6$ alkyl; and $R^{39}$-$R^{44}$ are independently selected from the group consisting of hydrogen, optionally substituted $C_1$-$C_6$ alkyl, optionally substituted $C_6$-$C_{20}$ aryl, and optionally substituted $C_5$-$C_2$ heteroaryl, or $R^{39}$, $R^{40}$ together with the carbon atom to which both are attached define a $C_3$-$C_6$ carbocyclo, and $R^{41}$-$R^{44}$ are as defined herein, or $R^{43}$, $R^{44}$ together with the carbon atom to which both are attached define a $C_3$-$C_6$ carbocyclo, and $R^{39}$-$R^{42}$ are as defined herein, or $R^{40}$ and $R^{41}$, or $R^{40}$ and $R^{43}$, or $R^{41}$ and $R^{43}$ to together with the carbon atom or heteroatom to which both are attached and the atoms intervening between those carbon atoms and/or heteroatoms define a $C_5$-$C_6$ carbocyclo or a $C_5$-$C_6$ heterocyclo, and $R^{39}$, $R^{44}$ and the remainder of $R^{40}$-$R^{43}$ are as defined herein, or $A_O$ is an α-amino or β-amino acid residue, wherein its amino nitrogen atom is covalently attached to the remainder of A, and its carboxylic acid carbonyl carbon is covalently attached to A', wherein both attachments are through amide functional groups.

37. The Ligand Drug Conjugate embodiment of claim 34 or 35, wherein $A_O$ is a second subunit of A that is present and is indicated as $A_2$ wherein $A_2$ is a β-amino acid residue having the structure of —$NHCH_2CH_2C$(=O)— or has the formula of -$L^P$(PEG)-, wherein $L^P$ is Parallel Connector Unit having the structure of a tri-functional amine-containing acid residue and PEG is a PEG Unit.

38. The Ligand Drug Conjugate embodiment of claim 37, wherein $A_2$ is -$L^P$(PEG)- having the structure of:

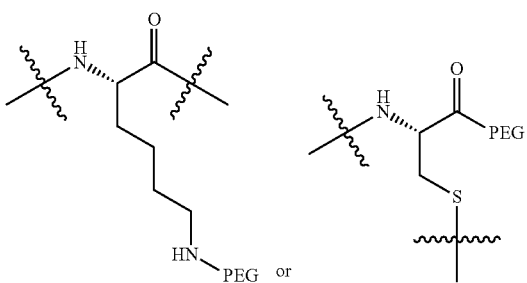

wherein the wavy line adjacent to the nitrogen atom indicates the site of covalent attachment to the first subunit of A and the wavy line to the carbonyl carbon atom or the sulfur atom indicates the site of covalent attachment to A' of $L_O$.

39. The Ligand Drug Conjugate composition of any one of embodiments 31 to 39, wherein A' is an alkylene diamine residue having the structure of formula 3b, formula 4b or formula 5b:

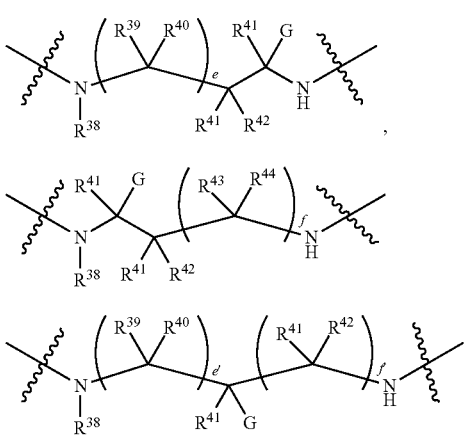

wherein subscript e and f range from 0 to 6; subscripts e' and f' range from 1 to 6; the wavy line next to the nitrogen atom of the amine residue to which $R^{38}$ is attached indicates the site of covalent attachment to a first optional Stretcher Unit that is present or to $A_O$, wherein $A_O$ is an optional second subunit of A that when present is indicated as $A_2$; and the wavy line adjacent to the nitrogen atom of the other amine residue indicates the site of covalent attachment to W, wherein both attachments are through amide functional groups;

G is hydrogen, —OH, —$OR^{PR}$, —$CO_2H$, —$CO_2R^{PR}$ or an optionally substituted $C_1$-$C_6$ alkyl, wherein the optional substituent when present is selected from the group consisting of —OH, —$OR^{PR}$, —$CO_2H$, and —$CO_2R^{PR}$; and wherein $R^{PR}$ is a suitable protecting, or G is $N(R^{PR})(R^{PR})$ or an optionally substituted $C_1$-$C_6$ alkyl, wherein the optional substituent when present is $N(R^{PR})(R^{PR})$, wherein $R^{PR}$ are independently a protecting group or $R^{PR}$ together form a suitable protecting group, or G is —$N(R^{45})(R^{46})$, or an optionally substituted $C_1$-$C_6$ alkyl, wherein the optional substituent when present is —$N(R^{45})(R^{46})$, wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl;

$R^{38}$ is hydrogen or optionally substituted $C_1$-$C_6$ alkyl; and $R^{39}$-$R^{44}$ are independently selected from the group consisting of hydrogen, optionally substituted $C_1$-$C_6$ alkyl, optionally substituted $C_6$-$C_{20}$ aryl, and optionally substituted $C_5$-$C_2$ heteroaryl, or $R^{39}$, $R^{40}$ together with the carbon atom to which both are attached define a $C_3$-$C_6$ carbocyclo, and $R^{41}$-$R^{44}$ are as defined herein, or $R^{43}$, $R^{44}$ together with the carbon atom to which both are attached define a $C_3$-$C_6$ carbocyclo, and $R^{39}$-$R^{42}$ are as defined herein, or $R^{40}$ and $R^{41}$, or $R^{40}$ and $R^{43}$, or $R^{41}$ and $R^{43}$ to together with the carbon atom or heteroatom to which both are attached and the atoms intervening between those carbon atoms and/or heteroatoms define a $C_5$-$C_6$ carbocyclo or a $C_5$-$C_6$ heterocyclo, and $R^{39}$, $R^{44}$ and the remainder of $R^{40}$-$R^{43}$ are as defined herein, or A' is an optionally substituted diamine residue, wherein one amino nitrogen atom is covalently attached to the remainder of A, and the other amino nitrogen atom is covalently attached to W, wherein both attachments are through amide functional groups.

40. The Ligand Drug Conjugate composition of embodiment 39, wherein -$A_2$-A'- has the structure of:

or a salt thereof, wherein the wavy line to the nitrogen atom of $L^P$(PEG) indicates the site of attachment to the remainder of A and the wavy line to the nitrogen atom of A' indicates the site of attachment to W, wherein both attachments are through amide functional groups.

41. The Ligand Drug Conjugate composition of any one of embodiments 31 to 40, wherein W is an amino acid sequence comprised of a dipeptide that provides a recognition site for a protease, wherein the dipeptide has the structure of:

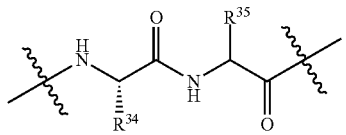

or a salt thereof, wherein the wavy line at the dipeptide N-terminal indicates the site of covalent attachment as an amide bond to an AF Drug Unit through its C-terminal component's carboxylic acid residue, wherein the amide bond is cleavable by the protease to release the Drug Unit as free drug; the wavy line at the dipeptide C-terminal indicates the site of covalent attachment to the remainder of the amino acid sequence or to A, or a subunit thereof, as when $A_O$ is present as $A_2$;

$R^{34}$ is hydrogen, or the side chain of a naturally occurring α-amino acid except proline, in particular —$CH_3$, —C($CH_3)_2$, —$CH_2COOH$, —$CH_2CH_2COOH$ or —$CH_2CH_2CH_2CH_2NH_2$; and $R^3$ is hydrogen, methyl, isopropyl, sec-butyl, benzyl, p-hydroxy-benzyl, —$CH_2OH$, —CH(OH)$CH_3$, —$CH_2CH_2SCH_3$, —$CH_2C$(=O)$NH_2$, —$CH_2COOH$, —$CH_2CH_2C$(=O)$NH_2$, —$CH_2CH_2COOH$, —$CH_2CH_2CH_2NHC$(=NH)$NH_2$, —$CH_2CH_2CH_2NH_2$, —$CH_2CH_2CH_2NH$—C(=O)$CH_3$, —$CH_2CH_2CH_2NH$—C(=O)H, —$CH_2CH_2CH_2CH_2NHC$(=NH)$NH_2$, —$CH_2CH_2CH_2CH_2NH_2$—, —$CH_2CH_2CH_2CH_2NH$—C(=O)$CH_3$, —$CH_2CH_2CH_2CH_2NH$—C(=O)H, —$CH_2CH_2CH_2NHC$(=O)$NH_2$, —$CH_2CH_2CH_2CH_2NHC$(=O)$NH_2$, —$CH_2CH_2CH$(OH)$CH_2NH_2$, 2-pyridylmethyl, 4-pyridylmethyl, phenyl or cyclohexyl, or $R^{35}$ has the structure of one of:

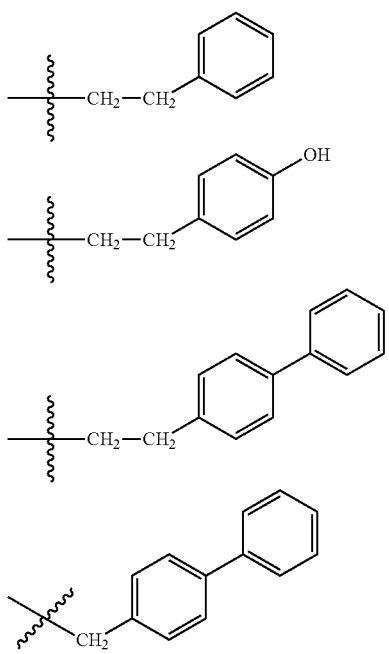

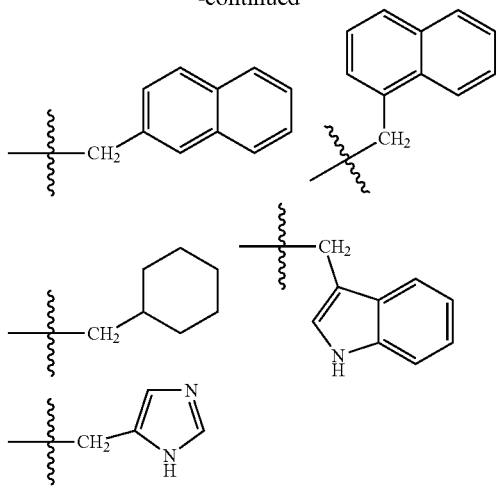

wherein the wavy line indicates the site of covalent attachment to the dipeptide backbone.

42. The Ligand Drug Conjugate composition of any one of embodiments 31 to 40, wherein W is a glutamic acid residue, an aspartic acid or a peptide sequence comprised of an N-terminal glutamic acid or aspartic acid residue covalently attached to the hydrophobic AF Drug Unit C-terminal component's carboxylic acid residue through the glutamic acid or aspartic acid α-amino nitrogen atom and to the remainder of the peptide sequence or to A', which is an optional second Stretcher Unit that is present, through the glutamic acid or aspartic acid α-carboxyl, wherein both attachments are through amide bonds, wherein the amide bond to the C-terminal component is cleavable by a protease to release the Drug Unit as free drug, and wherein A' is a $C_2$-$C_{12}$ alkylene diamine, in particular a $C_2$-$C_6$ or a $C_2$-$C_4$ alkylene diamine having a carboxylic acid side chain so that the nitrogen atom of one of its amines is covalently attached as an amide bond to the glutamic acid residue, and the nitrogen atom of the other amine is covalently attached A, or a subunit thereof, as when $A_O$ is present as $A_2$.

43. The Ligand Drug Conjugate composition of any one of embodiments 31 to 38, wherein -A'-W— has the structure of:

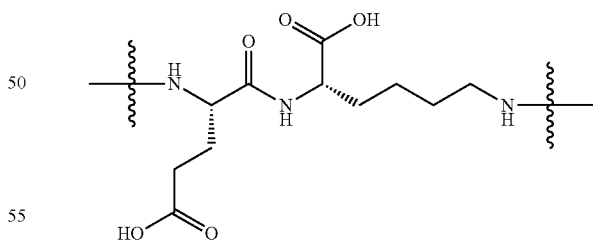

or a salt thereof, wherein the wavy line adjacent to the glutamic acid alpha-amino nitrogen atom indicates the site of covalent attachment as an amide bond to the hydrophobic AF Drug Unit through it C-terminal component's carboxylic acid residue, wherein the amide bond is cleavable by the protease to release the Drug Unit as free drug; and the wavy line adjacent the lysine epsilon amine nitrogen atom indicates the site of covalent attachment to a first optional Stretcher Unit (A) or subunit thereof that is present.

44. The Ligand Drug Conjugate composition of embodiment 30, wherein its drug linker moieties are represented by the structure(s) of:

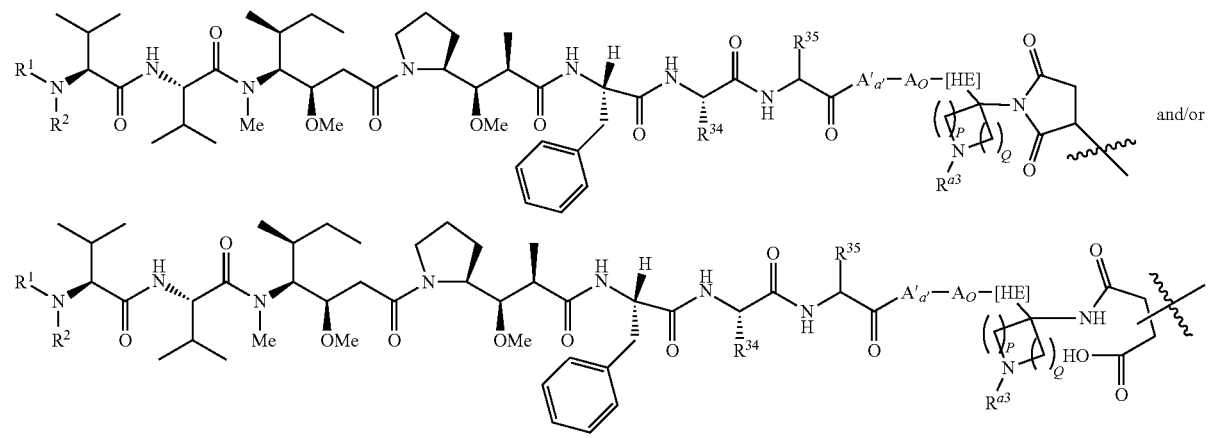

or a salt thereof, wherein HE is an optional Hydrolysis Enhancing Unit; $A_O$ is absent or is a second subunit of A; A' is a second optional Stretcher Unit; subscript a' is 0 or 1, indicating the absence or presence of A', respectively; subscript P is 1 or 2; subscript Q ranges from 1 to 6; $R^{a3}$ is —H, optionally substituted $C_1$-$C_6$ alkyl, optionally substituted —$C_1$-$C_4$ alkylene-($C_6$-$C_{10}$ aryl), or —$R^{PEG}$—O—($CH_2CH_2O)_{1-36}$—$R^{PEG2}$, wherein $R^{PEG1}$ is $C_1$-$C_4$ alkylene, $R^{PEG2}$ is —H or $C_1$-$C_4$ alkylene, wherein the basic nitrogen bonded to $R^{a3}$ is optionally protonated or is in a salt form,
$R^{34}$ is —$CH_3$, —$C(CH_3)_2$, —$CH_2COOH$, —$CH_2CH_2COOH$ or —$CH_2CH_2CH_2CH_2NH_2$; and $R^{35}$ is methyl, isopropyl, —$CH_2C(=O)NH_2$, —$CH_2COOH$, —$CH_2CH_2C(=O)NH_2$, —$CH_2CH_2COOH$, —$CH_2CH_2CH_2NHC(=NH)NH_2$, —$CH_2CH_2CH_2NH_2$, —$CH_2CH_2CH_2NH$—$C(=O)CH_3$, —$CH_2CH_2CH_2NH$—$C(=O)H$, —$CH_2CH_2CH_2CH_2NHC(=NH)NH_2$, —$CH_2CH_2CH_2CH_2NH_2$—, —$CH_2CH_2CH_2CH_2NH$—$C(=O)CH_3$, —$CH_2CH_2CH_2CH_2NH$—$C(=O)H$, —$CH_2CH_2CH_2NHC(=O)NH_2$, —$CH_2CH_2CH_2CH_2NHC(=O)NH_2$ or —$CH_2CH_2CH(OH)CH_2NH_2$;

$R^2$ is methyl; and $R^1$ is $C_1$-$C_9$ alkyl, optionally substituted by a $C_3$-$C_6$ carbocyclyl to provide a (carbocyclyl)-alkylene- of up to 9 total carbon atoms, or $R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in the (carbocyclyl)alkyl(ene) moieties of $R^1$ is between 4 and 10 and $R^1$ is not methyl, or $R^1$ is a first non-aromatic hydrophobic moiety; and $R^2$ is a second non-aromatic hydrophobic moiety, wherein the first and second hydrophobic moieties provide the hydrophobic AF compound characterized by a clogP value of between about 4.4 to about 7.2.

45. The Ligand Drug Conjugate composition of embodiment 30, wherein its drug linker moieties are represented by the structure(s) of:

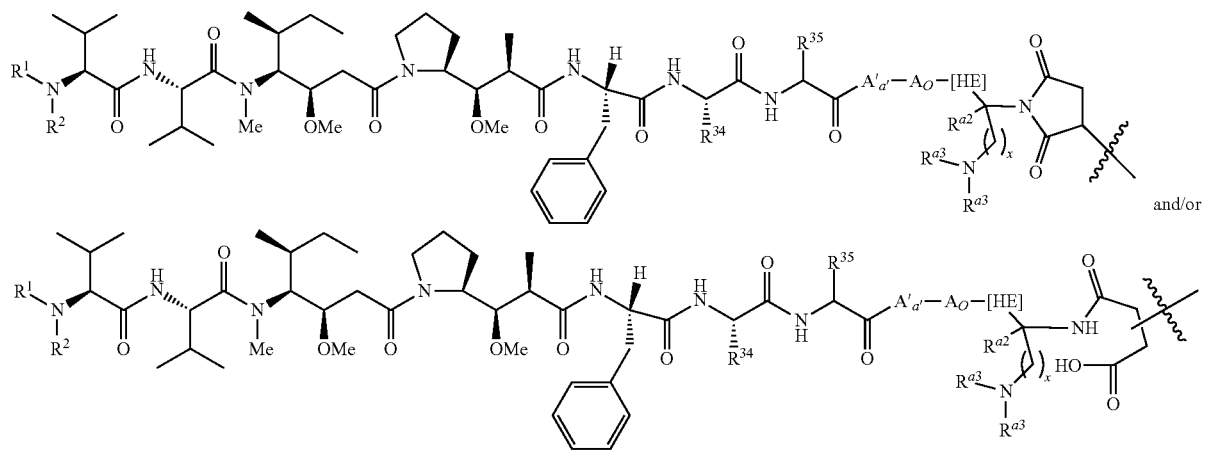

or a salt thereof, wherein HE is an optional Hydrolysis Enhancing Unit; $A_O$ is absent or is a second subunit of A; A' is a second optional Stretcher Unit; subscript a' is 0 or 1, indicating the absence or presence of A', respectively; subscript x is 1 or 2; $R^{a2}$ is hydrogen or —$CH_3$ or —$CH_2CH_3$; $R^{a3}$, at each instance, is independently hydrogen, —$CH_3$ or —$CH_2CH_3$, or both $R^a$ together with the nitrogen to which they are attached define an azetidinyl, pyrrolidinyl or piperidinyl heterocyclyl, in which a basic primary, secondary or tertiary amine so defined is optionally protonated as an acid addition salt form, $R^{34}$ is —$CH_3$, —$C(CH_3)_2$, —$CH_2COOH$, —$CH_2CH_2COOH$ or —$CH_2CH_2CH_2CH_2NH_2$; and $R^{35}$ is methyl, isopropyl, —$CH_2C(=O)NH_2$, —$CH_2COOH$, —$CH_2CH_2C(=O)NH_2$, —$CH_2CH_2COOH$, —$CH_2CH_2CH_2NHC(=NH)NH_2$, —$CH_2CH_2CH_2NH_2$, —$CH_2CH_2CH_2NH$—$C(=O)CH_3$, —$CH_2CH_2CH_2NH$—$C(=O)H$, —$CH_2CH_2CH_2CH_2NHC(=NH)NH_2$, —$CH_2CH_2CH_2CH_2NH_2$—, —$CH_2CH_2CH_2CH_2NH$—$C(=O)CH_3$, —$CH_2CH_2CH_2CH_2NH$—$C(=O)H$, —$CH_2CH_2CH_2NHC(=O)NH_2$, —$CH_2CH_2CH_2CH_2NHC(=O)NH_2$ or —$CH_2CH_2CH(OH)CH_2NH_2$;

$R^2$ is methyl; and $R^1$ is $C_1$-$C_9$ alkyl, optionally substituted by a $C_3$-$C_6$ carbocyclyl to provide a (carbocyclyl)-alkylene- of up to 9 total carbon atoms, or $R^1$ is —$(C_2$-$C_6$ alkylene)-X—$R^4$, wherein X is an amide or carbamate functional group and $R^4$ is $C_1$-$C_6$ alkyl, with the proviso that the total number of carbon atoms in the (carbocyclyl)alkyl(ene) moieties of $R^1$ is between 4 and 10 and $R^1$ is not methyl, or $R^1$ is a first non-aromatic hydrophobic moiety; and $R^2$ is a second non-aromatic hydrophobic moiety, wherein the first and second hydrophobic moieties provide the hydrophobic AF compound characterized by a clogP value of between about 4.4 to about 7.2.

46. The Ligand Drug Conjugate composition of embodiment 30, wherein a plurality of its drug linker moieties are represented by the structure(s) of:

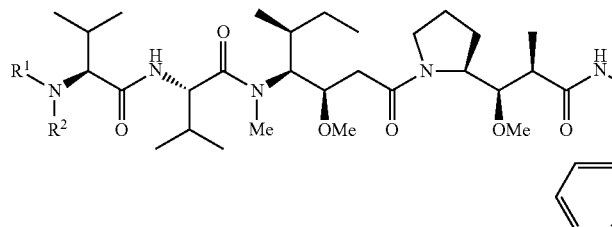
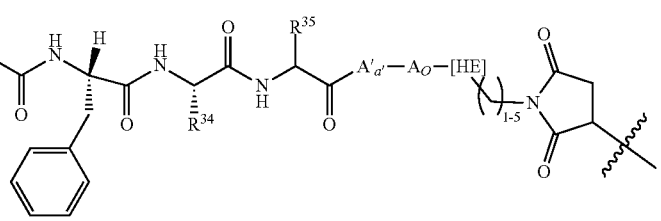

or a salt thereof, wherein HE is an optional Hydrolysis Enhancing Unit; $A_O$ is absent or is a second subunit of A; A' is a second optional Stretcher Unit; subscript a' is 0 or 1, indicating the absence or presence of A';

$R^{34}$ is —$CH_3$, —$C(CH_3)_2$, —$CH_2COOH$, —$CH_2CH_2COOH$ or —$CH_2CH_2CH_2CH_2NH_2$; and $R^{35}$ is methyl, isopropyl, —$CH_2C(=O)NH_2$, —$CH_2COOH$, —$CH_2CH_2C(=O)NH_2$, —$CH_2CH_2COOH$, —$CH_2CH_2CH_2NHC(=NH)NH_2$, —$CH_2CH_2CH_2NH_2$, —$CH_2CH_2CH_2NH$—$C(=O)CH_3$, —$CH_2CH_2CH_2NH$—$C(=O)H$, —$CH_2CH_2CH_2CH_2NHC(=NH)NH_2$, —$CH_2CH_2CH_2CH_2NH_2$—, —$CH_2CH_2CH_2CH_2NH$—$C(=O)CH_3$, —$CH_2CH_2CH_2CH_2NH$—$C(=O)H$, —$CH_2CH_2CH_2NHC(=O)NH_2$, —$CH_2CH_2CH_2CH_2NHC(=O)NH_2$ or —$CH_2CH_2CH(OH)CH_2NH_2$;

$R^2$ is methyl; and $R^1$ is $C_1$-$C_9$ alkyl, optionally substituted by a $C_3$-$C_6$ carbocyclyl to provide a (carbocyclyl)-alkylene- of up to 9 total carbon atoms, or $R^1$ is —$(C_2$-$C_6$ alkylene)-X—$R^4$, wherein X is an amide or carbamate functional group and $R^4$ is $C_1$-$C_6$ alkyl, with the proviso that the total number of carbon atoms in the (carbocyclyl)alkyl(ene) moieties of $R^1$ is between 4 and 10 and $R^1$ is not methyl, or $R^1$ is a first non-aromatic hydrophobic moiety; and $R^2$ is a second non-aromatic hydrophobic moiety, wherein the first and second hydrophobic moieties provide the hydrophobic AF compound characterized by a clogP value of between about 4.4 to about 7.2.

47. The Ligand Drug Conjugate composition of embodiment 44, wherein a plurality of its drug linker moieties is represented by the structure of:

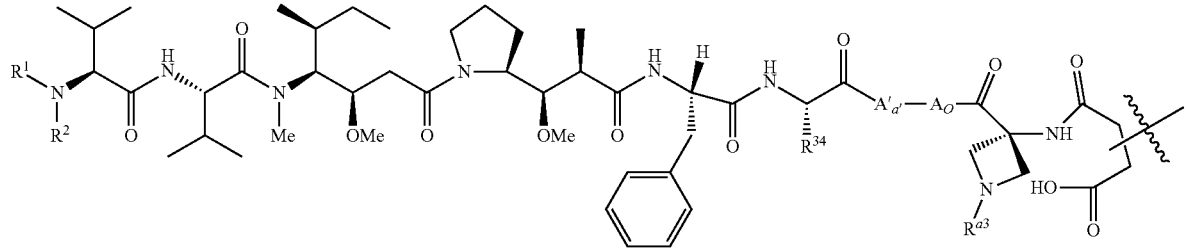

or a salt thereof, wherein $R^{a3}$ is hydrogen, —$CH_3$ or —$CH_2CH_3$, wherein the secondary or tertiary amine so defined is optionally protonated as an acid addition salt form; $A_O$ is a absent or is a second subunit of A having the structure of an α-amino acid or a β-amino acid residue; A' is a second optional Stretcher Unit that is present having the structure of an optionally substituted $C_2$-$C_6$ alkylene diamine residue, wherein one amino nitrogen atom is covalently attached to $A_O$, and the other amino nitrogen atom is covalently attached to the $R^{34}$-containing amino acid residue, wherein both attachments are through amide functional groups; $R^{34}$ is —$CH_2CO_2H$ or —$CH_2CH_2CO_2H$;

$R^2$ is methyl; and $R^1$ is $C_1$-$C_9$ alkyl, optionally substituted by a $C_3$-$C_6$ carbocyclyl to provide a (carbocyclyl)-alkylene- of up to 9 total carbon atoms, or $R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in the (carbocyclyl)alkyl(ene) moieties of $R^1$ is between 4 and 10 and $R^1$ is not methyl, or $R^1$ is a first non-aromatic hydrophobic moiety; and $R^2$ is a second non-aromatic hydrophobic moiety, wherein the first and second hydrophobic moieties provide the hydrophobic AF compound characterized by a clogP value of between about 4.4 to about 7.2.

48. The Ligand Drug Conjugate composition of embodiment 45, wherein a plurality of its drug linker moieties is represented by the structure of:

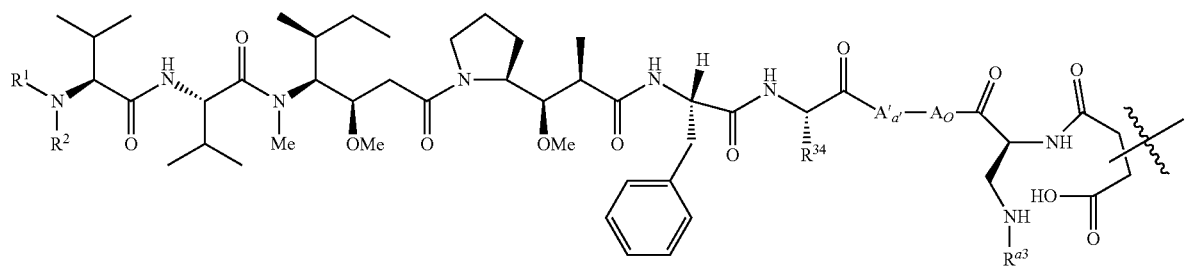

or a salt thereof, wherein $R^{a3}$ is hydrogen, —$CH_3$ or —$CH_2CH_3$, wherein the primary or secondary amine so defined is optionally protonated as an acid addition salt form; $A_O$ is absent or is a second subunit of A having the structure of an α-amino acid or a β-amino acid residue; A' is a second optional Stretcher Unit that is present having the structure of an optionally substituted $C_2$-$C_6$ alkylene diamine residue, wherein one amino nitrogen atom is covalently attached to $A_O$, and the other amino nitrogen atom is covalently attached to the $R^{34}$-containing amino acid residue, wherein both attachments are through amide functional groups; $R^{34}$ is —$CH_2CO_2H$ or —$CH_2CH_2CO_2H$;

$R^2$ is methyl; and $R^1$ is $C_1$-$C_9$ alkyl, optionally substituted by a $C_3$-$C_6$ carbocyclyl to provide a (carbocyclyl)-alkylene- of up to 9 total carbon atoms, or $R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in the (carbocyclyl)alkyl(ene) moieties of $R^1$ is between 4 and 10 and $R^1$ is not methyl, or $R^1$ is a first non-aromatic hydrophobic moiety; and $R^2$ is a second non-aromatic hydrophobic moiety, wherein the first and second hydrophobic moieties provide the hydrophobic AF compound characterized by a clogP value of between about 4.4 to about 7.2.

49. The Ligand Drug Conjugate composition of embodiment 46, wherein a plurality of its drug linker moieties is represented by the structure of:

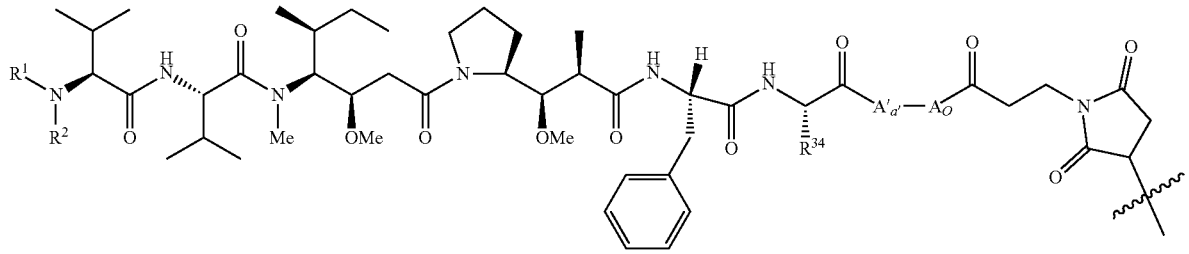

or a salt thereof, wherein $A_O$ is absent or is a second subunit of A having the structure of an α-amino acid or a β-amino acid residue; A' is a second optional Stretcher Unit that is present having the structure of an optionally substituted $C_2$-$C_6$ alkylene diamine residue, wherein one amino nitrogen atom is covalently attached to $A_O$, and the other amino nitrogen atom is covalently attached to the $R^{34}$-containing amino acid residue, wherein both attachments are through amide functional groups; $R^{34}$ is —$CH_2CO_2H$ or —$CH_2CH_2CO_2H$;

$R^2$ is methyl; and $R^1$ is $C_1$-$C_9$ alkyl, optionally substituted by a $C_3$-$C_6$ carbocyclyl to provide a (carbocyclyl)-alkylene- of up to 9 total carbon atoms, or $R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in the (carbocyclyl)alkyl(ene) moieties of $R^1$ is between 4 and 10 and $R^1$ is not methyl, or $R^1$ is a first non-aromatic hydrophobic moiety; and $R^2$ is a second non-aromatic hydrophobic moiety, wherein the first and second hydrophobic moieties provide the hydrophobic AF compound characterized by a clogP value of between about 4.4 to about 7.2.

50. The Ligand Drug Conjugate composition of embodiment 47, wherein a plurality of its drug linker moieties is represented by the structure of:

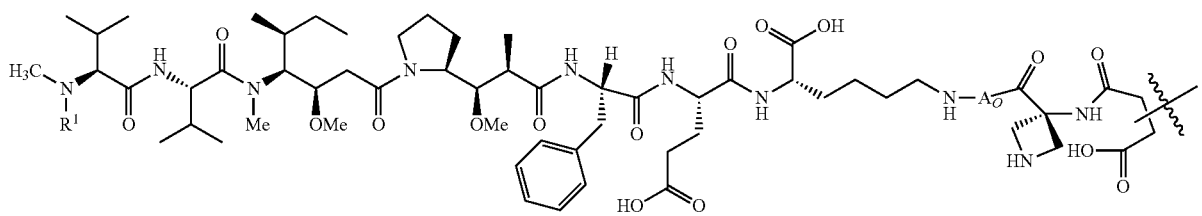

or a salt thereof.

51. The Ligand Drug Conjugate composition of claim 48, wherein a plurality of its drug linker moieties is represented by the structure of:

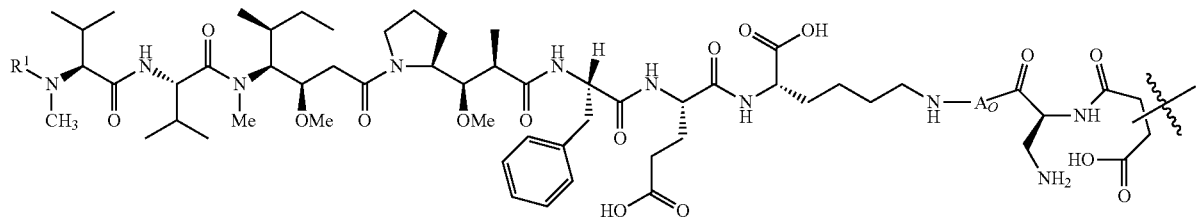

or a salt thereof.

52. The Ligand Drug Conjugate composition of embodiment 49, wherein a plurality of its drug linker moieties is represented by the structure of:

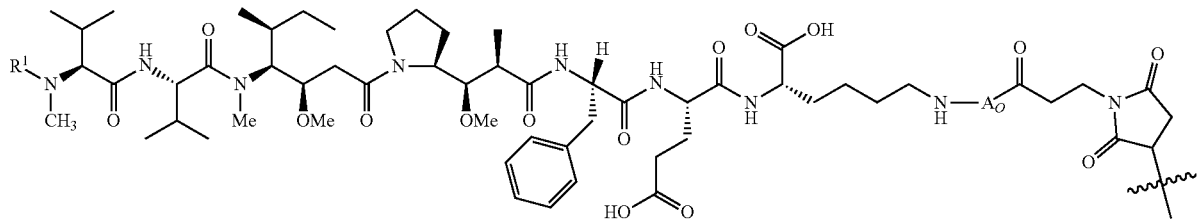

or a salt thereof.

53. The Ligand Drug Conjugate composition of any one of embodiments 45 to 52, wherein $R^1$ is —$CH_2CH_2CH_2CH_3$, —$CH_2CH_2CH_2CH_2CH_3$, $CH_2CH_2CH_2C(CH_3)_2$, —$CH_2CH_2CH_2CH_2N(CH_3)$—C(=O)—O-t-Bu, —$CH_2CH_2CH_2CH_2N(CH_3)$—C(=O)-t-Bu, —$CH_2CH_2CH_2N(CH_3)$—C(=O)—O-t-Bu, —$CH_2CH_2CH_2NH$—C(=O)—O-t-Bu, or has the structure of:

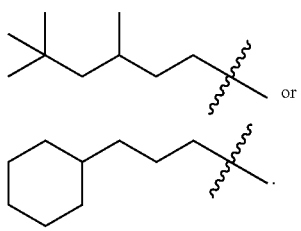

54. The Ligand Drug Conjugate composition of embodiment 30, wherein a plurality of its drug linker moieties has the structure of:

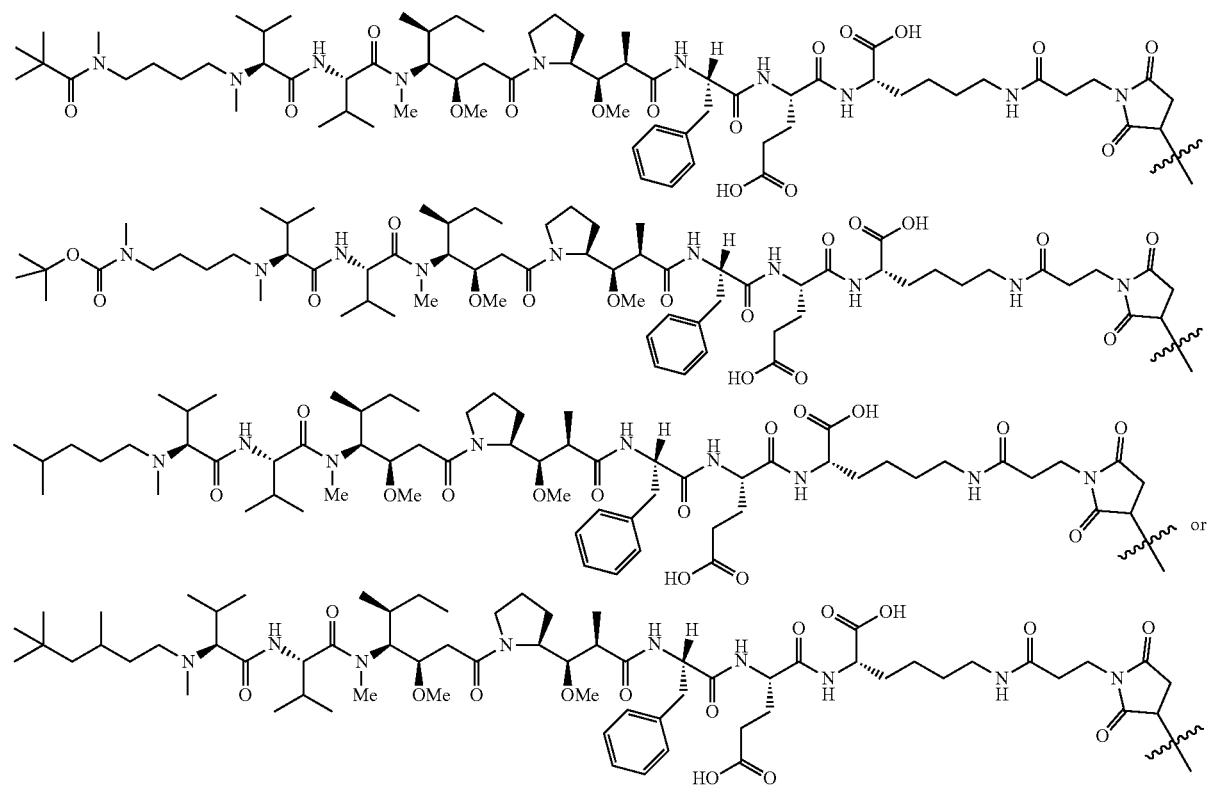

or a salt thereof.

55. The Ligand Drug Conjugate composition of any one of embodiments 30 to 54, wherein L is an antibody Ligand Unit of an intact antibody or an antigen-binding fragment thereof.

56. The Ligand Drug Conjugate composition of embodiment 55, wherein the antibody Ligand Unit is of an intact chimeric, humanized or human antibody.

57. The Ligand Drug Conjugate composition of any one of embodiments 30 to 56, wherein subscript p ranges from about 2 to about 12, or from about 2 to about 10, or from about 2 to about 8.

58. The Ligand Drug Conjugate composition of embodiment 57, wherein subscript p is about 2, about 4 or about 8.

59. The Ligand Drug Conjugate composition of any one of embodiments 55 to 58, wherein the antibody or fragment thereof is capable of selectively binding to a cancer cell antigen.

60. A pharmaceutically acceptable formulation, wherein the formulation comprises an effective amount of a Ligand Drug Conjugate composition of any one of claims 30 to 59 and at least one pharmaceutically acceptable excipient.

61. The pharmaceutically acceptable formulation of claim 60, wherein the formulation is a liquid suitable for lyophilization or administration to a subject in need thereof.

62. The pharmaceutically acceptable formulation of claim 61, wherein the formulation is a solid from lyophilization of the liquid formulation, wherein the at least one excipient of the solid formulation is a lyoprotectant.

63. A Drug Linker compound of Formula IA:

wherein $L_B'$ is an ligand covalent binding moiety precursor; A is a first optional Stretcher Unit; subscript a is 0 or 1 indicating the absence of presence of A, respectively; B is an optional Branching Unit; subscript b is 0 or 1, indicating the absence of presence of B, respectively; $L_O$ is an optional secondary linker moiety; subscript q is an integer ranging from 1 to 4; D is a hydrophobic AF Drug Unit having the structure of any one of claims 1 to 29 conjugated through its C-terminal component's carboxylic acid functional group.

64. The Drug Linker compound of embodiment 63, wherein $L_O$ is a secondary linker that is present and has the formula of:

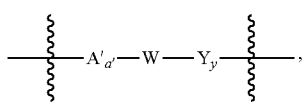

wherein the wavy line adjacent to Y indicates the site of covalent attachment of $L_O$ to the hydrophobic auristatin Drug Unit and the wavy line adjacent A' to indicates the site of covalent attachment of $L_O$ to the remainder of the drug linker moiety; A' is a second optional Stretcher Unit, subscript a' is 0 or 1, indicating the absence or presence of A', respectively; W is a peptide Cleavable Unit; Y is a peptide Spacer Unit; and subscript y is 0 or 1, indicating the absence or presence of Y, respectively.

65. The Drug Linker compound of embodiment 64, wherein the compound has the structure of:

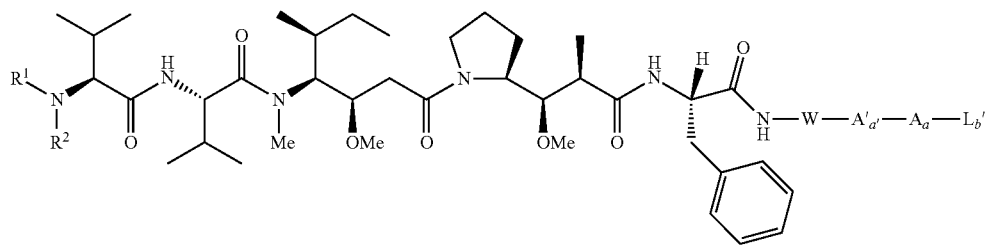

or a salt thereof, in particular a pharmaceutically acceptable salt, wherein $R^2$ is methyl; and $R^1$ is $C_3$-$C_9$ alkyl, optionally substituted by a $C_3$-$C_6$ carbocyclyl to provide a (carbocyclyl)-alkylene- of up to 9 total carbon atoms, or $R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in the (carbocyclyl)alkyl(ene) moiety of $R^1$ is between 4 and 10.

66. The Drug Linker compound of embodiment 65, wherein $L_b'$-A- has or is comprised of one of the structures of:

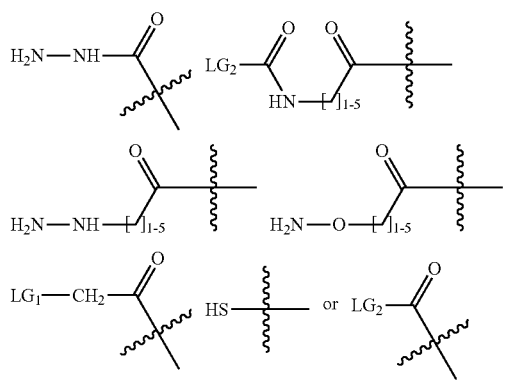

or a salt thereof, wherein $LG_1$ is a leaving group suitable for nucleophillic displacement by a targeting agent nucleophile; $LG_2$ is a leaving group suitable for amide bond formation to a targeting agent, or —OH to provide an activateable carboxylic acid suitable for amide bond formation to a targeting agent; and the wavy line indicates the site of covalent attachment to the remainder of the Drug Linker compound structure.

67. The Drug Linker compound of embodiment 65, wherein $L_b'$-A- has the structure of:

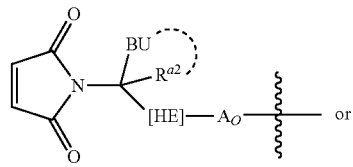

or

-continued

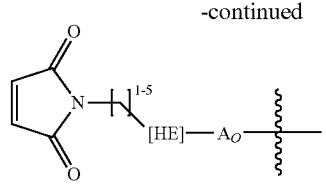

or a salt thereof, wherein the wavy line adjacent to $A_O$ indicates the site of covalent attachments to $L_O$; and the other wavy line indicates the site of covalent attachment to a sulfur atom of a Ligand Unit; $A_O$ is an optional second subunit of A; [HE] is an optional Hydrolysis Enhancing Unit, which is a component provided by A or a first subunit thereof; BU is a Basic Unit; $R^{a2}$ is an optionally substituted $C_1$-$C_{12}$ alkyl group; and the dotted curved line indicates optional cyclization so that in the absence of said cyclization, wherein BU is an acyclic Basic Unit having a primary, secondary or tertiary amine functional group as the basic function group of the acyclic Basic Unit, or in the presence of said cyclization BU is a cyclized Basic Unit in which $R^{a2}$ and BU together with the carbon atom to which both are attached, define an optionally substituted spiro $C_3$-$C_{20}$ heterocyclo containing a skeletal basic nitrogen atom of a secondary or tertiary amine functional group as the basic function group of the cyclic Basic Unit, wherein the basic nitrogen atom of the acyclic Basic Unit or cyclic Basic Unit is optionally suitably protected by a nitrogen protecting group, dependent on the degree of substitution of the basic nitrogen atom, or is optionally protonated as an acid addition salt.

68. The Drug Linker compound of embodiment 67, wherein $L_b'$-A- has the structure of:

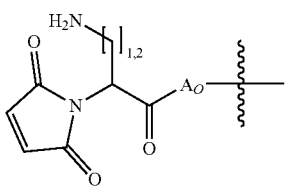

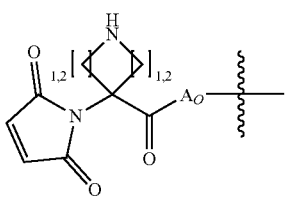

or a salt thereof, in particular as an acid addition salt, or wherein $L_b'$-A- has the structure of:

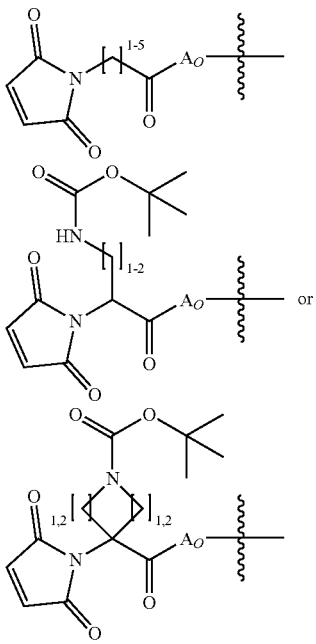

69. The Drug Linker compound of embodiment 67 or 68, wherein $A_O$ is a second subunit of A that is present and is indicated as $A_2$, wherein $A_2$ is an amine-containing acid residue having the structure of formula 3a, formula 4a or formula 5a:

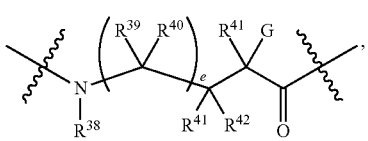

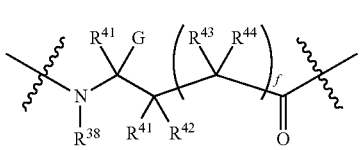

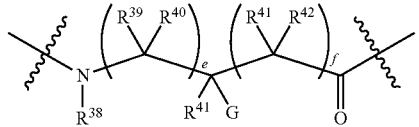

wherein the wavy line adjacent to the nitrogen atom indicates the site of covalent attachment to [HE] of the first subunit of A, wherein [HE] is —C(=O)— and the wavy line adjacent to the carbonyl carbon atom indicates the site of covalent attachment to $L_O$, wherein both attachments are through amide functional groups; subscripts e and f are independently 0 or 1; and G is hydrogen, —OH, —$OR^{PR}$, —$CO_2H$, —$CO_2R^{PR}$ or an optionally substituted $C_1$-$C_6$ alkyl, wherein the optional substituent when present is selected from the group consisting of —OH, —$OR^{PR}$, —$CO_2H$, and —$CO_2R^{PR}$; and wherein $R^{PR}$ is a suitable protecting, or G is $N(R^{PR})(R^{PR})$ or an optionally substituted $C_1$-$C_6$ alkyl, wherein the optional substituent when present is $N(R^{PR})(R^{PR})$, wherein $R^{PR}$ are independently a protecting group or $R^{PR}$ together form a suitable protecting group, or G is —$N(R^{45})(R^{46})$, or an optionally substituted $C_1$-$C_6$ alkyl, wherein the optional substituent when present is —$N(R^{45})(R^{46})$, wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl;

$R^{38}$ is hydrogen or optionally substituted $C_1$-$C_6$ alkyl; and $R^{39}$-$R^{44}$ are independently selected from the group consisting of hydrogen, optionally substituted $C_1$-$C_6$ alkyl, optionally substituted $C_6$-$C_{20}$ aryl, and optionally substituted $C_5$-$C_2$ heteroaryl, or $R^{39}$, $R^{40}$ together with the carbon atom to which both are attached define a $C_3$-$C_6$ carbocyclo, and $R^{41}$-$R^{44}$ are as defined herein, or $R^{43}$, $R^1$ together with the carbon atom to which both are attached define a $C_3$-$C_6$ carbocyclo, and $R^{39}$-$R^{42}$ are as defined herein, or $R^{40}$ and $R^{41}$, or $R^{40}$ and $R^{43}$, or $R^{41}$ and $R^{43}$ to together with the carbon atom or heteroatom to which both are attached and the atoms intervening between those carbon atoms and/or heteroatoms define a $C_5$-$C_6$ carbocyclo or a $C_5$-$C_6$ heterocyclo, and $R^{39}$, $R^{44}$ and the remainder of $R^{40}$-$R^{43}$ are as defined herein, or $A_O$ is an α-amino or 3-amino acid residue, wherein its amino nitrogen atom is covalently attached to the remainder of A, and its carboxylic acid carbonyl carbon is covalently attached to A', wherein both attachments are through amide functional groups.

70. The Drug Linker compound of embodiment 67 or 68, wherein $A_O$ is a second subunit of A that is present and is indicated as $A_2$ wherein $A_2$ is a β-amino acid residue having the structure of —$NHCH_2CH_2C(=O)$— or has the formula of -$L^P$(PEG)-, wherein $L^P$ is Parallel Connector Unit having the structure of a tri-functional amine-containing acid residue and PEG is a PEG Unit.

71. The Drug Linker compound of embodiment 70, wherein $A_2$ is -$L^P$(PEG)- having the structure of:

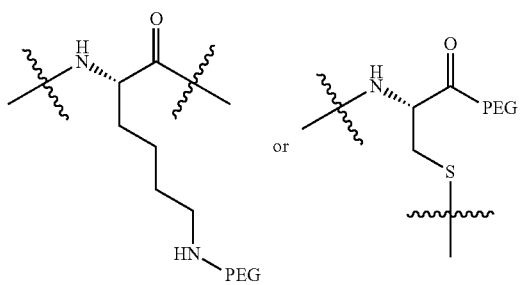

wherein the wavy line adjacent to the nitrogen atom indicates the site of covalent attachment to the first subunit of A and the wavy line to the carbonyl carbon atom or the sulfur atom indicates the site of covalent attachment to A' of $L_O$.

72. The Drug Linker compound of any one of embodiments 64 to 71, wherein A' is an alkylene diamine residue having the structure of formula 3b, formula 4b or formula 5b:

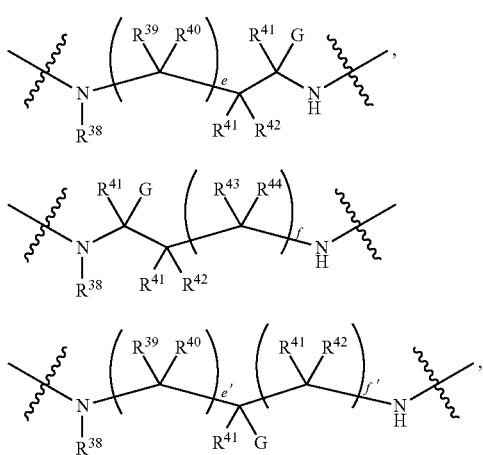

wherein subscript e and f range from 0 to 6; subscripts e' and f' range from 1 to 6; the wavy line next to the nitrogen atom of the amine residue to which $R^{38}$ is attached indicates the site of covalent attachment to a first optional Stretcher Unit that is present or to $A_O$, wherein $A_O$ is an optional second subunit of A that when present is indicated as $A_2$; the wavy line adjacent to the nitrogen atom of the other amine residue indicates the site of covalent attachment to W, wherein both attachments are through amide functional groups;

G is hydrogen, —OH, —$OR^{PR}$, —$CO_2H$, —$CO_2R^{PR}$ or an optionally substituted $C_1$-$C_6$ alkyl, wherein the optional substituent when present is selected from the group consisting of —OH, —$OR^{PR}$, —$CO_2H$, and —$CO_2R^{PR}$; and wherein $R^{PR}$ is a suitable protecting, or G is $N(R^{PR})(R^{PR})$ or an optionally substituted $C_1$-$C_6$ alkyl, wherein the optional substituent when present is $N(R^{PR})(R^{PR})$, wherein $R^{PR}$ are independently a protecting group or $R^{PR}$ together form a suitable protecting group, or G is —$N(R^{45})(R^{46})$, or an optionally substituted $C_1$-$C_6$ alkyl, wherein the optional substituent when present is —$N(R^{45})(R^{46})$, wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl;

$R^{38}$ is hydrogen or optionally substituted $C_1$-$C_6$ alkyl; and $R^{39}$-$R^{44}$ are independently selected from the group consisting of hydrogen, optionally substituted $C_1$-$C_6$ alkyl, optionally substituted $C_6$-$C_{20}$ aryl, and optionally substituted $C_5$-$C_{20}$ heteroaryl, or $R^{39}$, $R^{40}$ together with the carbon atom to which both are attached define a $C_3$-$C_6$ carbocyclo, and $R^{41}$-$R^{44}$ are as defined herein, or $R^{43}$, $R^{44}$ together with the carbon atom to which both are attached define a $C_3$-$C_6$ carbocyclo, and $R^{39}$-$R^{42}$ are as defined herein, or $R^{40}$ and $R^{41}$, or $R^{40}$ and $R^{43}$, or $R^{41}$ and $R^{43}$ to together with the carbon atom or heteroatom to which both are attached and the atoms intervening between those carbon atoms and/or heteroatoms define a $C_5$-$C_6$ carbocyclo or a $C_5$-$C_6$ heterocyclo, and $R^{39}$, $R^{44}$ and the remainder of $R^{40}$-$R^{43}$ are as defined herein, or A' is an optionally substituted diamine residue, wherein one amino nitrogen atom is covalently attached to the remainder of A, and the other amino nitrogen atom is covalently attached to W, wherein both attachments are through amide functional groups.

73. The Drug Linker compound of embodiments 71, wherein -$A_2$-A'- has the structure of:

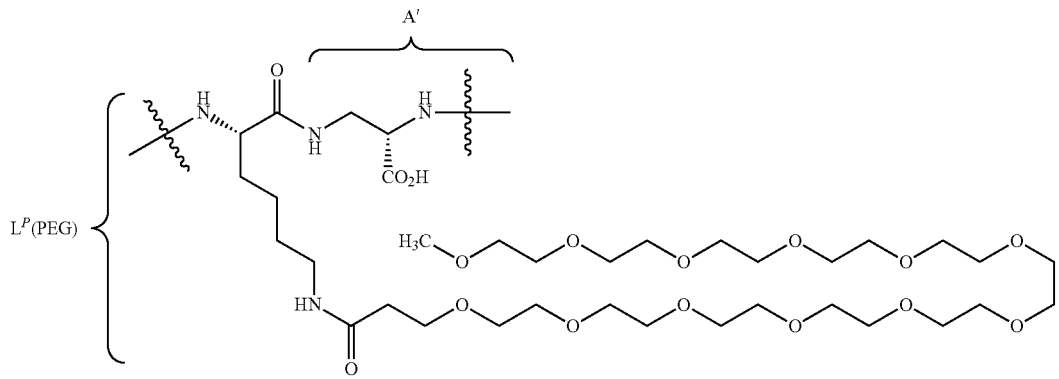

or a salt thereof, wherein the wavy line to the nitrogen atom of $L^P$(PEG) indicates the site of attachment to the remainder of A and the wavy line to the nitrogen atom of A' indicates the site of attachment to W, wherein both attachments are through amide functional groups.

74. The Drug Linker compound of any one of embodiments 64 to 73, wherein W is an amino acid sequence comprised of a dipeptide that provides a recognition site for a protease, wherein the dipeptide has the structure of:

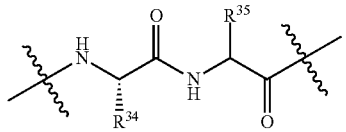

or a salt thereof, wherein the wavy line at the dipeptide N-terminal indicates the site of covalent attachment as an amide bond to an AF Drug Unit through its C-terminal component's carboxylic acid residue, wherein the amide bond is cleavable by the protease to release the Drug Unit as free drug; the wavy line at the dipeptide C-terminal indicates the site of covalent attachment to the remainder of the amino acid sequence or to A, or a subunit thereof, as when $A_O$ is present as $A_2$;

$R^{34}$ is hydrogen, or the side chain of a naturally occurring α-amino acid except proline, in particular —CH$_3$, —C(CH$_3$)$_2$, —CH$_2$COOH, —CH$_2$CH$_2$COOH or —CH$_2$CH$_2$CH$_2$CH$_2$NH$_2$—; and $R^3$ is hydrogen, methyl, isopropyl, sec-butyl, benzyl, p-hydroxy-benzyl, —CH$_2$OH, —CH(OH)CH$_3$, —CH$_2$CH$_2$SCH$_3$, —CH$_2$C(=O)NH$_2$, —CH$_2$COOH, —CH$_2$CH$_2$C(=O)NH$_2$, —CH$_2$CH$_2$COOH, —CH$_2$CH$_2$CH$_2$NHC(=NH)NH$_2$, —CH$_2$CH$_2$CH$_2$NH$_2$, —CH$_2$CH$_2$CH$_2$NH—C(=O)CH$_3$, —CH$_2$CH$_2$CH$_2$NH—C(=O)H, —CH$_2$CH$_2$CH$_2$CH$_2$NHC(=NH)NH$_2$, —CH$_2$CH$_2$CH$_2$CH$_2$NH$_2$, —CH$_2$CH$_2$CH$_2$CH$_2$NH—C(=O)CH$_3$, —CH$_2$CH$_2$CH$_2$CH$_2$NH—C(=O)H, —CH$_2$CH$_2$CH$_2$NHC(=O)NH$_2$, —CH$_2$CH$_2$CH$_2$CH$_2$NHC(=O)NH$_2$, —CH$_2$CH$_2$CH(OH)CH$_2$NH$_2$, 2-pyridylmethyl, 4-pyridylmethyl, phenyl or cyclohexyl, or $R^{35}$ has the structure of one of:

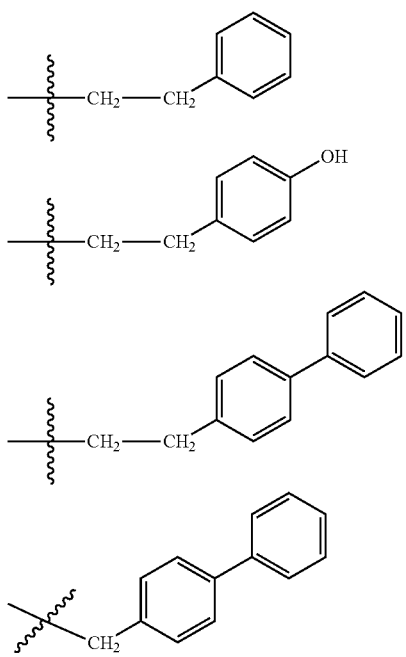

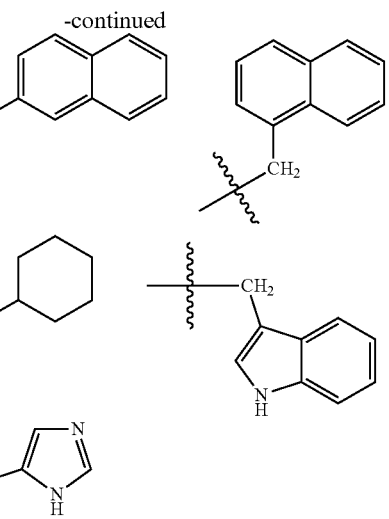

wherein the wavy line indicates the site of covalent attachment to the dipeptide backbone.

75. The Drug Linker compound of any one of embodiments 64 to 73, wherein W is a glutamic acid residue, an aspartic acid or a peptide sequence comprised of an N-terminal glutamic acid or aspartic acid residue covalently attached to the hydrophobic AF Drug Unit C-terminal component's carboxylic acid residue through the glutamic acid or aspartic acid α-amino nitrogen atom and to the remainder of the peptide sequence or to A', which is an optional second Stretcher Unit that is present, through the glutamic acid or aspartic acid α-carboxyl, wherein both attachments are through amide bonds, wherein the amide bond to the C-terminal component is cleavable by a protease to release the Drug Unit as free drug, and wherein A' is diamine having a carboxylic acid side chain so that the nitrogen atom of one of its amines is covalently attached as an amide bond to the glutamic acid residue, and the nitrogen atom of the other amine is covalently attached A, or a subunit thereof, as when $A_O$ is present as $A_2$.

76. The Drug Linker compound any one of embodiments 64 to 70, wherein -A'-W— has the structure of:

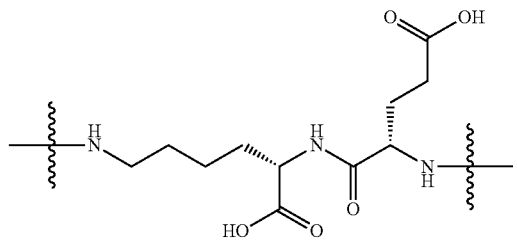 [SMILES: *NCCCC[C@H](NC(=O)[C@H](CCC(=O)O)N*)C(=O)O]

or a salt thereof, wherein the wavy line adjacent to the glutamic acid alpha-amino nitrogen atom indicates the site of covalent attachment as an amide bond to the hydrophobic AF Drug Unit through its C-terminal component's carboxylic acid residue, wherein the amide bond is cleavable by the protease to release the Drug Unit as free drug; and the wavy line adjacent the lysine epsilon amine nitrogen atom indicates the site of covalent attachment to a first optional Stretcher Unit (A) or subunit thereof that is present.

77. The Drug Linker compound of embodiment 63, wherein the compound has the structure of:

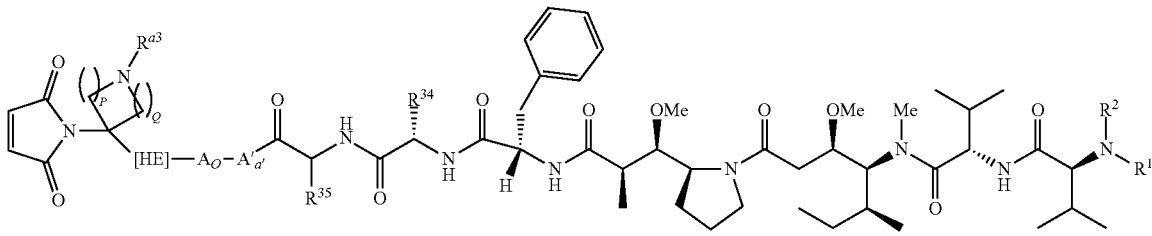

or a salt thereof, wherein HE is an optional Hydrolysis Enhancing Unit; $A_O$ is absent or is a second subunit of A; A' is a second optional Stretcher Unit; subscript a' is 0 or 1, indicating the absence or presence of A', respectively; subscript P is 1 or 2; subscript Q ranges from 1 to 6; R' is —H, optionally substituted $C_1$-$C_6$ alkyl, optionally substituted —$C_1$-$C_4$ alkylene-($C_6$-$C_{10}$ aryl), or —$R^{PEG1}$—O—$(CH_2CH_2O)_{1-36}$-$R^{PEG2}$, wherein $R^{PEG1}$ is $C_1$-$C_4$ alkylene, $R^{PEG2}$ is —H or $C_1$-$C_4$ alkylene, wherein the basic nitrogen bonded to $R^{a3}$ is optionally protonated as an acid addition salt or is optionally protected by an acid-labile protecting group, $R^{34}$ is —$CH_3$, —$C(CH_3)_2$, —$CH_2COOH$, —$CH_2CH_2COOH$ or —$CH_2CH_2CH_2CH_2NH_2$; and $R^{35}$ is methyl, isopropyl, —$CH_2C(=O)NH_2$, —$CH_2COOH$, —$CH_2CH_2C(=O)NH_2$, —$CH_2CH_2COOH$, —$CH_2CH_2CH_2NHC(=NH)NH_2$, —$CH_2CH_2CH_2NH_2$, —$CH_2CH_2CH_2NH$—$C(=O)CH_3$, —$CH_2CH_2CH_2NH$—$C(=O)H$, —$CH_2CH_2CH_2CH_2NHC(=NH)NH_2$, —$CH_2CH_2CH_2CH_2NH_2$—, —$CH_2CH_2CH_2CH_2NH$—$C(=O)CH_3$, —$CH_2CH_2CH_2CH_2NH$—$C(=O)H$, —$CH_2CH_2CH_2NHC(=O)NH_2$, —$CH_2CH_2CH_2CH_2NHC(=O)NH_2$ or —$CH_2CH_2CH(OH)CH_2NH_2$;

$R^2$ is methyl; and $R^1$ is $C_1$-$C_9$ alkyl, optionally substituted by a $C_3$-$C_6$ carbocyclyl to provide a (carbocyclyl)-alkylene- of up to 9 total carbon atoms, or $R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in the (carbocyclyl)alkyl(ene) moieties of $R^1$ is between 4 and 10 and $R^1$ is not methyl, or $R^1$ is a first non-aromatic hydrophobic moiety; and $R^2$ is a second non-aromatic hydrophobic moiety, wherein the first and second hydrophobic moieties provide the hydrophobic AF compound characterized by a clogP value of between about 4.4 to about 7.2.

78. The Drug Linker compound of embodiment 63, wherein the compound has the structure of:

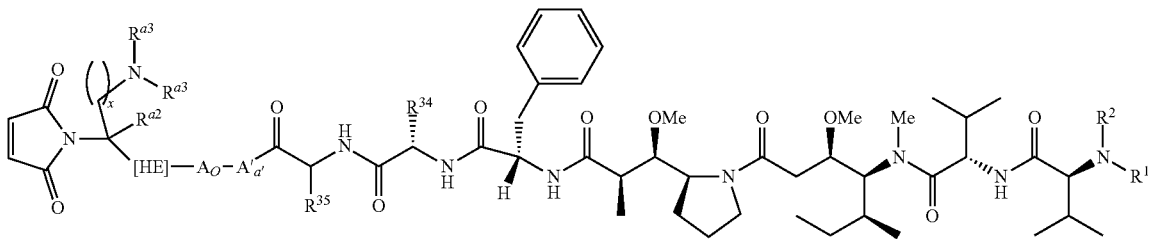

or a salt thereof, wherein HE is an optional Hydrolysis Enhancing Unit; $A_O$ is absent or is a second subunit of A; A' is a second optional Stretcher Unit; subscript a' is 0 or 1, indicating the absence or presence of A', respectively; subscript x is 1 or 2; $R^{a2}$ is hydrogen or —$CH_3$ or —$CH_2CH_3$; $R^a$, at each instance, is independently hydrogen, —$CH_3$ or —$CH_2CH_3$, or both $R^a$ together with the nitrogen to which they are attached define an azetidinyl, pyrrolidinyl or piperidinyl heterocyclyl, in which the basic primary, secondary or tertiary amine so defined is optionally protonated as an acid addition salt form, or in which the basic primary or secondary amine is optionally protected by an acid-labile protecting group;

$R^{34}$ is —$CH_3$, —$C(CH_3)_2$, —$CH_2COOH$, —$CH_2CH_2COOH$ or —$CH_2CH_2CH_2CH_2NH_2$; and $R^{35}$ is methyl, isopropyl, —$CH_2C(=O)NH_2$, —$CH_2COOH$, —$CH_2CH_2C(=O)NH_2$, —$CH_2CH_2COOH$, —$CH_2CH_2CH_2NHC(=NH)NH_2$, —$CH_2CH_2CH_2NH_2$, —$CH_2CH_2CH_2NH$—$C(=O)CH_3$, —$CH_2CH_2CH_2NH$—$C(=O)H$, —$CH_2CH_2CH_2CH_2NHC(=NH)NH_2$, —$CH_2CH_2CH_2CH_2NH_2$—, —$CH_2CH_2CH_2CH_2NH$—$C(=O)CH_3$, —$CH_2CH_2CH_2CH_2NH$—$C(=O)H$, —$CH_2CH_2CH_2NHC(=O)NH_2$, —$CH_2CH_2CH_2CH_2NHC(=O)NH_2$ or —$CH_2CH_2CH(OH)CH_2NH_2$;

$R^2$ is methyl; and $R^1$ is $C_1$-$C_9$ alkyl, optionally substituted by a $C_3$-$C_6$ carbocyclyl to provide a (carbocyclyl)-alkylene- of up to 9 total carbon atoms, or $R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in the (carbocyclyl)alkyl(ene) moieties of $R^1$ is between 4 and 10 and $R^1$ is not methyl, or $R^1$ is a first non-aromatic hydrophobic moiety; and $R^2$ is a second non-aromatic hydrophobic moiety, wherein the first and second hydrophobic moieties provide the hydrophobic AF compound characterized by a clogP value of between about 4.4 to about 7.2.

79. The Drug Linker compound of embodiment 63, wherein the compound has the structure of:

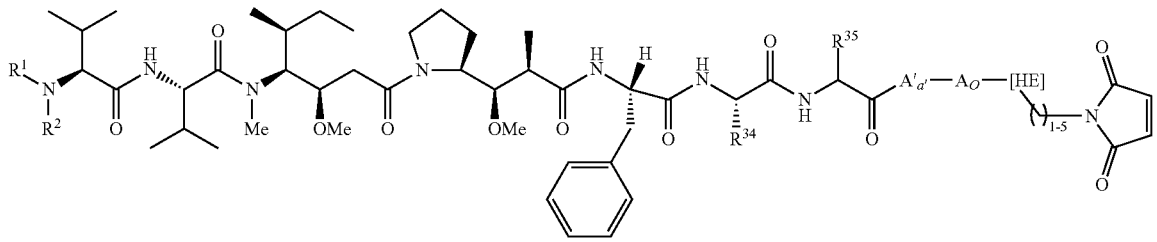

or a salt thereof, wherein HE is an optional Hydrolysis Enhancing Unit; $A_O$ is absent or is a second subunit of A; A' is a second optional Stretcher Unit; subscript a' is 0 or 1, indicating the absence or presence of A';
$R^{34}$ is —$CH_3$, —$C(CH_3)_2$, —$CH_2COOH$, —$CH_2CH_2COOH$, or —$CH_2CH_2CH_2CH_2NH_2$; and $R^{35}$ is methyl, isopropyl, —$CH_2C(=O)NH_2$, —$CH_2COOH$, —$CH_2CH_2C(=O)NH_2$, —$CH_2CH_2COOH$, —$CH_2CH_2CH_2NHC(=NH)NH_2$, —$CH_2CH_2CH_2NH_2$, —$CH_2CH_2CH_2NH$—$C(=O)$$CH_3$, —$CH_2CH_2CH_2NH$—$C(=O)H$, —$CH_2CH_2CH_2CH_2NHC(=NH)NH_2$, —$CH_2CH_2CH_2CH_2NH_2$—, —$CH_2CH_2CH_2CH_2NH$—$C(=O)CH_3$, —$CH_2CH_2CH_2CH_2NH$—$C(=O)H$, —$CH_2CH_2CH_2NHC(=O)NH_2$, —$CH_2CH_2CH_2CH_2NHC(=O)NH_2$ or —$CH_2CH_2CH(OH)CH_2NH_2$;

$R^2$ is methyl; and $R^1$ is $C_1$-$C_9$ alkyl, optionally substituted by a $C_3$-$C_6$ carbocyclyl to provide a (carbocyclyl)-alkylene- of up to 9 total carbon atoms, or $R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in the (carbocyclyl)alkyl(ene) moieties of $R^1$ is between 4 and 10 and $R^1$ is not methyl, or $R^1$ is a first non-aromatic hydrophobic moiety; and $R^2$ is a second non-aromatic hydrophobic moiety, wherein the first and second hydrophobic moieties provide the hydrophobic AF compound characterized by a clogP value of between about 4.4 to about 7.2.

80. The Drug Linker compound of embodiment 77, wherein the compound has the structure of:

or a salt thereof, wherein $R^{a3}$ is hydrogen, —$CH_3$ or —$CH_2CH_3$, wherein the secondary or tertiary amine so defined is optionally protonated as an acid addition salt form, or wherein the secondary amine so defined is optionally protected by an acid-labile protecting group; $A_O$ is a absent or is a second subunit of A having the structure of an α-amino acid or a β-amino acid residue; A' is a second optional Stretcher Unit that is present having the structure of an optionally substituted $C_2$-$C_6$ alkylene diamine residue, wherein one amino nitrogen atom is covalently attached to $A_O$, and the other amino nitrogen atom is covalently attached to the $R^{34}$-containing amino acid residue, wherein both attachments are through amide functional groups; $R^{34}$ is —$CH_2CO_2H$ or —$CH_2CH_2CO_2H$;

$R^2$ is methyl; and $R^1$ is $C_1$-$C_9$ alkyl, optionally substituted by a $C_3$-$C_6$ carbocyclyl to provide a (carbocyclyl)-alkylene- of up to 9 total carbon atoms, or $R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in the (carbocyclyl)-alkyl(ene) moieties of $R^1$ is between 4 and 10 and $R^1$ is not methyl, or $R^1$ is a first non-aromatic hydrophobic moiety; and $R^2$ is a second non-aromatic hydrophobic moiety, wherein the first and second hydrophobic moieties provide the hydrophobic AF compound characterized by a clogP value of between about 4.4 to about 7.2.

81. The Drug Linker compound of embodiment 78, wherein the compound has the structure of:

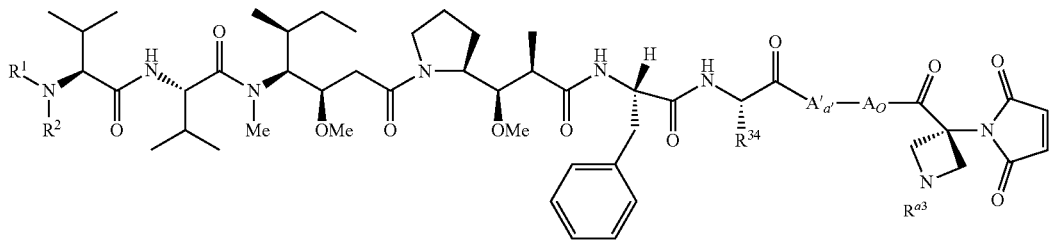

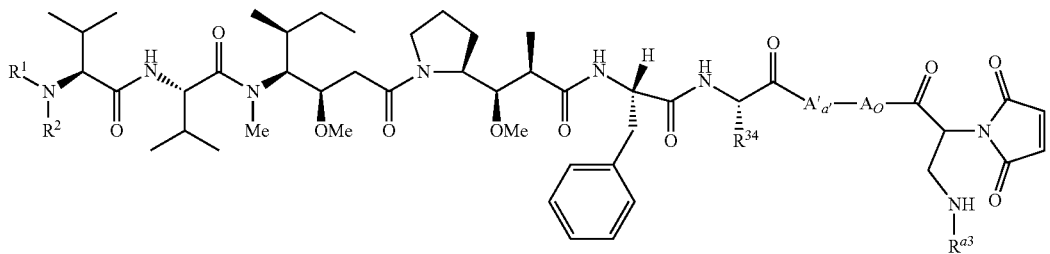

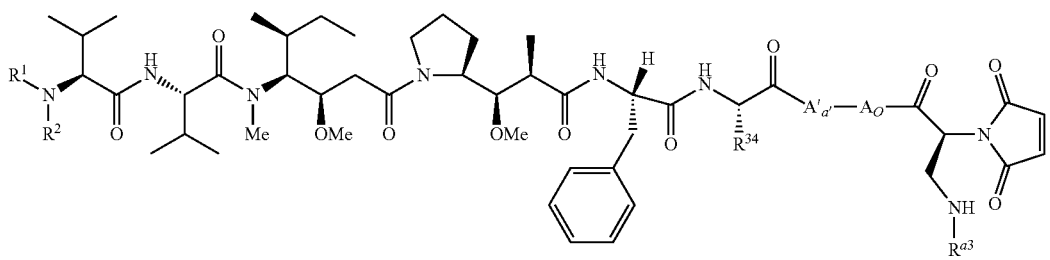

or a salt thereof, wherein $R^{a3}$ is hydrogen, —$CH_3$ or —$CH_2CH_3$, wherein the primary or secondary amine so defined is optionally protonated as an acid addition salt form or optionally protected by an acid-labile protecting group; $A_O$ is absent or is a second subunit of A having the structure of an α-amino acid or a β-amino acid residue; A' is a second optional Stretcher Unit that is present having the structure of an optionally substituted $C_2$-$C_6$ alkylene diamine residue, wherein one amino nitrogen atom is covalently attached to $A_O$, and the other amino nitrogen atom is covalently attached to the $R^{34}$-containing amino acid residue, wherein both attachments are through amide functional groups; $R^{34}$ is —$CH_2CO_2H$ or —$CH_2CH_2CO_2H$;

$R^2$ is methyl; and $R^1$ is $C_1$-$C_9$ alkyl, optionally substituted by a $C_3$-$C_6$ carbocyclyl to provide a (carbocyclyl)-alkylene- of up to 9 total carbon atoms, or $R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in the (carbocyclyl)alkyl(ene) moieties of $R^1$ is between 4 and 10 and $R^1$ is not methyl, or $R^1$ is a first non-aromatic hydrophobic moiety; and $R^2$ is a second non-aromatic hydrophobic moiety, wherein the first and second hydrophobic moieties provide the hydrophobic AF compound characterized by a clogP value of between about 4.4 to about 7.2.

82. The Drug Linker compound of embodiment 79, wherein the compound has the structure of:

or a salt thereof, wherein $A_O$ is absent or is a second subunit of A having the structure of an α-amino acid or a β-amino acid residue; A' is a second optional Stretcher Unit that is present having the structure of an optionally substituted $C_2$-$C_6$ alkylene diamine residue, wherein one amino nitrogen atom is covalently attached to $A_O$, and the other amino nitrogen atom is covalently attached to the $R^{34}$-containing amino acid residue, wherein both attachments are through amide functional groups; $R^{34}$ is —$CH_2CO_2H$ or —$CH_2CH_2CO_2H$; $R^2$ is methyl; and $R^1$ is $C_1$-$C_9$ alkyl, optionally substituted by a $C_3$-$C_6$ carbocyclyl to provide a (carbocyclyl)-alkylene- of up to 9 total carbon atoms, or $R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in the (carbocyclyl)alkyl (ene) moieties of $R^1$ is between 4 and 10 and $R^1$ is not methyl, or $R^1$ is a first non-aromatic hydrophobic moiety; and $R^2$ is a second non-aromatic hydrophobic moiety, wherein the first and second hydrophobic moieties provide the hydrophobic AF compound characterized by a clogP value of between about 4.4 to about 7.2.

83. The Drug Linker compound of embodiment 80, wherein the compound has the structure of:

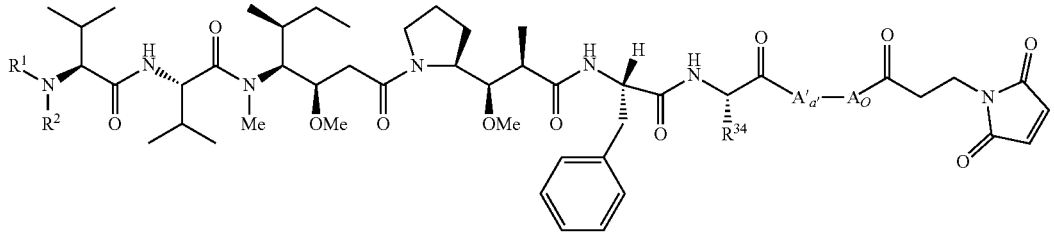

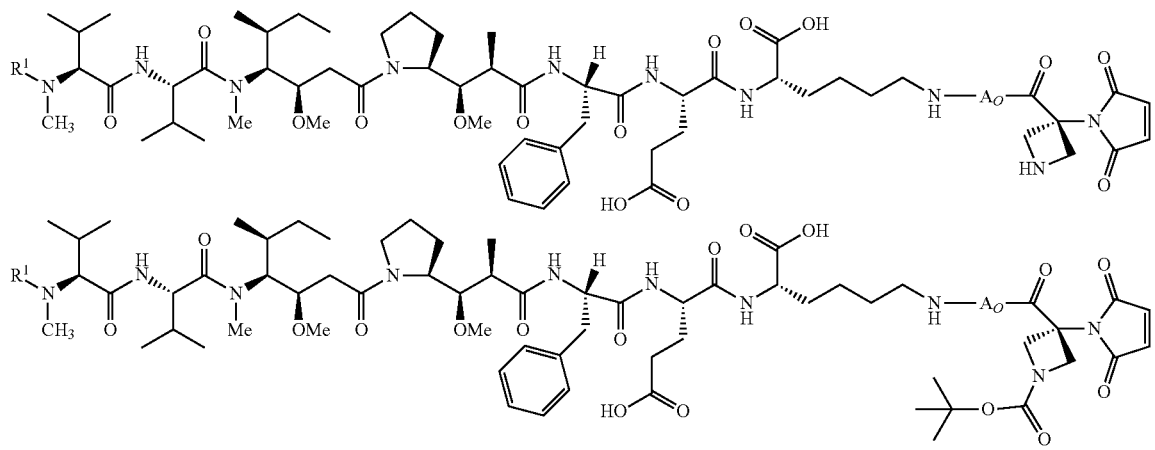

or a salt thereof.

84. The Drug Linker compound of embodiment 81, wherein the compound has the structure of:

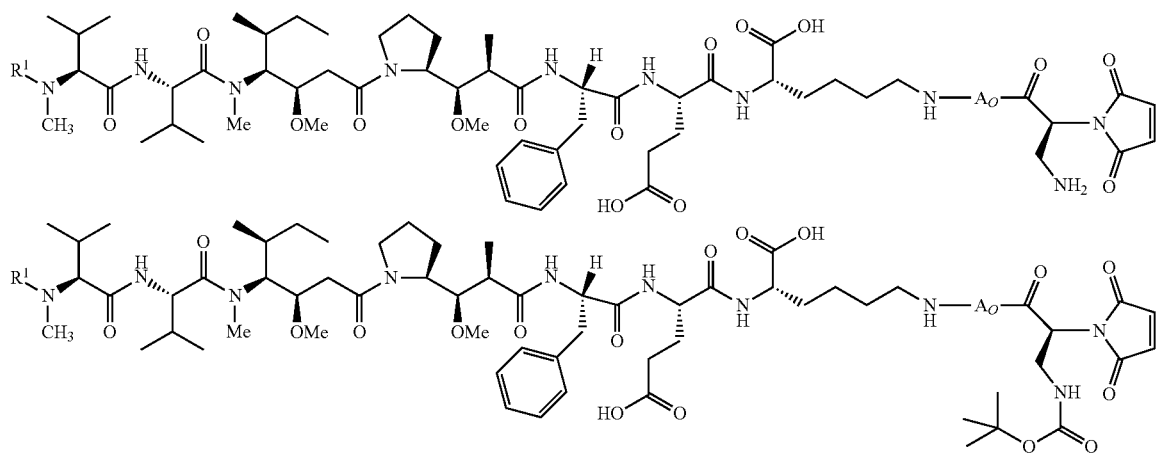

or a salt thereof.

85. The Drug Linker compound of embodiment 82, wherein the compound has the structure of:

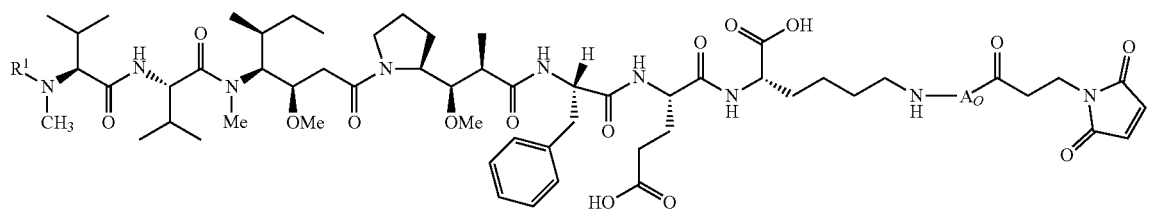

or a salt thereof.

86. The Drug Linker compound of any one of embodiments 63 to 85, wherein $R^1$ is —CH$_2$CH$_2$CH$_2$CH$_3$, —CH$_2$CH$_2$CH$_2$CH$_2$CH$_3$, CH$_2$CH$_2$CH$_2$C(CH$_3$)$_2$, —CH$_2$CH$_2$CH$_2$CH$_2$N(CH$_3$)—C(=O)—O-t-Bu, —CH$_2$CH$_2$CH$_2$CH$_2$N(CH$_3$)—C(=O)-t-Bu, —CH$_2$CH$_2$CH$_2$N(CH$_3$)—C(=O)—O-t-Bu, —CH$_2$CH$_2$CH$_2$NH—C(=O)—O-t-Bu, or has the structure

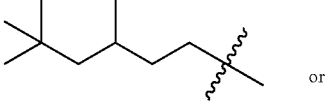 or

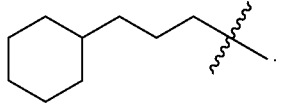

of:

87. The Drug Linker compound of embodiment 63, wherein the compound has the structure of:

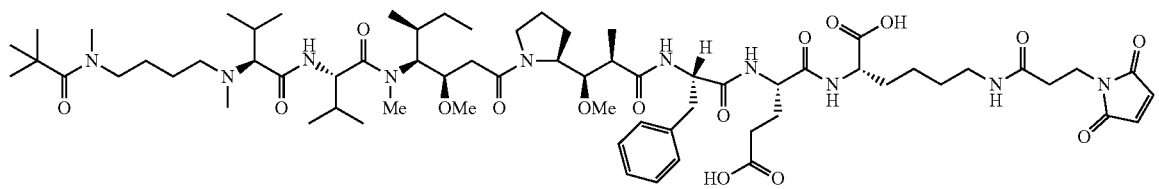 [SMILES: CC[C@H](C)[C@@H]([C@@H](CC(=O)N1CCC[C@H]1[C@H](OC)[C@@H](C)C(=O)N[C@@H](Cc1ccccc1)C(=O)N[C@@H](CCC(=O)O)C(=O)N[C@@H](CCCCNC(=O)CCN1C(=O)C=CC1=O)C(=O)O)OC)N(C)C(=O)[C@@H](NC(=O)[C@H](C(C)C)N(C)CCCCN(C)C(=O)C(C)(C)C)C(C)C]

or a salt thereof.

88. The Drug Linker compound of embodiment 63, wherein the compound has the structure of:

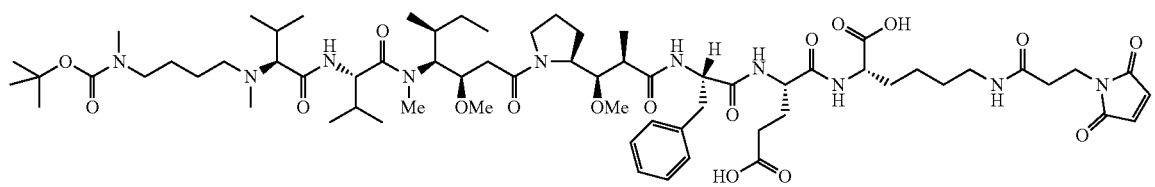 [SMILES: CC[C@H](C)[C@@H]([C@@H](CC(=O)N1CCC[C@H]1[C@H](OC)[C@@H](C)C(=O)N[C@@H](Cc1ccccc1)C(=O)N[C@@H](CCC(=O)O)C(=O)N[C@@H](CCCCNC(=O)CCN1C(=O)C=CC1=O)C(=O)O)OC)N(C)C(=O)[C@@H](NC(=O)[C@H](C(C)C)N(C)CCCCN(C)C(=O)OC(C)(C)C)C(C)C]

or a salt thereof.

89. The Drug Linker compound of embodiment 63, wherein the compound has the structure of:

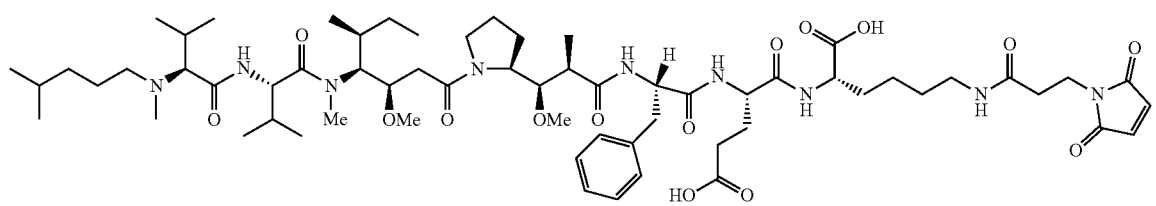 [SMILES: CC[C@H](C)[C@@H]([C@@H](CC(=O)N1CCC[C@H]1[C@H](OC)[C@@H](C)C(=O)N[C@@H](Cc1ccccc1)C(=O)N[C@@H](CCC(=O)O)C(=O)N[C@@H](CCCCNC(=O)CCN1C(=O)C=CC1=O)C(=O)O)OC)N(C)C(=O)[C@@H](NC(=O)[C@H](C(C)C)N(C)CCCC(C)C)C(C)C]

or a salt thereof.

90. The Drug Linker compound of embodiment 63, wherein the compound has the structure of:

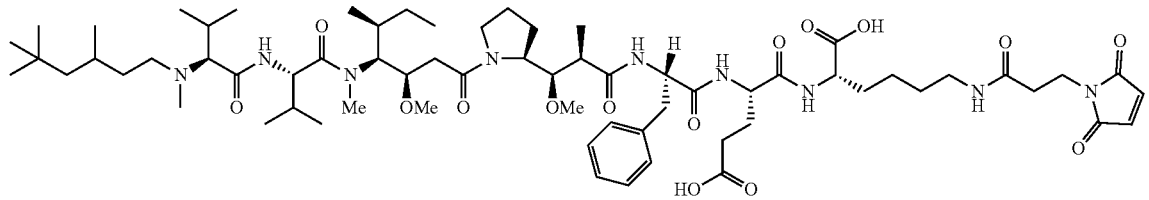 [SMILES: CC[C@H](C)[C@@H]([C@@H](CC(=O)N1CCC[C@H]1[C@H](OC)[C@@H](C)C(=O)N[C@H](Cc1ccccc1)C(=O)N[C@@H](CCC(=O)O)C(=O)N[C@@H](CCCCNC(=O)CCN1C(=O)C=CC1=O)C(=O)O)OC)N(C)C(=O)[C@@H](NC(=O)[C@H](C(C)C)N(C)CCC(C)CC(C)(C)C)C(C)C]

or a salt thereof.

EXAMPLES

General Information.

All commercially available anhydrous solvents were used without further purification. Commercially available chlorotrityl resin and aldehydes were purchased from MilliporeSigma and used without further purification. D-Series SynPhase Lanterns™ were purchased from Mimotopes™. 4-Methylpentanal was synthesized by the oxidation of 4-methylpentanol (Meyer et al., *J. Org. Chem.* 1994, 59, 7549-7552). Auristatins and drug linkers were synthesized according to our previous reports (Doronina et al WO2009117531A$_1$; Doronina et al., *Bioconjugate Chem.* 2006, 17, 114-124 and Doronina et al, *Bioconjugate Chem.* 2008, 19, 1960-1963). UPLC-MS system 1 consisted of a Waters SQ mass detector interfaced to an Acquity Ultra Performance LC equipped with an Acquity UPLC BEH C18 2.1×50 mm, 1.7 μm reverse phase column. The acidic mobile phase (0.1% formic acid) consisted of a gradient of 3% acetonitrile/97% water to 100% acetonitrile (flow rate=0.5 mL/min). UPLC-MS system 2 consisted of a Waters Xevo G2 ToF mass spectrometer interfaced to a Waters Acquity H-Class Ultra Performance LC equipped with an Acquity UPLC BEH C18 2.1×50 mm, 1.7 μm reverse phase column (Column 1) or CORTECS UPLC C18 2.1×50 mm, 1.6 μm reverse phase column (Column 2). Preparative HPLC was carried out on a Waters 2545 Binary Gradient Module with a Waters 2998 Photodiode Array Detector. Products were purified over a C12 Phenomenex Synergi™ 250×10.0 mm, 4 μm, 80 Å reverse phase column (Column 1) or a C12 Phenomenex Synergi 250×50 mm, 10 μm, 80 Å reverse phase column (Column 2) eluting with 0.1% trifluoroacetic acid in water (solvent A) and 0.1% trifluoroacetic acid in acetonitrile (solvent B). The purification methods generally consisted of linear gradients of solvent A to solvent B, ramping from 90% aqueous solvent A to 10% solvent A. The flow rate was 4.6 m/min with monitoring at 254 nm. NMR spectral data were collected on a Varian Mercury 400 MHz spectrometer. Coupling constants (J) are reported in hertz.

The cytotoxicity of an auristatin Ligand Drug Conjugate or free auristatin drug was measured by a cell proliferation assay employing the protocol described in Promega Corp. Technical Bulletin TB288; Mendoza et al., 2002, Cancer Res. 62:5485-5488), the methods of which is specifically incorporated by reference herein. Briefly, an aliquot of 100 μl of cell culture containing about 104 cells (e.g., HL-60, SK-MEL-5, etc.) in medium is deposited in each well of a 96-well, opaque-walled plate. Control wells were prepared containing medium and without cells. Free Drug or conjugate is added to the experimental wells and incubated for 96 h and are then equilibrated to room temperature for approximately 30 minutes whereupon a volume of CellTiter-Glo™ reagent equal to the volume of cell culture medium present in each well is added. The contents are mixed for 2 minutes on an orbital shaker to induce cell lysis and the plate is incubated at room temperature for 10 minutes to stabilize the luminescence signal for recordation.

Part A. General Procedure for Preparation of Hydrophobic AF Compounds

Scheme 1. Solid Phase Synthesis of Hydrophobic Auristatin F Compounds

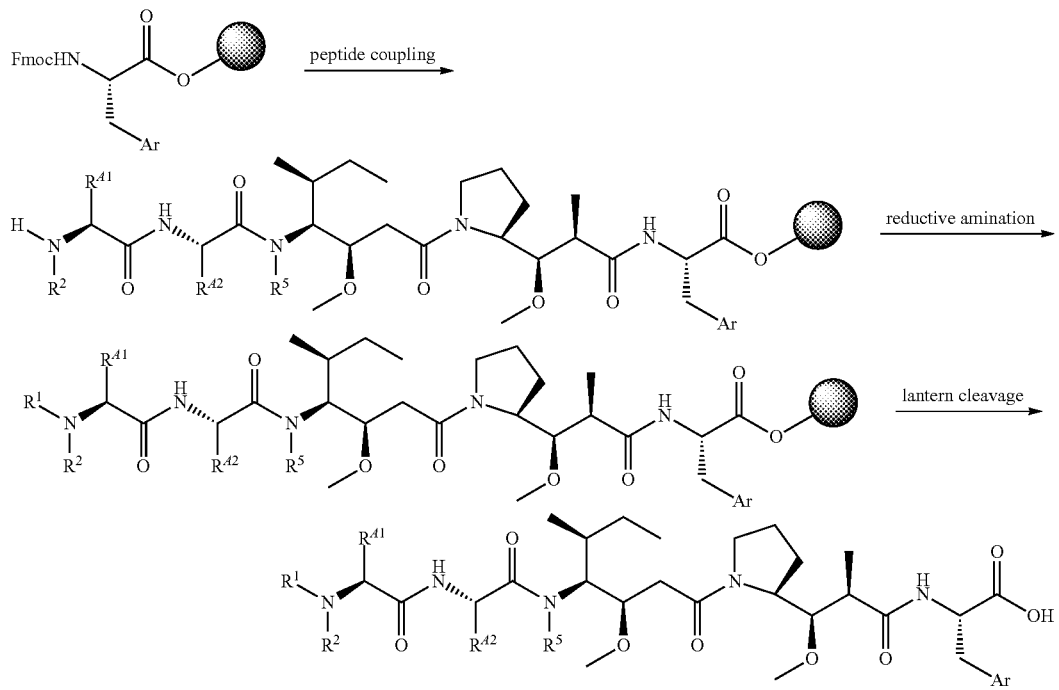

Example 1. General Procedure for Lantern Loading

A D-series trityl alcohol lantern (8 μmol/lantern) was treated with 0.5 mL solution of 10% (V/V) acetyl chloride in dry DCM at RT for 3 h. The solution was filtered and the lanterns were washed with dry DCM (3×3 mL) and used immediately without drying.

The lantern was treated with 0.5 mL of a solution of Fmoc-amino acid (0.14 M, 70 μmol, 8.75 equiv) and DIPEA (0.5 M, 260 μmol, 33 equiv) in DCM at RT for 2 h. The solution was filtered and the lanterns were washed with DMF (3×3 min) and DCM (3×3) min and vacuum-dried in a desiccator.

Example 2. General Procedure for Fmoc Deprotection

The lantern was treated with a 0.5 mL solution of 20% (V/V) piperidine in DMF and shaken for 30 min. The solution was removed and the lantern was subjected to the same deprotection conditions. The solution was filtered and the lanterns are washed with DMF (3×3 min) and DCM (3×3) min and vacuum-dried in a desiccator.

Example 3. General Procedure for Amide Coupling

Fmoc-amino acid (128 μmol, 16 equiv) was dissolved in dry DMF (0.6 mL, 0.2 M final concentration) and DIPEA (217 μmol, 27 equiv), and HATU (124 μmol, 15.5 equiv) were added successively and the reaction was stirred for 5 min. The lantern was treated with the solution of activated Fmoc-amino acid and shaken for 2 h. The solution was filtered and the lanterns were washed with DMF (3×3 min) and DCM (3×3) min and vacuum-dried in a desiccator.

Example 4. General Procedure for Reductive Amination

Aldehyde (40 μmol, 5 equiv) was dissolved in a 0.6 mL solution of 1% (V/V) AcOH in DMF, followed by the addition of $NaBH_3CN$ (32 μmol, 4 equiv). The lantern was treated with the solution and shaken for 2 h. The solution was filtered and the lanterns were washed with DMF (3×3 min) and DCM (3×3 min) and vacuum-dried in a desiccator.

Example 5. General Procedure for Cleavage of Lantern

Lanterns are placed individually in 96-well plates and treated with 0.5 mL solution of 20% (V/V) HFIP in DCM for 1 h. Lanterns are removed and the cleaved products are concentrated using a stream of $N_2$. Samples were dissolved for UPLC analysis and preparative HPLC.

The following compounds were prepared according to the general procedures of Part A.

Example 6. Ethyl-AF

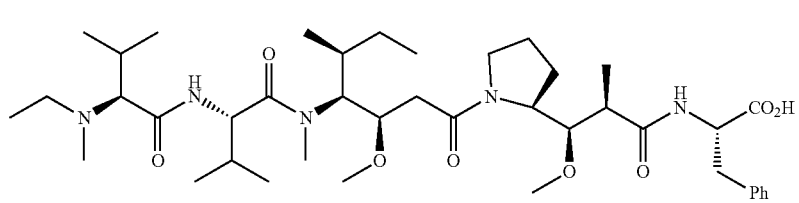

(4)

Ethyl-AF (4) was prepared by reductive amination with acetaldehyde. Yield: 3.2 mg (52%) Analytical UPLC-MS (UPLC 1): tr=1.37 min, m/z (ES+) calculated 760.52 $(M+H)^+$, found 760.47.

Example 7. Propyl-AF

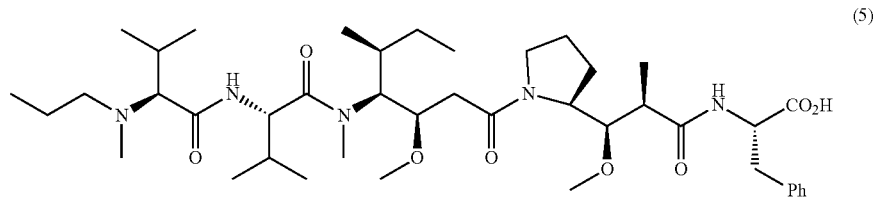 [SMILES: CCCN(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

(5)

Propyl-AF (5) was prepared by reductive amination with propionaldehyde. Yield: 2.4 mg (38%) Analytical UPLC-MS (UPLC 1): tr=1.38 min, m/z (ES+) calculated 774.53 $(M)^+$, found 774.54.

Example 8. Butyl-AF

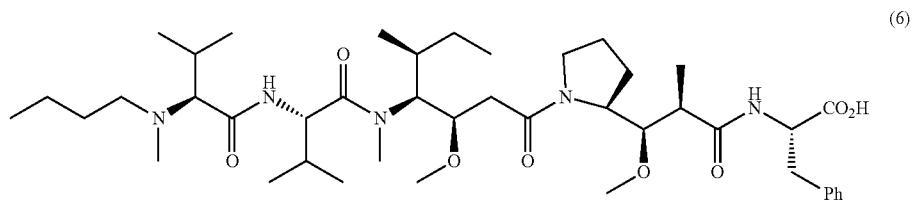 [SMILES: CCCCN(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

(6)

Butyl-AF was prepared by reductive amination with butyraldehyde. Yield: 2.9 mg (46%) Analytical UPLC-MS (UPLC 1): tr=1.43 min, m/z (ES+) calculated 788.55 $(M+H)^+$, found 788.51.

Example 9. Pentyl-AF

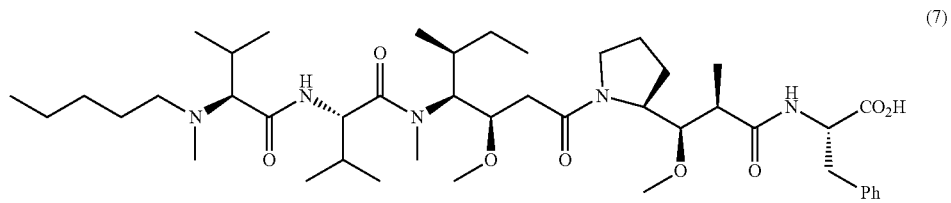 [SMILES: CCCCCN(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

(7)

Pentyl-AF (7) was prepared by reductive amination with valeraldehyde. Yield: 2.2 mg (34%) Analytical UPLC-MS (UPLC 1): tr=1.50 min, m/z (ES+) calculated 802.56 $(M+H)^+$, found 802.19.

Example 10. Hexyl-AF

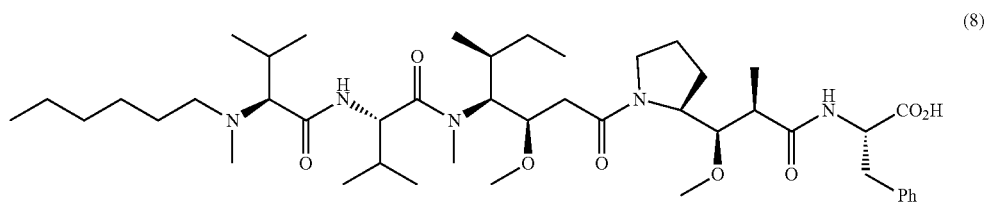 [SMILES: CCCCCCN(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

(8)

Hexyl-AF (8) was prepared by reductive amination with hexanal. Yield: 3.0 mg (46%) Analytical UPLC-MS (UPLC 1): tr=1.55 min, m/z (ES+) calculated 816.58 $(M+H)^+$, found 816.45.

Example 11. Heptyl-AF

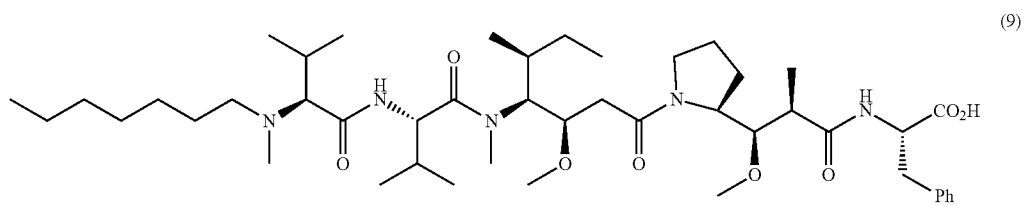 [SMILES: CCCCCCCN(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

(9)

Heptyl-AF (9) was prepared by reductive amination with heptanal. Yield: 3.8 mg (57%) Analytical UPLC-MS (UPLC 1): tr=1.65 min, m/z (ES+) calculated 830.60 $(M+H)^+$, found 830.67.

Example 12. Octyl-AF

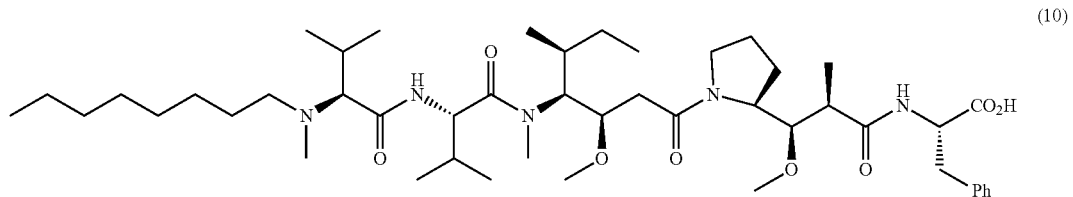 [SMILES: CCCCCCCCN(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

(10)

Octyl-AF (10) was prepared by reductive amination with octanal. Yield: 1.2 mg (17%) Analytical UPLC-MS (UPLC 1): tr=1.72 min, m/z (ES+) calculated 844.61 (M+H)$^+$, found 844.45.

Example 13. Nonyl-AF

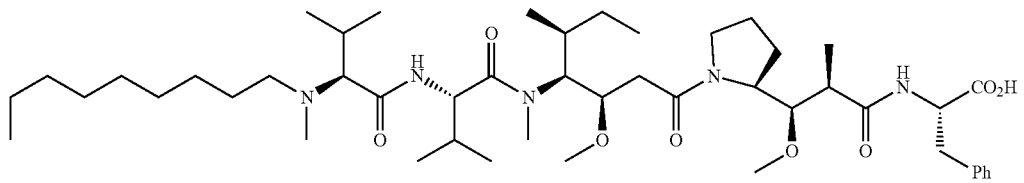

(11)

Nonyl-AF (11) was prepared by reductive amination with nonanal. Yield: 1.5 mg (22%) Analytical UPLC-MS (UPLC 1): tr=1.80 min, m/z (ES+) calculated 858.63 (M+H)$^+$, found 858.35.

Example 14. Decyl-AF

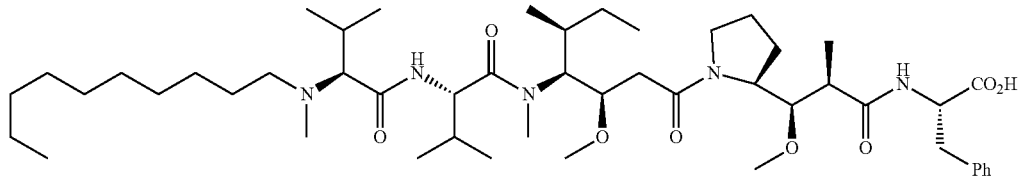

(12)

Decyl-AF (12) was prepared by reductive amination with decanal. Yield: 4.0 mg (57%) Analytical UPLC-MS (UPLC 1): tr=1.87 min, m/z (ES+) calculated 872.64 (M+H)$^+$, found 872.51.

Example 15. Undecyl-AF

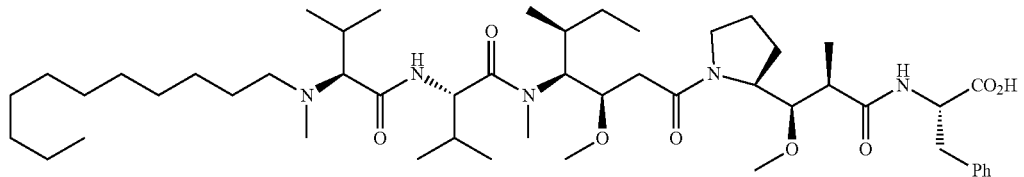

(13)

Undecyl-AF (13) was prepared by reductive amination with undecanal. Yield: 2.7 mg (38%) Analytical UPLC-MS (UPLC 1): tr=1.96 min, m/z (ES+) calculated 886.66 (M+H)$^+$, found 886.58.

Example 16. Dodecyl-AF

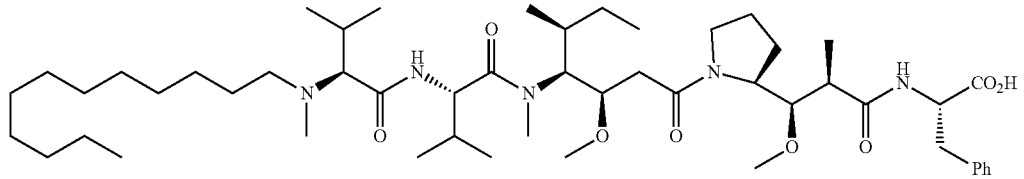

(14)

Dodecyl-AF (14) was prepared by reductive amination with dodecanal. Yield: 2.4 mg (33%) Analytical UPLC-MS (UPLC 1): tr=2.06 min, m/z (ES+) calculated 900.67 (M+H)+, found 900.65.

Example 17. Pentadecyl-AF

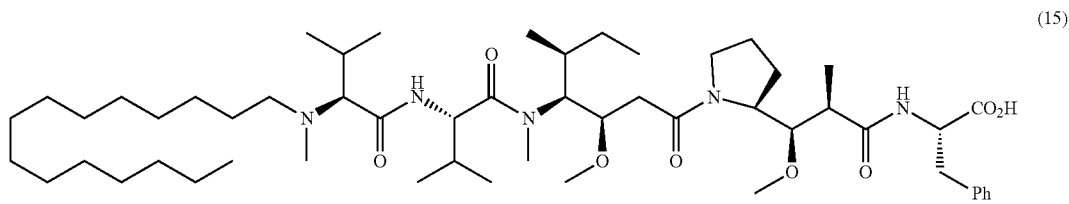 [SMILES: CCCCCCCCCCCCCCCN(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]
(15)

Pentadecyl-AF (15) was prepared by reductive amination with pentadecanal. Yield: 2.1 mg (28%) Analytical UPLC-MS (UPLC 1): tr=2.27 min, m/z (ES+) calculated 942.72 (M+H)+, found 942.75.

Example 18. 4-Methylpentyl-AF

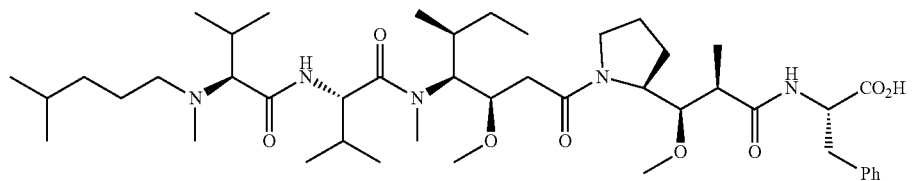
(19)

4-Methylpentyl-AF (19) was prepared by reductive amination with 4-methylpentanal. Yield: 3.7 mg (57%) Analytical UPLC-MS (UPLC 1): tr=1.55 min, m/z (ES+) calculated 816.58 (M+H)+, found 816.45.

Example 19. 3-Methybutyl-AF

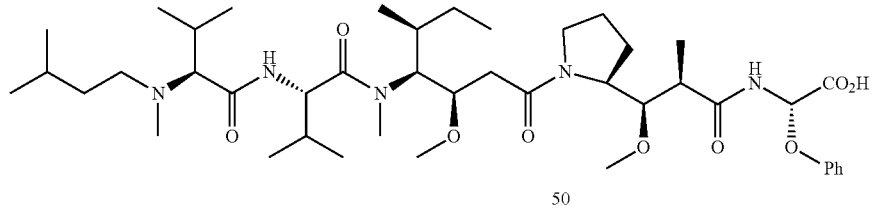
(21)

3-Methylbutyl-AF (21) was prepared by reductive amination with 3-methylbutanal. Yield: 4.1 mg (64%) Analytical UPLC-MS (UPLC 1): tr=1.48 min, m/z (ES+) calculated 802.56 (M+H)+, found 802.48.

Example 20. Bis(ethyl)-AF

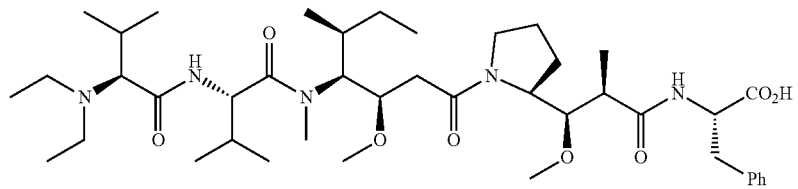
(22)

Bis(ethyl)-AF (22) was prepared by reductive amination with acetaldehyde. Yield: 3.5 mg (57%) Analytical UPLC-MS (UPLC 1): tr=1.48 min, m/z (ES+) calculated 774.53 (M+H)+, found 774.44.

Example 21. Bis(propyl)-AF

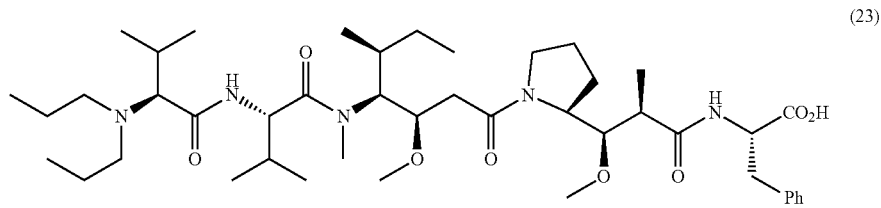 [SMILES: CCCN(CCC)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

(23)

Bis(propyl)-AF was prepared by reductive amination with propionaldehyde. Yield: 2.6 mg (41%) Analytical UPLC-MS (UPLC 1): tr=1.50 min, m/z (ES+) calculated 802.56 (M+H)+, found 802.80.

Example 22. 3,5,5-Trimethylhexyl-AF

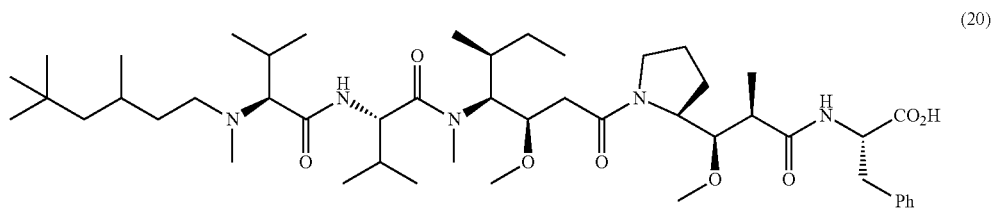 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCC(C)CC(C)(C)C)C(C)C]

(20)

3,5,5-Trimethylhexyl-AF (20) was prepared by reductive amination with 3,5,5-trimethylhexanal. Yield: 2.8 mg (41%) Analytical UPLC-MS (UPLC 1): tr=1.71 min, m/z (ES+) calculated 858.63 (M+H)+, found 858.64.

Example 23. N-Boc-propyl-AF

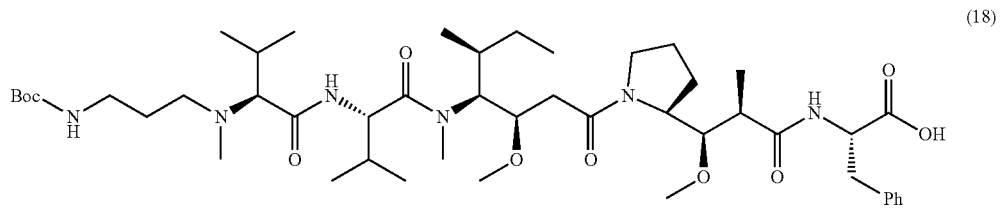 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCCNC(=O)OC(C)(C)C)C(C)C]

(18)

N-Boc-propyl-AF (18) was prepared by reductive amination with N-(4-oxopropyl)pivalamide. Yield: 2.2 mg (31%) Analytical UPLC-MS (UPLC 1): tr=1.47 min, m/z (ES+) calculated 889.60 (M+H)+, found 889.39.

Part B. General Procedure for Preparation of Hydrophobic AF Compounds from Monomethyl Auristatin F Scheme 2. Solid Phase Reductive Amination of MMAF

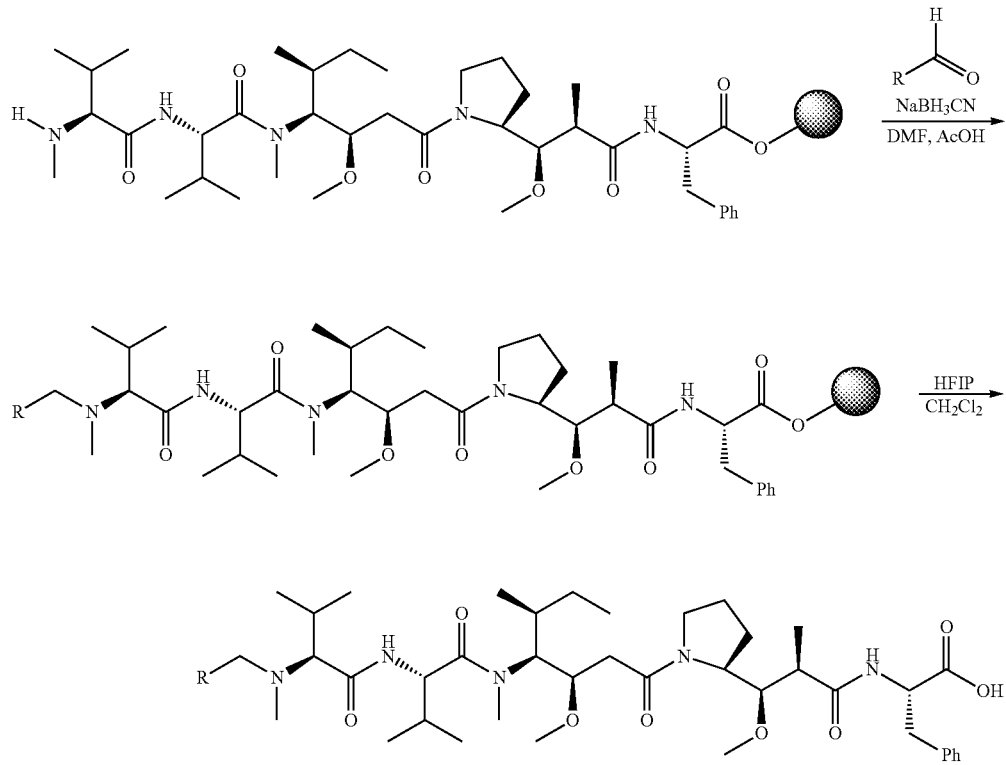

Example 24. General Procedure for Reductive Amination of MMAF on Resin

A general peptide coupling with FMOC-amino acids and HATU, and the intermediate MMAF on Cl-trityl resin was prepared as previously described (WO 2009117531A1). Aldehyde (1.4 mmol, 2 equiv) was dissolved in a 10 mL solution of 1% (V/V) AcOH in DMF, followed by the addition of NaBH$_3$CN (1.2 mmol, 1.8 equiv). The solution was added to a syringe with a PET frit containing resin (1 g, 0.7 mmol/g), and the mixture is agitated for about 2 h. The resin was filtered, washed with DMF, DCM and ethyl ether, and dried in a vacuum desiccator.

A solution of 20% (V/V) HFIP in DCM was added to the resin for 1 h and filter. Resin was washed with DCM and the combined organic layers were dried in vacuo. Samples were dissolved for UPLC analysis and preparative HPLC.

The following compounds were prepared according to the general procedures of Part B.

Example 25. (Boc-N-methyl)-butyl-AF

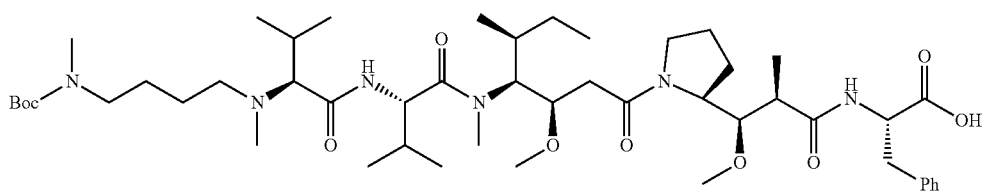

(16)

(Boc-N-methyl)-butyl-AF (16) was prepared by reductive amination with N-methyl-N-(4-oxobutyl)pivalamide. Yield: 17 mg (68%) Analytical UPLC-MS (UPLC 2, Column 1): tr=1.21 min, m/z (ES+) calculated 917.63 (M+H)$^+$, found 917.67.

Example 26. (Boc-N-methyl)-butyl-AF

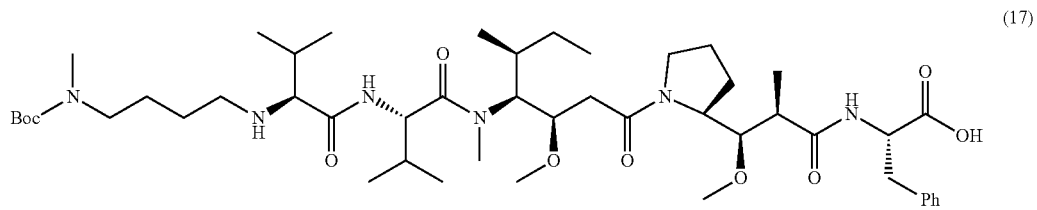 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H](NCCCCN(C)C(=O)OC(C)(C)C)C(C)C)C(C)C]

(17)

(Boc-N-methyl)-butyl-AF (17) was prepared by reductive amination with N-methyl-N-(4-oxobutyl)pivalamide. Yield: 14 mg (56%) Analytical UPLC-MS (UPLC 2, Column 1): tr=1.24 min, m/z (ES+) calculated 903.61 (M+H)$^+$, found 903.65.

Example 27. (Boc-N-methyl)-ethyl-AF

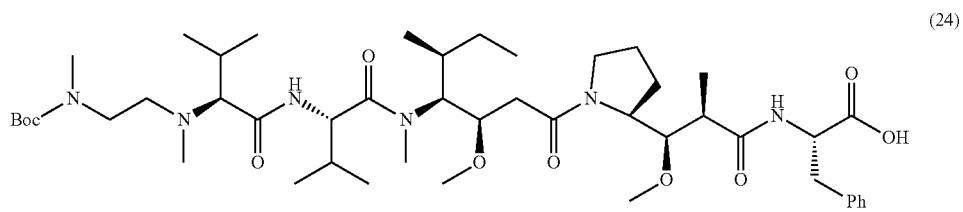 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCN(C)C(=O)OC(C)(C)C)C(C)C]

(24)

Boc-(N-methyl-ethyl)-AF (24) was prepared by reductive amination with N-methyl-N-(4-oxoethyl)pivalamide. Yield: 4 mg (32%) Analytical UPLC-MS (UPLC 2, Column 1): tr=1.28 min, m/z (ES+) calculated 889.60 (M+H)$^+$, found 889.66.

Example 28. (Boc-N-methyl)-propyl-AF

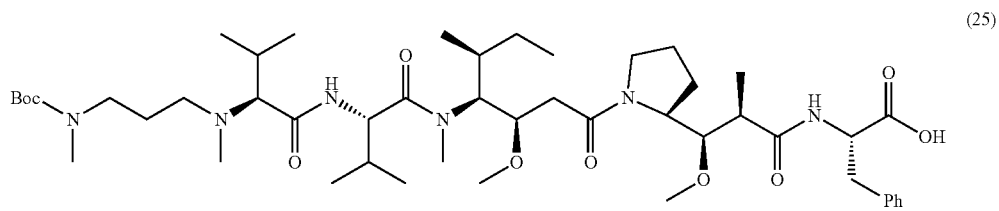 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCCN(C)C(=O)OC(C)(C)C)C(C)C]

(25)

(Boc-N-methyl)-propyl-AF (25) was prepared by reductive amination with N-methyl-N-(4-oxopropyl)pivalamide. Yield: 7 mg (55%) Analytical UPLC-MS (UPLC 2, Column 1): tr=1.23 min, m/z (ES+) calculated 903.61 (M+H)$^+$, found 903.68.

Example 29. (Boc-N-methyl)-pentyl-AF

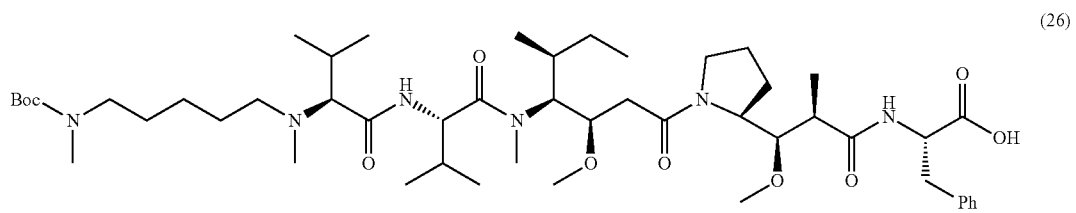 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCCCCN(C)C(=O)OC(C)(C)C)C(C)C]

(26)

(Boc-N-methyl)-pentyl-AF (26) was prepared by reductive amination with N-methyl-N-(4-oxopentyl)pivalamide. Yield: 3 mg (25%) Analytical UPLC-MS (UPLC 2, Column 1): tr=1.29 min, m/z (ES+) calculated 931.64 (M+H)$^+$, found 931.71.

Example 30. 4-(N-Methylpivalamido)-butyl-AF

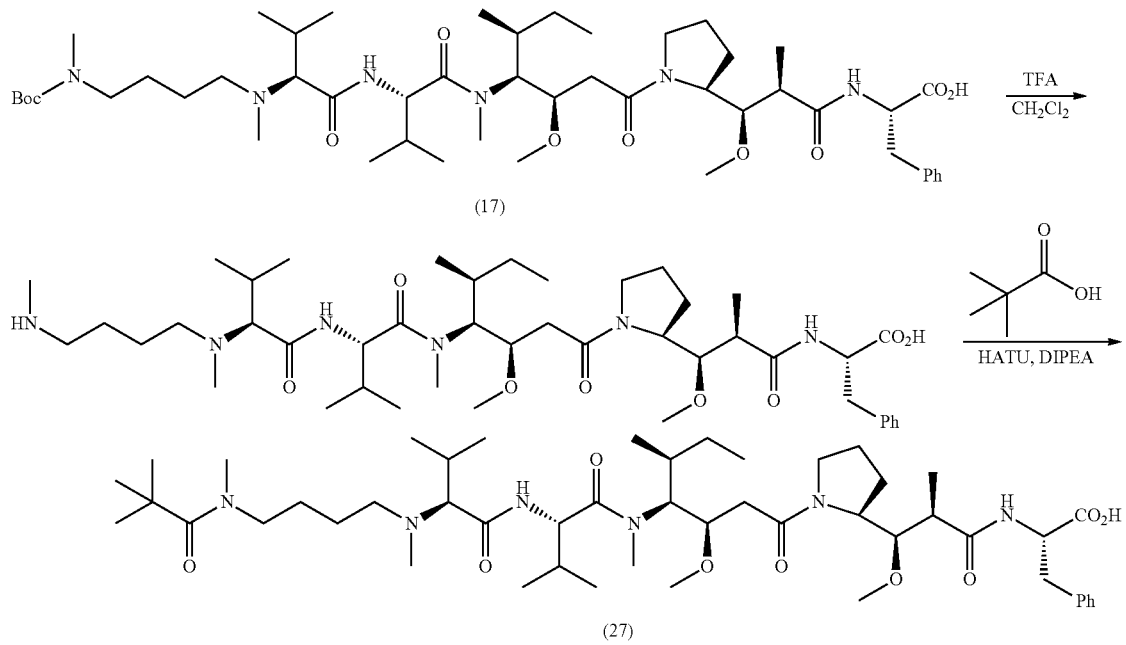

A 4 mL vial was charged with compound 17 (25 mg, 0.027 mmol) and DCM (0.3 mL). TFA (1 mL, 20% in DCM) was added to the mixture and the reaction was stirred for 1 h at RT. Solvent was removed in vacuo. The residue was dissolved in DMSO (3 mL) and purified by preparative HPLC to afford (N-Methyl)-butyl-AF). Yield: 17 mg (76%) Analytical UPLC-MS (UPLC 2, Column 1): tr=1.23 min, m/z (ES+) calculated 817.58 (M+H)$^+$, found 817.67.

A 4 mL vial was charged with pivalaldehyde (2.7 μL, 0.025 mmol), DIPEA (11 μL, 0.066 mmol), HATU (8 mg, 0.021 mmol) and DMF (0.3 mL). The reaction was stirred for 15 min at RT and N-methyl-butyl-AF (11 mg, 0.016 mmol) was added to the reaction. The reaction was stirred for 4 h at RT, and solvent was removed in vacuo. The residue was dissolved in DMSO (3 mL) and purified by preparative HPLC to afford the title compound (27). Yield: 5 mg (33%) Analytical UPLC-MS (UPLC 2, Column 1): tr=1.23 min, m/z (ES+) calculated 901.63 (M+H)$^+$, found 901.69.

Part C. General Procedure for Preparation of Hydrophobic AF Drug Linker Compounds Scheme 3. Synthesis of Drug Linker Compounds Having a -A'-W— Protease Recognition Site

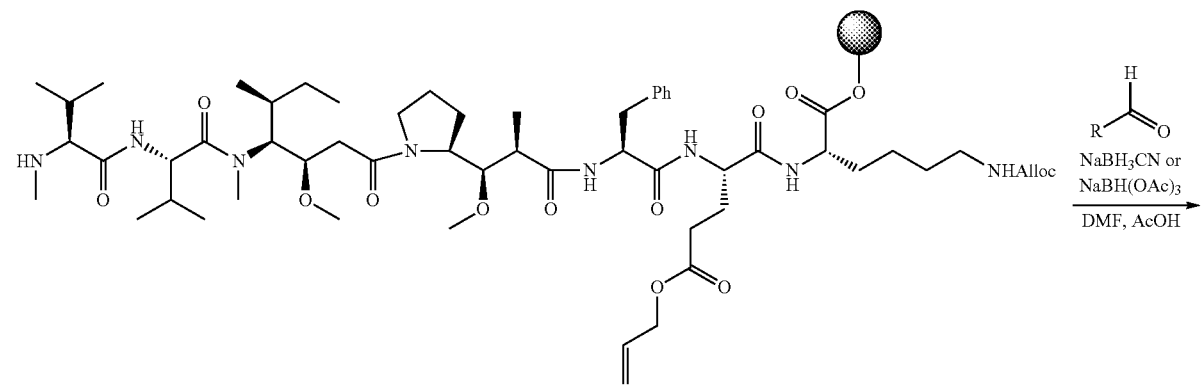

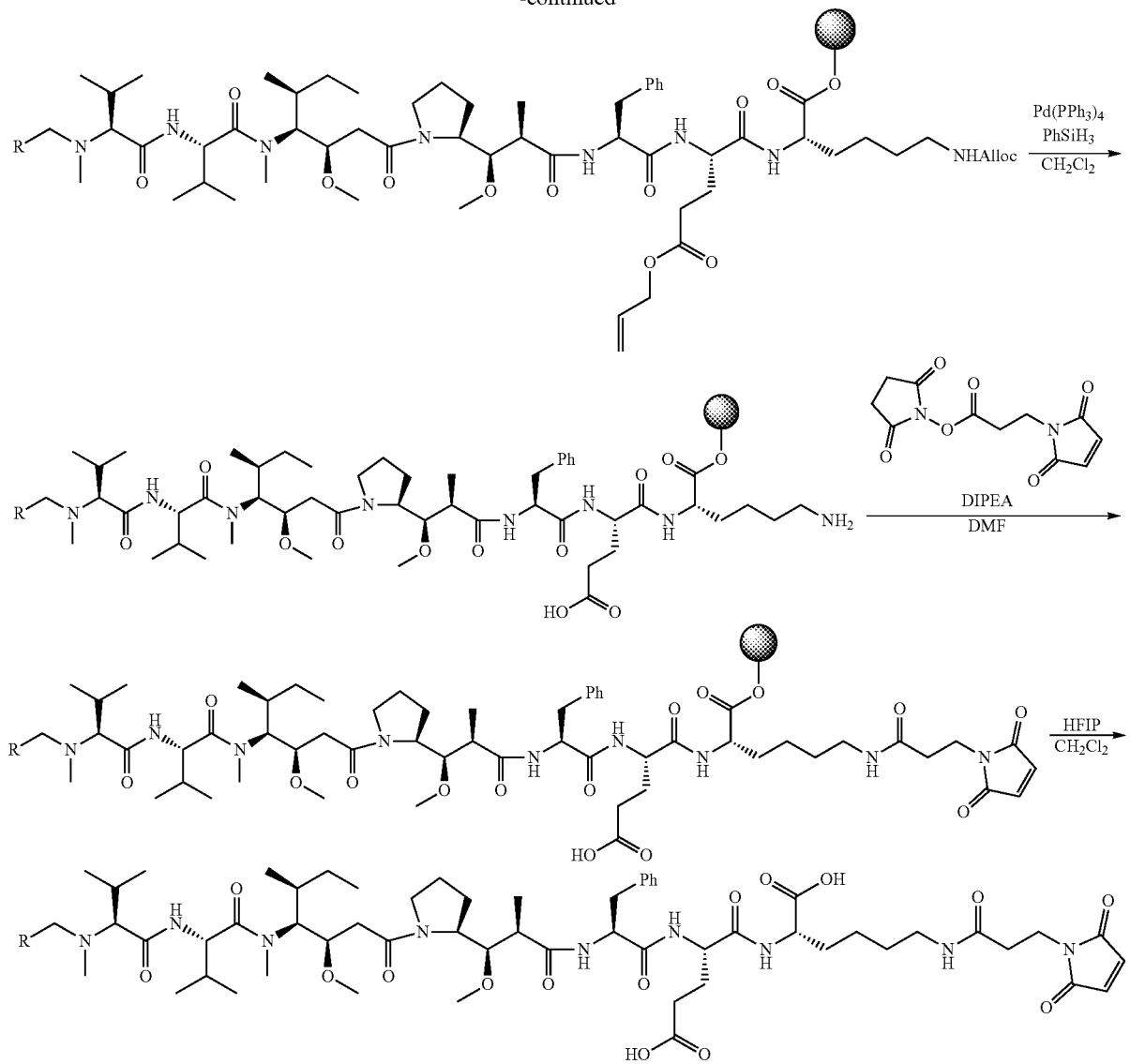

Example 32. General Procedure for Reductive of -A'-W-D Drug Linker Compound Intermediates A general peptide coupling with Fmoc-amino acids and HATU, and the intermediate auristratin on Cl-trityl resin was prepared as previously described (WO 2009117531A1).

Aldehyde (0.14 mmol, 2 equiv) was dissolved in a 10 mL solution of 1% (V/V) AcOH in DMF, followed by the addition of NaBH₃CN (0.12 mmol, 1.8 equiv). The solution was added to a syringe with a PET frit containing resin (0.1 g, 0.07 mmol/g), and the mixture was agitated for about 2 h. The resin was filtered, washed with DMF, DCM and ethyl ether, and dried in a vacuum desiccator.

Example 33. General Procedure for Removing Allylic Protecting Groups

Phenylsilane (0.7 mmol, 10 equiv) was dissolved in 1.4 mL of DCM, and the solution was added to a syringe with a PET frit containing resin (0.1 g, 0.07 mmol/g), and the mixture was agitated for 5 min. Pd(PPh)₃ (14 µmol, 0.2 equiv) was dissolved in 0.3 mL of DCM and added to the resin mixture. The resin was agitated for 2 h, filtered, washed with DMF, DCM and ethyl ether, and dried in a vacuum desiccator.

Example 34. General Procedure for Maleimide Coupling and Resin Cleavage 3-(Maleimido)propionic acid N-hydroxysuccinimide ester (0.09 mmol, 1.2 equiv) and DIPEA (0.14 mmol, 1.7 equiv) were dissolved in 1.0 mL DMF, and the solution was added to a syringe with a PET frit containing resin (0.1 g, 0.07 mmol/g). The mixture was agitated for 2 h, filtered, washed with DMF, DCM and ethyl ether, and dried in a vacuum desiccator. A solution of 20% (V/V) HFIP in DCM was added to the resin for 1 h and filtered. Resin was washed with DCM and the combined organic layers were dried in vacuo. Samples were dissolved in ACN for UPLC analysis and DMSO for preparative HPLC.

The following compounds were prepared according to the general procedures of Part C.

Example 35. (Boc-N-Methyl)-butyl-AF-glutamic acid-lysine-propionyl maleimide

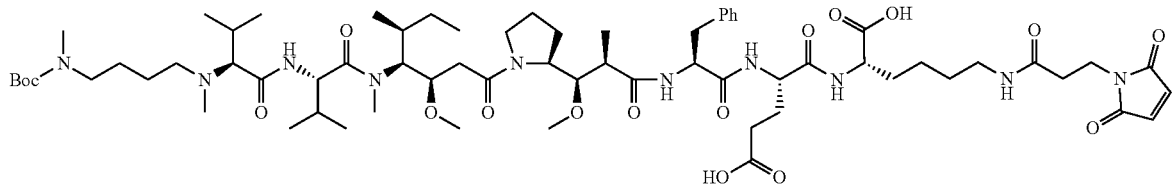 [SMILES: CC[C@H](C)[C@@H]([C@@H](CC(=O)N1CCC[C@H]1[C@H](OC)[C@@H](C)C(=O)N[C@@H](Cc1ccccc1)C(=O)N[C@@H](CCC(=O)O)C(=O)N[C@@H](CCCCNC(=O)CCN1C(=O)C=CC1=O)C(=O)O)OC)N(C)C(=O)[C@@H](NC(=O)[C@H](C(C)C)N(C)CCCCN(C)C(=O)OC(C)(C)C)C(C)C]

Title compound (35) was prepared by reductive amination with N-methyl-N-(4-oxobutyl)pivalamide. Yield: 27 mg (29%) Analytical UPLC-MS (UPLC 2, Column 1): tr=1.19 min, m/z (ES+) calculated 1325.79 (M+H)$^+$, found 1325.87.

Example 36. (3-Methylbutyl)-AF-Glutamic Acid-Lysine-Propionyl Maleimide

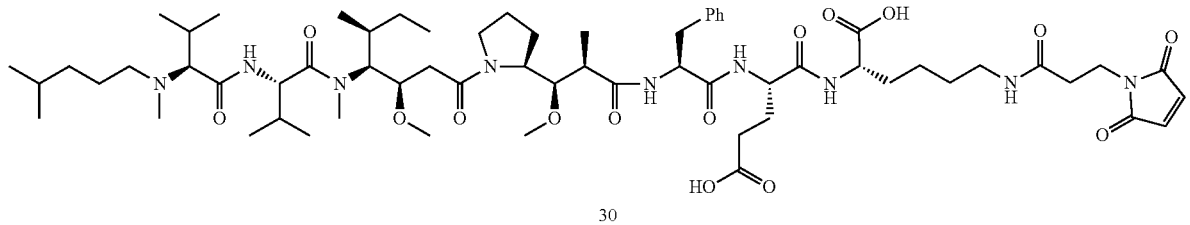

Title compound (36) was prepared by reductive amination with 3-methylbutanal. Yield: 11 mg (12%) Analytical UPLC-MS (UPLC 1): tr=1.69 min m/z (ES+) calculated 1224.74 (M+H)$^+$, found 1224.55.

Example 37. (3,5,5-Trimethylhexyl)-AF-glutamic acid-lysine-propionyl maleimide

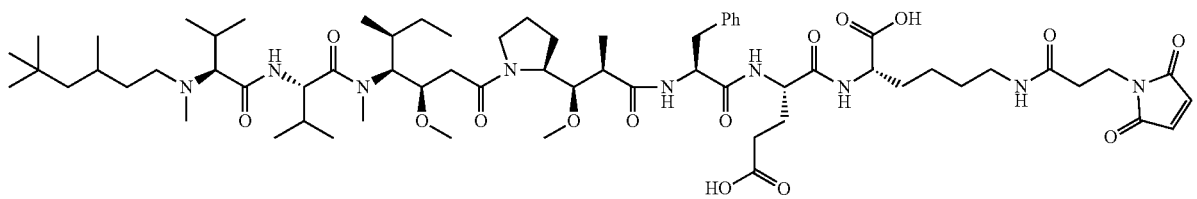 [SMILES: CC[C@H](C)[C@@H]([C@@H](CC(=O)N1CCC[C@H]1[C@H](OC)[C@@H](C)C(=O)N[C@@H](Cc1ccccc1)C(=O)N[C@@H](CCC(=O)O)C(=O)N[C@@H](CCCCNC(=O)CCN1C(=O)C=CC1=O)C(=O)O)OC)N(C)C(=O)[C@@H](NC(=O)[C@H](C(C)C)N(C)CCC(C)CC(C)(C)C)C(C)C]

Title compound (37) was prepared by reductive amination with 3,5,5-trimethylhexanal. Yield: 33 mg (79%) Analytical UPLC-MS (UPLC 2, Column 1): tr=1.26 min, m/z (ES+) calculated 1266.79 (M+H)$^+$, found 1266.96.

Example 38. (Boc-N-methyl)propyl-AF-glutamic acid-lysine-propionyl maleimide

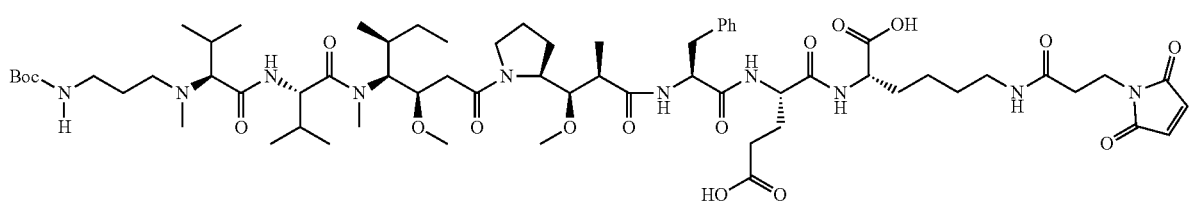 [SMILES: CC[C@H](C)[C@@H]([C@@H](CC(=O)N1CCC[C@H]1[C@H](OC)[C@@H](C)C(=O)N[C@@H](Cc1ccccc1)C(=O)N[C@@H](CCC(=O)O)C(=O)N[C@@H](CCCCNC(=O)CCN1C(=O)C=CC1=O)C(=O)O)OC)N(C)C(=O)[C@@H](NC(=O)[C@H](C(C)C)N(C)CCCNC(=O)OC(C)(C)C)C(C)C]

Title compound (38) was prepared by reductive amination with N-(4-oxopropyl)pivalamide. Yield: 1.2 mg (4% from 0.024 mmol resin) Analytical UPLC-MS (UPLC 2, Column 1): tr=1.56 min, m/z (ES+) calculated 1297.76 (M+H)+, found 1297.52.

Example 40. 4-[(Boc-N-Methyl)pivalamido]-butyl-AF-glutamic acid-2,3-diaminopropionic acid-propionyl maleimide

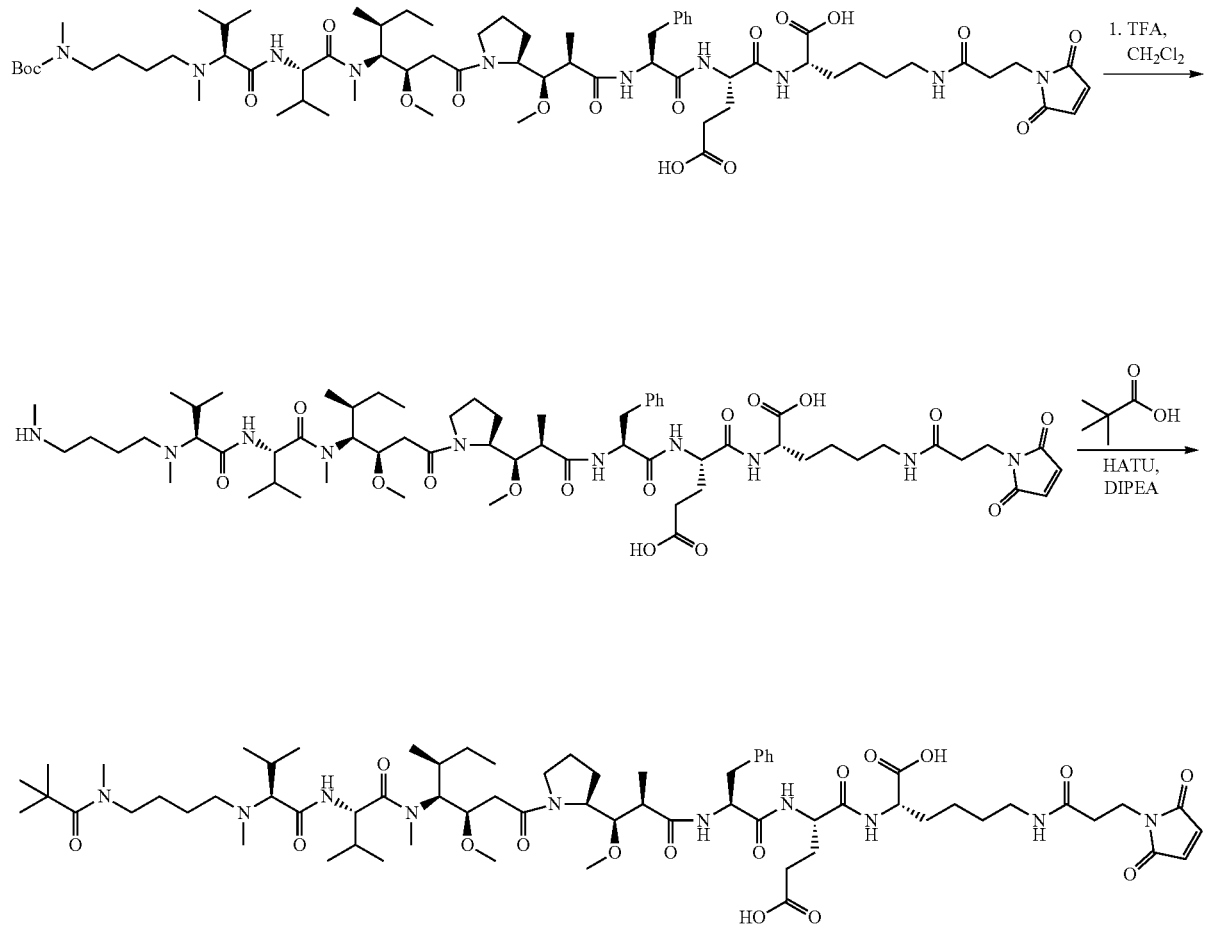

A 4 mL vial was charged with Boc-N-methyl-butyl-AF (25 mg, 0.027 mmol) and DCM (0.3 mL). TFA (1 mL, 20% in DCM) was added to the mixture and the reaction was stirred for 1 h at RT. Solvent was removed in vacuo. A 4 mL vial was charged with pivalaldehyde (2.7 µL, 0.025 mmol), DIPEA (11 µL, 0.066 mmol), HATU (8 mg, 0.021 mmol) and DMF (0.3 mL). The reaction was stirred for 15 min at RT and N-methyl-butyl-AF (11 mg, 0.016 mmol) was added to the auristatin drug linker residue. The reaction was stirred for 4 h at RT, and solvent was removed in vacuo. The residue was dissolved in DMSO (3 mL) and purified by preparative HPLC to afford the title compound (40).

Yield: 10 mg (11%) Analytical UPLC-MS (UPLC 2, Column 1): tr=1.13 min, m/z (ES+) calculated 1309.80 (M+H)+, found 1309.88.

Example 41. Activity of Auristatin Free Drugs on Genetically Paired MDR- and MDR+ Cancer Cell

TABLE 2

In vitro $IC_{50}$ (nM) values for auristatin free drugs on MDR- HL60 and MDR+ HL60/RV acute myeloid leukemia cell lines.

| Compound No. | HL60 (MDR-) | HL60/RV (MDR+) |
|---|---|---|
| 4 | 23.2 | 145 |
| 5 | 24.5 | 82.1 |
| 6 | 14.3 | 47.9 |
| 7 | 6.6 | 35.7 |
| 8 | 6.9 | 40.9 |
| 9 | 7.7 | 88.5 |
| 10 | 3.9 | 55.9 |
| 11 | 1.8 | 35.4 |

TABLE 2-continued

In vitro IC$_{50}$ (nM) values for auristatin free drugs on MDR$^-$ HL60 and MDR$^+$ HL60/RV acute myeloid leukemia cell lines.

| Compound No. | HL60 (MDR$^-$) | HL60/RV (MDR$^+$) |
|---|---|---|
| 12 | 1.0 | 59.2 |
| 13 | 1.0 | 60.2 |
| 14 | 1.4 | 138 |
| 15 | 4.7 | 294 |
| 19 | 4.9 | 20.5 |
| 20 | 1.0 | 17 |
| 21 | 9.0 | 46.3 |
| 22 | 13.6 | 202 |
| 23 | 6.2 | 437 |
| 1 (AF) | 137 | 388 |
| 3 (MMAE) | 1 | 180 |

Example 41. Activity of Auristatin Free Drugs on Other MDR$^+$ Cell Lines

TABLE 3

In vitro IC$_{50}$ (nM) values for auristatin free drugs on melanoma and colon cancer cell lines.

| Compound No. | SK-MEL-28 Melanoma | SK-MEL-5 Melanoma | A2058 Melanoma | A375 Melanoma | IGR-37 Melanoma | Colo-853 Colon Cancer |
|---|---|---|---|---|---|---|
| 16 | 4.4 | 0.4 | 0.9 | 0.7 | 2.5 | 6.2 |
| 17 | 77.3 | 26.2 | 20.3 | 14.8 | 62.7 | 66.2 |
| 18 | 21 | 4 | 9.1 | 4.9 | 13.7 | 17.5 |
| 24 | 13.9 | 5.7 | 5.2 | 4.9 | 23.1 | 19.6 |
| 25 | 17.2 | 6.1 | 4 | 5.9 | 16.1 | 15.1 |
| 26 | 9.6 | 0.9 | 0.9 | 2.1 | 6.5 | 12.5 |
| 2 (MMAF) | 138 | 35.6 | 84.2 | 48.9 | 72.5 | 90.2 |
| 3 (MMAE) | 0.1 | 0.1 | 0.1 | 0.1 | 0.2 | 0.1 |

Example 42. Activity of Auristatin ADCs Targeting CD70$^+$ Cancer Cells

The efficacy of cAC10 conjugates were evaluated in admixed Karpas/KarpasBVR (Hodgkin lymphoma) xenografts. Conjugates with an average of 4 drug moieties per antibody were used. The admixed tumor model was implanted subcutaneously into SCID mice with a mixture containing Karpas 299 (2.5×10$^6$ cells per mouse) and KarpasBVR (5×10$^6$ cells per mouse). Treatment was initiated when the average tumor size reached at least 100 mm$^3$ for tumor efficacy studies. Tumor volumes are calculated using the formula (0.5×L×W$^2$) where L and W are the longer and shorter of two bidirectional measurements.

TABLE 4

In vitro IC$_{50}$ (ng/mL) values for 4-load auristatin ADCs on renal cell carcinoma and Hodgkin lymphoma cell lines.

| Conjugate | 786-O Renal Cell Carcinoma | A498 Renal Cell Carcinoma | L428 Hodgkin Lymphoma |
|---|---|---|---|
| h1F6-35(4) | 7 | 23 | 2 |
| h1F6-36(4) | 4 | 9 | 1 |
| h1F6-37(4) | 23 | 39 | 2 |
| h1F6-38(4) | 12 | 36 | 2 |
| h1F6-mc-vc-MMAF(4) | 5 | 8 | 7 |
| h1F6-mc-vc-MMAE(4) | >1000 | >1000 | >1000 |

What is claimed is:

1. A Ligand Drug Conjugate compound represented by Formula 1:

$$L-[LU-D']_{p'} \qquad (1)$$

or a salt thereof, wherein

L is a Ligand Unit;

subscript p' is an integer ranging from 1 to 24:

each -LU-D' is a drug-linker moiety of Formula 1A:

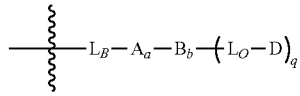

(1A)

or a salt thereof, wherein the wavy line indicates covalent attachment to L;

L$_B$ is a ligand covalent binding moiety;

A is a first optional Stretcher Unit;

subscript a is 0 or 1, indicating the absence or presence of A, respectively;

B is an optional Branching Unit;

subscript b is 0 or 1, indicating the absence or presence of B, respectively;

L$_O$ is an optional secondary linker moiety;

subscript q is an integer ranging from 1 to 4;

D is a hydrophobic auristatin F compound represented by the structure of:

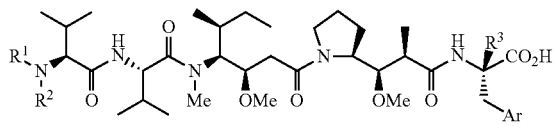

(H-AF₁)

or a salt thereof, wherein
the hydrophobic auristatin F compound is conjugated to the remainder of the drug-linker moiety through its C-terminal component's carboxylic acid carbon atom:
Ar is phenyl, thienyl, 1-napthyl, 2-napthyl, or benzo[b]thiophen-3-yl;
$R^3$ is independently selected from the group consisting of hydrogen and $C_1$-$C_2$ alkyl:
$R^1$ is $C_1$-$C_9$ alkyl, or
$R^1$ is ($C_3$-$C_6$ carbocyclyl)-alkylene- of up to 9 total carbon atoms, or
$R^1$ is —($C_2$-$C_6$ alkylene)-X—$R^4$, wherein X is an amide or carbamate functional group and $R^4$ is $C_1$-$C_6$ alkyl; and
$R^2$ is $C_1$-$C_2$ alkyl,
with the proviso that the total number of carbon atoms in $R^2$ and the (carbocyclyl)alkyl(ene) moiety of $R^1$ is between 4 and 10, and $R^1$ and $R^2$ are not each methyl,
wherein, when present, $L_O$ has the formula of:

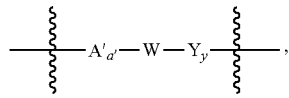

wherein the wavy line adjacent to Y indicates the site of covalent attachment to the hydrophobic auristatin F compound, and the wavy line adjacent to A' indicates the site of covalent attachment to the remainder of the drug linker moiety;
A' is a second optional Stretcher Unit,
subscript a' is 0 or 1, indicating the absence or presence of A', respectively;
W is a peptide Cleavable Unit;
Y is a peptide Spacer Unit; and
subscript y is 0 or 1, indicating the absence or presence of Y, respectively.

2. The Ligand Drug Conjugate compound of claim 1, wherein each of the drug linker moieties has the structure of:

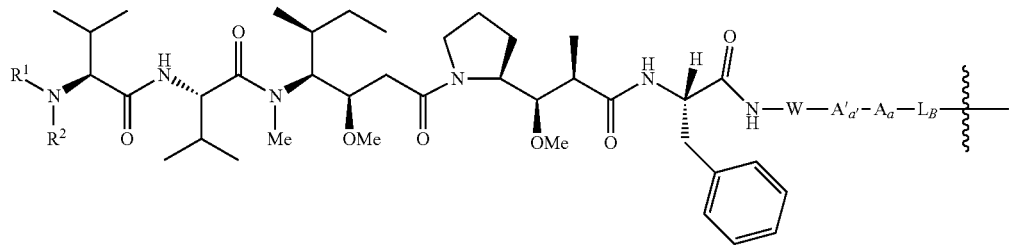

or a pharmaceutically acceptable salt thereof, wherein
$R^2$ is methyl; and
$R^1$ is $C_3$-$C_9$ alkyl, or
$R^1$ is ($C_3$-$C_6$ carbocyclyl)-alkylene- of up to 9 total carbon atoms, or
$R^1$ is —($C_2$-$C_6$ alkylene)-X—$R^4$, wherein X is an amide or carbamate functional group and $R^4$ is $C_1$-$C_6$ alkyl;
with the proviso that the total number of carbon atoms in $R^2$ and the (carbocyclyl)alkyl(ene) moiety of $R^1$ is between 4 and 10.

3. The Ligand Drug Conjugate compound of claim 2, wherein:
(a) L-$L_B$-A- comprises one of the structures of:

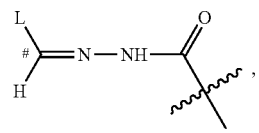

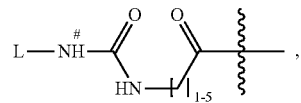

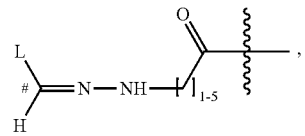

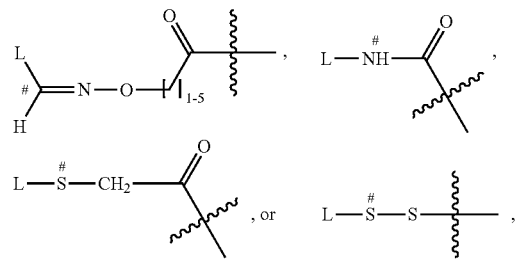

wherein the nitrogen, carbon, or sulfur atom indicated by #is from the Ligand Unit; and wherein the wavy line indicates the site of covalent attachment to the remainder of the Ligand Drug Conjugate compound; or (b) each -L_B-A- has the structure of:

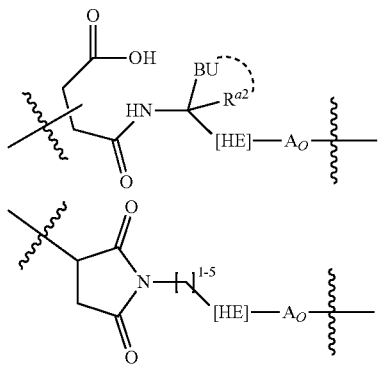

or wherein
the wavy line adjacent to $A_O$ indicates the site of covalent attachment to $L_O$; and the other wavy line indicates the site of covalent attachment to a sulfur atom of a Ligand Unit;
$A_O$ is an optional second subunit of A;
[HE] is an optional Hydrolysis Enhancing Unit, which is a component provided by A or a first subunit thereof; and
BU is an acyclic Basic Unit moiety comprising a primary, secondary, or tertiary amine as the basic functional group; the dotted curved line is absent; and $R^{a2}$ is a substituted $C_1$-$C_{12}$ alkyl group; or
$R^{a2}$ and BU, together with the carbon atom to which both are attached, define a substituted or unsubstituted spiro $C_3$-$C_{20}$ heterocyclo Basic Unit moiety comprising an annular secondary or tertiary amine as the basic functional group,
wherein the basic amine of the Basic Unit is protonated, unprotonated, or suitably protected by a nitrogen protecting group; or
(c) [HE] is —C(=O)—, and -L_B-A- has the structure of:

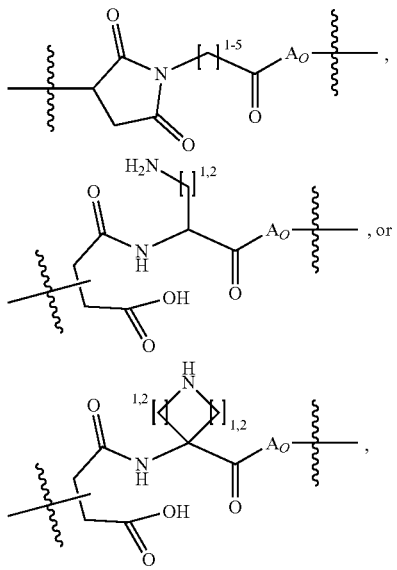

wherein $A_O$ is optional.
4. The Ligand Drug Conjugate composition of claim 3, wherein $A_O$ is a second subunit of A that is present and is indicated as $A_2$, wherein $A_2$ is an amine-containing acid residue having the structure of formula 3a, formula 4a or formula 5a:

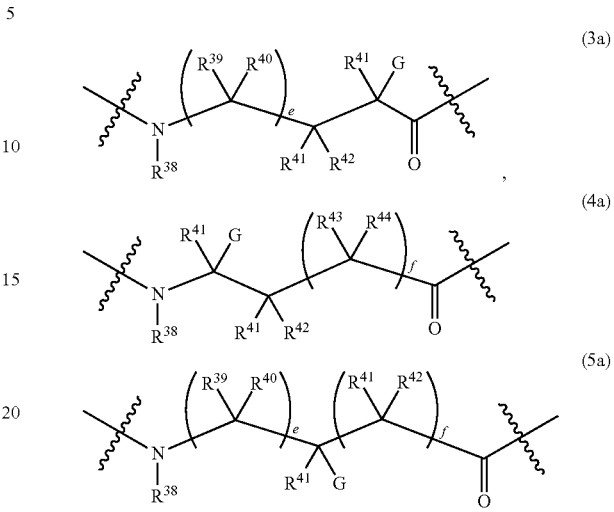

wherein the wavy line adjacent to the nitrogen atom indicates the site of covalent attachment to [HE] of the first submit of A, wherein [HE] is —C(=O)— and the wavy line adjacent to the carbonyl carbon atom indicates the site of covalent attachment to $L_O$, wherein both attachments are through amide functional groups;
subscripts e and f are independently 0 or 1; and
G is hydrogen, —OH, —OR^{PR}, —CO_2H, —CO_2R^{PR} or an optionally substituted $C_1$-$C_6$ alkyl, wherein the optional substituent when present is selected from the group consisting of —OH, —OR^{PR}, —CO_2H, and —CO_2R^{PR}; and wherein $R^{PR}$ is a suitable protecting, or
G is N(R^{PR})(R^{PR}) or an optionally substituted $C_1$-$C_6$ alkyl, wherein the optional substituent when present is N(R^{PR})(R^{PR}), wherein $R^{PR}$ are independently a protecting group or $R^{PR}$ together form a suitable protecting group, or
G is —N(R^{45})(R^{46}), or an optionally substituted $C_1$-$C_6$ alkyl, wherein the optional substituent when present is —N(R^{45})(R^{46}), wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl;
$R^{38}$ is hydrogen or optionally substituted $C_1$-$C_6$ alkyl; and
$R^{39}$-$R^{44}$ are independently selected from the group consisting of hydrogen, optionally substituted $C_1$-$C_6$ alkyl, optionally substituted $C_6$-$C_{20}$ aryl, and optionally substituted $C_5$-$C_{20}$ heteroaryl, or
$R^{39}$, $R^{40}$ together with the carbon atom to which both are attached define a $C_3$-$C_6$ carbocyclo, and $R^{41}$-$R^{44}$ are as defined herein, or
$R^{43}$, $R^{44}$ together with the carbon atom to which both are attached define a $C_3$-$C_6$ carbocyclo, and $R^{39}$-$R^{42}$ are as defined herein, or
$R^{40}$ and $R^{41}$, or $R^{40}$ and $R^{43}$, or $R^{41}$ and $R^{43}$ to together with the carbon atom or heteroatom to which both are attached and the atoms intervening between those carbon atoms and/or heteroatoms define a $C_5$-$C_6$ carbocyclo or a $C_5$-$C_6$ heterocyclo, and $R^{39}$, $R^{44}$ and the remainder of $R^{40}$-$R^{43}$ are as defined herein,
or $A_O$ is an α-amino or β-amino acid residue, wherein its amino nitrogen atom is covalently attached to the remainder of A, and its carboxylic acid carbonyl carbon is covalently attached to A', wherein both attachments are through amide functional groups, or $A_O$ is a second subunit of A that is present and is indicated as $A_2$ wherein $A_2$ is a β-amino acid residue having the structure of —NHCH$_2$CH$_2$C(=O)— or has the formula of -L$^P$(PEG)-, wherein L$^P$ is Parallel Connector Unit having the structure of a tri-functional amine-containing acid residue and PEG is a PEG Unit, in particular, -L$^P$(PEG)- has the structure of:

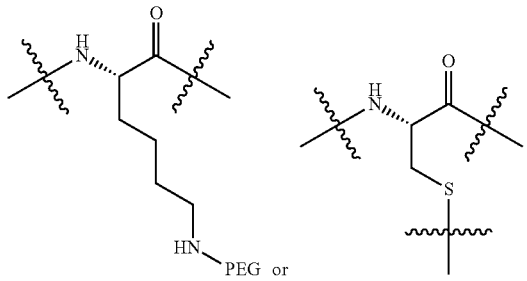

wherein the wavy line adjacent to the nitrogen atom indicates the site of covalent attachment to the first subunit of A and the wavy line to the carbonyl carbon atom or the sulfur atom indicates the site of covalent attachment to A' of $L_O$, wherein A' is preferably an alkylene diamine residue having the structure of formula 3b, formula 4b or formula 5b:

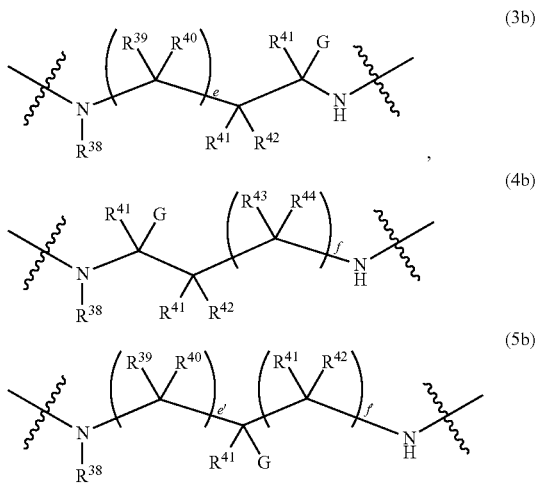

wherein subscript e and f range from 0 to 6;
subscripts e' and f' range from 1 to 6;
the wavy line next to the nitrogen atom of the amine residue to which $R^{38}$ is attached indicates the site of covalent attachment to a first optional Stretcher Unit that is present or to $A_O$, wherein $A_O$ is an optional second subunit of A that when present is indicated as A2;
the wavy line adjacent to the nitrogen atom of the other amine residue indicates the site of covalent attachment to W,
wherein both attachments are through amide functional groups;
G is hydrogen, —OH, —OR$^{PR}$, —CO$_2$H$_5$, —CO$_2$R$^{PR}$ or an optionally substituted C$_1$-C$_6$ alkyl, wherein the optional substituent when present is selected from the group consisting of —OH, —OR$^{PR}$, —CO$_2$H, and —CO$_2$R$^{PR}$; and wherein R$^{PR}$ is a suitable protecting, or
G is N(R$^{PR}$)(R$^{PR}$) or an optionally substituted C$_1$-C$_6$ alkyl, where in the optional substituent when present is —N(R$^{PR}$)(R$^{PR}$), wherein R$^{PR}$ are independently a protecting group or R$^{PR}$ together form a suitable protecting group, or
G is —N(R$^{45}$)(R$^{46}$), or an optionally substituted C$_1$-C$_6$ alkyl, where in the optional substituent when present is —N(R$^{45}$)(R$^{46}$), wherein one of R$^{45}$, R$^{46}$ is hydrogen or R$^{PR}$, wherein R$^{PR}$ is a suitable protecting group, and the other is hydrogen or optionally substituted C$_1$-C$_6$ alkyl;
R$^{38}$ is hydrogen or optionally substituted C$_1$-C$_6$ alkyl; and R$^{39}$-R$^{44}$ are independently selected from the group consisting of hydrogen, optionally substituted C$_1$-C$_6$ alkyl, optionally substituted C$_6$-C$_{20}$ aryl, and optionally substituted C$_5$-C$_{20}$ heteroaryl, or
R$^{39}$, R$^{40}$ together with the carbon atom to which both are attached define a C$_3$-C$_6$ carbocyclo, and R$^{41}$-R$^{44}$ are as defined herein, or
R$^{43}$, R$^{44}$ together with the carbon atom to which both are attached define a C$_3$-C$_6$ carbocyclo, and R$^{39}$-R$^{42}$ are as defined herein, or
R$^{40}$ and R$^{41}$, or R$^{40}$ and R$^{43}$, or R$^{41}$ and R$^{43}$ to together with the carbon atom or heteroatom to which both are attached and the atoms intervening between those carbon atoms and/or heteroatoms define a C$_5$-C$_6$ carbocyclo or a C$_5$-C$_6$ heterocyclo, and R$^{39}$, R$^{44}$ and the remainder of R$^{40}$-R$^{43}$ are as defined herein,
or A' is an optionally substituted diamine residue, wherein one amino nitrogen atom is covalently attached to the remainder of A, and the other amino nitrogen atom is covalently attached to W, wherein both attachments are through amide functional groups.

5. The Ligand Drug Conjugate composition of claim 4, wherein -A$_2$-A'- has the structure of:

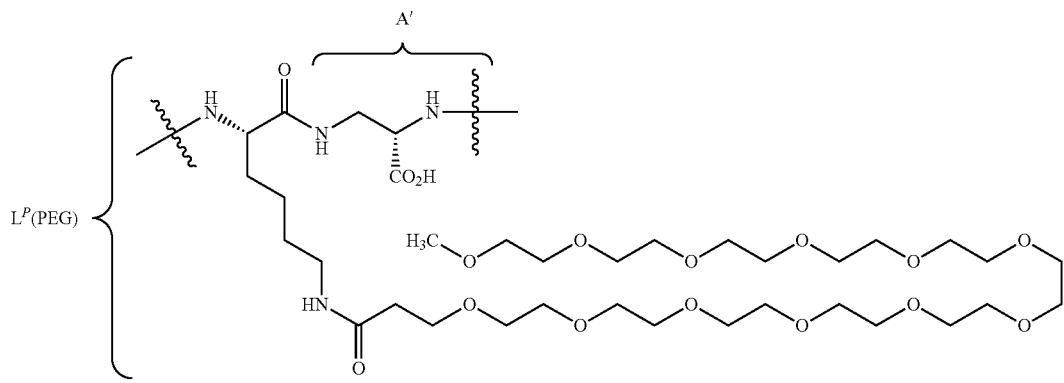 [SMILES: *N[C@@H](CNC(=O)[C@H](CCCCNC(=O)CCOCCOCCOCCOCCOCCOCCOCCOCCOCCOCCOCCOC)N*)C(=O)O]

or a salt thereof, wherein the wavy line to the nitrogen atom of $L^P$(PEG) indicates the site of attachment to the remainder of A and the wavy line to the nitrogen atom of A' indicates the site of attachment to W, wherein both attachments are through amide functional groups.

6. The Ligand Drug Conjugate compound of claim 1, wherein (a) W is an amino acid sequence comprising a dipeptide, wherein the dipeptide has the structure of:

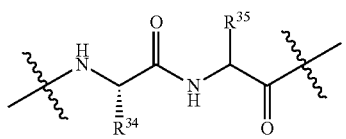

wherein the wavy line at the dipeptide N-terminus indicates the site of covalent attachment via an amide bond to an auristatin F compound through its C-terminal component's carboxylic acid residue;

the wavy line at the dipeptide C-terminus indicates the site of covalent attachment to the remainder W or to A, or a subunit thereof, as when $A_O$ is present as $A_2$;

$R^{34}$ is hydrogen, or the side chain of a naturally occurring α-amino acid except proline, in particular —CH$_3$, —C(CH$_3$)$_2$, —CH$_2$COOH, —CH$_2$CH$_2$COOH, or —CH$_2$CH$_2$CH$_2$NH$_2$; and $R^{35}$ is hydrogen, methyl, isopropyl, sec-butyl, benzyl, p-hydroxy-benzyl, —CH$_2$OH, —CH(OH)CH$_3$, —CH$_2$CH$_2$SCH$_3$, —CH$_2$C(=O)NH$_2$, —CH$_2$COOH, —CH$_2$CH$_2$C(=O)NH$_2$, —CH$_2$CH$_2$COOH, —CH$_2$CH$_2$CH$_2$NHC(=NH)NH$_2$, —CH$_2$CH$_2$CH$_2$NH$_2$, —CH$_2$CH$_2$CH$_2$NH—C(=O)CH$_3$, —CH$_2$CH$_2$CH$_2$NH—C(=O)H, —CH$_2$CH$_2$CH$_2$CH$_2$NHC(=NH)NH$_2$, —CH$_2$CH$_2$CH$_2$CH$_2$NH$_2$—, —CH$_2$CH$_2$CH$_2$CH$_2$NH—C(=O)CH$_3$, —CH$_2$CH$_2$CH$_2$CH$_2$NH—C(=O)H, —CH$_2$CH$_2$CH$_2$NHC(=O)NH$_2$, —CH$_2$CH$_2$CH$_2$CH$_2$NHC(=O)NH$_2$, —CH$_2$CH$_2$CH(OH)CH$_2$NH$_2$, 2-pyridylmethyl, 4-pyridylmethyl, phenyl, or cyclohexyl, or $R^{35}$ has the structure of one of:

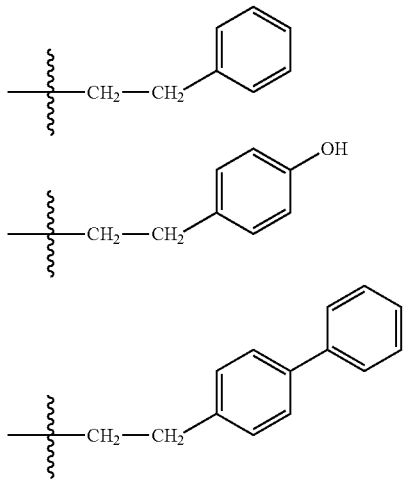

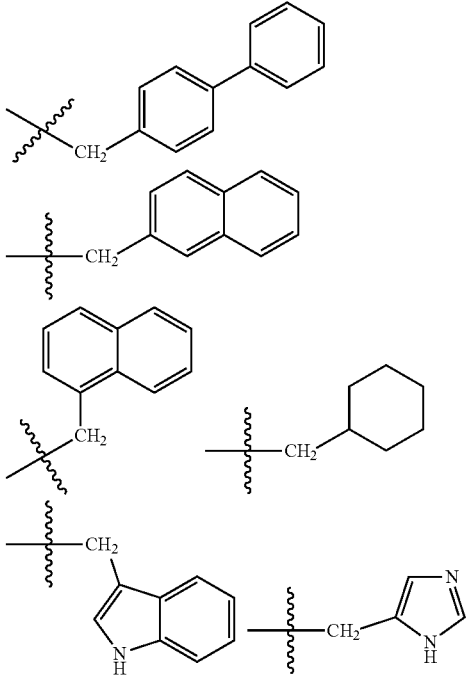

wherein the wavy line indicates the site of covalent attachment to the dipeptide backbone; or (b) W is a glutamic acid residue, an aspartic acid residue, or a peptide sequence comprising an N-terminal glutamic acid residue or N-terminal aspartic acid residue, wherein W is covalently attached through its α-amino nitrogen atom to the hydrophobic auristatin F compound C-terminal component's carboxylic acid residue, and wherein W is covalently attached through its a-carboxyl carbon atom to A', wherein both attachments are through amide bonds, wherein A' is a $C_2$-$C_{12}$ alkylene diamine, in particular a $C_2$-$C_6$ or a $C_2$-$C_4$ alkylene diamine having a carboxylic acid substituent, wherein the nitrogen atom of one of the amines of A' is covalently attached via an amide bond to W, and the nitrogen atom of the other amine of A' is covalently attached to A, or a subunit thereof, as when $A_O$ is present as $A_2$; or (c) -A'-W— has the structure of:

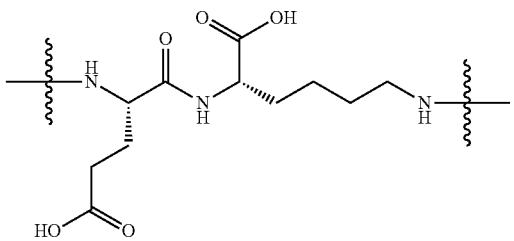 [SMILES: *NCCCC[C@H](NC(=O)[C@H](CCC(=O)O)N*)C(=O)O]

wherein the wavy line adjacent to the glutamic acid alpha-amino nitrogen atom indicates the site of covalent attachment via an amide bond to the hydrophobic auristatin F compound through its C-terminal component's carboxylic acid residue, and the wavy line adjacent to the lysine epsilon amine nitrogen atom indicates the site of covalent attachment to A or subunit thereof as when $A_O$ is present as $A_2$.

7. The Ligand Drug Conjugate composition of claim 1, wherein its drug linker moieties are represented by the structure(s) of:

or a salt thereof, wherein HE is an optional Hydrolysis Enhancing Unit;

$A_O$ is absent or is a second subunit of A;

A' is a second optional Stretcher Unit;

subscript a' is 0 or 1, indicating the absence or presence of A', respectively;

subscript P is 1 or 2;

subscript Q ranges from 1 to 6;

$R^{a3}$ is —H, optionally substituted $C_1$-$C_6$ alkyl, optionally substituted —$C_1$-$C_4$ alkylene-($C_6$-$C_{10}$ aryl), or —$R^{PEG1}$—O—($CH_2CH_2O)_{1-36}$—$R^{PEG2}$, wherein $R^{PEG1}$ is $C_1$-$C_4$ alkylene, $R^{PEG2}$ is —H or $C_1$-$C_4$ alkylene, wherein the basic nitrogen bonded to $R^{a3}$ is optionally protonated or is in a salt form, $R^{34}$ is —$CH_3$, —$C(CH_3)_2$, —$CH_2COOH$, —$CH_2CH_2COOH$ or —$CH_2CH_2CH_2CH_2NH_2$; and $R^{35}$ is methyl, isopropyl, —$CH_2C(=O)NH_2$, —$CH_2COOH$, —$CH_2CH_2C(=O)NH_2$, —$CH_2CH_2COOH$, —$CH_2CH_2CH_2NHC(=NH)NH_2$, —$CH_2CH_2CH_2NH_2$, —$CH_2CH_2CH_2NH$—$C(=O)CH_3$, —$CH_2CH_2CH_2NH$—$C(=O)H$, —$CH_2CH_2CH_2CH_2NHC(=NH)NH_2$, —$CH_2CH_2CH_2CH_2NH_2$—, —$CH_2CH_2CH_2CH_2NH$—$C(=O)CH_3$, —$CH_2CH_2CH_2CH_2NH$—$C(=O)H$, —$CH_2CH_2CH_2NHC(=O)NH_2$, —$CH_2CH_2CH_2CH_2NHC(=O)NH_2$ or —$CH_2CH_2CH(OH)CH_2NH_2$;

$R^2$ is methyl; and $R^1$ is $C_1$-$C_9$ alkyl, optionally substituted by a $C_3$-$C_6$ carbocyclyl to provide a (carbocyclyl)-alkylene- of up to 9 total carbon atoms, or $R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in the (carbocyclyl)alkyl(ene) moieties of $R^1$ is between 4 and 10 and $R^1$ is not methyl, or $R^1$ is a first non-aromatic hydrophobic moiety; and $R^2$ is a second non-aromatic hydrophobic moiety, wherein the first and second hydrophobic moieties provide the hydrophobic AF compound characterized by a clogP value of between about 4.4 to about 7.2, or wherein its drug linker moieties are represented by the structure(s) of:

or a salt thereof,
wherein HE is an optional Hydrolysis Enhancing Unit,
$A_O$ is absent or is a second subunit of A;
A' is a second optional Stretcher Unit;
subscript a' is 0 or 1, indicating the absence or presence of A', respectively;
subscript x is 1 or 2;
$R^{a2}$ is hydrogen or —$CH_3$ or —$CH_2CH_3$;
$R^{a3}$, at each instance, is independently hydrogen, —$CH_3$ or —$CH_2CH_3$, or both $R^{a3}$ together with the nitrogen to which they are attached define an azetidinyl, pyrrolidinyl or piperidinyl heterocyclyl, in which a basic primary, secondary or tertiary amine so defined is optionally protonated as an acid addition salt form,
$R^{34}$ is —$CH_3$, —$C(CH_3)_2$, —$CH_2COOH$, —$CH_2CH_2COOH$ or —$CH_2CH_2CH_2NH_2$; and
$R^{35}$ is methyl, isopropyl, —$CH_2C(=O)NH_2$, —$CH_2COOH$, —$CH_2CH_2C(=O)NH_2$, —$CH_2CH_2COOH$, —$CH_2CH_2CH_2NHC(=NH)NH_2$, —$CH_2CH_2CH_2NH_2$, —$CH_2CH_2CH_2NH$—$C(=O)CH_3$, —$CH_2CH_2CH_2NH$—$C(=O)H$, —$CH_2CH_2CH_2NHC(=NH)NH$-2, —$CH_2CH_2CH_2CH_2NH_2$—, —$CH_2CH_2CH_2CH_2NH$—$C(=O)CH_3$, —$CH_2CH_2CH_2CH_2NH$—$C(=O)H$, —$CH_2CH_2CH_2NHC(=O)NH_2$, —$CH_2CH_2CH_2CH_2NHC(=O)NH_2$ or —$CH_2CH_2CH(OH)CH_2NH_2$;
$R^2$ is methyl; and
$R^1$ is $C_1$-$C_9$ alkyl, optionally substituted by a $C_3$-$C_6$ carbocyclyl to provide a (carbocyclyl)-alkylene- of up to 9 total carbon atoms, or
$R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in the (carbocyclyl)alkyl(ene) moieties of $R^1$ is between 4 and 10 and $R^1$ is not methyl, or
$R^1$ is a first non-aromatic hydrophobic moiety; and
$R^2$ is a second non-aromatic hydrophobic moiety,
wherein the first and second hydrophobic moieties provide the hydrophobic AF compound characterized by a clogP value of between about 4.4 to about 7.2.

8. The Ligand Drug Conjugate compound of claim 1, wherein:
(a) each drug linker moiety is represented by the structure of:

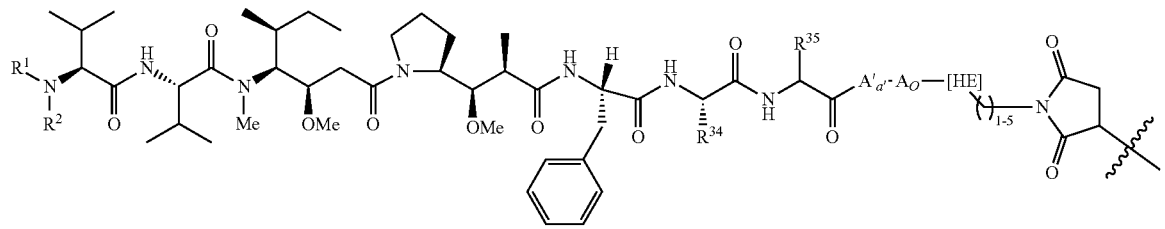

or a salt thereof, wherein
HE is an optional Hydrolysis Enhancing Unit, which is a component provided by A or a first subunit thereof;
$A_O$ is an optional second subunit of A;
A' is a second optional Stretcher Unit;
subscript a' is 0 or 1, indicating the absence or presence of A', respectively;
$R^{34}$ is —$CH_3$, —$C(CH_3)_2$, —$CH_2COOH$, —$CH_2CH_2COOH$, or —$CH_2CH_2CH_2NH_2$;
$R^{35}$ is methyl, isopropyl, —$CH_2C(=O)NH_2$, —$CH_2COOH$, —$CH_2CH_2C(=O)NH_2$, —$CH_2CH_2COOH$, —$CH_2CH_2CH_2NHC(=NH)NH_2$, —$CH_2CH_2CH_2NH_2$, —$CH_2CH_2CH_2NH$—$C(=O)CH_3$, —$CH_2CH_2CH_2NH$—$C(=O)H$, —$CH_2CH_2CH_2CH_2NHC(=NH)NH_2$, —$CH_2CH_2CH_2CH_2NH_2$—, —$CH_2CH_2CH_2CH_2NH$—$C(=O)CH_3$, —$CH_2CH_2CH_2CH_2NH$—$C(=O)H$, —$CH_2CH_2CH_2NHC(=O)NH_2$, —$CH_2CH_2CH_2CH_2NHC(=O)NH_2$, or —$CH_2CH_2CH(OH)CH_2NH_2$;
$R^2$ is methyl; and
$R^1$ is $C_1$-$C_9$ alkyl, or
$R^1$ is ($C_3$-$C_6$ carbocyclyl)-alkylene- of up to 9 total carbon atoms, or
$R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in $R^2$ and the (carbocyclyl)alkyl(ene) moiety of $R^1$ is between 4 and 10, and $R^1$ is not methyl, or

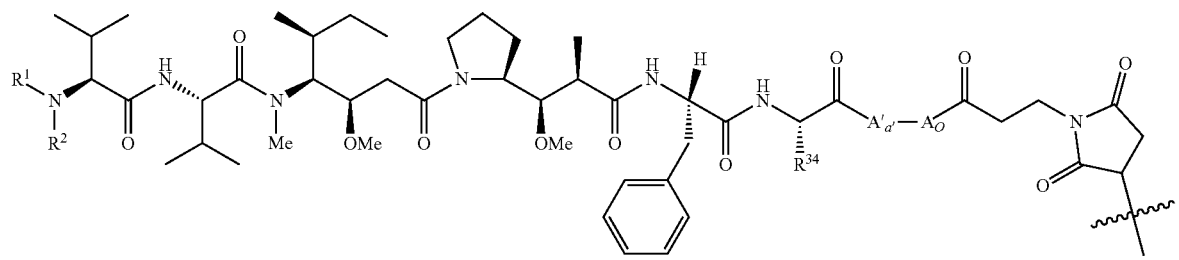

or a salt thereof, wherein $A_O$ is absent or an α-amino acid or a β-amino acid residue;

A' is present substituted or unsubstituted $C_2$-$C_6$ alkylene diamine residue;

$R^{34}$ is —$CH_2CO_2H$ or —$CH_2CH_2CO_2H$;

$R^2$ is methyl; and $R^1$ is $C_1$-$C_9$ alkyl, or $R^1$ is ($C_3$-$C_6$ carbocyclyl)-alkylene- of up to 9 total carbon atoms, or $R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in $R^2$ and the (carbocyclyl)alkyl(ene) moiety of $R^1$ is between 4 and 10, and $R^1$ is not methyl, or (c) each drug linker moiety is represented by the structure of:

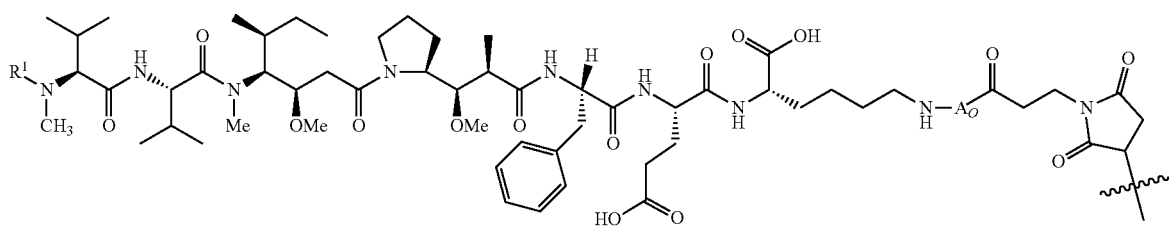

or a salt thereof, wherein $A_O$ is absent or is an α-amino acid or a β-amino acid residue; and $R^1$ is $C_1$-$C_9$ alkyl, or $R^1$ is ($C_3$-$C_6$ carbocyclyl)-alkylene- of up to 9 total carbon atoms, or $R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in $R^2$ and the (carbocyclyl)alkyl(ene) moiety of $R^1$ is between 4 and 10, and $R^1$ is not methyl, or (d) each drug linker moiety is represented by the structure of:

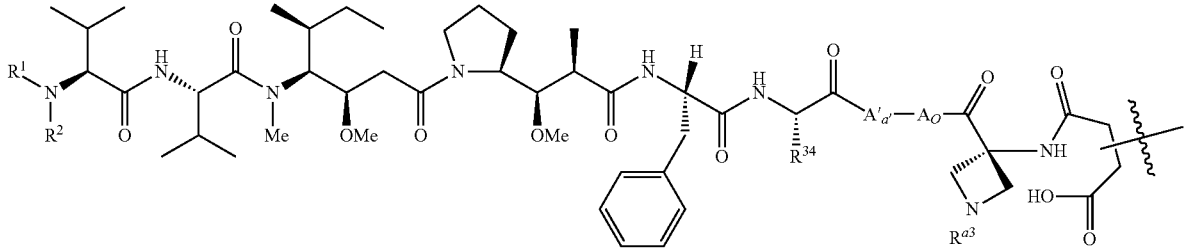

or a salt thereof, wherein
$R^{a3}$ is hydrogen, —$CH_3$, or —$CH_2CH_3$, wherein the secondary or tertiary amine so defined is optionally protonated as an acid addition salt form;
$A_O$ is absent or is an α-amino acid or a β-amino acid residue;
A' is a substituted or unsubstituted $C_2$-$C_6$ alkylene diamine residue
$R^{34}$ is —$CH_2CO_2H$ or —$CH_2CH_2CO_2H$;
$R^2$ is methyl; and $R^1$ is $C_1$-$C_9$ alkyl, or
R is ($C_3$-$C_6$ carbocyclyl)-alkylene- of up to 9 total carbon atoms, or
$R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in $R^2$ and the (carbocyclyl)alkyl(ene) moiety of $R^1$ is between 4 and 10, and $R^1$ is not methyl, or
(e) each drug linker moiety is represented by the structure of

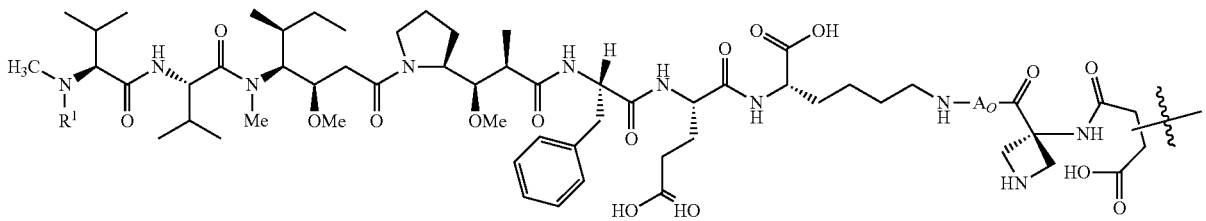

or a salt thereof, wherein
$A_O$ is absent or is an α-amino acid or a β-amino acid residue; and
$R^1$ is $C_1$-$C_9$ alkyl, or
$R^1$ is ($C_3$-$C_6$ carbocyclyl)-alkylene- of up to 9 total carbon atoms, or
$R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in $R^2$ and the (carbocyclyl)alkyl(ene) moiety of $R^1$ is between 4 and 10, and $R^1$ is not methyl,
or
(f) each drug linker moiety is represented by the structure of:

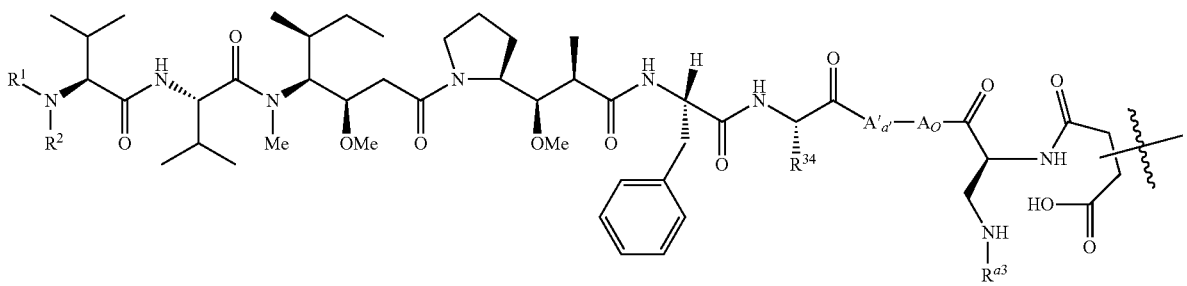

or a salt thereof, wherein
$R^{a3}$ is hydrogen, —$CH_3$, or —$CH_2CH_3$, wherein the primary or secondary amine so defined is optionally protonated as an acid addition salt form;
$A_O$ is absent or is an α-amino acid or a β-amino acid residue;
A' is substituted or unsubstituted $C_2$-$C_6$ alkylene diamine residue
$R^{34}$ is —$CH_2CO_2H$ or —$CH_2CH_2CO_2H$;
$R^2$ is methyl; and
$R^1$ is $C_1$-$C_9$ alkyl, or
$R^1$ is ($C_3$-$C_6$ carbocyclyl)-alkylene- of up to 9 total carbon atoms, or
$R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in $R^2$ and the (carbocyclyl)alkyl(ene) moiety of $R^1$ is between 4 and 10, and $R^1$ is not methyl, or (g) each drug linker moiety is represented by the structure of:

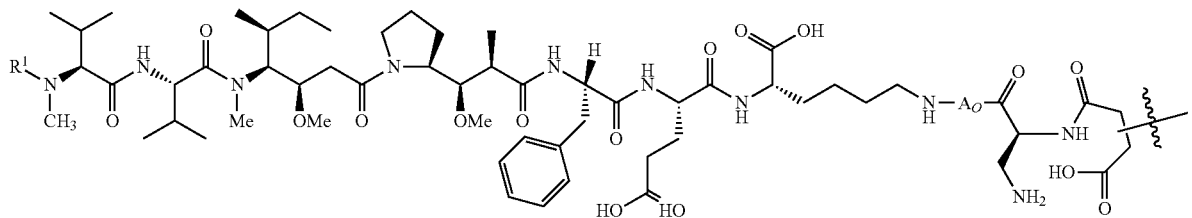

or a salt thereof, wherein $A_O$ is absent or is an α-amino acid or a β-amino acid residue; and $R^1$ is $C_1$-$C_9$ alkyl, or $R^1$ is ($C_3$-$C_6$ carbocyclyl)-alkylene- of up to 9 total carbon atoms, or $R^1$ is —($C_2$-$C_6$ alkylene)-X—$R^4$, wherein X is an amide or carbamate functional group and $R^4$ is $C_1$-$C_6$ alkyl, with the proviso that the total number of carbon atoms in $R^2$ and the (carbocyclyl)alkyl(ene) moiety of $R^1$ is between 4 and 10, and $R^1$ is not methyl.

9. The Ligand Drug Conjugate compound of claim 8, wherein $R^1$ is —CH₂CH₂CH₂CH₃, —CH₂CH₂CH₂CH₂CH₃, CH₂CH₂CH₂C(CH₃)₂, —CH₂CH₂CH₂CH₂N(CH₃)—C(=O)—O-t-Bu, —CH₂CH₂CH₂CH₂N(CH₃)—C(=O)-t-Bu, —CH₂CH₂CH₂N(CH₃)—C(=O)—O-t-Bu, —CH₂CH₂CH₂NH—C(=O)—O-t-Bu, or has the structure of:

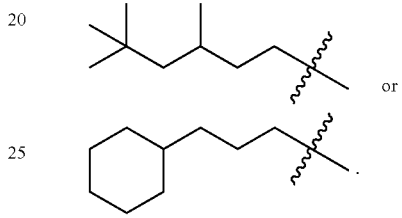

10. The Ligand Drug Conjugate compound of claim 1, wherein each drug linker moiety has the structure of:

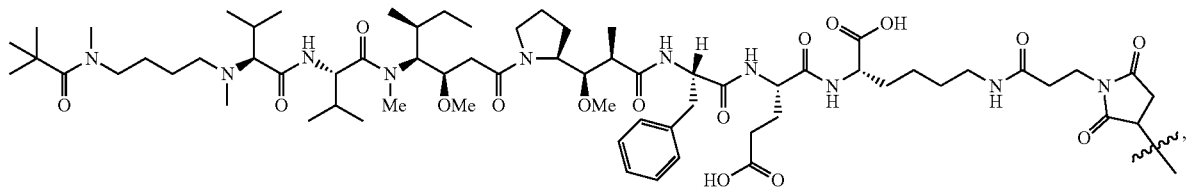

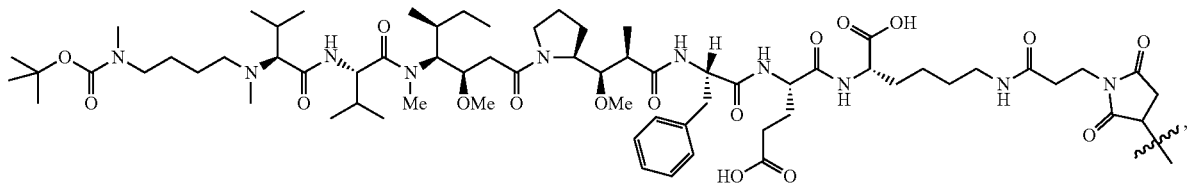

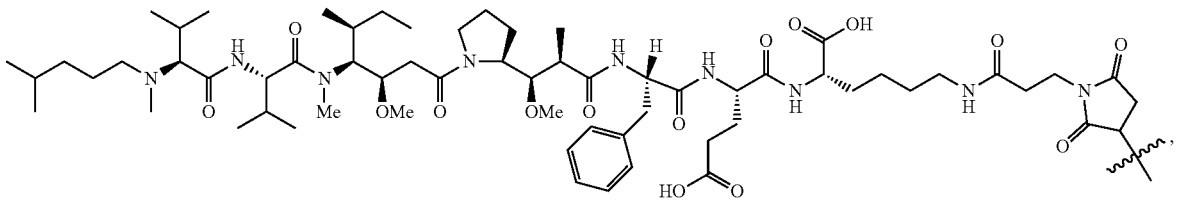

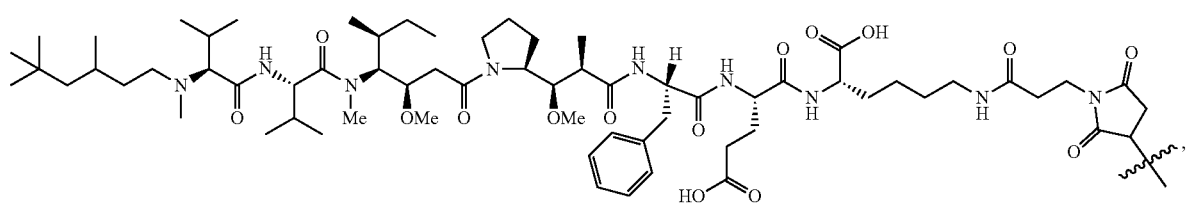

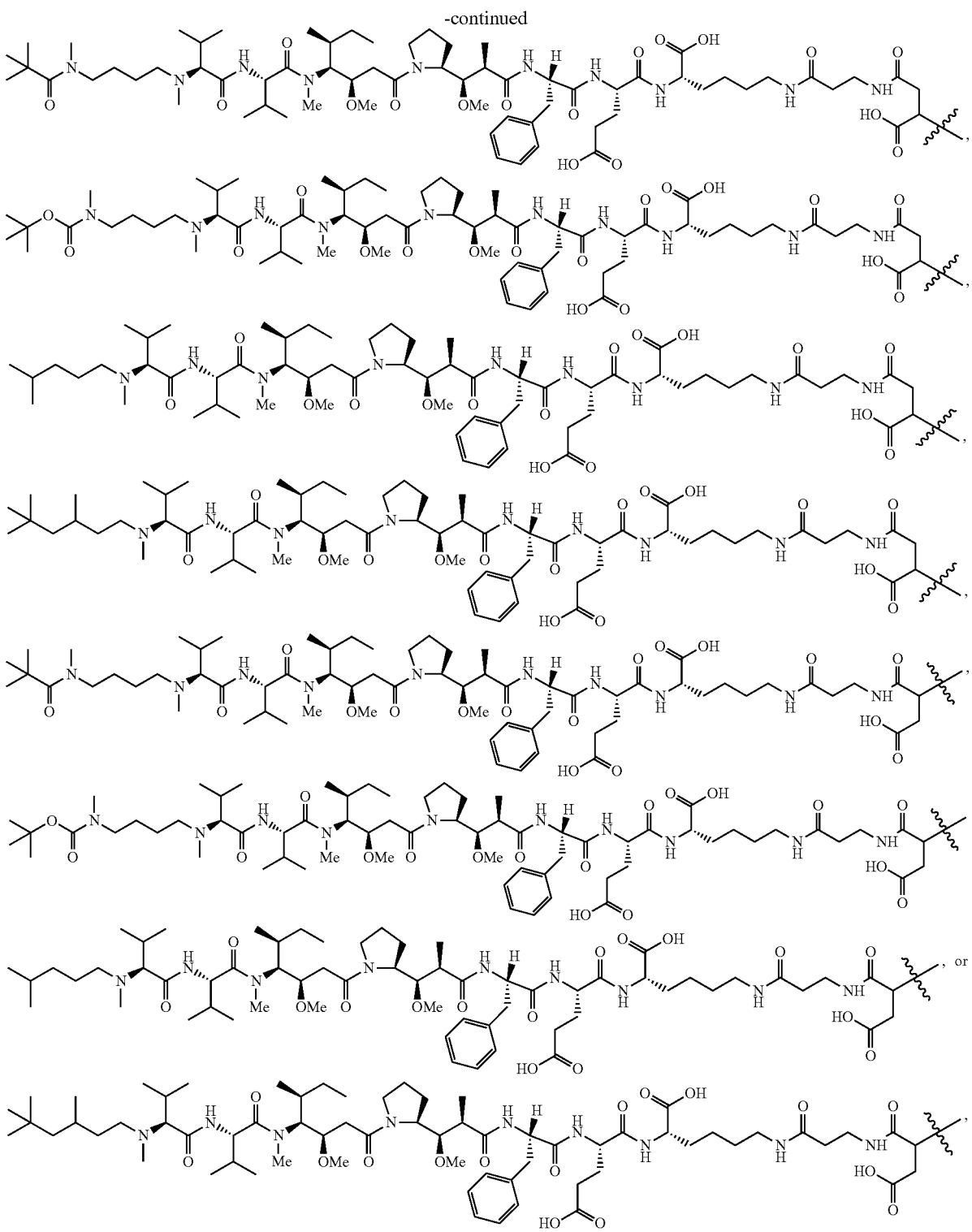

or a salt thereof.

11. The Ligand Drug Conjugate compound of claim 1, wherein L is an antibody Ligand Unit of an intact antibody or an antigen-binding fragment thereof, that is capable of selectively binding to a cancer cell antigen, in particular, the antibody the Ligand Unit is an intact chimeric, humanized, or human antibody.

12. The Ligand Drug Conjugate compound of claim 11, wherein subscript p' is from about 2 to about 12, or from about 2 to about 10, or from about 2 to about 8, in particular, subscript p' is about 2, about 4, or about 8.

* * * * *